US011168135B2

(12) United States Patent
Bowman et al.

(10) Patent No.: US 11,168,135 B2
(45) Date of Patent: *Nov. 9, 2021

(54) PD1 AND/OR LAG3 BINDERS

(71) Applicant: Merck Sharp & Dohme Corp., Rahway, NJ (US)

(72) Inventors: Edward Bowman, Redwood City, CA (US); Maribel Beaumont, San Mateo, CA (US); Marie-Ange Buyse, Merelbeke (BE); Carlo Boutton, Wielsbeke (BE); Bruno Dombrecht, Heusden (BE); Robert A. Kastelein, Portola Valley, CA (US); David Vlerick, Gentbrugge (BE)

(73) Assignee: Merck Sharp & Dohme Corp., Rahway, NJ (US)

( * ) Notice: Subject to any disclaimer, the term of this patent is extended or adjusted under 35 U.S.C. 154(b) by 228 days.

This patent is subject to a terminal disclaimer.

(21) Appl. No.: 16/415,455

(22) Filed: May 17, 2019

(65) Prior Publication Data

US 2019/0330339 A1    Oct. 31, 2019

Related U.S. Application Data

(62) Division of application No. 15/353,919, filed on Nov. 17, 2016, now Pat. No. 10,323,090.

(60) Provisional application No. 62/257,009, filed on Nov. 18, 2015.

(51) Int. Cl.
| | | |
|---|---|---|
| *C07K 16/28* | (2006.01) | |
| *C07K 16/18* | (2006.01) | |
| *A61K 39/395* | (2006.01) | |
| *A61K 45/06* | (2006.01) | |
| *C07K 16/46* | (2006.01) | |

(52) U.S. Cl.
CPC ...... *C07K 16/2803* (2013.01); *A61K 39/3955* (2013.01); *A61K 45/06* (2013.01); *C07K 16/18* (2013.01); *C07K 16/2818* (2013.01); *C07K 16/468* (2013.01); *C07K 2317/22* (2013.01); *C07K 2317/24* (2013.01); *C07K 2317/31* (2013.01); *C07K 2317/33* (2013.01); *C07K 2317/34* (2013.01); *C07K 2317/565* (2013.01); *C07K 2317/569* (2013.01); *C07K 2317/62* (2013.01); *C07K 2317/76* (2013.01); *C07K 2317/92* (2013.01)

(58) Field of Classification Search
CPC ........ C07K 16/00–468; C07K 16/2803; C07K 16/2818; C07K 2317/22; C07K 2317/569
See application file for complete search history.

(56) References Cited

U.S. PATENT DOCUMENTS

| | | | |
|---|---|---|---|
| 5,665,862 A | 11/1997 | Mahurkar | |
| 5,869,050 A | 2/1999 | de Boer et al. | |
| 6,632,927 B2 | 10/2003 | Adair et al. | |
| 6,824,779 B1 | 11/2004 | Freeman et al. | |
| 8,907,065 B2 * | 12/2014 | Hermans | C07K 16/2818 530/387.1 |
| 10,087,251 B2 * | 10/2018 | Hermans | A61K 47/643 |
| 10,323,090 B2 * | 6/2019 | Bowman | A61P 31/00 |
| 10,544,222 B2 * | 1/2020 | Punnonen | A61P 31/12 |
| 2002/0006403 A1 | 1/2002 | Yu et al. | |
| 2004/0083084 A1 | 4/2004 | West | |
| 2009/0055944 A1 | 2/2009 | Korman et al. | |
| 2014/0093511 A1 | 4/2014 | Lonberg et al. | |
| 2014/0271635 A1 | 9/2014 | Brogdon et al. | |
| 2015/0010546 A1 | 1/2015 | Kolkman et al. | |
| 2015/0158948 A9 | 6/2015 | Descamps et al. | |
| 2015/0210769 A1 | 7/2015 | Freeman et al. | |
| 2015/0266958 A1 | 9/2015 | Hermans et al. | |
| 2016/0222121 A1 | 8/2016 | Johnson et al. | |
| 2017/0137520 A1 | 5/2017 | Punnonen et al. | |
| 2017/0137521 A1 | 5/2017 | Punnonen et al. | |

FOREIGN PATENT DOCUMENTS

| | | |
|---|---|---|
| CA | 2924524 A1 | 3/2015 |
| CA | 2932966 A1 | 6/2015 |
| CA | 2734335 C | 1/2018 |
| CN | 102176921 B | 5/2014 |
| EP | 2139918 | 6/2010 |
| EP | 3486257 A1 | 5/2019 |
| EP | 3081576 B1 | 8/2019 |
| WO | 199404678 | 3/1994 |
| WO | 2002051871 | 7/2002 |
| WO | 2002078731 A1 | 10/2002 |
| WO | 2003042402 | 5/2003 |
| WO | 200441865 | 5/2004 |
| WO | 2006040153 A2 | 4/2006 |

(Continued)

OTHER PUBLICATIONS

Edwards et al, J Mol Biol 334:103-118 (Year: 2003).*
Marchalonis et al., Dev & Comp Immunol 30:223-247 (Year: 2006).*
Almagro & Fransson, Frontiers in Bioscience 13:1619-33 (Year: 2008).*

(Continued)

*Primary Examiner* — Jessica H Roark
(74) *Attorney, Agent, or Firm* — John David Reilly; Anna L. Cocuzzo

(57) ABSTRACT

The present invention provides molecules, such as ISVDs and Nanobodies, that bind to PD1 and LAG3 and, optionally to human serum albumin. These molecules have been engineered so as to reduce the incidence of binding by pre-existing antibodies in the bodies of a subject administered such a molecule. Methods for increasing immune response, treating cancer and/or treating an infectious disease with such molecules are provided.

16 Claims, 66 Drawing Sheets

Specification includes a Sequence Listing.

(56) References Cited

FOREIGN PATENT DOCUMENTS

| WO | 2006122787 | | 11/2006 |
|---|---|---|---|
| WO | 2007049017 | A2 | 5/2007 |
| WO | 2008071447 | A2 | 6/2008 |
| WO | 2008071447 | | 8/2008 |
| WO | 2010007376 | | 1/2010 |
| WO | 201019570 | | 2/2010 |
| WO | 2010019570 | | 2/2010 |
| WO | 2010027828 | A2 | 3/2010 |
| WO | 2008096158 | A2 | 6/2010 |
| WO | 201106915 | | 1/2011 |
| WO | 2012176400 | | 12/2012 |
| WO | 2013024059 | | 2/2013 |
| WO | 2014030049 | | 2/2014 |
| WO | 2014043509 | | 3/2014 |
| WO | 2014111550 | | 7/2014 |
| WO | 2015026684 | A1 | 2/2015 |
| WO | 2015044386 | | 2/2015 |
| WO | 2015042246 | | 3/2015 |
| WO | 2015044386 | | 4/2015 |
| WO | 2015070060 | A1 | 5/2015 |
| WO | 2015085847 | A1 | 6/2015 |
| WO | 2015112800 | A1 | 7/2015 |
| WO | 2015112900 | | 7/2015 |
| WO | 2015173325 | | 11/2015 |
| WO | 2015200119 | | 12/2015 |
| WO | 2016023960 | A1 | 2/2016 |
| WO | 2016024228 | A1 | 2/2016 |
| WO | 2016024231 | A1 | 2/2016 |
| WO | 2016028656 | A1 | 2/2016 |
| WO | 2016168716 | A1 | 10/2016 |
| WO | 2017017623 | A1 | 2/2017 |
| WO | 2017017624 | A1 | 2/2017 |
| WO | 2017025051 | A1 | 2/2017 |
| WO | 2017040790 | A1 | 3/2017 |
| WO | 2017055404 | A1 | 4/2017 |
| WO | 2017055443 | A1 | 4/2017 |
| WO | 2017058859 | A1 | 4/2017 |
| WO | 2017093478 | A1 | 6/2017 |
| WO | 2017106061 | A1 | 6/2017 |
| WO | 2017106656 | A1 | 6/2017 |
| WO | 2017194641 | A1 | 11/2017 |
| WO | 2017198741 | A1 | 11/2017 |
| WO | 2018005973 | A1 | 1/2018 |
| WO | 2018013017 | A1 | 1/2018 |
| WO | 2018050027 | A1 | 3/2018 |
| WO | 2018053106 | A1 | 3/2018 |
| WO | 2018053405 | A1 | 3/2018 |
| WO | 2018185043 | A1 | 10/2018 |

OTHER PUBLICATIONS

S. Muylderman, Annu. Rev. Biochem. 82:775-97 (Year: 2013).*
International Search Report for PC/TUS2016/062394, dated Feb. 22, 2017; 7 pages.
Abrams et al., Blockade of T Lymphocyte Costimulation with Cytotoxic T Lymphocyte-associated Antigen 4-Immunoglobulin (CTLA4Ig) Reverses the Cellular Pathology of Psoriatic Plaques, Including the Activation of Keratinocytes, Dendritic Cells, and Endothelial Cells, J. Exp. Med., 2000, pp. 681-693, vol. 192.
Adorini et al., Therapeutic Aspects of Apoptosls, Idrugs, 2000, pp. 496-498, vol. 3.
Alegre et al., T-Cell Regulation by CD28 and CTLA-4, Nat. Rev. Immunol., 2001, pp. 220-228, vol. 1.
Butte et al., Programmed Death-1 Ligand 1 Interacts Specifically with the B7-1 Costimulatory Molecule to Inhibit T Cell Responses, Immunity, 2007, pp. 111-122, vol. 27.
Chambers et al., CTLA-4-Mediated Inhibition in Regulation of T Cell Responses: Mechanisms and Manipulation in Tumor Immunotherapy, Annu. Rev. Immunol., 2001, pp. 565-594, vol. 19.
Choi et al., Activation of Naive CD4T Cells in Vivo by a Self-Peptide Mimic: Mechanism of Tolerance Maintenance and Preservation of Immunity, J. Immunol., 2004, pp. 7399-7407, vol. 172.
Collins et al., The Interaction Properties of Costimulatory Molecules Revisited, Immunity, 2002, pp. 201-210, vol. 17.
Conrath et al., Camel Single-domain Antibodies as Modular Building Units in Bispecific and Bivalent Antibody Constructs, The Journal of Biological Chemistry, 2001, pp. 7346-7350, vol. 276(10).
Coyle et al., The expanding B7 superfamily: Increasing complexity in costimulatory signals regulating T cell function, Nature Immunology, 2001, pp. 203-209, vol. 2/3.
Coyle et al., The role of ICOS and other costimulatory molecules in allergy and asthma, Immune, 2004, pp. 349-359, vol. 25.
Curran et al., PD1 and CTLA4 combination blockade expands infiltrating T cells and reduces regulatory T and myeloid cells within B16 melanoma tumors, PNAS, 2010, pp. 4275-4280, vol. 107.
Database WPI, Thomson XP002766907, Oct. 21, 2015—Abstract.
Dincq et al., Expression and Purification of Monospecific and Bispecific Recombinant Antibody Fragments Derived from Antibodies That Block the CD80,CD86-CD28 Costimulatoly Pathway, Protein Expression and Purification, 2001, pp. 11-24, vol. 22.
Duraiswamy et al., Dual Blockade of PD-1 and CTLA-4 Combined with Tumor Vaccine Effective Restores T-Cell Rejection Function in Tumors, Cancer Research, 2013, pp. 3591-3603, vol. 73.
Friedberg et al., Updated Results from a Phase II Study of Galixmab (anti-CD80) in Combination with Rituximob for Relapsed for Refractory, Follicular NHL, Blood, 2005, p. 2435, vol. 106.
Furukawa et al., Association of B7-1 Co-Stimulation with the Development of Graft Arterial Disease Studies Using Mice Lacking B7-1, B7-2, or B7-1,B7-2, Am. J. of Pathology, 2000, pp. 473-484, vol. 157.
Gottlieb et al., Abstracts for the 61st Annual Meeting of the Society for Investigative Dermatology, J. Invest. Dermatology, J. Invest. Dermatol., 2001, p. 840, vol. 111.
Howard et al., Therapeutic Blockade of TCR Signal Transduction and Co-Stimulation in Autoimmune Disease, Current Drug Targets, 2005, pp. 85-94, vol. 4.
Hufton et al., Development and application of cytotoxic T lymphocyte-associated antigen 4 as a protein scaffold for the generation of novel binding ligands, Febs Lett., 2000, pp. 225-231, vol. 475.
Kang et al., The Synthetic Peptide Trp-Lys-Tyr-Met-Val-D-Met Inhibits Human Monocyte-Derived Dendritic Cell Maturation via Formyl Peptide Receptor and Formyl Peptide Receptor-Like, J. Immunol., 2005, pp. 685-692, vol. 175.
Karandikar et al., Targeting the B7,CD28:CTLA-4 costimulatory system in CNS autoimmune disease, J. of Neuroimmunology, 1998, pp. 10-15, vol. 89.
Keler et al., Activity and Safety of CTLA-4 Blockade Combined with Vaccines in Cynomologus Macaques, J. Immunol., 2003, pp. 6251-6259, vol. 171.
Kopf et al., Inducible Costimulator Protein (ICOS) Controls T Helper Cell Subset Polarization after Virus and Parasite Infection, J, Exp. Med., 2000, pp. 53-61. vol. 192.
Larkin et al., Combined Nivolumab and Ipilmumab or Monotherapy in Untreated Melanoma, The New England Journal of Medicine, Jul. 2, 2015, pp. 23-34, vol. 373.
Larsen et al., Rational Development of LEA29Y (belatacepl), a High-Affinity Variant of CTLA4-Ig with Potent Immunosuppressive Properties, Am. J. Transplant, 2005, pp. 443-453, vol. 5.
Oosterwegel et al., CTLA-4 and T cell activation, Current Opinion in Immunology, 1999, pp. 294-300, vol. 11.
Ozkaynak et al., Importance of ICOS—B7RP-1 costimulation in acute and chronic allograft rejection, Naturo Immunology, 2001, pp. 591-596, vol. 2.
Panka et al., Variable region framework differences result in decreased or increased affinity of variant anti-digoxin antibodies, Proc. Natl. Acad. Sci. USA, 1988, pp. 3080-3084, vol. 85.
Park et al., Targeting and Blocking B7 Costimulatory Molecules on Antigen-Presenting Cells Using CTLA4Ig-Conjugated Liposomes: In Vitro Characterization and in Vivo Factors Affecting Biodistribution, Pharmaceutical Research, 2003, pp. 1239-1248, vol. 20.
Polojil et al., CD4 T Cell Expressed CD80 Regulates Central Nervous System Effector Function and Survival during Experimental AutoImmune Encephalomyelitis, J. of Immunology, 2006, pp. 2948-2958, vol. 177.

(56) References Cited

OTHER PUBLICATIONS

Polojil et al., CD86 and beta 2-adrenergic receptor stimulation regulate B-cell activity cooperatively, Trends in Immunology, 2005, pp. 180-185, vol. 26.
Rao et al., Novel cyclic and linear oligopeptides that bind to Integrin beta 1 chain and either inhibit or costimulate T lymphocytes, Int. Immunopharmacol, 2003, pp. 435-443, vol. 3.
Rottman et al., The costimulatory molecule ICOS plays an important role in the immunopathogenesis of EAE, Nature Immunology, 2001, pp. 605-611, vol. 2.
Rudikoff, Single amino acid substitution altering antigen-binding specificity, PNAS, 1982, pp. 1979-1983, vol. 79.
S. Muyldermans, Single domain camel antibodies: current status, Molecular Biology, 2001, pp. 277-302, vol. 74.
Salama et al., Challenges to achieving clinical transplantation tolerance, J. of Clinical Investigation, 2001, pp. 943-948, vol. 108.
Stuart et al., Targeting T Cell Costimulation in Autoimmune Disease, Anti-inflammatory, 2002, Issue No. 3, pp. 275-289, vol. 6.
Van Den Beucken et al., Building Novel Binding Ligands to B7.1 and B7.2 Based on Human Antibody Single Variable Light Chain Domains, J. Mol. Biology, 2001, pp. 591-601, vol. 310.
Waldmann et al., Effective Cancer Therapy Through Immunomodulation, Annu. Rev. Med., 2005, pp. 65-81, vol. 57(1).
Webb et al., Prevention and amelioration of collagen-inducedarthritis by blockade of the CD28 co-stimulatory pathway: requirement for both B7-1 and B7-2, Eur. J. Immunol., 1996, pp. 2320-2328, vol. 26.
Wolchok et al., Nivolumab plus Ipilimumab in Advanced Melanoma, The New England Jouranl of Medicine, 2013, pp. 122-133, vol. 369(2).
Yamada et al., The Role of Novel T Cell Costimulatory Pathways in Autoimmunity and Transplantation, J. Am. Soc. Nephrol., 2002, pp. 559-575, vol. 13.
Zhang et al., Crystal structure of the receptor-binding domain of human B7-2: Insights into organization and signaling, PNAS, 2003, pp. 2586-2591, vol. 100.
Shin et al., The Evolution of Checkpoint Blockade as a Cancer Therapy: What's here, What's next?, Current Opinion in Immunology, vol. 33, 2016, pp. 23-35.
Tesaro and AbaptysBio Expand Collaboration with Novel Antibody Candidate, Retrieved from the Internet on May 4, 2017: URL:https://immuno-oncologynews.com/2014/1/2/04/tesaro-anaptysbic-expand-collaboration-novel-bispecific-antibody-candidate/, XP055369219, 2017, p. 2.
La Motte-Mohs et al., MGD2013, a Bispecific PD-1 x LAG-3 Dual-Affinity Re-Targeting (DART) Protein with T-cell Immunomodulatory Activity for Cancer Treatment, 2016, Poser, Retrieved from Internet on May 4, 2017: URL:http://titles.shareholder.com/downloads/AMDA-278VRP/0X0X886238/9181C668-BC8D-4410-88B2-BD08E68ABDEE/MacroGenics_AACR_2016_MGD013 PD-1_x_LAG-3 dart.pdf.
Woo et al., Immune Inhibitory Molecules LAG-3 and PD-1 Synergistically Regulate T-cell Function to Promote Tumoral Immune Escape, Cancer Research, vol. 72. No. 4, 2011, 917-927.
Vincke, et al., Journal of Biological Chemistry, vol. 284, No. 5, 2008, pp. 3273-3284.
Cordy, et al., Clinical and Experimental Immunology, vol. 182, No. 2, 2015, pp. 139-148.
Holland, et al., Journal of Clinical Immunology, vol. 33, No. 7, 2013, pp. 1192-1203.

* cited by examiner

| Numbering according to Kabat (VH) | Numbering according to Chotia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: http://www.bioc.uzh.ch/plueckthun/antibody/Numbering/NumFrame.html

FIG.1

| SEQ ID NO | Description | Sequence |
|---|---|---|
| 1 | WO 2008/071447, SEQ ID NO:348 (102C12) | EVQLVESGGGLVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTQVTVSS |
| 2 | referenceA | EVQLVESGGGLVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVSS |
| 3 | CDR1 (Kabat) | IHAMG |
| 4 | CDR2 (Kabat) | VITWSGGITYYADSVKG |
| 5 | CDR3 (Kabat/Abm) | DKHQSSWYDY |
| 6 | CDR1 (Abm) | GSIASIHAMG |
| 7 | CDR2 (Abm) | VITWSGGITY |
| 8 | CDR3 (Kabat/Abm) | DKHQSSWYDY |
| 9 | Reference A (89T) | EVQLVESGGGLVQAGGSLRLSCAASGSIASIHAMGWFRQAPGKEREFVAVITWSGGITYYADSVKGRFTISRDNAKNTVYLQMNSLKPEDTATYYCAGDKHQSSWYDYWGQGTLVTVSS |
| 10 | Reference A (11V + 110K) | EVQLVESGGGLVQAGGSLRLSCAASGSIASIHAMGWFRQAPGKEREFVAVITWSGGITYYADSVKGRFTISRDNAKNTVYLQMNSLKPEDTATYYCAGDKHQSSWYDYWGQGTLVKVSS |
| 11 | Reference A (11V + 110Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVQVSS |
| 12 | Reference A (11V + 112K) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVTVKS |
| 13 | Reference A (11V + 112Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTLVTVQS |

FIG.2-1

| SEQ ID NO | Description | Sequence |
|---|---|---|
| 14 | Reference A (89L + 110K) | EVQLVESGGGLVQAGGSLRLSCAASGSIASIHAMGWFRQAP GKEQEFVADIRTSAGRTYYADSVKGRFTISRDNAKNTVYLQ MNSLKPEDTALYYCAAEMSGISGWDYWGQGTLVKVSS |
| 15 | Reference A (89L + 110Q) | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVQVSS |
| 16 | Reference A (89L + 112K) | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVKS |
| 17 | Reference A (11V + 112Q) | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVQS |
| 18 | Reference A (11V + 89L) | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVSS |
| 19 | Reference A (11V + 89L + 110K) | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVKVSS |
| 20 | Reference A (11V + 89L + 110Q) | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVQVSS |
| 21 | Reference A (11V + 89L + 112K) | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVKS |
| 22 | Reference A (11V + 89L + 112Q) | EVQLVESGGGVVQPGGSLRLSCAASGGTFSFYGMGWFRQAP GKEQEFVADIRTSAGRTYYADSVKGRFTISRDNSKNTVYLQ MNSLRPEDTALYYCAAEMSGISGWDYWGQGTLVTVQS |
| 23 | PD1 binder/binding moiety | EVQLVESGGGVVQPGGSLRLSCAASGGTFSFYGMGWFRQAP GKEREFVADIRTSAGRTYYADSVKGRFTISRDNSKNTVYLQ MNSLRPEDTALYYCAAEMSGISGWDYWGQGTLVTVSS |

FIG.2-2

| SEQ ID NO | Description | Sequence |
|---|---|---|
| 24 | PD1 binder/binding moiety | DVQLVESGGGVVQPGGSLRLSCAASGGTFSFYGMGWFRQAP GKEQEFVADIRTSAGRTYYADSVKGRFTISRDNSKNTVYLQ MNSLRPEDTALYYCAAEMSGISGWDYWGQGTLVTVSS |
| 25 | Reference A (89T)+ A | DVQLVESGGGVVQPGGSLRLSCAASGGTFSFYGMGWFRQAP GKEREFVADIRTSAGRTYYADSVKGRFTISRDNSKNTVYLQ MNSLRPEDTALYYCAAEMSGISGWDYWGQGTLVTSSA |
| 26 | Reference A (11V + 110K)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTATYYCAAEMSGISGWDYWGQGTLVKVSSA |
| 27 | Reference A (11V + 110Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTLVQVSSA |
| 28 | Reference A (11V + 112K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTLVTVKSA |
| 29 | Reference A (11V + 112Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTLVTVQSA |
| 30 | Reference A (89L + 110K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTLVKVSSA |
| 31 | Reference A (89L + 110Q)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVQVSSA |
| 32 | Reference A (89L + 112K)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVKSA |
| 33 | Reference A (89L + 112Q)+A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVQSA |

FIG.2-3

| SEQ ID NO | Description | Sequence |
|---|---|---|
| 34 | Reference A (11V + 89L)+A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVSSA |
| 35 | Reference A (11V + 89L + 110K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVKVSSA |
| 36 | Reference A (11V + 89L + 110Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVQVSSA |
| 37 | Reference A (11V + 89L + 112K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVKSA |
| 38 | Reference A (11V + 89L + 112Q)+A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVQSA |
| 39 | PD1 binder/binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTLVTVSSA |
| 40 | PD1 binder/binding moiety | EVQLVESGGGVVQPGGSLRLSCAASGGTFSFYGMGWFRQAP GKEQEFVADIRTSAGRTYYADSVKGRFTISRDNSKNTVYLQ MNSLRPEDTALYYCAAEMSGISGWDYWGQGTLVTVSSA |

FIG.2-4

| SEQ ID NO | Description | Sequence |
|---|---|---|
| 41 | HIS6-FLAG3 tag | HHHHHHGAADYKDHDGDYKDHDIDYKDDDDKGAA |
| 42 | C-terminal end | VTVKS |
| 43 | C-terminal end | VTVQS |
| 44 | C-terminal end | VKVSS |
| 45 | C-terminal end | VQVSS |
| 46 | C-terminal end | VTVKSX(n) |
| 47 | C-terminal end | VTVQSX(n) |
| 48 | C-terminal end | VKVSSX(n) |
| 49 | C-terminal end | VQVSSX(n) |
| 50 | C-terminal end | VTVKSA |
| 51 | C-terminal end | VTVQSA |
| 52 | C-terminal end | VKVSSA |
| 53 | C-terminal end | VQVSSA |
| 54 | C-terminal end | VTVSS |
| 55 | C-terminal end | VTVSSX(n) |
| 56 | C-terminal end | VTVSSA |

FIG.2-5

|   |   | 20 |   | 40 |   | 60 |   |
|---|---|---|---|---|---|---|---|
| SEQIDNO:1 | EVQLVESGGG | LVQAGGSLRL | SCAASGSIAS | IHAMGWFRQA | PGKEREFVAV | ITWSGGITYY | 60 |
| SEQIDNO:2 | .......... | .......... | .......... | .......... | .......... | .......... | 60 |
| SEQIDNO:9 | .......... | .......... | .......... | .......... | .......... | .......... | 60 |
| SEQIDNO:10 | .......... | V......... | .......... | .......... | .......... | .......... | 60 |
| SEQIDNO:11 | .......... | V......... | .......... | .......... | .......... | .......... | 60 |
| SEQIDNO:12 | .......... | V......... | .......... | .......... | .......... | .......... | 60 |
| SEQIDNO:13 | .......... | V......... | .......... | .......... | .......... | .......... | 60 |
| SEQIDNO:14 | .......... | .......... | .......... | .......... | .......... | .......... | 60 |
| SEQIDNO:15 | .......... | .......... | .......... | .......... | .......... | .......... | 60 |
| SEQIDNO:16 | .......... | .......... | .......... | .......... | .......... | .......... | 60 |
| SEQIDNO:17 | .......... | .......... | .......... | .......... | .......... | .......... | 60 |
| SEQIDNO:18 | .......... | V......... | .......... | .......... | .......... | .......... | 60 |
| SEQIDNO:19 | .......... | V......... | .......... | .......... | .......... | .......... | 60 |
| SEQIDNO:20 | .......... | V......... | .......... | .......... | .......... | .......... | 60 |
| SEQIDNO:21 | .......... | V......... | .......... | .......... | .......... | .......... | 60 |
| SEQIDNO:22 | .......... | V......... | .......... | .......... | .......... | .......... | 60 |
| SEQIDNO:23 | .......... | V..P...... | .......... | .......... | .......... | .......... | 60 |
| SEQIDNO:24 | .......... | .......... | .......... | .......... | .......... | .......... | 60 |
| SEQIDNO:25 | .......... | V......... | .......... | .......... | .......... | .......... | 60 |
| SEQIDNO:26 | .......... | V......... | .......... | .......... | .......... | .......... | 60 |
| SEQIDNO:27 | .......... | V......... | .......... | .......... | .......... | .......... | 60 |
| SEQIDNO:28 | .......... | V......... | .......... | .......... | .......... | .......... | 60 |
| SEQIDNO:29 | .......... | .......... | .......... | .......... | .......... | .......... | 60 |
| SEQIDNO:30 | .......... | .......... | .......... | .......... | .......... | .......... | 60 |
| SEQIDNO:31 | .......... | .......... | .......... | .......... | .......... | .......... | 60 |
| SEQIDNO:32 | .......... | .......... | .......... | .......... | .......... | .......... | 60 |
| SEQIDNO:33 | .......... | V......... | .......... | .......... | .......... | .......... | 60 |
| SEQIDNO:34 | .......... | V......... | .......... | .......... | .......... | .......... | 60 |
| SEQIDNO:35 | .......... | V......... | .......... | .......... | .......... | .......... | 60 |
| SEQIDNO:36 | .......... | V......... | .......... | .......... | .......... | .......... | 60 |
| SEQIDNO:37 | .......... | V......... | .......... | .......... | .......... | .......... | 60 |
| SEQIDNO:38 | .......... | V..P...... | .......... | .......... | .......... | .......... | 60 |

FIG.3A

```
                              80              100             120
                              |               |               |
SEQIDNO:1  ADSVKGRFTI SRDNAKNTVY LQMNSLKPED TAIYYCAGDK HQSSWYDYWG QGTQVTVSS- 119
SEQIDNO:2  .......... .......... .......... .......... .......... ...L.....- 119
SEQIDNO:9  .......... .......... .......... ..T....... .......... ...L.....- 119
SEQIDNO:10 .......... .......... .......... .......... .......... ...L.K...- 119
SEQIDNO:11 .......... .......... .......... .......... .......... ...L.Q...- 119
SEQIDNO:12 .......... .......... .......... .......... .......... ...L...K.- 119
SEQIDNO:13 .......... .......... .......... .......... .......... ...L...Q.- 119
SEQIDNO:14 .......... .......... .......... ....V..... .......... ...L.K...- 119
SEQIDNO:15 .......... .......... .......... ....V..... .......... ...L.Q...- 119
SEQIDNO:16 .......... .......... .......... ....V..... .......... ...L...K.- 119
SEQIDNO:17 .......... .......... .......... ....V..... .......... ...L...Q.- 119
SEQIDNO:18 .......... .......... .......... ....V..... .......... ...L.....- 119
SEQIDNO:19 .......... .......... .......... ....V..... .......... ...L.K...- 119
SEQIDNO:20 .......... .......... .......... ....V..... .......... ...L.Q...- 119
SEQIDNO:21 .......... .......... .......... ....V..... .......... ...L...K.- 119
SEQIDNO:22 .......... .......... .......... ....V..... .......... ...L...Q.- 119
SEQIDNO:23 .......... ....S..... ......R... ..L....... .......... ...L.....- 119
SEQIDNO:24 .......... .......... .......... ..T....... .......... ...L.....A 120
SEQIDNO:25 .......... .......... .......... .......... .......... ...L.K...A 120
SEQIDNO:26 .......... .......... .......... .......... .......... ...L.Q...A 120
SEQIDNO:27 .......... .......... .......... .......... .......... ...L...K.A 120
SEQIDNO:28 .......... .......... .......... .......... .......... ...L...Q.A 120
SEQIDNO:29 .......... .......... .......... ....V..... .......... ...L.K...A 120
SEQIDNO:30 .......... .......... .......... ....V..... .......... ...L.Q...A 120
SEQIDNO:31 .......... .......... .......... ....V..... .......... ...L...K.A 120
SEQIDNO:32 .......... .......... .......... ....V..... .......... ...L...Q.A 120
SEQIDNO:33 .......... .......... .......... ....V..... .......... ...L.....A 120
SEQIDNO:34 .......... .......... .......... ....V..... .......... ...L.K...A 120
SEQIDNO:35 .......... .......... .......... ....V..... .......... ...L.Q...A 120
SEQIDNO:36 .......... .......... .......... ....V..... .......... ...L...K.A 120
SEQIDNO:37 .......... .......... .......... ....V..... .......... ...L...Q.A 120
SEQIDNO:38 .......... ....S..... ......R... ..L....... .......... ...L.....A 120
```

FIG.3B

F023700275: 1PD102C12(A14P,A74S,K83R)-FLAG3-HIS6
F023700706: 1PD102C12(L11V,A14P,A74S,K83R,I89L)-FLAG3-HIS6

F0237611B09-*FLAG3-HIS6*
F023700842: F0237611B09(L11V,A14P,R41P,N43K,A62S,A74S,K83R,V89L)-FLAG3-HIS6

F0237611B09-*FLAG3-HIS6*
F023700842: F0237611B09(L11V,A14P,R41P,N43K,A62S,A74S,K83R,V89L)-FLAG3-HIS6

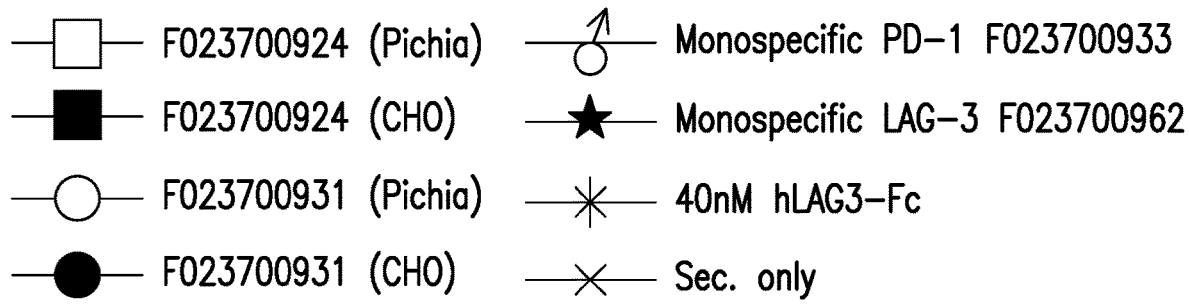
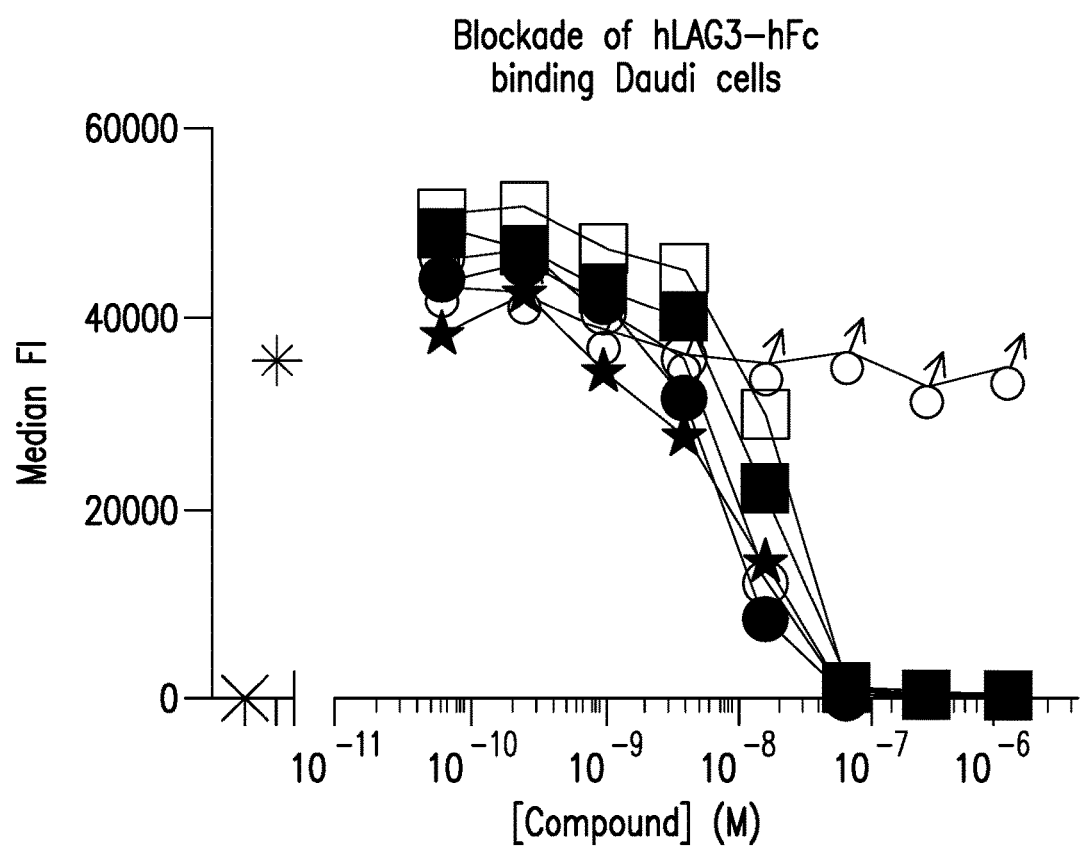
FIG.10B

F023700706: 1PD102C12(L11V,A14P,A74S,K83R,I89L)-FLAG3-HIS6

F023700706: 1PD102C12(L11V,A14P,A74S,K83R,I89L)-FLAG3-HIS6
F023701192: 1PD102C12(E1D,L11V,A14P,W52aV,N73Q,A74S,K83R,I89L,W100aF)-HIS6
F023701193: 1PD102C12(E1D,L11V,A14P,W52aV,N73P,A74S,K83R,I89L,W100aF)-HIS6

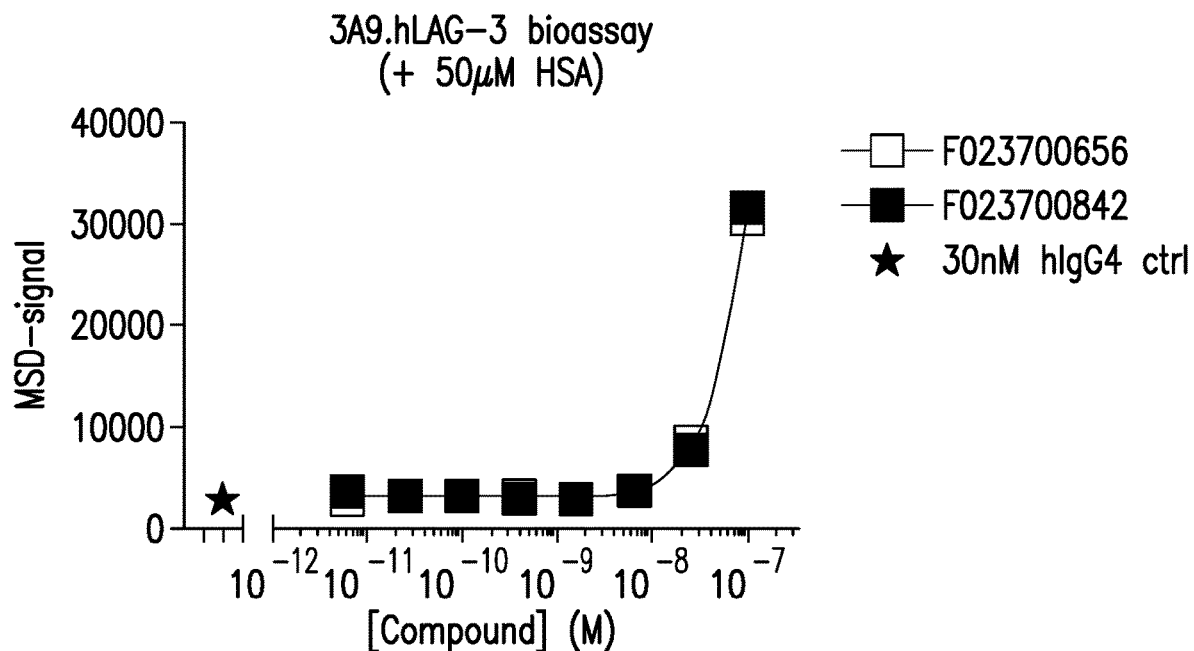
FIG.15A
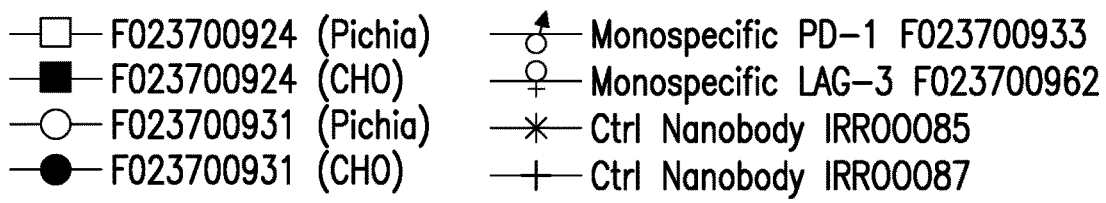
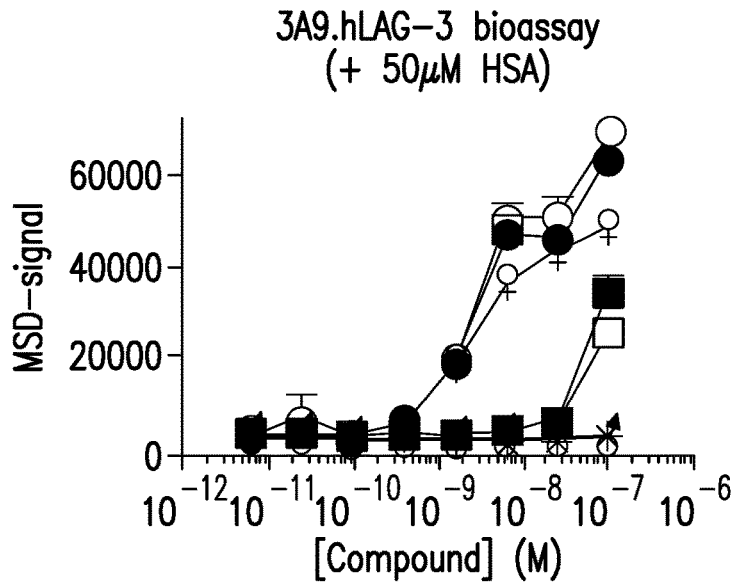
FIG.15B

| Reagent | Description | Target | Sequence |
|---|---|---|---|
| Parent 611B09 | F0237611B09-FLAG3-HIS6 (SEQ ID NO: 128) | hLAG-3 | EVQLVESGGGLVQAGGSLRLSCAASGRTFSDYVMGWFRQARGNEREFVAAISESGGR THYADAVKGRFTISRDNAKNTLYLQMNSLKPEDTAVYYCATTLLWWTSEYAPIKAND YDYWGQGTLVTVSSAAADYKDHDGDYKDHDIDYKDDDDKGAAHHHHHH |
| 611B09 with E1D | F0237611B09(E1D)-HIS6 (SEQ ID NO: 129) | hLAG-3 | DVQLVESGGGLVQAGGSLRLSCAASGRTFSDYVMGWFRQARGNEREFVAAISESGGR THYADAVKGRFTISRDNAKNTLYLQMNSLKPEDTAVYYCATTLLWWTSEYAPIKAND YDYWGQGTLVTVSSAAAHHHHHH |
| SO 611B09 monomer | F0237700842 F0237611B09(L11V,A14P,R41P,N43K,A62S,A74S,K83R,V89L)-FLAG3-HIS6 (SEQ ID NO: 130) | hLAG-3 | EVQLVESGGGVVQPGGSLRLSCAASGRTFSDYVMGWFRQAPGKEREFVAAISESGGR THYADSVKGRFTISRDNSKNTLYLQMNSLRPEDTALYYCATTLLWWTSEYAPIKAND YDYWGQGTLVTVSSAAADYKDHDGDYKDHDIDYKDDDDKGAAHHHHHH |
| Monovalent SO 611B09 + ALB201 | F0237701128 F0237611B09(E1D,L11V,A14P,R41P,N43K,A62S,A74S,K83R,V89L)-35GS-ALB11002-A (SEQ ID NO: 96) | hLAG-3 | DVQLVESGGGVVQPGGSLRLSCAASGRTFSDYVMGWFRQAPGKEREFVAAISESGGR THYADSVKGRFTISRDNSKNTLYLQMNSLRPEDTALYYCATTLLWWTSEYAPIKAND YDYWGQGTLVTVSSGGGGSGGGGSGGGGSGGGGSGGGGSGGGGSEVQLVESG GGVVQPGNSLRLSCAASGFTFSSFGMSWRQAPGKGLEWVSSISGSGSDTLYADSVK GRFTISRDNAKTTLYLQMNSLRPEDTALYYCTIGGSLSRSSQGTLVTVSSA |

FIG. 18A

| | | | |
|---|---|---|---|
| Bivalent SO 611B09 + ALB201 | F023700962 | F023761IB09(E1D,L11V,A14P,R41P,N43K,A62S,A74S,K83R,V89L)-35GS-F023761IB09(L11V,A14P,R41P,N43K,A62S,A74S,K83R,V89L)-35GS-ALB11002-A (SEQ ID NO: 97) | hLAG-3 | DVQLVESGGGVVQPGGSLRLSCAASGRTFSDYVMGWFRQAPGKEREFVAAISESGRTHYADSVKGRFTISRDNSKNTLYLQMNSLRPEDTALYYCATTLLWTSEYAPIKANDYDYWGQGTLVTVSSGGGGSGGGGSGGGGSGGGGSEVQLVESGGGVVQPGGSLRLSCAASGRTFSDYVMGWFRQAPGKEREFVAAISESGRTHYADSVKGRFTISRDNSKNTLYLQMNSLRPEDTALYYCATTLLWTSEYAPIKANDYDYWGQGTLVTVSSGGGGSGGGGSGGGGSGGGGSEVQLVESGGGVVQPGNSLRLSCAASGFTFSSFGMSWRQAPGKGLEWVSSISGSGSDTLYADSVKGRFTISRDNAKTTLYLQMNSLRPEDTALYYCTIGGSLSRSSQGTLVTVSSA |
| Partial SO 1PD102C12 | F023700275 | 1PD102C12(A14P,A74S,K83R)-FLAG3-HIS6 (SEQ ID NO: 131) | hPD-1 | EVQLVESGGGLVQPGGSLRLSCAASGSIASIHAMGWFRQAPGKEREFVAVITWSGGITYYADSVKGRFTISRDKNTVYLQMNSLRPEDTAYYCAGDKHQSSWYDYWGQGTLVTVSSAAADYKDHDGDYKDHDIDYKDDDDKGAAHHHHHH |
| SO 1PD102C12 monomer | F023700706 | 1PD102C12(L11V,A14P,A74S,K83R,I89L)-FLAG3-HIS6 (SEQ ID NO: 132) | hPD-1 | EVQLVESGGGVVQPGGSLRLSCAASGSIASIHAMGWFRQAPGKEREFVAVITWSGGITYYADSVKGRFTISRDKNTVYLQMNSLRPEDTALYYCAGDKHQSSWYDYWGQGTLVTVSSAAADYKDHDGDYKDHDIDYKDDDDKGAAHHHHHH |

FIG. 18B

| | | | |
|---|---|---|---|
| SO 1PD102C12 monomer | F023700929 | 1PD102C12(L11V,A14P,A74S,K83R,I89L)-HIS6 (SEQ ID NO: 133) | hPD-1 | EVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSHHHHHH |
| Monovalent SO 1PD102C12 + ALB201 | F023701127 | 1PD102C12(E1D,L11V,A14P,A74S,K83R,I89L)-35GS-ALB11002-A (SEQ ID NO: 101) | hPD-1 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSGGGGSGGGGSGGGGSGGGGSGGGGSEVQLVESGGGVVQPGNS LRLSCAASGFTFSSFGMSWVRQAPGKGLEWVSSISGSGSDTLYADSVKGRFTISRDN AKTTLYLQMNSLRPEDTALYYCTIGGSLSRSSQGTLVTVSSA |
| Bivalent SO 1PD102C12 + ALB201 | F023700933 | 1PD102C12(E1D,L11V,A14P,A74S,K83R,I89L)-35GS-1PD102C12(L11V,A14P,A74S,K83R,I89L)-35GS-ALB11002-A (SEQ ID NO: 102) | hPD-1 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSGGGGSGGGGSGGGGSGGGGSGGGGSEVQLVESGGGVVQPGGS LRLSCAASGSIASIHAMGWFRQAPGKEREFVAVITWSGGITYYADSVKGRFTISRDN SKNTVYLQMNSLRPEDTALYYCAGDKHQSSWYDYWGQGTLVTVSSGGGGSGGGGSGG GGSGGGGSGGGGSEVQLVESGGGVVQPGNSLRLSCAASGFTFSSFGM SWVRQAPGKGLEWVSSISGSGSDTLYADSVKGRFTISRDNAKTTLYLQMNSLRPEDT ALYYCTIGGSLSRSSQGTLVTVSSA |

FIG. 18C

| Enhanced S0 1PD102C12 monomer | F023701190 | 1PD102C12(E1D,L11V,A14P, W52aV,A74S,K83R,I89L,W10 0aF)-HIS6 (SEQ ID NO: 134) | hPD-1 | DVQLVESGGGVVQPGGSLRLSCAASGSIASIHAMGWFRQAPGKEREFVAVITVSGI TYYADSVKGRFTISRDNSKNTVYLQMNSLRPEDTALYYCAGDKHQSSFYDYWGQGTL VTVSSAAHHHHHH |
| --- | --- | --- | --- | --- |
| Enhanced S0 1PD102C12 monomer | F023701192 | 1PD102C12(E1D,L11V,A14P, W52aV,N73Q,A74S,K83R,I89 L,W100aF)-HIS6 (SEQ ID NO: 135) | hPD-1 | DVQLVESGGGVVQPGGSLRLSCAASGSIASIHAMGWFRQAPGKEREFVAVITVSGI TYYADSVKGRFTISRDQSKNTVYLQMNSLRPEDTALYYCAGDKHQSSFYDYWGQGTL VTVSSAAHHHHHH |
| Enhanced S0 1PD102C12 monomer | F023701193 | 1PD102C12(E1D,L11V,A14P, W52aV,N73P,A74S,K83R,I89 L,W100aF)-HIS6 (SEQ ID NO: 136) | hPD-1 | DVQLVESGGGVVQPGGSLRLSCAASGSIASIHAMGWFRQAPGKEREFVAVITVSGI TYYADSVKGRFTISRDPSKNTVYLQMNSLRPEDTALYYCAGDKHQSSFYDYWGQGTL VTVSSAAHHHHHH |

FIG.18D

| Pentamer #1 | F023700899 | 1PD102C12(A14P,A74S,K83R)-35GS-1PD102C12(A14P,A74S,K83R)-35GS-F023761lB09-35GS-F023761lB09-35GS-ALB11 (SEQ ID NO: 106) | hPD-1/hLAG3 | EVQLVESGGGLVQPGGSLRLSCAASGSIASIHAMGWFRQAPGKEREFVAVITWSGGI TYYADSVKGRFTISRDNSKNTVYLQMNSLRPEDTAIYYCAGDKHQSSWYDYWGQGTL VTVSSGGGGSGGGGSGGGGSGGGGSGGGGSEVQLVESGGGLVQPGGS LRLSCAASGSIASIHAMGWFRQAPGKEREFVAVITWSGGITYYADSVKGRFTISRDN SKNTVYLQMNSLRPEDTAIYYCAGDKHQSSWYDYWGQGTLVTVSSGGGGSGGGGSGG GGSGGGGSGGGGSEVQLVESGGGLVQAGGSLRLSCAASGRTFSDYM GWFRQARGNEREFVAAISESGGRTHYADAVKGRFTISRDNAKNTLYLQMNSLKPEDT AVYYCATTLLWWTSEYAPIKANDYDYWGQGTLVTVSSGGGGSGGGGSGGGGSGGGGS GGGGSGGGGSEVQLVESGGGLVQAGGSLRLSCAASGRTFSDYMGWFRQARG NEREFVAAISESGGRTHYADAVKGRFTISRDNAKNTLYLQMNSLKPEDTAVYYCATT LLWWTSEYAPIKANDYDYWGQGTLVTVSSGGGGSGGGGSGGGGSGGGGSGGGGSGGG GSGGGGSEVQLVESGGGLVQPGNSLRLSCAASGFTFSSFGMSWVRQAPGKGLEWVSS ISGSGSDTLYADSVKGRFTISRDNAKTITLYLQMNSLRPEDTAVYYCTIGGSLSRSSQ GTLVTVSS |

FIG.18E

| | | hPD-1/hLAG-3 |
|---|---|---|
| Pentamer | F023700931<br>1PD102C12<br>(E1D,L11V,A14P,A74S,K83R,I89L)-35GS-1PD102C12<br>(L11V,A14P,A74S,K83R,I89L)-35GS-F0237600B09<br>(L11V,A14P,R41P,N43K,A62S,A74S,K83R,V89L)-35GS-F0237611B09<br>(L11V,A14P,R41P,N43K,A62S,A74S,K83R,V89L)-35GS-ALB11002-A<br>(SEQ ID NO: 107) | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSGGGGSGGGGSGGGGSGGGGSGGGGSEVQLVESGGGVVQPGGSGITYYADSVKGRFTISRDN LRLSCAASGSIASIHAMGWFRQAPGKEREFVAVITWSGGITYYADSVKGRFTISRDN SKNTVYLQMNSLRPEDTALYYCAGDKHQSSWYDYWGQGTLVTVSSGGGGSGGGGSGG GGSGGGGSGGGGSGGGGSEVQLVESGGGVVQPGGSLRLSCAASGRTFSDYM GWFRQAPGKEREFVAAISESGGRTHYADSVKGRFTISRDNSKNTLYLQMNSLRPEDT ALYYCATTLLWWTSEYAPIKANDYDYWGQGTLVTVSSGGGGSGGGGSGGGGS GGGGSGGGGSGGGGSEVQLVESGGGVVQPGGSLRLSCAASGRTFSDYMGWFRQAPG KEREFVAAISESGGRTHYADSVKGRFTISRDNSKNTLYLQMNSLRPEDTALYYCATT LLWWTSEYAPIKANDYDYWGQGTLVTVSSGGGGSGGGGSGGGGSGGGGSGGGGSGGG ISGSGSDTLYADSVKGRFTISRDNAKTTLYLQMNSLRPEDTALYYCTIGGSLSRSSQ GTLVTVSSA |

FIG. 18F

| Pentamer with 20GS | F023701016 | 102C12(E1D,L11V,A14P,A74S,K83R,I89L)-20GS-<br>102C12(L11V,A14P,A74S,K83R,I89L)-20GS-<br>F0237611B09(L11V,A14P,R41P,N43K,A62S,A74S,K83R,V89L)-20GS-<br>F0237611B09(L11V,A14P,R41P,N43K,A62S,A74S,K83R,V89L)-20GS-ALB11002-A<br>(SEQ ID NO: 108) | hPD-1/hLAG-3 | DVQLVESGGGVVQPGGSLRLSCAASGSIASIHAMGWFRQAPGKEREFVAVITWSGGI<br>TYYADSVKGRFTISRDNSKNTVYLQMNSLRPEDTALYYCAGDKHQSSMYDYWGQGTL<br>VTVSSGGGGSGGGGSGGGGSGGGGSEVQLVESGGGVVQPGGSLRLSCAASGSIASIH<br>AMGWFRQAPGKEREFVAVITWSGGITYYADSVKGRFTISRDNSKNTVYLQMNSLRPE<br>DTALYYCAGDKHQSSMYDYWGQGTLVTVSSGGGGSGGGGSGGGGSGGGGSEVQLVES<br>GGGVVQPGGSLRLSCAASGRTFSDYVMGWFRQAPGKEREFVAAISESGGRTHYADSV<br>KGRFTISRDNSKNTLYLQMNSLRPEDTALYYCATTLLWWTSEYAPIKANDYDWGQG<br>TLVTVSSGGGGSGGGGSGGGGSGGGGSEVQLVESGGGVVQPGGSLRLSCAASGRTFS<br>DYVMGWFRQAPGKEREFVAAISESGGRTHYADSVKGRFTISRDNSKNTLYLQMNSLR<br>PEDTALYYCATTLLWWTSEYAPIKANDYDWGQGTLVTVSSGGGGSGGGGSGGGGSG<br>GGGSEVQLVESGGGVVQPGNSLRLSCAASGFTFSSFGMSWVRQAPGKGLEWVSSISG<br>SGSDTLYADSVKGRFTISRDNAKTTLYLQMNSLRPEDTALYYCTIGGSLSRSSQGTL<br>VTVSSA |

FIG.18G

| | | | |
|---|---|---|---|
| Pentamer with 9GS | F023701017 | 102C12(E1D,L11V,A14P,A74S,K83R,I89L)-9GS-102C12(L11V,A14P,A74S,K83R,I89L)-9GS-F0237611B09(L11V,A14P,R41P,N43K,A62S,A74S,K83R,V89L)-9GS-F0237611B09(L11V,A14P,R41P,N43K,A62S,A74S,K83R,V89L)-9GS-ALB11002-A (SEQ ID NO: 109) | hPD-1/hLAG-3 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSMYDYWGQGTL VTVSSGGGGSGGGGSEVQLVESGGGVVQPGGSLRLSCAASGSIASIHAMGWFRQAPGK EREFVAVITWSGGITYYADSVKGRFTISRDNSKNTVYLQMNSLRPEDTALYYCAGDK HQSSMYDYWGQGTLVTVSSGGGGSGGGGSEVQLVESGGGVVQPGGSEVQLVESGGGRTF SDYVMGWFRQAPGKEREFVAAISESGGRTHYADSVKGRFTISRDNSKNTLYLQMNSL RPEDTALYYCATTLLWWTSEYAPIKANDYDWGQGTLVTVSSGGGGSGGGGSEVQLVE SGGGVVQPGGSLRLSCAASGRTFSDYVMGWFRQAPGKEREFVAAISESGGRTHYADS VKGRFTISRDNSKNTLYLQMNSLRPEDTALYYCATTLLWWTSEYAPIKANDYDWGQ GTLVTVSSGGGGSGGGGSEVQLVESGGGSDTLYADSVKGRFTISRDNAKTTLYLQMNSLRPEDTALYYCT PGKGLEWSSISGSGSDTLYADSVKGRFTISRDNAKTTLYLQMNSLRPEDTALYYCT IGGSLSRSSQGTLVTVSSA |
| Trimer | F023700924 | 1PD102C12 (E1D,L11V,A14P,A74S,K83R,I89L)-35GS-F0237611B09 (L11V,A14P,R41P,N43K,A62S,A74S,K83R,V89L)-35GS-ALB11002-A (SEQ ID NO: 110) | hPD-1/hLAG-3 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSMYDYWGQGTL VTVSSGGGGSGGGGSGGGGSGGGGSGGGGSGGGGSEVQLVESGGGVVQPGGS LRLSCAASGRTFSDYVMGWFRQAPGKEREFVAAISESGGRTHYADSVKGRFTISRDN SKNTLYLQMNSLRPEDTALYYCATTLLWWTSEYAPIKANDYDWGQGTLVTVSSGGG GSGGGGSGGGGSGGGGSGGGGSGGGGSGGGGSEVQLVESGGGVVQPGNSLRLSCAAS GFTFSSFGMSWRQAPGKGLEWSSISGSGSDTLYADSVKGRFTISRDNAKTTLYLQ MNSLRPEDTALYYCTIGGSLSRSSQGTLVTVSSA |

FIG. 18H

| | | | |
|---|---|---|---|
| Trimer with 20GS | F023700969 | 102C12(E1D,L11V,A14P,A74S,K83R,I89L)-20GS-F0237611B09(L11V,A14P,R41P,N43K,A62S,A74S,K83R,V89L)-20GS-ALB11002-A (SEQ ID NO: 111) | hPD-1/hLAG-3 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSGGGGSGGGGSGGGGSGGGGSEVQLVESGGGVVQPGGSLRLSCAASGRTFSDY VMGWFRQAPGKEREFVAAISESGGRTHYADSVKGRFTISRDNSKNTLYLQMNSLRPE DTALYYCATTLLWWTSEYAPIKANDYDYWGQGTLVTVSSGGGGSGGGGSGGGGSGGG GSEVQLVESGGGVVQPGNSLRLSCAASGFTFSSFGMSWRQAPGKGLEWVSSISGSG SDTLYADSVKGRFTISRDNAKTTLYLQMNSLRPEDTALYYCTIGGSLSRSSQGTLVT VSSA |
| Trimer with 9GS | F023700970 | 102C12(E1D,L11V,A14P,A74S,K83R,I89L)-9GS-F0237611B09(L11V,A14P,R41P,N43K,A62S,A74S,K83R,V89L)-9GS-ALB11002-A (SEQ ID NO: 112) | hPD-1/hLAG-3 | DVQLVESGGGVVQPGGSLRLSCAASGSIASIHAMGWFRQAPGKEREFVAVITWSGGI TYYADSVKGRFTISRDNSKNTVYLQMNSLRPEDTALYYCAGDKHQSSWYDYWGQGTL VTVSSGGGGSGGGSEVQLVESGGGVVQPGGSLRLSCAASGRTFSDYVMGWFRQAPGK EREFVAAISESGGRTHYADSVKGRFTISRDNSKNTLYLQMNSLRPEDTALYYCATTL LWWTSEYAPIKANDYDYWGQGTLVTVSSGGGGSGGGSEVQLVESGGGVVQPGNSLRL SCAASGFTFSSFGMSWRQAPGKGLEWVSSISGSGSDTLYADSVKGRFTISRDNAKT TLYLQMNSLRPEDTALYYCTIGGSLSRSSQGTLVTVSSA |

FIG. 18I

| | | |
|---|---|---|
| Pentamer /35GS | F023701163 | 1PD102C12 (E1D, L11V, A14P, W52aV, N73P, A74S, K83R, I89L, W100aF)-35GS-1PD102C12 (L11V, A14P, W52aV, N73P, A74S, K83R, I89L, W100aF)-35GS-F023700842-35GS-F023700842-35GS-ALB11002-A (SEQ ID NO: 113) | hPD-1/hLAG-3 | DVQLVESGGGVVQPGGSLRLSCAASGSIASIHAMGWFRQAPGKEREFVAVITVSGGI TYYADSVKGRFTISRDPSKNTVYLQMNSLRPEDTALYYCAGDKHQSSFYDYWGQGTL VTVSSGGGGSGGGGSGGGGSGGGGSGGGGSEVQLVESGGGVVQPGGS LRLSCAASGSIASIHAMGWFRQAPGKEREFVAVITVSGGITYYADSVKGRFTISRDP SKNTVYLQMNSLRPEDTALYYCAGDKHQSSFYDYWGQGTLVTVSSGGGGSGGGGSGG GGSGGGGSGGGGSEVQLVESGGGVVQPGGSLRLSCAASGRTFSDYM GWFRQAPGKEREFVAAISESGGRTHYADSVKGRFTISRDNSKNTLYLQMNSLRPEDT ALYYCATTLLWWTSEYAPIKANDYDYWGQGTLVTVSSGGGGSGGGGSGGGGS GGGGSGGGGSGGGGSEVQLVESGGGVVQPGGSLRLSCAASGRTFSDYMGWFRQAPG KEREFVAAISESGGRTHYADSVKGRFTISRDNSKNTLYLQMNSLRPEDTALYYCATT LLWWTSEYAPIKANDYDYWGQGTLVTVSSGGGGSGGGGSGGGGSGGGGSGGGGSGGG GSGGGGSDTLYADSVKGRFTISRDNAKTTLYLQMNSLRPEDTALYYCTIGGSLSRSSQ GTLVTVSSA |

FIG.18J

| | | | | |
|---|---|---|---|---|
| Pentamer /9GS | F023701168 | 1PD102C12 (E1D, L11V, A14P, W52aV, N73P, A74S, K83R, I89L, W100aF)-9GS-1PD102C12 (L11V, A14P, W52aV, N73P, A74S, K83R, I89L, W100aF)-9GS-F023700842-9GS-F023700842-9GS-ALB11002-A (SEQ ID NO: 114) | hPD-1/hLAG-3 | DVQLVESGGGVVQPGGSLRLSCAASGSIASIHAMGWFRQAPGKEREFVAVITVSGGI<br>TYYADSVKGRFTISRDPSKNTVYLQMNSLRPEDTALYYCAGDKHQSSFYDYWGQGTL<br>VTVSSGGGGSGGGSEVQLVESGGGVVQPGGSLRLSCAASGSIASIHAMGWFRQAPGK<br>EREFVAVITVSGGITYYADSVKGRFTISRDPSKNTVYLQMNSLRPEDTALYYCAGDK<br>HQSSFYDYWGQGTLVTVSSGGGGSGGGSEVQLVESGGGVVQPGGSLRLSCAASGRTF<br>SDYVMGWFRQAPGKEREFVAAISESGGRTHYADSVKGRFTISRDNSKNTLYLQMNSL<br>RPEDTALYYCATTLLWWTSEYAPIKANDYDYWGQGTLVTVSSGGGGSGGGSEVQLVE<br>SGGGVVQPGGSLRLSCAASGRTFSDYVMGWFRQAPGKEREFVAAISESGGRTHYADS<br>VKGRFTISRDNSKNTLYLQMNSLRPEDTALYYCATTLLWWTSEYAPIKANDYDYWGQ<br>GTLVTVSSGGGGSGGGSEVQLVESGGGVVQPGNSLRLSCAASGFTFSSFGMSWVRQA<br>PGKGLEWVSSISGSGSDTLYADSVKGRFTISRDNAKTTLYLQMNSLRPEDTALYYCT<br>IGGSLSRSSQGTLVTVSSA |
| Trimer/ 35GS | F023701173 | 1PD102C12 (E1D, L11V, A14P, W52aV, N73P, A74S, K83R, I89L, W100aF)-35GS-F023700842-35GS-ALB11002-A (SEQ ID NO: 115) | hPD-1/hLAG-3 | DVQLVESGGGVVQPGGSLRLSCAASGSIASIHAMGWFRQAPGKEREFVAVITVSGGI<br>TYYADSVKGRFTISRDPSKNTVYLQMNSLRPEDTALYYCAGDKHQSSFYDYWGQGTL<br>VTVSSGGGGSGGGGSGGGGSGGGGSGGGGSGGGGSGGGGSEVQLVESGGGVVQPGGS<br>LRLSCAASGRTFSDYVMGWFRQAPGKEREFVAAISESGGRTHYADSVKGRFTISRDN<br>SKNTLYLQMNSLRPEDTALYYCATTLLWWTSEYAPIKANDYDYWGQGTLVTVSSGGG<br>GSGGGGSGGGGSGGGGSGGGGSGGGGSGGGGSEVQLVESGGGVVQPGNSLRLSCAAS<br>GFTFSSFGMSWVRQAPGKGLEWVSSISGSGSDTLYADSVKGRFTISRDNAKTTLYLQ<br>MNSLRPEDTALYYCTIGGSLSRSSQGTLVTVSSA |

FIG.18K

| | | | |
|---|---|---|---|
| Trimer /9GS | F023701178 | 1PD102C12 (E1D, L11V, A14P, W52aV, N73P, A74S, K83R, I89L, W100aF)-9GS-F023700842-9GS-ALB11002-A (SEQ ID NO: 116) | hPD-1/hLAG-3 | DVQLVESGGGVVQPGGSLRLSCAASGSIASIHAMGWFRQAPGKEREFVAVITVSGGI TYYADSVKGRFTISRDPSKNTVYLQMNSLRPEDTALYYCAGDKHQSSFYDYWGQGTL VTVSSGGGGSGGGGSGGGGSEVQLVESGGGVVQPGGSLRLSCAASGRTFSDYVMGWFRQAPGK EREFVAAISESGGRTHYADSVKGRFTISRDNSKNTLYLQMNSLRPEDTALYYCATTL LWWTSEYAPIKANDYDYWGQGTLVTVSSGGGGSGGGGSEVQLVESGGGVVQPGNSLRL SCAASGFTFSSFGMSWVRQAPGKGLEWVSSISGSGSDTLYADSVKGRFTISRDNAKT TLYLQMNSLRPEDTALYYCTIGGSLSRSSQGTLVTVSSA |
| Pentamer /35GS | F023701161 | 1PD102C12 (E1D, L11V, A14P, W52aV, N73Q, A74S, K83R, I89L, W100aF)-35GS-1PD102C12 (L11V, A14P, W52aV, N73Q, A74S, K83R, I89L, W100aF)-35GS-F023700842-35GS-F023700842-35GS-ALB11002-A (SEQ ID NO: 117) | hPD-1/hLAG-3 | DVQLVESGGGVVQPGGSLRLSCAASGSIASIHAMGWFRQAPGKEREFVAVITVSGGI TYYADSVKGRFTISRDQSKNTVYLQMNSLRPEDTALYYCAGDKHQSSFYDYWGQGTL VTVSSGGGGSGGGGSGGGGSGGGGSGGGGSEVQLVESGGGVVQPGGSLRLSCAASGSIASIHAMGWFRQAPGKEREFVAVITVSGGITYYADSVKGRFTISRDQ SKNTVYLQMNSLRPEDTALYYCAGDKHQSSFYDYWGQGTLVTVSSGGGGSGGGGSGG GGSGGGGSGGGGSEVQLVESGGGVVQPGGSLRLSCAASGRTFSDYVM GWFRQAPGKEREFVAAISESGGRTHYADSVKGRFTISRDNSKNTLYLQMNSLRPEDT ALYYCATTLLWWTSEYAPIKANDYDYWGQGTLVTVSSGGGGSGGGGSGGGGSGGGGS GGGGSGGGGSEVQLVESGGGVVQPGGSLRLSCAASGRTFSDYVMGWFRQAPG KEREFVAAISESGGRTHYADSVKGRFTISRDNSKNTLYLQMNSLRPEDTALYYCATT LLWWTSEYAPIKANDYDYWGQGTLVTVSSGGGGSGGGGSGGGGSGGGGSGGGGSGGG GSGGGGSEVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSRSSQ GTLVTVSSA |

FIG. 18L

| | | | | |
|---|---|---|---|---|
| Pentamer /9GS | F023701166 | 1PD102C12 (E1D, L11V, A14P, W52aV, N73Q, A74S, K83R, I89L, W100aF)-9GS-1PD102C12 (L11V, A14P, W52aV, N73Q, A74S, K83R, I89L, W100aF)-9GS-F023700842-9GS-F023700842-9GS-ALB11002-A (SEQ ID NO: 118) | hPD-1/hLAG-3 | DVQLVESGGGVVQPGGSLRLSCAASGSIASIHAMGWFRQAPGKEREFVAVITVSGGI<br>TYYADSVKGRFTISRDQSKNTVYLQMNSLRPEDTALYYCAGDKHQSSFYDYWGQGTL<br>VTVSSGGGGSGGGSEVQLVESGGGVVQPGGSLRLSCAASGSIASIHAMGWFRQAPGK<br>EREFVAVITVSGGITYYADSVKGRFTISRDQSKNTVYLQMNSLRPEDTALYYCAGDK<br>HQSSFYDYWGQGTLVTVSSGGGGSGGGSEVQLVESGGGVVQPGGSLRLSCAASGRTF<br>SDYVMGWFRQAPGKEREFVAAISESGGRTHYADSVKGRFTISRDNSKNTLYLQMNSL<br>RPEDTALYYCATTLLWWTSEYAPIKANDYDYWGQGTLVTVSSGGGGSGGGSEVQLVE<br>SGGGVVQPGGSLRLSCAASGRTFSDYVMGWFRQAPGKEREFVAAISESGGRTHYADS<br>VKGRFTISRDNSKNTLYLQMNSLRPEDTALYYCATTLLWWTSEYAPIKANDYDYWGQ<br>GTLVTVSSGGGGSGGGSEVQLVESGGGVVQPGNSLRLSCAASGFTFSSFGMSWVRQA<br>PGKGLEWVSSISGSGSDTLYADSVKGRFTISRDNAKTTLYLQMNSLRPEDTALYYCT<br>IGGSLSRSSQGTLVTVSSA |
| Trimer /35GS | F023701171 | 1PD102C12 (E1D, L11V, A14P, W52aV, N73Q, A74S, K83R, I89L, W100aF)-35GS-F023700842-35GS-ALB11002-A (SEQ ID NO: 119) | hPD-1/hLAG-3 | DVQLVESGGGVVQPGGSLRLSCAASGSIASIHAMGWFRQAPGKEREFVAVITVSGGI<br>TYYADSVKGRFTISRDQSKNTVYLQMNSLRPEDTALYYCAGDKHQSSFYDYWGQGTL<br>VTVSSGGGGSGGGGSGGGGSGGGGSGGGGSGGGGSGGGGSEVQLVESGGGVVQPGGS<br>LRLSCAASGRTFSDYVMGWFRQAPGKEREFVAAISESGGRTHYADSVKGRFTISRDN<br>SKNTLYLQMNSLRPEDTALYYCATTLLWWTSEYAPIKANDYDYWGQGTLVTVSSGGG<br>GSGGGGSGGGGSGGGGSGGGGSGGGGSGGGGSEVQLVESGGGVVQPGNSLRLSCAAS<br>GFTFSSFGMSWVRQAPGKGLEWVSSISGSGSDTLYADSVKGRFTISRDNAKTTLYLQ<br>MNSLRPEDTALYYCTIGGSLSRSSQGTLVTVSSA |

FIG.18M

| | | | |
|---|---|---|---|
| Trimer /9GS | F023701176 | 1PD102C12 (E1D, L11V, A14P, W52aV, N73Q, A74S, K83R, I89L, W100aF)-9GS-F023700842-9GS-ALB11002-A (SEQ ID NO: 120) | hPD-1/hLAG-3 | DVQLVESGGGVVQPGGSLRLSCAASGSIASIHAMGWFRQAPGKEREFVAVITVSGGI TYYADSVKGRFTISRDQSKNTVYLQMNSLRPEDTALYYCAGDKHQSSFYDYWGQGTL VTVSSGGGSGGGSEVQLVESGGGVVQPGGSLRLSCAASGRTFSDYVMGWFRQAPGK EREFVAAISESGGRTHYADSVKGRFTISRDNSKNTLYLQMNSLRPEDTALYYCATTL LWWTSEYAPIKANDYDYWGQGTLVTVSSGGGSGGGSEVQLVESGGGVVQPGNSLRL SCAASGFTFSSFGMSWVRQAPGKGLEWVSSISGSGSDTLYADSVKGRFTISRDNAKT TLYLQMNSLRPEDTALYYCTIGGSLSRSSQGTLVTVSSA |
| Pentamer /35GS | F023701162 | 1PD102C12 (E1D, L11V, A14P, W52aV, N73S, A74S, K83R, I89L, W100aF)-35GS-1PD102C12 (L11V, A14P, W52aV, N73S, A74S, K83R, I89L, W100aF)-35GS-F023700842-35GS-F023700842-35GS-ALB11002-A (SEQ ID NO: 121) | hPD-1/hLAG-3 | DVQLVESGGGVVQPGGSLRLSCAASGSIASIHAMGWFRQAPGKEREFVAVITVSGGI TYYADSVKGRFTISRDSSKNTVYLQMNSLRPEDTALYYCAGDKHQSSFYDYWGQGTL VTVSSGGGSGGGSGGGSGGGSGGGSGGGSEVQLVESGGGVVQPGGSLRLSCAASGSIASIHAMGWFRQAPGKEREFVAVITVSGGITYYADSVKGRFTISRDS SKNTVYLQMNSLRPEDTALYYCAGDKHQSSFYDYWGQGTLVTVSSGGGSGGGSGGG SGGGSGGGSGGGSEVQLVESGGGVVQPGGSLRLSCAASGRTFSDYVM GWFRQAPGKEREFVAAISESGGRTHYADSVKGRFTISRDNSKNTLYLQMNSLRPEDT ALYYCATTLLWWTSEYAPIKANDYDYWGQGTLVTVSSGGGSGGGSGGGSGGGSGGGS GGGSGGGSEVQLVESGGGVVQPGGSLRLSCAASGRTFSDYVMGWFRQAPG KEREFVAAISESGGRTHYADSVKGRFTISRDNSKNTLYLQMNSLRPEDTALYYCATT LLWWTSEYAPIKANDYDYWGQGTLVTVSSGGGSGGGSGGGSGGGSGGGSGGGSGGG SGGGSEVQLVESGGGVVQPGNSLRLSCAASGFTFSSFGMSWVRQAPGKGLEWVSS ISGSGSDTLYADSVKGRFTISRDNAKTTLYLQMNSLRPEDTALYYCTIGGSLSRSSQ GTLVTVSSA |

FIG. 18N

| | | | |
|---|---|---|---|
| Pentamer /9GS | F023701167 | 1PD102C12 (E1D, L11V, A14P, W52aV, N73S, A74S, K83R, I89L, W100aF)-9GS-F023700842-9GS-F023700842-9GS-1PD102C12 (L11V, A14P, W52aV, N73S, A74S, K83R, I89L, W100aF)-9GS-F023700842-9GS-F023700842-9GS-ALB11002-A (SEQ ID NO: 122) | hPD-1/hLAG-3 | DVQLVESGGGVVQPGGSLRLSCAASGSIASIHAMGWFRQAPGKEREFVAVITVSGGI TYYADSVKGRFTISRDSSKNTVYLQMNSLRPEDTALYYCAGDKHQSSFYDYWGQGTL VTVSSGGGGSGGGGSEVQLVESGGGVVQPGGSLRLSCAASGSIASIHAMGWFRQAPGK EREFVAVITVSGGITYYADSVKGRFTISRDSSKNTVYLQMNSLRPEDTALYYCAGDK HQSSFYDYWGQGTLVTVSSGGGGSGGGGSEVQLVESGGGVVQPGGSLRLSCAASGRTF SDYVMGWFRQAPGKEREFVAAISESGGRTHYADSVKGRFTISRDNSKNTLYLQMNSL RPEDTALYYCATTLLWWTSEYAPIKANDYDYWGQGTLVTVSSGGGGSGGGGSEVQLVE SGGGVVQPGGSLRLSCAASGRTFSDYVMGWFRQAPGKEREFVAAISESGGRTHYADS VKGRFTISRDNSKNTLYLQMNSLRPEDTALYYCATTLLWWTSEYAPIKANDYDYWGQ GTLVTVSSGGGGSGGGGSEVQLVESGSGDTLYADSVKGRFTISRDNAKTTLYLQMNSLRPEDTALYYCT IGGSLSRSSQGTLVTVSSA |
| Trimer /35GS | F023701172 | 1PD102C12 (E1D, L11V, A14P, W52aV, N73S, A74S, K83R, I89L, W100aF)-35GS-F023700842-35GS-ALB11002-A (SEQ ID NO: 123) | hPD-1/hLAG-3 | DVQLVESGGGVVQPGGSLRLSCAASGSIASIHAMGWFRQAPGKEREFVAVITVSGGI TYYADSVKGRFTISRDSSKNTVYLQMNSLRPEDTALYYCAGDKHQSSFYDYWGQGTL VTVSSGGGGSGGGGSGGGGSGGGGSGGGGSGGGGSEVQLVESGGGVVQPGGS LRLSCAASGRTFSDYVMGWFRQAPGKEREFVAAISESGGRTHYADSVKGRFTISRDN SKNTLYLQMNSLRPEDTALYYCATTLLWWTSEYAPIKANDYDYWGQGTLVTVSSGGG GSGGGGSGGGGSGGGGSGGGGSGGGGSGGGGSEVQLVESGSGDTLYADSVKGRFTISRDNAKTTLYLQ GFTFSSFGMSWRQAPGKGLEWSSISGSGSDTLYADSVKGRFTISRDNAKTTLYLQ MNSLRPEDTALYYCTIGGSLSRSSQGTLVTVSSA |

FIG. 18O

| Trimer /9GS | F023701177 | 1PD102C12 (E1D, L11V, A14P, W52aV, N73S, A74S, K83R, I89L, W100aF)-9GS-F023700842-9GS-ALB1102-A (SEQ ID NO: 123) | hPD-1/hLAG-3 | DVQLVESGGGVVQPGGSLRLSCAASGSIASIHAMGWFRQAPGKEREFVAVITVSGGI TYYADSVKGRFTISRDSSKNTVYLQMNSLRPEDTALYYCAGDKHQSSFYDYWGQGTL VTVSSGGGGSGGGSEVQLVESGGGVVQPGGSLRLSCAASGRTFSDYMGWFRQAPGK EREFVAAISESGGRTHYADSVKGRFTISRDNSKNTLYLQMNSLRPEDTALYYCATTL LWWTSEYAPIKANDYDYWGQGTLVTVSSGGGGSGGGGSEVQLVESGGGVVQPGNSLRL SCAASGFTFSSFGMSWRQAPGKGLEWVSSISGSGSDTLYADSVKGRFTISRDNAKT TLYLQMNSLRPEDTALYYCTIGGSLSRSSQGTLVTVSSA |

FIG. 18P

SEQUENCE LISTING

<160> NUMBER OF SEQ ID NOS: 154

<210> SEQ ID NO 1
<211> LENGTH: 119
<212> TYPE: PRT
<213> ORGANISM: Artificial Sequence
<220> FEATURE:
<223> OTHER INFORMATION: humanized Lama

<400> SEQUENCE: 1

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110
```

Thr Gln Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: humanized Lama

<400> SEQUENCE: 2

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 3
<211> LENGTH: 5
<212> TYPE: PRT
<213> ORGANISM: Lama sp.

<400> SEQUENCE: 3

Ile His Ala Met Gly
1               5

<210> SEQ ID NO 4
<211> LENGTH: 17
<212> TYPE: PRT
<213> ORGANISM: Lama sp.
<220> FEATURE:
<221> NAME/KEY: MISC_FEATURE
<222> LOCATION: (4)..(4)
<223> OTHER INFORMATION: X is W or V

<400> SEQUENCE: 4

Val Ile Thr Xaa Ser Gly Gly Ile Thr Tyr Tyr Ala Asp Ser Val Lys
1               5                   10                  15

Gly

<210> SEQ ID NO 5
<211> LENGTH: 10
<212> TYPE: PRT
<213> ORGANISM: Lama sp.
<220> FEATURE:
<221> NAME/KEY: MISC_FEATURE
<222> LOCATION: (7)..(7)
<223> OTHER INFORMATION: X is W or F

<400> SEQUENCE: 5

Asp Lys His Gln Ser Ser Xaa Tyr Asp Tyr
1               5                   10

<210> SEQ ID NO 6
<211> LENGTH: 10
<212> TYPE: PRT
<213> ORGANISM: Lama sp.

<400> SEQUENCE: 6

Gly Ser Ile Ala Ser Ile His Ala Met Gly
1               5                   10

<210> SEQ ID NO 7
<211> LENGTH: 10
<212> TYPE: PRT
<213> ORGANISM: Lama sp.
<220> FEATURE:
<221> NAME/KEY: MISC_FEATURE
<222> LOCATION: (4)..(4)
<223> OTHER INFORMATION: X is W or V

<400> SEQUENCE: 7

Val Ile Thr Xaa Ser Gly Gly Ile Thr Tyr
1               5                   10

<210> SEQ ID NO 8
<211> LENGTH: 10
<212> TYPE: PRT
<213> ORGANISM: Lama sp.
<220> FEATURE:
<221> NAME/KEY: MISC_FEATURE
<222> LOCATION: (7)..(7)
<223> OTHER INFORMATION: X is W or F

<400> SEQUENCE: 8

Asp Lys His Gln Ser Ser Xaa Tyr Asp Tyr
1               5                   10

<210> SEQ ID NO 9
<211> LENGTH: 119
<212> TYPE: PRT
<213> ORGANISM: Artificial Sequence
<220> FEATURE:
<223> OTHER INFORMATION: humanized Lama

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 10
<211> LENGTH: 119

```
<212> TYPE: PRT
<213> ORGANISM: Artificial Sequence
<220> FEATURE:
<223> OTHER INFORMATION: humanized Lama

<400> SEQUENCE: 10
```

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
            85                  90                  95

Ala Gly Asp Lys His Gln Ser Ser Trp Tyr Asp Tyr Trp Gly Gln Gly
        100                 105                 110

Thr Leu Val Lys Val Ser Ser
            115

```
<210> SEQ ID NO 11
<211> LENGTH: 119
<212> TYPE: PRT
<213> ORGANISM: Artificial Sequence
<220> FEATURE:
<223> OTHER INFORMATION: humanized Lama

<400> SEQUENCE: 11
```

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
            85                  90                  95

Ala Gly Asp Lys His Gln Ser Ser Trp Tyr Asp Tyr Trp Gly Gln Gly
        100                 105                 110

Thr Leu Val Gln Val Ser Ser
            115

```
<210> SEQ ID NO 12
<211> LENGTH: 119
<212> TYPE: PRT
<213> ORGANISM: Artificial Sequence
<220> FEATURE:
<223> OTHER INFORMATION: humanized Lama

<400> SEQUENCE: 12
```

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His

```
                    20                  25                  30
Ala Met Gly Trp Phe Arg Gln Ala Pro Gly Lys Glu Arg Glu Phe Val
                35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                    85                  90                  95

Ala Gly Asp Lys His Gln Ser Ser Trp Tyr Asp Tyr Trp Gly Gln Gly
                100                 105                 110

Thr Leu Val Thr Val Lys Ser
            115

<210> SEQ ID NO 13
<211> LENGTH: 119
<212> TYPE: PRT
<213> ORGANISM: Artificial Sequence
<220> FEATURE:
<223> OTHER INFORMATION: humanized Lama

<400> SEQUENCE: 13

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                    85                  90                  95

Ala Gly Asp Lys His Gln Ser Ser Trp Tyr Asp Tyr Trp Gly Gln Gly
                100                 105                 110

Thr Leu Val Thr Val Gln Ser
            115

<210> SEQ ID NO 14
<211> LENGTH: 119
<212> TYPE: PRT
<213> ORGANISM: Artificial Sequence
<220> FEATURE:
<223> OTHER INFORMATION: humanized Lama

<400> SEQUENCE: 14

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: humanized Lama

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: humanized Lama

<400> SEQUENCE: 16

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser
        115

<210> SEQ ID NO 17
```

```
<211> LENGTH: 119
<212> TYPE: PRT
<213> ORGANISM: Artificial Sequence
<220> FEATURE:
<223> OTHER INFORMATION: humanized Lama

<400> SEQUENCE: 17

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser
        115

<210> SEQ ID NO 18
<211> LENGTH: 119
<212> TYPE: PRT
<213> ORGANISM: Artificial Sequence
<220> FEATURE:
<223> OTHER INFORMATION: humanized Lama

<400> SEQUENCE: 18

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: humanized Lama

<400> SEQUENCE: 19

Glu Val Gln Leu Val Glu Ser Gly Gly Gly Val Val Gln Ala Gly Gly
1               5                   10                  15
```

```
Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser
            115

<210> SEQ ID NO 20
<211> LENGTH: 119
<212> TYPE: PRT
<213> ORGANISM: Artificial Sequence
<220> FEATURE:
<223> OTHER INFORMATION: humanized Lama

<400> SEQUENCE: 20

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser
            115

<210> SEQ ID NO 21
<211> LENGTH: 119
<212> TYPE: PRT
<213> ORGANISM: Artificial Sequence
<220> FEATURE:
<223> OTHER INFORMATION: humanized Lama

<400> SEQUENCE: 21

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser
        115
```

<210> SEQ ID NO 22
<211> LENGTH: 119
<212> TYPE: PRT
<213> ORGANISM: Artificial Sequence
<220> FEATURE:
<223> OTHER INFORMATION: humanized Lama

<400> SEQUENCE: 22

```
Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser
        115
```

<210> SEQ ID NO 23
<211> LENGTH: 119
<212> TYPE: PRT
<213> ORGANISM: Artificial Sequence
<220> FEATURE:
<223> OTHER INFORMATION: humanized Lama

<400> SEQUENCE: 23

```
Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115
```

-continued

```
<210> SEQ ID NO 24
<211> LENGTH: 119
<212> TYPE: PRT
<213> ORGANISM: Artificial Sequence
<220> FEATURE:
<223> OTHER INFORMATION: humanized Lama

<400> SEQUENCE: 24

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 25
<211> LENGTH: 120
<212> TYPE: PRT
<213> ORGANISM: Artificial Sequence
<220> FEATURE:
<223> OTHER INFORMATION: humanized Lama

<400> SEQUENCE: 25

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
        115                 120

<210> SEQ ID NO 26
<211> LENGTH: 120
<212> TYPE: PRT
<213> ORGANISM: Artificial Sequence
<220> FEATURE:
<223> OTHER INFORMATION: humanized Lama

<400> SEQUENCE: 26

Glu Val Gln Leu Val Glu Ser Gly Gly Gly Val Val Gln Ala Gly Gly
1               5                   10                  15
```

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
            85                  90                  95

Ala Gly Asp Lys His Gln Ser Ser Trp Tyr Asp Tyr Trp Gly Gln Gly
            100                 105                 110

Thr Leu Val Lys Val Ser Ser Ala
            115                 120

<210> SEQ ID NO 27
<211> LENGTH: 120
<212> TYPE: PRT
<213> ORGANISM: Artificial Sequence
<220> FEATURE:
<223> OTHER INFORMATION: humanized Lama

<400> SEQUENCE: 27

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
            85                  90                  95

Ala Gly Asp Lys His Gln Ser Ser Trp Tyr Asp Tyr Trp Gly Gln Gly
            100                 105                 110

Thr Leu Val Gln Val Ser Ser Ala
            115                 120

<210> SEQ ID NO 28
<211> LENGTH: 120
<212> TYPE: PRT
<213> ORGANISM: Artificial Sequence
<220> FEATURE:
<223> OTHER INFORMATION: humanized Lama

<400> SEQUENCE: 28

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser Ala
            115                 120

<210> SEQ ID NO 29
<211> LENGTH: 120
<212> TYPE: PRT
<213> ORGANISM: Artificial Sequence
<220> FEATURE:
<223> OTHER INFORMATION: humanized Lama

<400> SEQUENCE: 29

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser Ala
            115                 120

<210> SEQ ID NO 30
<211> LENGTH: 120
<212> TYPE: PRT
<213> ORGANISM: Artificial Sequence
<220> FEATURE:
<223> OTHER INFORMATION: humanized Lama

<400> SEQUENCE: 30

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser Ala
            115                 120
```

<210> SEQ ID NO 31
<211> LENGTH: 120
<212> TYPE: PRT
<213> ORGANISM: Artificial Sequence
<220> FEATURE:
<223> OTHER INFORMATION: humanized Lama

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser Ala
        115                 120

<210> SEQ ID NO 32
<211> LENGTH: 120
<212> TYPE: PRT
<213> ORGANISM: Artificial Sequence
<220> FEATURE:
<223> OTHER INFORMATION: humanized Lama

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser Ala
        115                 120

<210> SEQ ID NO 33
<211> LENGTH: 120
<212> TYPE: PRT
<213> ORGANISM: Artificial Sequence
<220> FEATURE:
<223> OTHER INFORMATION: humanized Lama

<400> SEQUENCE: 33

Glu Val Gln Leu Val Glu Ser Gly Gly Gly Leu Val Gln Ala Gly Gly

-continued

```
              1               5                  10                 15
         Ser Leu Arg Leu Ser Cys Ala Ala Ser Gly Ser Ile Ala Ser Ile His
                     20                  25                 30

Ala Met Gly Trp Phe Arg Gln Ala Pro Gly Lys Glu Arg Glu Phe Val
                     35                  40                 45

Ala Val Ile Thr Trp Ser Gly Gly Ile Thr Tyr Tyr Ala Asp Ser Val
                     50                  55                 60

Lys Gly Arg Phe Thr Ile Ser Arg Asp Asn Ala Lys Asn Thr Val Tyr
          65                  70                  75                 80

Leu Gln Met Asn Ser Leu Lys Pro Glu Asp Thr Ala Leu Tyr Tyr Cys
                         85                  90                 95

Ala Gly Asp Lys His Gln Ser Ser Trp Tyr Asp Tyr Trp Gly Gln Gly
                        100                 105                110

Thr Leu Val Thr Val Gln Ser Ala
                        115                 120

<210> SEQ ID NO 34
<211> LENGTH: 120
<212> TYPE: PRT
<213> ORGANISM: Artificial Sequence
<220> FEATURE:
<223> OTHER INFORMATION: humanized Lama

<400> SEQUENCE: 34

Glu Val Gln Leu Val Glu Ser Gly Gly Gly Val Val Gln Ala Gly Gly
          1               5                  10                 15

Ser Leu Arg Leu Ser Cys Ala Ala Ser Gly Ser Ile Ala Ser Ile His
                     20                  25                 30

Ala Met Gly Trp Phe Arg Gln Ala Pro Gly Lys Glu Arg Glu Phe Val
                     35                  40                 45

Ala Val Ile Thr Trp Ser Gly Gly Ile Thr Tyr Tyr Ala Asp Ser Val
                     50                  55                 60

Lys Gly Arg Phe Thr Ile Ser Arg Asp Asn Ala Lys Asn Thr Val Tyr
          65                  70                  75                 80

Leu Gln Met Asn Ser Leu Lys Pro Glu Asp Thr Ala Leu Tyr Tyr Cys
                         85                  90                 95

Ala Gly Asp Lys His Gln Ser Ser Trp Tyr Asp Tyr Trp Gly Gln Gly
                        100                 105                110

Thr Leu Val Thr Val Ser Ser Ala
                        115                 120

<210> SEQ ID NO 35
<211> LENGTH: 120
<212> TYPE: PRT
<213> ORGANISM: Artificial Sequence
<220> FEATURE:
<223> OTHER INFORMATION: humanized Lama

<400> SEQUENCE: 35

Glu Val Gln Leu Val Glu Ser Gly Gly Gly Val Val Gln Ala Gly Gly
          1               5                  10                 15

Ser Leu Arg Leu Ser Cys Ala Ala Ser Gly Ser Ile Ala Ser Ile His
                     20                  25                 30

Ala Met Gly Trp Phe Arg Gln Ala Pro Gly Lys Glu Arg Glu Phe Val
                     35                  40                 45

Ala Val Ile Thr Trp Ser Gly Gly Ile Thr Tyr Tyr Ala Asp Ser Val
                     50                  55                 60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Lys Val Ser Ser Ala
            115                 120

<210> SEQ ID NO 36
<211> LENGTH: 120
<212> TYPE: PRT
<213> ORGANISM: Artificial Sequence
<220> FEATURE:
<223> OTHER INFORMATION: humanized Lama

<400> SEQUENCE: 36

Glu Val Gln Leu Val Glu Ser Gly Gly Gly Val Val Gln Ala Gly Gly
  1               5                  10                  15

Ser Leu Arg Leu Ser Cys Ala Ala Ser Gly Ser Ile Ala Ser Ile His
                 20                  25                  30

Ala Met Gly Trp Phe Arg Gln Ala Pro Gly Lys Glu Arg Glu Phe Val
             35                  40                  45

Ala Val Ile Thr Trp Ser Gly Gly Ile Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Gln Val Ser Ser Ala
            115                 120

<210> SEQ ID NO 37
<211> LENGTH: 120
<212> TYPE: PRT
<213> ORGANISM: Artificial Sequence
<220> FEATURE:
<223> OTHER INFORMATION: humanized Lama

<400> SEQUENCE: 37

Glu Val Gln Leu Val Glu Ser Gly Gly Gly Val Val Gln Ala Gly Gly
  1               5                  10                  15

Ser Leu Arg Leu Ser Cys Ala Ala Ser Gly Ser Ile Ala Ser Ile His
                 20                  25                  30

Ala Met Gly Trp Phe Arg Gln Ala Pro Gly Lys Glu Arg Glu Phe Val
             35                  40                  45

Ala Val Ile Thr Trp Ser Gly Gly Ile Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Lys Ser Ala
            115                 120
```

<210> SEQ ID NO 38
<211> LENGTH: 120
<212> TYPE: PRT
<213> ORGANISM: Artificial Sequence
<220> FEATURE:
<223> OTHER INFORMATION: humanized Lama

<400> SEQUENCE: 38

```
Glu Val Gln Leu Val Glu Ser Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser Ala
        115                 120
```

<210> SEQ ID NO 39
<211> LENGTH: 120
<212> TYPE: PRT
<213> ORGANISM: Artificial Sequence
<220> FEATURE:
<223> OTHER INFORMATION: humanized Lama

<400> SEQUENCE: 39

```
Glu Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
        115                 120
```

<210> SEQ ID NO 40
<211> LENGTH: 120
<212> TYPE: PRT
<213> ORGANISM: Artificial Sequence
<220> FEATURE:
<223> OTHER INFORMATION: humanized Lama

<400> SEQUENCE: 40

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
            115                 120

<210> SEQ ID NO 41
<211> LENGTH: 34
<212> TYPE: PRT
<213> ORGANISM: Artificial Sequence
<220> FEATURE:
<223> OTHER INFORMATION: HIS6-FLAG3 tag

<400> SEQUENCE: 41

His His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 42
<211> LENGTH: 5
<212> TYPE: PRT
<213> ORGANISM: Lama sp.

<400> SEQUENCE: 42

Val Thr Val Lys Ser
1               5

<210> SEQ ID NO 43
<211> LENGTH: 5
<212> TYPE: PRT
<213> ORGANISM: Lama sp.

<400> SEQUENCE: 43

Val Thr Val Gln Ser
1               5

<210> SEQ ID NO 44
<211> LENGTH: 5
<212> TYPE: PRT
<213> ORGANISM: Lama sp.

<400> SEQUENCE: 44

Val Lys Val Ser Ser
1               5

<210> SEQ ID NO 45
<211> LENGTH: 5
<212> TYPE: PRT

```
<213> ORGANISM: Lama sp.

<400> SEQUENCE: 45

Val Gln Val Ser Ser
1               5

<210> SEQ ID NO 46
<211> LENGTH: 6
<212> TYPE: PRT
<213> ORGANISM: Lama sp.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 46

Val Thr Val Lys Ser Xaa
1               5

<210> SEQ ID NO 47
<211> LENGTH: 6
<212> TYPE: PRT
<213> ORGANISM: Lama sp.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 47

Val Thr Val Gln Ser Xaa
1               5

<210> SEQ ID NO 48
<211> LENGTH: 6
<212> TYPE: PRT
<213> ORGANISM: Lama sp.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 48

Val Lys Val Ser Ser Xaa
1               5

<210> SEQ ID NO 49
<211> LENGTH: 6
<212> TYPE: PRT
<213> ORGANISM: Lama sp.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 49

Val Gln Val Ser Ser Xaa
1               5

<210> SEQ ID NO 50
<211> LENGTH: 6
<212> TYPE: PRT
<213> ORGANISM: Lama sp.

<400> SEQUENCE: 50

Val Thr Val Lys Ser Ala
1               5
```

```
<210> SEQ ID NO 51
<211> LENGTH: 6
<212> TYPE: PRT
<213> ORGANISM: Lama sp.

<400> SEQUENCE: 51

Val Thr Val Gln Ser Ala
1               5

<210> SEQ ID NO 52
<211> LENGTH: 6
<212> TYPE: PRT
<213> ORGANISM: Lama sp.

<400> SEQUENCE: 52

Val Lys Val Ser Ser Ala
1               5

<210> SEQ ID NO 53
<211> LENGTH: 6
<212> TYPE: PRT
<213> ORGANISM: Lama sp.

<400> SEQUENCE: 53

Val Gln Val Ser Ser Ala
1               5

<210> SEQ ID NO 54
<211> LENGTH: 5
<212> TYPE: PRT
<213> ORGANISM: Lama sp.

<400> SEQUENCE: 54

Val Thr Val Ser Ser
1               5

<210> SEQ ID NO 55
<211> LENGTH: 6
<212> TYPE: PRT
<213> ORGANISM: Lama sp.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 55

Val Thr Val Ser Ser Xaa
1               5

<210> SEQ ID NO 56
<211> LENGTH: 6
<212> TYPE: PRT
<213> ORGANISM: Lama sp.

<400> SEQUENCE: 56

Val Thr Val Ser Ser Ala
1               5

<210> SEQ ID NO 57
<211> LENGTH: 119
<212> TYPE: PRT
<213> ORGANISM: Artificial Sequence
<220> FEATURE:
<223> OTHER INFORMATION: humanized Lama

<400> SEQUENCE: 57
```

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115
```

<210> SEQ ID NO 58
<211> LENGTH: 35
<212> TYPE: PRT
<213> ORGANISM: Artificial Sequence
<220> FEATURE:
<223> OTHER INFORMATION: 35GS linker

<400> SEQUENCE: 58

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser
        35
```

<210> SEQ ID NO 59
<211> LENGTH: 116
<212> TYPE: PRT
<213> ORGANISM: Artificial Sequence
<220> FEATURE:
<223> OTHER INFORMATION: humanized Lama
<220> FEATURE:
<221> NAME/KEY: MISC_FEATURE
<222> LOCATION: (11)..(11)
<223> OTHER INFORMATION: X is L or V
<220> FEATURE:
<221> NAME/KEY: MISC_FEATURE
<222> LOCATION: (93)..(93)
<223> OTHER INFORMATION: X is L or V

<400> SEQUENCE: 59

```
Glu Val Gln Leu Val Glu Ser Gly Gly Gly Xaa Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Xaa Tyr Tyr Cys
                85                  90                  95
```

Thr Ile Gly Gly Ser Leu Ser Arg Ser Ser Gln Gly Thr Leu Val Thr
            100                 105                 110

Val Ser Ser Ala
        115

<210> SEQ ID NO 60
<211> LENGTH: 10
<212> TYPE: PRT
<213> ORGANISM: Lama sp.

<400> SEQUENCE: 60

Gly Phe Thr Phe Ser Ser Phe Gly Met Ser
1               5                   10

<210> SEQ ID NO 61
<211> LENGTH: 17
<212> TYPE: PRT
<213> ORGANISM: Lama sp.

<400> SEQUENCE: 61

Ser Ile Ser Gly Ser Gly Ser Asp Thr Leu Tyr Ala Asp Ser Val Lys
1               5                   10                  15

Gly

<210> SEQ ID NO 62
<211> LENGTH: 6
<212> TYPE: PRT
<213> ORGANISM: Lama sp.

<400> SEQUENCE: 62

Gly Gly Ser Leu Ser Arg
1               5

<210> SEQ ID NO 63
<211> LENGTH: 128
<212> TYPE: PRT
<213> ORGANISM: Artificial Sequence
<220> FEATURE:
<223> OTHER INFORMATION: humanized Lama

<400> SEQUENCE: 63

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Arg Gly Asn Glu Arg Glu Phe Val
        35                  40                  45

Ala Ala Ile Ser Glu Ser Gly Gly Arg Thr His Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
            115                 120                 125

<210> SEQ ID NO 64
<211> LENGTH: 128
<212> TYPE: PRT

<213> ORGANISM: Artificial Sequence
<220> FEATURE:
<223> OTHER INFORMATION: humanized Lama

<400> SEQUENCE: 64

```
Glu Val Gln Leu Val Glu Ser Gly Gly Val Val Gln Pro Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Pro Gly Lys Glu Arg Glu Phe Val
        35                  40                  45

Ala Ala Ile Ser Glu Ser Gly Gly Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Thr Thr Leu Leu Trp Trp Thr Ser Glu Tyr Ala Pro Ile Lys Ala
                100                 105                 110

Asn Asp Tyr Asp Tyr Trp Gly Gln Gly Thr Leu Val Thr Val Ser Ser
            115                 120                 125
```

<210> SEQ ID NO 65
<211> LENGTH: 10
<212> TYPE: PRT
<213> ORGANISM: Lama sp.

<400> SEQUENCE: 65

```
Gly Arg Thr Phe Ser Asp Tyr Val Met Gly
1               5                   10
```

<210> SEQ ID NO 66
<211> LENGTH: 17
<212> TYPE: PRT
<213> ORGANISM: Lama sp.
<220> FEATURE:
<221> NAME/KEY: MISC_FEATURE
<222> LOCATION: (14)..(14)
<223> OTHER INFORMATION: X is A or S

<400> SEQUENCE: 66

```
Ala Ile Ser Glu Ser Gly Gly Arg Thr His Tyr Ala Asp Xaa Val Lys
1               5                   10                  15

Gly
```

<210> SEQ ID NO 67
<211> LENGTH: 19
<212> TYPE: PRT
<213> ORGANISM: Lama sp.

<400> SEQUENCE: 67

```
Thr Leu Leu Trp Trp Thr Ser Glu Tyr Ala Pro Ile Lys Ala Asn Asp
1               5                   10                  15

Tyr Asp Tyr
```

<210> SEQ ID NO 68
<211> LENGTH: 34
<212> TYPE: PRT
<213> ORGANISM: Artificial Sequence
<220> FEATURE:
<223> OTHER INFORMATION: humanized Lama

```
<400> SEQUENCE: 68

Ala Ala Ala Asp Tyr Lys Asp His Asp Gly Asp Tyr Lys Asp His Asp
1               5                   10                  15

Ile Asp Tyr Lys Asp Asp Asp Asp Lys Gly Ala Ala His His His His
            20                  25                  30

His His

<210> SEQ ID NO 69
<211> LENGTH: 9
<212> TYPE: PRT
<213> ORGANISM: Artificial Sequence
<220> FEATURE:
<223> OTHER INFORMATION: HisX6 tag sequence

<400> SEQUENCE: 69

Ala Ala Ala His His His His His His
1               5

<210> SEQ ID NO 70
<211> LENGTH: 35
<212> TYPE: PRT
<213> ORGANISM: Artificial Sequence
<220> FEATURE:
<223> OTHER INFORMATION: 35GS linker

<400> SEQUENCE: 70

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 71
<211> LENGTH: 11
<212> TYPE: PRT
<213> ORGANISM: Rattus sp.

<400> SEQUENCE: 71

Lys Thr Ser Gln Asn Ile Phe Glu Asn Leu Ala
1               5                   10

<210> SEQ ID NO 72
<211> LENGTH: 7
<212> TYPE: PRT
<213> ORGANISM: Rattus sp.

<400> SEQUENCE: 72

Asn Ala Ser Pro Leu Gln Ala
1               5

<210> SEQ ID NO 73
<211> LENGTH: 8
<212> TYPE: PRT
<213> ORGANISM: Rattus sp.

<400> SEQUENCE: 73

His Gln Tyr Tyr Ser Gly Tyr Thr
1               5

<210> SEQ ID NO 74
<211> LENGTH: 10
<212> TYPE: PRT
```

```
<213> ORGANISM: Rattus sp.

<400> SEQUENCE: 74

Gly Phe Thr Phe Ser Asp Tyr His Met Ala
1               5                   10

<210> SEQ ID NO 75
<211> LENGTH: 17
<212> TYPE: PRT
<213> ORGANISM: Rattus sp.

<400> SEQUENCE: 75

Ser Ile Thr Leu Asp Ala Thr Tyr Thr Tyr Tyr Arg Asp Ser Val Arg
1               5                   10                  15
Gly

<210> SEQ ID NO 76
<211> LENGTH: 10
<212> TYPE: PRT
<213> ORGANISM: Rattus sp.

<400> SEQUENCE: 76

His Arg Gly Phe Ser Val Trp Leu Asp Tyr
1               5                   10

<210> SEQ ID NO 77
<211> LENGTH: 10
<212> TYPE: PRT
<213> ORGANISM: Rattus sp.

<400> SEQUENCE: 77

Gly Tyr Ile Phe Thr Asp Tyr Ala Met His
1               5                   10

<210> SEQ ID NO 78
<211> LENGTH: 16
<212> TYPE: PRT
<213> ORGANISM: Rattus sp.

<400> SEQUENCE: 78

Thr Phe Ile Pro Leu Leu Asp Thr Ser Asp Tyr Asn Gln Asn Phe Lys
1               5                   10                  15

<210> SEQ ID NO 79
<211> LENGTH: 11
<212> TYPE: PRT
<213> ORGANISM: Rattus sp.

<400> SEQUENCE: 79

Met Gly Val Thr His Ser Tyr Val Met Asp Ala
1               5                   10

<210> SEQ ID NO 80
<211> LENGTH: 11
<212> TYPE: PRT
<213> ORGANISM: Rattus sp.

<400> SEQUENCE: 80

Arg Ala Ser Gln Pro Ile Ser Ile Ser Val His
1               5                   10

<210> SEQ ID NO 81
<211> LENGTH: 7
<212> TYPE: PRT
```

```
<213> ORGANISM: Rattus sp.

<400> SEQUENCE: 81

Phe Ala Ser Gln Ser Ile Ser
1               5

<210> SEQ ID NO 82
<211> LENGTH: 9
<212> TYPE: PRT
<213> ORGANISM: Rattus sp.

<400> SEQUENCE: 82

Gln Gln Thr Phe Ser Leu Pro Tyr Thr
1               5

<210> SEQ ID NO 83
<211> LENGTH: 10
<212> TYPE: PRT
<213> ORGANISM: Mus sp.

<400> SEQUENCE: 83

Gly Phe Ile Ile Lys Ala Thr Tyr Met His
1               5                   10

<210> SEQ ID NO 84
<211> LENGTH: 17
<212> TYPE: PRT
<213> ORGANISM: Mus sp.

<400> SEQUENCE: 84

Arg Ile Asp Pro Ala Asn Gly Glu Thr Lys Tyr Asp Pro Lys Phe Gln
1               5                   10                  15

Val

<210> SEQ ID NO 85
<211> LENGTH: 7
<212> TYPE: PRT
<213> ORGANISM: Mus sp.

<400> SEQUENCE: 85

Tyr Ala Trp Tyr Phe Asp Val
1               5

<210> SEQ ID NO 86
<211> LENGTH: 11
<212> TYPE: PRT
<213> ORGANISM: Mus sp.

<400> SEQUENCE: 86

Arg Ala Ser Glu Asn Ile Tyr Ser Phe Leu Ala
1               5                   10

<210> SEQ ID NO 87
<211> LENGTH: 7
<212> TYPE: PRT
<213> ORGANISM: Mus sp.

<400> SEQUENCE: 87

His Ala Lys Thr Leu Ala Glu
1               5

<210> SEQ ID NO 88
<211> LENGTH: 9
<212> TYPE: PRT
```

```
<213> ORGANISM: Mus sp.

<400> SEQUENCE: 88

Gln His Tyr Tyr Gly Ser Pro Leu Thr
1               5

<210> SEQ ID NO 89
<211> LENGTH: 447
<212> TYPE: PRT
<213> ORGANISM: Artificial Sequence
<220> FEATURE:
<223> OTHER INFORMATION: humanized mouse

<400> SEQUENCE: 89

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

-continued

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 90
<211> LENGTH: 218
<212> TYPE: PRT
<213> ORGANISM: Artificial Sequence
<220> FEATURE:
<223> OTHER INFORMATION: humanized mouse

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 91
<211> LENGTH: 440
<212> TYPE: PRT
<213> ORGANISM: Homo sapiens
```

<400> SEQUENCE: 91

| | | | | | | | | | | | | | | |
|---|---|---|---|---|---|---|---|---|---|---|---|---|---|---|
|Gln|Val|Gln|Leu|Val|Glu|Ser|Gly|Gly|Gly|Val|Val|Gln|Pro|Gly|Arg|
|1| | | |5| | | | |10| | | | |15|

Ser Leu Arg Leu Asp Cys Lys Ala Ser Gly Ile Thr Phe Ser Asn Ser
           20                 25                 30

Gly Met His Trp Val Arg Gln Ala Pro Gly Lys Gly Leu Glu Trp Val
           35                 40                 45

Ala Val Ile Trp Tyr Asp Gly Ser Lys Arg Tyr Tyr Ala Asp Ser Val
 50                     55                 60

Lys Gly Arg Phe Thr Ile Ser Arg Asp Asn Ser Lys Asn Thr Leu Phe
65                  70                 75                 80

Leu Gln Met Asn Ser Leu Arg Ala Glu Asp Thr Ala Val Tyr Tyr Cys
           85                 90                 95

Ala Thr Asn Asp Asp Tyr Trp Gly Gln Gly Thr Leu Val Thr Val Ser
          100                105              110

Ser Ala Ser Thr Lys Gly Pro Ser Val Phe Pro Leu Ala Pro Cys Ser
         115                120              125

Arg Ser Thr Ser Glu Ser Thr Ala Ala Leu Gly Cys Leu Val Lys Asp
     130                135              140

Tyr Phe Pro Glu Pro Val Thr Val Ser Trp Asn Ser Gly Ala Leu Thr
145                  150                155              160

Ser Gly Val His Thr Phe Pro Ala Val Leu Gln Ser Ser Gly Leu Tyr
         165                170              175

Ser Leu Ser Ser Val Val Thr Val Pro Ser Ser Ser Leu Gly Thr Lys
     180                185              190

Thr Tyr Thr Cys Asn Val Asp His Lys Pro Ser Asn Thr Lys Val Asp
         195                200              205

Lys Arg Val Glu Ser Lys Tyr Gly Pro Pro Cys Pro Pro Cys Pro Ala
     210                215              220

Pro Glu Phe Leu Gly Gly Pro Ser Val Phe Leu Phe Pro Pro Lys Pro
225                  230                235              240

Lys Asp Thr Leu Met Ile Ser Arg Thr Pro Glu Val Thr Cys Val Val
         245                250              255

Val Asp Val Ser Gln Glu Asp Pro Glu Val Gln Phe Asn Trp Tyr Val
         260                265              270

Asp Gly Val Glu Val His Asn Ala Lys Thr Lys Pro Arg Glu Glu Gln
     275                280              285

Phe Asn Ser Thr Tyr Arg Val Val Ser Val Leu Thr Val Leu His Gln
     290                295              300

Asp Trp Leu Asn Gly Lys Glu Tyr Lys Cys Lys Val Ser Asn Lys Gly
305                  310                315              320

Leu Pro Ser Ser Ile Glu Lys Thr Ile Ser Lys Ala Lys Gly Gln Pro
         325                330              335

Arg Glu Pro Gln Val Tyr Thr Leu Pro Pro Ser Gln Glu Glu Met Thr
         340                345              350

Lys Asn Gln Val Ser Leu Thr Cys Leu Val Lys Gly Phe Tyr Pro Ser
     355                360              365

Asp Ile Ala Val Glu Trp Glu Ser Asn Gly Gln Pro Glu Asn Asn Tyr
         370                375              380

Lys Thr Thr Pro Pro Val Leu Asp Ser Asp Gly Ser Phe Phe Leu Tyr
385                  390                395              400

Ser Arg Leu Thr Val Asp Lys Ser Arg Trp Gln Glu Gly Asn Val Phe

```
                    405                 410                 415
Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 92
<211> LENGTH: 214
<212> TYPE: PRT
<213> ORGANISM: Homo sapiens

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 6
<212> TYPE: PRT
<213> ORGANISM: Artificial Sequence
<220> FEATURE:
<223> OTHER INFORMATION: HisX6 tag

<400> SEQUENCE: 93

His His His His His His
1               5

<210> SEQ ID NO 94
<211> LENGTH: 18
<212> TYPE: PRT
<213> ORGANISM: Artificial Sequence
<220> FEATURE:
<223> OTHER INFORMATION: HisX18 tag
```

```
<400> SEQUENCE: 94

His His His His His His His His His His His His His His His
1               5                   10                  15

His His

<210> SEQ ID NO 95
<211> LENGTH: 7
<212> TYPE: PRT
<213> ORGANISM: Artificial Sequence
<220> FEATURE:
<223> OTHER INFORMATION: humanized Lama

<400> SEQUENCE: 95

Asp Tyr Lys Asp Asp Asp Lys
1               5

<210> SEQ ID NO 96
<211> LENGTH: 279
<212> TYPE: PRT
<213> ORGANISM: Artificial Sequence
<220> FEATURE:
<223> OTHER INFORMATION: humanized Lama

<400> SEQUENCE: 96

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Pro Gly Lys Glu Arg Glu Phe Val
        35                  40                  45

Ala Ala Ile Ser Glu Ser Gly Gly Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Gly Gly
145                 150                 155                 160

Gly Gly Ser Glu Val Gln Leu Val Glu Ser Gly Gly Gly Val Val Gln
                165                 170                 175

Pro Gly Asn Ser Leu Arg Leu Ser Cys Ala Ala Ser Gly Phe Thr Phe
            180                 185                 190

Ser Ser Phe Gly Met Ser Trp Val Arg Gln Ala Pro Gly Lys Gly Leu
        195                 200                 205

Glu Trp Val Ser Ser Ile Ser Gly Ser Gly Ser Asp Thr Leu Tyr Ala
    210                 215                 220

Asp Ser Val Lys Gly Arg Phe Thr Ile Ser Arg Asp Asn Ala Lys Thr
225                 230                 235                 240

Thr Leu Tyr Leu Gln Met Asn Ser Leu Arg Pro Glu Asp Thr Ala Leu
                245                 250                 255

Tyr Tyr Cys Thr Ile Gly Gly Ser Leu Ser Arg Ser Ser Gln Gly Thr
```

Leu Val Thr Val Ser Ser Ala
            275

<210> SEQ ID NO 97
<211> LENGTH: 442
<212> TYPE: PRT
<213> ORGANISM: Artificial Sequence
<220> FEATURE:
<223> OTHER INFORMATION: humanized Lama

<400> SEQUENCE: 97

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Pro Gly Lys Glu Arg Glu Phe Val
        35                  40                  45

Ala Ala Ile Ser Glu Ser Gly Gly Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Gly Gly
145                 150                 155                 160

Gly Gly Ser Glu Val Gln Leu Val Glu Ser Gly Gly Val Val Gln
                165                 170                 175

Pro Gly Gly Ser Leu Arg Leu Ser Cys Ala Ala Ser Gly Arg Thr Phe
            180                 185                 190

Ser Asp Tyr Val Met Gly Trp Phe Arg Gln Ala Pro Gly Lys Glu Arg
        195                 200                 205

Glu Phe Val Ala Ala Ile Ser Glu Ser Gly Gly Arg Thr His Tyr Ala
    210                 215                 220

Asp Ser Val Lys Gly Arg Phe Thr Ile Ser Arg Asp Asn Ser Lys Asn
225                 230                 235                 240

Thr Leu Tyr Leu Gln Met Asn Ser Leu Arg Pro Glu Asp Thr Ala Leu
                245                 250                 255

Tyr Tyr Cys Ala Thr Thr Leu Leu Trp Trp Thr Ser Glu Tyr Ala Pro
            260                 265                 270

Ile Lys Ala Asn Asp Tyr Asp Tyr Trp Gly Gln Gly Thr Leu Val Thr
        275                 280                 285

Val Ser Ser Gly Gly Gly Gly Ser Gly Gly Gly Gly Ser Gly Gly Gly
    290                 295                 300

Gly Ser Gly Gly Gly Gly Ser Gly Gly Gly Gly Ser Gly Gly Gly Gly
305                 310                 315                 320

Ser Gly Gly Gly Gly Ser Glu Val Gln Leu Val Glu Ser Gly Gly Gly
                325                 330                 335

Val Val Gln Pro Gly Asn Ser Leu Arg Leu Ser Cys Ala Ala Ser Gly

-continued

```
                   340                 345                 350

Phe Thr Phe Ser Ser Phe Gly Met Ser Trp Val Arg Gln Ala Pro Gly
            355                 360                 365

Lys Gly Leu Glu Trp Val Ser Ser Ile Ser Gly Ser Gly Ser Asp Thr
        370                 375                 380

Leu Tyr Ala Asp Ser Val Lys Gly Arg Phe Thr Ile Ser Arg Asp Asn
385                 390                 395                 400

Ala Lys Thr Thr Leu Tyr Leu Gln Met Asn Ser Leu Arg Pro Glu Asp
                405                 410                 415

Thr Ala Leu Tyr Tyr Cys Thr Ile Gly Gly Ser Leu Ser Arg Ser Ser
            420                 425                 430

Gln Gly Thr Leu Val Thr Val Ser Ser Ala
        435                 440

<210> SEQ ID NO 98
<211> LENGTH: 119
<212> TYPE: PRT
<213> ORGANISM: Artificial Sequence
<220> FEATURE:
<223> OTHER INFORMATION: humanized Lama

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Artificial Sequence
<220> FEATURE:
<223> OTHER INFORMATION: humanized Lama

<400> SEQUENCE: 99

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 100
<211> LENGTH: 20
<212> TYPE: PRT
<213> ORGANISM: Artificial Sequence
<220> FEATURE:
<223> OTHER INFORMATION: 20GS linker

<400> SEQUENCE: 100

Gly Gly Gly Gly Ser Gly Gly Gly Ser Gly Gly Gly Gly Ser Gly
1               5                   10                  15

Gly Gly Gly Ser
            20

<210> SEQ ID NO 101
<211> LENGTH: 270
<212> TYPE: PRT
<213> ORGANISM: Artificial Sequence
<220> FEATURE:
<223> OTHER INFORMATION: humanized Lama

<400> SEQUENCE: 101

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Asn Ser Leu Arg Leu Ser Cys
                165                 170                 175

Ala Ala Ser Gly Phe Thr Phe Ser Ser Phe Gly Met Ser Trp Val Arg
            180                 185                 190

Gln Ala Pro Gly Lys Gly Leu Glu Trp Val Ser Ser Ile Ser Gly Ser
        195                 200                 205

Gly Ser Asp Thr Leu Tyr Ala Asp Ser Val Lys Gly Arg Phe Thr Ile
    210                 215                 220

Ser Arg Asp Asn Ala Lys Thr Thr Leu Tyr Leu Gln Met Asn Ser Leu
225                 230                 235                 240
```

Arg Pro Glu Asp Thr Ala Leu Tyr Tyr Cys Thr Ile Gly Gly Ser Leu
            245                 250                 255

Ser Arg Ser Ser Gln Gly Thr Leu Val Thr Val Ser Ser Ala
        260                 265                 270

<210> SEQ ID NO 102
<211> LENGTH: 424
<212> TYPE: PRT
<213> ORGANISM: Artificial Sequence
<220> FEATURE:
<223> OTHER INFORMATION: humanized Lama

<400> SEQUENCE: 102

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

Gly Gly Ile Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Gly Val Val
305                 310                 315                 320

Gln Pro Gly Asn Ser Leu Arg Leu Ser Cys Ala Ala Ser Gly Phe Thr
                325                 330                 335

-continued

```
Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
        355                 360                 365

Ala Asp Ser Val Lys Gly Arg Phe Thr Ile Ser Arg Asp Asn Ala Lys
    370                 375                 380

Thr Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
            405                 410                 415

Thr Leu Val Thr Val Ser Ser Ala
            420

<210> SEQ ID NO 103
<211> LENGTH: 119
<212> TYPE: PRT
<213> ORGANISM: Artificial Sequence
<220> FEATURE:
<223> OTHER INFORMATION: humanized Lama

<400> SEQUENCE: 103

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser
        115

<210> SEQ ID NO 104
<211> LENGTH: 119
<212> TYPE: PRT
<213> ORGANISM: Artificial Sequence
<220> FEATURE:
<223> OTHER INFORMATION: humanized Lama

<400> SEQUENCE: 104

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
```

```
                    85                  90                  95

Ala Gly Asp Lys His Gln Ser Ser Phe Tyr Asp Tyr Trp Gly Gln Gly
            100                 105                 110

Thr Leu Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: humanized Lama

<400> SEQUENCE: 105

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser
        115

<210> SEQ ID NO 106
<211> LENGTH: 749
<212> TYPE: PRT
<213> ORGANISM: Artificial Sequence
<220> FEATURE:
<223> OTHER INFORMATION: humanized Lama

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140
```

```
Gly Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
            165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Ile Tyr Tyr Cys Ala Gly Asp Lys His Gln
            245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Ser Gly Gly Gly Gly Ser Gly
            290                 295                 300

Gly Gly Gly Ser Glu Val Gln Leu Val Glu Ser Gly Gly Gly Leu Val
305                 310                 315                 320

Gln Ala Gly Gly Ser Leu Arg Leu Ser Cys Ala Ala Ser Gly Arg Thr
            325                 330                 335

Phe Ser Asp Tyr Val Met Gly Trp Phe Arg Gln Ala Arg Gly Asn Glu
            340                 345                 350

Arg Glu Phe Val Ala Ala Ile Ser Glu Ser Gly Gly Arg Thr His Tyr
            355                 360                 365

Ala Asp Ala Val Lys Gly Arg Phe Thr Ile Ser Arg Asp Asn Ala Lys
            370                 375                 380

Asn Thr Leu Tyr Leu Gln Met Asn Ser Leu Lys Pro Glu Asp Thr Ala
385                 390                 395                 400

Val Tyr Tyr Cys Ala Thr Thr Leu Leu Trp Trp Thr Ser Glu Tyr Ala
            405                 410                 415

Pro Ile Lys Ala Asn Asp Tyr Asp Tyr Trp Gly Gln Gly Thr Leu Val
            420                 425                 430

Thr Val Ser Ser Gly Gly Gly Gly Ser Gly Gly Gly Gly Ser Gly Gly
            435                 440                 445

Gly Gly Ser Gly Gly Gly Gly Ser Gly Gly Gly Gly Ser Gly Gly Gly
            450                 455                 460

Gly Ser Gly Gly Gly Gly Ser Glu Val Gln Leu Val Glu Ser Gly Gly
465                 470                 475                 480

Gly Leu Val Gln Ala Gly Gly Ser Leu Arg Leu Ser Cys Ala Ala Ser
            485                 490                 495

Gly Arg Thr Phe Ser Asp Tyr Val Met Gly Trp Phe Arg Gln Ala Arg
            500                 505                 510

Gly Asn Glu Arg Glu Phe Val Ala Ala Ile Ser Glu Ser Gly Gly Arg
            515                 520                 525

Thr His Tyr Ala Asp Ala Val Lys Gly Arg Phe Thr Ile Ser Arg Asp
            530                 535                 540

Asn Ala Lys Asn Thr Leu Tyr Leu Gln Met Asn Ser Leu Lys Pro Glu
545                 550                 555                 560

Asp Thr Ala Val Tyr Tyr Cys Ala Thr Thr Leu Leu Trp Trp Thr Ser
```

```
                    565                 570                 575
Glu Tyr Ala Pro Ile Lys Ala Asn Asp Tyr Asp Tyr Trp Gly Gln Gly
            580                 585                 590

Thr Leu Val Thr Val Ser Ser Gly Gly Gly Ser Gly Gly Gly Gly
        595                 600                 605

Ser Gly Gly Gly Ser Gly Gly Gly Ser Gly Gly Gly Ser
    610                 615                 620

Gly Gly Gly Gly Ser Gly Gly Gly Ser Glu Val Gln Leu Val Glu
625                 630                 635                 640

Ser Gly Gly Gly Leu Val Gln Pro Gly Asn Ser Leu Arg Leu Ser Cys
            645                 650                 655

Ala Ala Ser Gly Phe Thr Phe Ser Ser Phe Gly Met Ser Trp Val Arg
            660                 665                 670

Gln Ala Pro Gly Lys Gly Leu Glu Trp Val Ser Ser Ile Ser Gly Ser
            675                 680                 685

Gly Ser Asp Thr Leu Tyr Ala Asp Ser Val Lys Gly Arg Phe Thr Ile
            690                 695                 700

Ser Arg Asp Asn Ala Lys Thr Thr Leu Tyr Leu Gln Met Asn Ser Leu
705                 710                 715                 720

Arg Pro Glu Asp Thr Ala Val Tyr Tyr Cys Thr Ile Gly Gly Ser Leu
                725                 730                 735

Ser Arg Ser Ser Gln Gly Thr Leu Val Thr Val Ser Ser
            740                 745
```

<210> SEQ ID NO 107
<211> LENGTH: 750
<212> TYPE: PRT
<213> ORGANISM: Artificial Sequence
<220> FEATURE:
<223> OTHER INFORMATION: humanized Lama

<400> SEQUENCE: 107

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
```

```
                  180                 185                 190
Gln Ala Pro Gly Lys Glu Arg Glu Phe Val Ala Val Ile Thr Trp Ser
            195                 200                 205
Gly Gly Ile Thr Tyr Tyr Ala Asp Ser Val Lys Gly Arg Phe Thr Ile
        210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
Ser Ser Trp Tyr Asp Tyr Trp Gly Gln Gly Thr Leu Val Thr Val Ser
            260                 265                 270
Ser Gly Gly Gly Gly Ser Gly Gly Gly Ser Gly Gly Gly Gly Ser
        275                 280                 285
Gly Gly Gly Gly Ser Gly Gly Gly Ser Gly Gly Gly Gly Ser Gly
        290                 295                 300
Gly Gly Gly Ser Glu Val Gln Leu Val Glu Ser Gly Gly Val Val
305                 310                 315                 320
Gln Pro Gly Gly Ser Leu Arg Leu Ser Cys Ala Ala Ser Gly Arg Thr
                325                 330                 335
Phe Ser Asp Tyr Val Met Gly Trp Phe Arg Gln Ala Pro Gly Lys Glu
                340                 345                 350
Arg Glu Phe Val Ala Ala Ile Ser Glu Ser Gly Arg Thr His Tyr
            355                 360                 365
Ala Asp Ser Val Lys Gly Arg Phe Thr Ile Ser Arg Asp Asn Ser Lys
        370                 375                 380
Asn Thr Leu Tyr Leu Gln Met Asn Ser Leu Arg Pro Glu Asp Thr Ala
385                 390                 395                 400
Leu Tyr Tyr Cys Ala Thr Thr Leu Leu Trp Trp Thr Ser Glu Tyr Ala
                405                 410                 415
Pro Ile Lys Ala Asn Asp Tyr Asp Tyr Trp Gly Gln Gly Thr Leu Val
            420                 425                 430
Thr Val Ser Ser Gly Gly Gly Gly Ser Gly Gly Gly Gly Ser Gly Gly
            435                 440                 445
Gly Gly Ser Gly Gly Gly Gly Ser Gly Gly Gly Gly Ser Gly Gly Gly
        450                 455                 460
Gly Ser Gly Gly Gly Gly Ser Glu Val Gln Leu Val Glu Ser Gly Gly
465                 470                 475                 480
Gly Val Val Gln Pro Gly Gly Ser Leu Arg Leu Ser Cys Ala Ala Ser
                485                 490                 495
Gly Arg Thr Phe Ser Asp Tyr Val Met Gly Trp Phe Arg Gln Ala Pro
                500                 505                 510
Gly Lys Glu Arg Glu Phe Val Ala Ala Ile Ser Glu Ser Gly Gly Arg
            515                 520                 525
Thr His Tyr Ala Asp Ser Val Lys Gly Arg Phe Thr Ile Ser Arg Asp
        530                 535                 540
Asn Ser Lys Asn Thr Leu Tyr Leu Gln Met Asn Ser Leu Arg Pro Glu
545                 550                 555                 560
Asp Thr Ala Leu Tyr Tyr Cys Ala Thr Thr Leu Leu Trp Trp Thr Ser
                565                 570                 575
Glu Tyr Ala Pro Ile Lys Ala Asn Asp Tyr Asp Tyr Trp Gly Gln Gly
                580                 585                 590
Thr Leu Val Thr Val Ser Ser Gly Gly Gly Gly Ser Gly Gly Gly Gly
            595                 600                 605
```

```
Ser Gly Gly Gly Gly Ser Gly Gly Gly Ser Gly Gly Gly Ser
    610                 615                 620

Gly Gly Gly Gly Ser Gly Gly Gly Ser Glu Val Gln Leu Val Glu
625                 630                 635                 640

Ser Gly Gly Gly Val Val Gln Pro Gly Asn Ser Leu Arg Leu Ser Cys
                645                 650                 655

Ala Ala Ser Gly Phe Thr Phe Ser Ser Phe Gly Met Ser Trp Val Arg
            660                 665                 670

Gln Ala Pro Gly Lys Gly Leu Glu Trp Val Ser Ser Ile Ser Gly Ser
        675                 680                 685

Gly Ser Asp Thr Leu Tyr Ala Asp Ser Val Lys Gly Arg Phe Thr Ile
    690                 695                 700

Ser Arg Asp Asn Ala Lys Thr Thr Leu Tyr Leu Gln Met Asn Ser Leu
705                 710                 715                 720

Arg Pro Glu Asp Thr Ala Leu Tyr Tyr Cys Thr Ile Gly Gly Ser Leu
                725                 730                 735

Ser Arg Ser Ser Gln Gly Thr Leu Val Thr Val Ser Ser Ala
            740                 745                 750

<210> SEQ ID NO 108
<211> LENGTH: 690
<212> TYPE: PRT
<213> ORGANISM: Artificial Sequence
<220> FEATURE:
<223> OTHER INFORMATION: humanized Lama

<400> SEQUENCE: 108

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Glu Val Gln Leu Val
    130                 135                 140

Glu Ser Gly Gly Val Val Gln Pro Gly Gly Ser Leu Arg Leu Ser
145                 150                 155                 160

Cys Ala Ala Ser Gly Ser Ile Ala Ser Ile His Ala Met Gly Trp Phe
                165                 170                 175

Arg Gln Ala Pro Gly Lys Glu Arg Glu Phe Val Ala Val Ile Thr Trp
            180                 185                 190

Ser Gly Gly Ile Thr Tyr Tyr Ala Asp Ser Val Lys Gly Arg Phe Thr
        195                 200                 205

Ile Ser Arg Asp Asn Ser Lys Asn Thr Val Tyr Leu Gln Met Asn Ser
    210                 215                 220
```

```
Leu Arg Pro Glu Asp Thr Ala Leu Tyr Tyr Cys Ala Gly Asp Lys His
225                 230                 235                 240

Gln Ser Ser Trp Tyr Asp Tyr Trp Gly Gln Gly Thr Leu Val Thr Val
            245                 250                 255

Ser Ser Gly Gly Gly Gly Ser Gly Gly Gly Ser Gly Gly Gly Gly
        260                 265                 270

Ser Gly Gly Gly Ser Glu Val Gln Leu Val Glu Ser Gly Gly Gly
    275                 280                 285

Val Val Gln Pro Gly Gly Ser Leu Arg Leu Ser Cys Ala Ala Ser Gly
290                 295                 300

Arg Thr Phe Ser Asp Tyr Val Met Gly Trp Phe Arg Gln Ala Pro Gly
305                 310                 315                 320

Lys Glu Arg Glu Phe Val Ala Ala Ile Ser Glu Ser Gly Gly Arg Thr
                325                 330                 335

His Tyr Ala Asp Ser Val Lys Gly Arg Phe Thr Ile Ser Arg Asp Asn
            340                 345                 350

Ser Lys Asn Thr Leu Tyr Leu Gln Met Asn Ser Leu Arg Pro Glu Asp
        355                 360                 365

Thr Ala Leu Tyr Tyr Cys Ala Thr Thr Leu Leu Trp Trp Thr Ser Glu
370                 375                 380

Tyr Ala Pro Ile Lys Ala Asn Asp Tyr Asp Tyr Trp Gly Gln Gly Thr
                385                 390                 395                 400

Leu Val Thr Val Ser Ser Gly Gly Gly Gly Ser Gly Gly Gly Gly Ser
                405                 410                 415

Gly Gly Gly Gly Ser Gly Gly Gly Ser Glu Val Gln Leu Val Glu
                420                 425                 430

Ser Gly Gly Gly Val Val Gln Pro Gly Gly Ser Leu Arg Leu Ser Cys
        435                 440                 445

Ala Ala Ser Gly Arg Thr Phe Ser Asp Tyr Val Met Gly Trp Phe Arg
    450                 455                 460

Gln Ala Pro Gly Lys Glu Arg Glu Phe Val Ala Ala Ile Ser Glu Ser
465                 470                 475                 480

Gly Gly Arg Thr His Tyr Ala Asp Ser Val Lys Gly Arg Phe Thr Ile
                485                 490                 495

Ser Arg Asp Asn Ser Lys Asn Thr Leu Tyr Leu Gln Met Asn Ser Leu
            500                 505                 510

Arg Pro Glu Asp Thr Ala Leu Tyr Tyr Cys Ala Thr Thr Leu Leu Trp
        515                 520                 525

Trp Thr Ser Glu Tyr Ala Pro Ile Lys Ala Asn Asp Tyr Asp Tyr Trp
    530                 535                 540

Gly Gln Gly Thr Leu Val Thr Val Ser Ser Gly Gly Gly Gly Ser Gly
545                 550                 555                 560

Gly Gly Gly Ser Gly Gly Gly Gly Ser Gly Gly Gly Ser Glu Val
                565                 570                 575

Gln Leu Val Glu Ser Gly Gly Gly Val Val Gln Pro Gly Asn Ser Leu
            580                 585                 590

Arg Leu Ser Cys Ala Ala Ser Gly Phe Thr Phe Ser Ser Phe Gly Met
        595                 600                 605

Ser Trp Val Arg Gln Ala Pro Gly Lys Gly Leu Glu Trp Val Ser Ser
    610                 615                 620

Ile Ser Gly Ser Gly Ser Asp Thr Leu Tyr Ala Asp Ser Val Lys Gly
625                 630                 635                 640
```

```
Arg Phe Thr Ile Ser Arg Asp Asn Ala Lys Thr Thr Leu Tyr Leu Gln
                    645                 650                 655

Met Asn Ser Leu Arg Pro Glu Asp Thr Ala Leu Tyr Tyr Cys Thr Ile
            660                 665                 670

Gly Gly Ser Leu Ser Arg Ser Ser Gln Gly Thr Leu Val Thr Val Ser
        675                 680                 685

Ser Ala
    690

<210> SEQ ID NO 109
<211> LENGTH: 646
<212> TYPE: PRT
<213> ORGANISM: Artificial Sequence
<220> FEATURE:
<223> OTHER INFORMATION: humanized Lama

<400> SEQUENCE: 109

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Ser
        115                 120                 125

Glu Val Gln Leu Val Glu Ser Gly Gly Gly Val Val Gln Pro Gly Gly
    130                 135                 140

Ser Leu Arg Leu Ser Cys Ala Ala Ser Gly Ser Ile Ala Ser Ile His
145                 150                 155                 160

Ala Met Gly Trp Phe Arg Gln Ala Pro Gly Lys Glu Arg Glu Phe Val
                165                 170                 175

Ala Val Ile Thr Trp Ser Gly Gly Ile Thr Tyr Tyr Ala Asp Ser Val
            180                 185                 190

Lys Gly Arg Phe Thr Ile Ser Arg Asp Asn Ser Lys Asn Thr Val Tyr
        195                 200                 205

Leu Gln Met Asn Ser Leu Arg Pro Glu Asp Thr Ala Leu Tyr Tyr Cys
    210                 215                 220

Ala Gly Asp Lys His Gln Ser Ser Trp Tyr Asp Tyr Trp Gly Gln Gly
225                 230                 235                 240

Thr Leu Val Thr Val Ser Ser Gly Gly Gly Ser Gly Gly Gly Ser
                245                 250                 255

Glu Val Gln Leu Val Glu Ser Gly Gly Gly Val Val Gln Pro Gly Gly
            260                 265                 270

Ser Leu Arg Leu Ser Cys Ala Ala Ser Gly Arg Thr Phe Ser Asp Tyr
        275                 280                 285

Val Met Gly Trp Phe Arg Gln Ala Pro Gly Lys Glu Arg Glu Phe Val
    290                 295                 300
```

```
Ala Ala Ile Ser Glu Ser Gly Gly Arg Thr His Tyr Ala Asp Ser Val
305                 310                 315                 320

Lys Gly Arg Phe Thr Ile Ser Arg Asp Asn Ser Lys Asn Thr Leu Tyr
            325                 330                 335

Leu Gln Met Asn Ser Leu Arg Pro Glu Asp Thr Ala Leu Tyr Tyr Cys
        340                 345                 350

Ala Thr Thr Leu Leu Trp Trp Thr Ser Glu Tyr Ala Pro Ile Lys Ala
        355                 360                 365

Asn Asp Tyr Asp Tyr Trp Gly Gln Gly Thr Leu Val Thr Val Ser Ser
    370                 375                 380

Gly Gly Gly Gly Ser Gly Gly Gly Ser Glu Val Gln Leu Val Glu Ser
385                 390                 395                 400

Gly Gly Gly Val Val Gln Pro Gly Gly Ser Leu Arg Leu Ser Cys Ala
                405                 410                 415

Ala Ser Gly Arg Thr Phe Ser Asp Tyr Val Met Gly Trp Phe Arg Gln
                420                 425                 430

Ala Pro Gly Lys Glu Arg Glu Phe Val Ala Ala Ile Ser Glu Ser Gly
            435                 440                 445

Gly Arg Thr His Tyr Ala Asp Ser Val Lys Gly Arg Phe Thr Ile Ser
450                 455                 460

Arg Asp Asn Ser Lys Asn Thr Leu Tyr Leu Gln Met Asn Ser Leu Arg
465                 470                 475                 480

Pro Glu Asp Thr Ala Leu Tyr Tyr Cys Ala Thr Thr Leu Leu Trp Trp
                485                 490                 495

Thr Ser Glu Tyr Ala Pro Ile Lys Ala Asn Asp Tyr Asp Tyr Trp Gly
            500                 505                 510

Gln Gly Thr Leu Val Thr Val Ser Ser Gly Gly Gly Gly Ser Gly Gly
        515                 520                 525

Gly Ser Glu Val Gln Leu Val Glu Ser Gly Gly Gly Val Val Gln Pro
    530                 535                 540

Gly Asn Ser Leu Arg Leu Ser Cys Ala Ala Ser Gly Phe Thr Phe Ser
545                 550                 555                 560

Ser Phe Gly Met Ser Trp Val Arg Gln Ala Pro Gly Lys Gly Leu Glu
                565                 570                 575

Trp Val Ser Ser Ile Ser Gly Ser Gly Ser Asp Thr Leu Tyr Ala Asp
                580                 585                 590

Ser Val Lys Gly Arg Phe Thr Ile Ser Arg Asp Asn Ala Lys Thr Thr
            595                 600                 605

Leu Tyr Leu Gln Met Asn Ser Leu Arg Pro Glu Asp Thr Ala Leu Tyr
        610                 615                 620

Tyr Cys Thr Ile Gly Gly Ser Leu Ser Arg Ser Ser Gln Gly Thr Leu
625                 630                 635                 640

Val Thr Val Ser Ser Ala
                645

<210> SEQ ID NO 110
<211> LENGTH: 433
<212> TYPE: PRT
<213> ORGANISM: Artificial Sequence
<220> FEATURE:
<223> OTHER INFORMATION: humanized Lama

<400> SEQUENCE: 110

Asp Val Gln Leu Val Glu Ser Gly Gly Gly Val Val Gln Pro Gly Gly
1               5                   10                  15
```

```
Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Arg Thr Phe Ser Asp Tyr Val Met Gly Trp Phe Arg
            180                 185                 190

Gln Ala Pro Gly Lys Glu Arg Glu Phe Val Ala Ala Ile Ser Glu Ser
        195                 200                 205

Gly Gly Arg Thr His Tyr Ala Asp Ser Val Lys Gly Arg Phe Thr Ile
    210                 215                 220

Ser Arg Asp Asn Ser Lys Asn Thr Leu Tyr Leu Gln Met Asn Ser Leu
225                 230                 235                 240

Arg Pro Glu Asp Thr Ala Leu Tyr Tyr Cys Ala Thr Thr Leu Leu Trp
                245                 250                 255

Trp Thr Ser Glu Tyr Ala Pro Ile Lys Ala Asn Asp Tyr Asp Tyr Trp
            260                 265                 270

Gly Gln Gly Thr Leu Val Thr Val Ser Ser Gly Gly Gly Gly Ser Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gly Gly Gly Gly Ser Glu Val Gln
305                 310                 315                 320

Leu Val Glu Ser Gly Gly Val Val Gln Pro Gly Asn Ser Leu Arg
            325                 330                 335

Leu Ser Cys Ala Ala Ser Gly Phe Thr Phe Ser Ser Phe Gly Met Ser
            340                 345                 350

Trp Val Arg Gln Ala Pro Gly Lys Gly Leu Glu Trp Val Ser Ser Ile
        355                 360                 365

Ser Gly Ser Gly Ser Asp Thr Leu Tyr Ala Asp Ser Val Lys Gly Arg
    370                 375                 380

Phe Thr Ile Ser Arg Asp Asn Ala Lys Thr Thr Leu Tyr Leu Gln Met
385                 390                 395                 400

Asn Ser Leu Arg Pro Glu Asp Thr Ala Leu Tyr Tyr Cys Thr Ile Gly
                405                 410                 415

Gly Ser Leu Ser Arg Ser Ser Gln Gly Thr Leu Val Thr Val Ser Ser
            420                 425                 430

Ala
```

<210> SEQ ID NO 111
<211> LENGTH: 403
<212> TYPE: PRT
<213> ORGANISM: Artificial Sequence
<220> FEATURE:
<223> OTHER INFORMATION: humanized Lama

<400> SEQUENCE: 111

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Val Val Gln Pro Gly Gly Ser Leu Arg Leu Ser
145                 150                 155                 160

Cys Ala Ala Ser Gly Arg Thr Phe Ser Asp Tyr Val Met Gly Trp Phe
                165                 170                 175

Arg Gln Ala Pro Gly Lys Glu Arg Glu Phe Val Ala Ala Ile Ser Glu
            180                 185                 190

Ser Gly Gly Arg Thr His Tyr Ala Asp Ser Val Lys Gly Arg Phe Thr
        195                 200                 205

Ile Ser Arg Asp Asn Ser Lys Asn Thr Leu Tyr Leu Gln Met Asn Ser
    210                 215                 220

Leu Arg Pro Glu Asp Thr Ala Leu Tyr Tyr Cys Ala Thr Thr Leu Leu
225                 230                 235                 240

Trp Trp Thr Ser Glu Tyr Ala Pro Ile Lys Ala Asn Asp Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Gly Gly Gly Gly Ser Glu
        275                 280                 285

Val Gln Leu Val Glu Ser Gly Gly Gly Val Val Gln Pro Gly Asn Ser
    290                 295                 300

Leu Arg Leu Ser Cys Ala Ala Ser Gly Phe Thr Phe Ser Ser Phe Gly
305                 310                 315                 320

Met Ser Trp Val Arg Gln Ala Pro Gly Lys Gly Leu Glu Trp Val Ser
                325                 330                 335

Ser Ile Ser Gly Ser Gly Ser Asp Thr Leu Tyr Ala Asp Ser Val Lys
            340                 345                 350

Gly Arg Phe Thr Ile Ser Arg Asp Asn Ala Lys Thr Thr Leu Tyr Leu
        355                 360                 365
```

Gln Met Asn Ser Leu Arg Pro Glu Asp Thr Ala Leu Tyr Tyr Cys Thr
        370                 375                 380

Ile Gly Gly Ser Leu Ser Arg Ser Ser Gln Gly Thr Leu Val Thr Val
385                 390                 395                 400

Ser Ser Ala

<210> SEQ ID NO 112
<211> LENGTH: 381
<212> TYPE: PRT
<213> ORGANISM: Artificial Sequence
<220> FEATURE:
<223> OTHER INFORMATION: humanized Lama

<400> SEQUENCE: 112

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Ser
        115                 120                 125

Glu Val Gln Leu Val Glu Ser Gly Gly Gly Val Val Gln Pro Gly Gly
    130                 135                 140

Ser Leu Arg Leu Ser Cys Ala Ala Ser Gly Arg Thr Phe Ser Asp Tyr
145                 150                 155                 160

Val Met Gly Trp Phe Arg Gln Ala Pro Gly Lys Glu Arg Glu Phe Val
                165                 170                 175

Ala Ala Ile Ser Glu Ser Gly Gly Arg Thr His Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Pro Glu Asp Thr Ala Leu Tyr Tyr Cys
    210                 215                 220

Ala Thr Thr Leu Leu Trp Trp Thr Ser Glu Tyr Ala Pro Ile Lys Ala
225                 230                 235                 240

Asn Asp Tyr Asp Tyr Trp Gly Gln Gly Thr Leu Val Thr Val Ser Ser
                245                 250                 255

Gly Gly Gly Gly Ser Gly Gly Gly Ser Glu Val Gln Leu Val Glu Ser
            260                 265                 270

Gly Gly Gly Val Val Gln Pro Gly Asn Ser Leu Arg Leu Ser Cys Ala
        275                 280                 285

Ala Ser Gly Phe Thr Phe Ser Ser Phe Gly Met Ser Trp Val Arg Gln
    290                 295                 300

Ala Pro Gly Lys Gly Leu Glu Trp Val Ser Ser Ile Ser Gly Ser Gly
305                 310                 315                 320

Ser Asp Thr Leu Tyr Ala Asp Ser Val Lys Gly Arg Phe Thr Ile Ser
            325                 330                 335

Arg Asp Asn Ala Lys Thr Thr Leu Tyr Leu Gln Met Asn Ser Leu Arg
        340                 345                 350

Pro Glu Asp Thr Ala Leu Tyr Tyr Cys Thr Ile Gly Gly Ser Leu Ser
        355                 360                 365

Arg Ser Ser Gln Gly Thr Leu Val Thr Val Ser Ser Ala
    370                 375                 380

<210> SEQ ID NO 113
<211> LENGTH: 750
<212> TYPE: PRT
<213> ORGANISM: Artificial Sequence
<220> FEATURE:
<223> OTHER INFORMATION: humanized Lama

<400> SEQUENCE: 113

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Val Ser
        195                 200                 205

Gly Gly Ile Thr Tyr Tyr Ala Asp Ser Val Lys Gly Arg Phe Thr Ile
    210                 215                 220

Ser Arg Asp Pro Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Phe Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly
    290                 295                 300

-continued

```
Gly Gly Gly Ser Glu Val Gln Leu Val Glu Ser Gly Gly Val Val
305             310             315             320

Gln Pro Gly Gly Ser Leu Arg Leu Ser Cys Ala Ala Ser Gly Arg Thr
            325             330             335

Phe Ser Asp Tyr Val Met Gly Trp Phe Arg Gln Ala Pro Gly Lys Glu
        340             345             350

Arg Glu Phe Val Ala Ala Ile Ser Glu Ser Gly Gly Arg Thr His Tyr
    355             360             365

Ala Asp Ser Val Lys Gly Arg Phe Thr Ile Ser Arg Asp Asn Ser Lys
370             375             380

Asn Thr Leu Tyr Leu Gln Met Asn Ser Leu Arg Pro Glu Asp Thr Ala
385             390             395             400

Leu Tyr Tyr Cys Ala Thr Thr Leu Leu Trp Trp Thr Ser Glu Tyr Ala
            405             410             415

Pro Ile Lys Ala Asn Asp Tyr Asp Tyr Trp Gly Gln Gly Thr Leu Val
        420             425             430

Thr Val Ser Ser Gly Gly Gly Ser Gly Gly Gly Ser Gly Gly
    435             440             445

Gly Gly Ser Gly Gly Gly Ser Gly Gly Gly Ser Gly Gly Gly
    450             455             460

Gly Ser Gly Gly Gly Ser Glu Val Gln Leu Val Glu Ser Gly Gly
465             470             475             480

Gly Val Val Gln Pro Gly Ser Leu Arg Leu Ser Cys Ala Ala Ser
            485             490             495

Gly Arg Thr Phe Ser Asp Tyr Val Met Gly Trp Phe Arg Gln Ala Pro
        500             505             510

Gly Lys Glu Arg Glu Phe Val Ala Ala Ile Ser Glu Ser Gly Gly Arg
    515             520             525

Thr His Tyr Ala Asp Ser Val Lys Gly Arg Phe Thr Ile Ser Arg Asp
    530             535             540

Asn Ser Lys Asn Thr Leu Tyr Leu Gln Met Asn Ser Leu Arg Pro Glu
545             550             555             560

Asp Thr Ala Leu Tyr Tyr Cys Ala Thr Thr Leu Leu Trp Trp Thr Ser
            565             570             575

Glu Tyr Ala Pro Ile Lys Ala Asn Asp Tyr Asp Tyr Trp Gly Gln Gly
        580             585             590

Thr Leu Val Thr Val Ser Ser Gly Gly Gly Ser Gly Gly Gly
    595             600             605

Ser Gly Gly Gly Ser Gly Gly Gly Ser Gly Gly Gly Ser
    610             615             620

Gly Gly Gly Ser Gly Gly Gly Ser Glu Val Gln Leu Val Glu
625             630             635             640

Ser Gly Gly Val Val Gln Pro Gly Asn Ser Leu Arg Leu Ser Cys
            645             650             655

Ala Ala Ser Gly Phe Thr Phe Ser Phe Gly Met Ser Trp Val Arg
        660             665             670

Gln Ala Pro Gly Lys Gly Leu Glu Trp Val Ser Ser Ile Ser Gly Ser
    675             680             685

Gly Ser Asp Thr Leu Tyr Ala Asp Ser Val Lys Gly Arg Phe Thr Ile
        690             695             700

Ser Arg Asp Asn Ala Lys Thr Thr Leu Tyr Leu Gln Met Asn Ser Leu
705             710             715             720

Arg Pro Glu Asp Thr Ala Leu Tyr Tyr Cys Thr Ile Gly Gly Ser Leu
```

```
                        725                 730                 735
Ser Arg Ser Ser Gln Gly Thr Leu Val Thr Val Ser Ser Ala
                740                 745                 750

<210> SEQ ID NO 114
<211> LENGTH: 646
<212> TYPE: PRT
<213> ORGANISM: Artificial Sequence
<220> FEATURE:
<223> OTHER INFORMATION: humanized Lama

<400> SEQUENCE: 114

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Ser Gly Gly Gly Ser
        115                 120                 125

Glu Val Gln Leu Val Glu Ser Gly Gly Val Val Gln Pro Gly Gly
    130                 135                 140

Ser Leu Arg Leu Ser Cys Ala Ala Ser Gly Ser Ile Ala Ser Ile His
145                 150                 155                 160

Ala Met Gly Trp Phe Arg Gln Ala Pro Gly Lys Glu Arg Glu Phe Val
                165                 170                 175

Ala Val Ile Thr Val Ser Gly Gly Ile Thr Tyr Tyr Ala Asp Ser Val
            180                 185                 190

Lys Gly Arg Phe Thr Ile Ser Arg Asp Pro Ser Lys Asn Thr Val Tyr
        195                 200                 205

Leu Gln Met Asn Ser Leu Arg Pro Glu Asp Thr Ala Leu Tyr Tyr Cys
    210                 215                 220

Ala Gly Asp Lys His Gln Ser Ser Phe Tyr Asp Tyr Trp Gly Gln Gly
225                 230                 235                 240

Thr Leu Val Thr Val Ser Ser Gly Gly Gly Ser Gly Gly Gly Ser
                245                 250                 255

Glu Val Gln Leu Val Glu Ser Gly Gly Val Val Gln Pro Gly Gly
            260                 265                 270

Ser Leu Arg Leu Ser Cys Ala Ala Ser Gly Arg Thr Phe Ser Asp Tyr
        275                 280                 285

Val Met Gly Trp Phe Arg Gln Ala Pro Gly Lys Glu Arg Glu Phe Val
    290                 295                 300

Ala Ala Ile Ser Glu Ser Gly Gly Arg Thr His Tyr Ala Asp Ser Val
305                 310                 315                 320

Lys Gly Arg Phe Thr Ile Ser Arg Asp Asn Ser Lys Asn Thr Leu Tyr
                325                 330                 335

Leu Gln Met Asn Ser Leu Arg Pro Glu Asp Thr Ala Leu Tyr Tyr Cys
```

```
                340             345             350
Ala Thr Thr Leu Leu Trp Trp Thr Ser Glu Tyr Ala Pro Ile Lys Ala
            355                 360                 365

Asn Asp Tyr Asp Tyr Trp Gly Gln Gly Thr Leu Val Thr Val Ser Ser
    370                 375                 380

Gly Gly Gly Gly Ser Gly Gly Ser Glu Val Gln Leu Val Glu Ser
385                 390                 395                 400

Gly Gly Gly Val Val Gln Pro Gly Gly Ser Leu Arg Leu Ser Cys Ala
                405                 410                 415

Ala Ser Gly Arg Thr Phe Ser Asp Tyr Val Met Gly Trp Phe Arg Gln
            420                 425                 430

Ala Pro Gly Lys Glu Arg Glu Phe Val Ala Ala Ile Ser Glu Ser Gly
            435                 440                 445

Gly Arg Thr His Tyr Ala Asp Ser Val Lys Gly Arg Phe Thr Ile Ser
        450                 455                 460

Arg Asp Asn Ser Lys Asn Thr Leu Tyr Leu Gln Met Asn Ser Leu Arg
465                 470                 475                 480

Pro Glu Asp Thr Ala Leu Tyr Tyr Cys Ala Thr Thr Leu Leu Trp Trp
                485                 490                 495

Thr Ser Glu Tyr Ala Pro Ile Lys Ala Asn Asp Tyr Asp Tyr Trp Gly
                500                 505                 510

Gln Gly Thr Leu Val Thr Val Ser Ser Gly Gly Gly Gly Ser Gly Gly
            515                 520                 525

Gly Ser Glu Val Gln Leu Val Glu Ser Gly Gly Gly Val Val Gln Pro
        530                 535                 540

Gly Asn Ser Leu Arg Leu Ser Cys Ala Ala Ser Gly Phe Thr Phe Ser
545                 550                 555                 560

Ser Phe Gly Met Ser Trp Val Arg Gln Ala Pro Gly Lys Gly Leu Glu
                565                 570                 575

Trp Val Ser Ser Ile Ser Gly Ser Gly Ser Asp Thr Leu Tyr Ala Asp
                580                 585                 590

Ser Val Lys Gly Arg Phe Thr Ile Ser Arg Asp Asn Ala Lys Thr Thr
            595                 600                 605

Leu Tyr Leu Gln Met Asn Ser Leu Arg Pro Glu Asp Thr Ala Leu Tyr
        610                 615                 620

Tyr Cys Thr Ile Gly Gly Ser Leu Ser Arg Ser Ser Gln Gly Thr Leu
625                 630                 635                 640

Val Thr Val Ser Ser Ala
                645

<210> SEQ ID NO 115
<211> LENGTH: 433
<212> TYPE: PRT
<213> ORGANISM: Artificial Sequence
<220> FEATURE:
<223> OTHER INFORMATION: humanized Lama

<400> SEQUENCE: 115

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
```

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Ser
    130                 135                 140

Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Arg Thr Phe Ser Asp Tyr Val Met Gly Trp Phe Arg
            180                 185                 190

Gln Ala Pro Gly Lys Glu Arg Glu Phe Val Ala Ala Ile Ser Glu Ser
            195                 200                 205

Gly Gly Arg Thr His Tyr Ala Asp Ser Val Lys Gly Arg Phe Thr Ile
            210                 215                 220

Ser Arg Asp Asn Ser Lys Asn Thr Leu Tyr Leu Gln Met Asn Ser Leu
225                 230                 235                 240

Arg Pro Glu Asp Thr Ala Leu Tyr Tyr Cys Ala Thr Thr Leu Leu Trp
                245                 250                 255

Trp Thr Ser Glu Tyr Ala Pro Ile Lys Ala Asn Asp Tyr Asp Tyr Trp
                260                 265                 270

Gly Gln Gly Thr Leu Val Thr Val Ser Ser Gly Gly Gly Gly Ser Gly
            275                 280                 285

Gly Gly Ser Gly Gly Gly Gly Ser Gly Gly Gly Gly Ser Gly Gly
    290                 295                 300

Gly Gly Ser Gly Gly Gly Ser Gly Gly Gly Gly Ser Glu Val Gln
305                 310                 315                 320

Leu Val Glu Ser Gly Gly Gly Val Val Gln Pro Gly Asn Ser Leu Arg
            325                 330                 335

Leu Ser Cys Ala Ala Ser Gly Phe Thr Phe Ser Ser Phe Gly Met Ser
            340                 345                 350

Trp Val Arg Gln Ala Pro Gly Lys Gly Leu Glu Trp Val Ser Ser Ile
            355                 360                 365

Ser Gly Ser Gly Ser Asp Thr Leu Tyr Ala Asp Ser Val Lys Gly Arg
            370                 375                 380

Phe Thr Ile Ser Arg Asp Asn Ala Lys Thr Thr Leu Tyr Leu Gln Met
385                 390                 395                 400

Asn Ser Leu Arg Pro Glu Asp Thr Ala Leu Tyr Tyr Cys Thr Ile Gly
                405                 410                 415

Gly Ser Leu Ser Arg Ser Ser Gln Gly Thr Leu Val Thr Val Ser Ser
            420                 425                 430

Ala

<210> SEQ ID NO 116
<211> LENGTH: 381
<212> TYPE: PRT
<213> ORGANISM: Artificial Sequence
<220> FEATURE:

<223> OTHER INFORMATION: humanized Lama

<400> SEQUENCE: 116

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Ser Gly Gly Gly Ser
        115                 120                 125

Glu Val Gln Leu Val Glu Ser Gly Gly Gly Val Val Gln Pro Gly Gly
    130                 135                 140

Ser Leu Arg Leu Ser Cys Ala Ala Ser Gly Arg Thr Phe Ser Asp Tyr
145                 150                 155                 160

Val Met Gly Trp Phe Arg Gln Ala Pro Gly Lys Glu Arg Glu Phe Val
                165                 170                 175

Ala Ala Ile Ser Glu Ser Gly Gly Arg Thr His Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Pro Glu Asp Thr Ala Leu Tyr Tyr Cys
    210                 215                 220

Ala Thr Thr Leu Leu Trp Trp Thr Ser Glu Tyr Ala Pro Ile Lys Ala
225                 230                 235                 240

Asn Asp Tyr Asp Tyr Trp Gly Gln Gly Thr Leu Val Thr Val Ser Ser
                245                 250                 255

Gly Gly Gly Gly Ser Gly Gly Gly Ser Glu Val Gln Leu Val Glu Ser
            260                 265                 270

Gly Gly Gly Val Val Gln Pro Gly Asn Ser Leu Arg Leu Ser Cys Ala
        275                 280                 285

Ala Ser Gly Phe Thr Phe Ser Ser Phe Gly Met Ser Trp Val Arg Gln
    290                 295                 300

Ala Pro Gly Lys Gly Leu Glu Trp Val Ser Ser Ile Ser Gly Ser Gly
305                 310                 315                 320

Ser Asp Thr Leu Tyr Ala Asp Ser Val Lys Gly Arg Phe Thr Ile Ser
                325                 330                 335

Arg Asp Asn Ala Lys Thr Thr Leu Tyr Leu Gln Met Asn Ser Leu Arg
            340                 345                 350

Pro Glu Asp Thr Ala Leu Tyr Tyr Cys Thr Ile Gly Gly Ser Leu Ser
        355                 360                 365

Arg Ser Ser Gln Gly Thr Leu Val Thr Val Ser Ser Ala
    370                 375                 380
```

<210> SEQ ID NO 117
<211> LENGTH: 750

```
<212> TYPE: PRT
<213> ORGANISM: Artificial Sequence
<220> FEATURE:
<223> OTHER INFORMATION: humanized Lama

<400> SEQUENCE: 117
```

| | | | | | | | | | | | | | | |
|---|---|---|---|---|---|---|---|---|---|---|---|---|---|---|
| Asp | Val | Gln | Leu | Val | Glu | Ser | Gly | Gly | Gly | Val | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Ser | Ile | Ala | Ser | Ile | His |
| | | | 20 | | | | | 25 | | | | | 30 | | |
| Ala | Met | Gly | Trp | Phe | Arg | Gln | Ala | Pro | Gly | Lys | Glu | Arg | Glu | Phe | Val |
| | | 35 | | | | | 40 | | | | | 45 | | | |
| Ala | Val | Ile | Thr | Val | Ser | Gly | Ile | Thr | Tyr | Tyr | Ala | Asp | Ser | Val | |
| 50 | | | | | 55 | | | | | 60 | | | | | |
| Lys | Gly | Arg | Phe | Thr | Ile | Ser | Arg | Asp | Gln | Ser | Lys | Asn | Thr | Val | Tyr |
| 65 | | | | | 70 | | | | | 75 | | | | | 80 |
| Leu | Gln | Met | Asn | Ser | Leu | Arg | Pro | Glu | Asp | Thr | Ala | Leu | Tyr | Tyr | Cys |
| | | | | 85 | | | | | 90 | | | | | 95 | |
| Ala | Gly | Asp | Lys | His | Gln | Ser | Ser | Phe | Tyr | Asp | Tyr | Trp | Gly | Gln | Gly |
| | | | 100 | | | | | 105 | | | | | 110 | | |
| Thr | Leu | Val | Thr | Val | Ser | Ser | Gly | Gly | Gly | Gly | Ser | Gly | Gly | Gly | Gly |
| | | | 115 | | | | | 120 | | | | | 125 | | |
| Ser | Gly | Gly | Gly | Gly | Ser | Gly | Gly | Gly | Gly | Ser | Gly | Gly | Gly | Gly | Ser |
| 130 | | | | | 135 | | | | | 140 | | | | | |
| Gly | Gly | Gly | Gly | Ser | Gly | Gly | Gly | Ser | Glu | Val | Gln | Leu | Val | Glu | |
| 145 | | | | | 150 | | | | | 155 | | | | | 160 |
| Ser | Gly | Gly | Gly | Val | Val | Gln | Pro | Gly | Gly | Ser | Leu | Arg | Leu | Ser | Cys |
| | | | | 165 | | | | | 170 | | | | | 175 | |
| Ala | Ala | Ser | Gly | Ser | Ile | Ala | Ser | Ile | His | Ala | Met | Gly | Trp | Phe | Arg |
| | | | 180 | | | | | 185 | | | | | 190 | | |
| Gln | Ala | Pro | Gly | Lys | Glu | Arg | Glu | Phe | Val | Ala | Val | Ile | Thr | Val | Ser |
| | | | 195 | | | | | 200 | | | | | 205 | | |
| Gly | Gly | Ile | Thr | Tyr | Tyr | Ala | Asp | Ser | Val | Lys | Gly | Arg | Phe | Thr | Ile |
| 210 | | | | | 215 | | | | | 220 | | | | | |
| Ser | Arg | Asp | Gln | Ser | Lys | Asn | Thr | Val | Tyr | Leu | Gln | Met | Asn | Ser | Leu |
| 225 | | | | | 230 | | | | | 235 | | | | | 240 |
| Arg | Pro | Glu | Asp | Thr | Ala | Leu | Tyr | Tyr | Cys | Ala | Gly | Asp | Lys | His | Gln |
| | | | | 245 | | | | | 250 | | | | | 255 | |
| Ser | Ser | Phe | Tyr | Asp | Tyr | Trp | Gly | Gln | Gly | Thr | Leu | Val | Thr | Val | Ser |
| | | | 260 | | | | | 265 | | | | | 270 | | |
| Ser | Gly | Gly | Gly | Gly | Ser | Gly | Gly | Gly | Gly | Ser | Gly | Gly | Gly | Gly | Ser |
| | | 275 | | | | | 280 | | | | | 285 | | | |
| Gly | Gly | Gly | Gly | Ser | Gly | Gly | Gly | Ser | Gly | Gly | Gly | Ser | Gly | | |
| | 290 | | | | | 295 | | | | | 300 | | | | |
| Gly | Gly | Gly | Ser | Glu | Val | Gln | Leu | Val | Glu | Ser | Gly | Gly | Val | Val | |
| 305 | | | | | 310 | | | | | 315 | | | | | 320 |
| Gln | Pro | Gly | Gly | Ser | Leu | Arg | Leu | Ser | Cys | Ala | Ala | Ser | Gly | Arg | Thr |
| | | | | 325 | | | | | 330 | | | | | 335 | |
| Phe | Ser | Asp | Tyr | Val | Met | Gly | Trp | Phe | Arg | Gln | Ala | Pro | Gly | Lys | Glu |
| | | | 340 | | | | | 345 | | | | | 350 | | |
| Arg | Glu | Phe | Val | Ala | Ala | Ile | Ser | Glu | Ser | Gly | Gly | Arg | Thr | His | Tyr |
| | | | 355 | | | | | 360 | | | | | 365 | | |
| Ala | Asp | Ser | Val | Lys | Gly | Arg | Phe | Thr | Ile | Ser | Arg | Asp | Asn | Ser | Lys |
| 370 | | | | | 375 | | | | | 380 | | | | | |

Asn Thr Leu Tyr Leu Gln Met Asn Ser Leu Arg Pro Glu Asp Thr Ala
385                 390                 395                 400

Leu Tyr Tyr Cys Ala Thr Thr Leu Leu Trp Trp Thr Ser Glu Tyr Ala
            405                 410                 415

Pro Ile Lys Ala Asn Asp Tyr Asp Tyr Trp Gly Gln Gly Thr Leu Val
            420                 425                 430

Thr Val Ser Ser Gly Gly Gly Ser Gly Gly Gly Ser Gly Gly
            435                 440                 445

Gly Gly Ser Gly Gly Gly Ser Gly Gly Gly Ser Gly Gly Gly
450                 455                 460

Gly Ser Gly Gly Gly Ser Glu Val Gln Leu Val Glu Ser Gly Gly
465                 470                 475                 480

Gly Val Val Gln Pro Gly Gly Ser Leu Arg Leu Ser Cys Ala Ala Ser
            485                 490                 495

Gly Arg Thr Phe Ser Asp Tyr Val Met Gly Trp Phe Arg Gln Ala Pro
            500                 505                 510

Gly Lys Glu Arg Glu Phe Val Ala Ala Ile Ser Glu Ser Gly Gly Arg
            515                 520                 525

Thr His Tyr Ala Asp Ser Val Lys Gly Arg Phe Thr Ile Ser Arg Asp
            530                 535                 540

Asn Ser Lys Asn Thr Leu Tyr Leu Gln Met Asn Ser Leu Arg Pro Glu
545                 550                 555                 560

Asp Thr Ala Leu Tyr Tyr Cys Ala Thr Thr Leu Leu Trp Trp Thr Ser
            565                 570                 575

Glu Tyr Ala Pro Ile Lys Ala Asn Asp Tyr Asp Tyr Trp Gly Gln Gly
            580                 585                 590

Thr Leu Val Thr Val Ser Ser Gly Gly Gly Ser Gly Gly Gly Gly
            595                 600                 605

Ser Gly Gly Gly Gly Ser Gly Gly Gly Ser Gly Gly Gly Gly Ser
610                 615                 620

Gly Gly Gly Gly Ser Gly Gly Gly Gly Ser Glu Val Gln Leu Val Glu
625                 630                 635                 640

Ser Gly Gly Gly Val Val Gln Pro Gly Asn Ser Leu Arg Leu Ser Cys
            645                 650                 655

Ala Ala Ser Gly Phe Thr Phe Ser Ser Phe Gly Met Ser Trp Val Arg
            660                 665                 670

Gln Ala Pro Gly Lys Gly Leu Glu Trp Val Ser Ser Ile Ser Gly Ser
            675                 680                 685

Gly Ser Asp Thr Leu Tyr Ala Asp Ser Val Lys Gly Arg Phe Thr Ile
            690                 695                 700

Ser Arg Asp Asn Ala Lys Thr Thr Leu Tyr Leu Gln Met Asn Ser Leu
705                 710                 715                 720

Arg Pro Glu Asp Thr Ala Leu Tyr Tyr Cys Thr Ile Gly Gly Ser Leu
            725                 730                 735

Ser Arg Ser Ser Gln Gly Thr Leu Val Thr Val Ser Ser Ala
            740                 745                 750

<210> SEQ ID NO 118
<211> LENGTH: 646
<212> TYPE: PRT
<213> ORGANISM: Artificial Sequence
<220> FEATURE:
<223> OTHER INFORMATION: humanized Lama

<400> SEQUENCE: 118

```
Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Val Ser Gly Ile Thr Tyr Tyr Ala Asp Ser Val
        50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Ser Gly Gly Gly Ser
            115                 120                 125

Glu Val Gln Leu Val Glu Ser Gly Gly Val Val Gln Pro Gly Gly
            130                 135                 140

Ser Leu Arg Leu Ser Cys Ala Ala Ser Gly Ser Ile Ala Ser Ile His
145                 150                 155                 160

Ala Met Gly Trp Phe Arg Gln Ala Pro Gly Lys Glu Arg Glu Phe Val
            165                 170                 175

Ala Val Ile Thr Val Ser Gly Gly Ile Thr Tyr Tyr Ala Asp Ser Val
            180                 185                 190

Lys Gly Arg Phe Thr Ile Ser Arg Asp Gln Ser Lys Asn Thr Val Tyr
            195                 200                 205

Leu Gln Met Asn Ser Leu Arg Pro Glu Asp Thr Ala Leu Tyr Tyr Cys
            210                 215                 220

Ala Gly Asp Lys His Gln Ser Ser Phe Tyr Asp Tyr Trp Gly Gln Gly
225                 230                 235                 240

Thr Leu Val Thr Val Ser Ser Gly Gly Gly Gly Ser Gly Gly Gly Ser
                245                 250                 255

Glu Val Gln Leu Val Glu Ser Gly Gly Gly Val Val Gln Pro Gly Gly
            260                 265                 270

Ser Leu Arg Leu Ser Cys Ala Ala Ser Gly Arg Thr Phe Ser Asp Tyr
            275                 280                 285

Val Met Gly Trp Phe Arg Gln Ala Pro Gly Lys Glu Arg Glu Phe Val
            290                 295                 300

Ala Ala Ile Ser Glu Ser Gly Gly Arg Thr His Tyr Ala Asp Ser Val
305                 310                 315                 320

Lys Gly Arg Phe Thr Ile Ser Arg Asp Asn Ser Lys Asn Thr Leu Tyr
                325                 330                 335

Leu Gln Met Asn Ser Leu Arg Pro Glu Asp Thr Ala Leu Tyr Tyr Cys
                340                 345                 350

Ala Thr Thr Leu Leu Trp Trp Thr Ser Glu Tyr Ala Pro Ile Lys Ala
                355                 360                 365

Asn Asp Tyr Asp Tyr Trp Gly Gln Gly Thr Leu Val Thr Val Ser Ser
            370                 375                 380

Gly Gly Gly Gly Ser Gly Gly Gly Ser Glu Gln Leu Val Glu Ser
385                 390                 395                 400

Gly Gly Gly Val Val Gln Pro Gly Gly Ser Leu Arg Leu Ser Cys Ala
                405                 410                 415

Ala Ser Gly Arg Thr Phe Ser Asp Tyr Val Met Gly Trp Phe Arg Gln
```

```
                420                 425                 430
Ala Pro Gly Lys Glu Arg Glu Phe Val Ala Ala Ile Ser Glu Ser Gly
                435                 440                 445

Gly Arg Thr His Tyr Ala Asp Ser Val Lys Gly Arg Phe Thr Ile Ser
            450                 455                 460

Arg Asp Asn Ser Lys Asn Thr Leu Tyr Leu Gln Met Asn Ser Leu Arg
465                 470                 475                 480

Pro Glu Asp Thr Ala Leu Tyr Tyr Cys Ala Thr Thr Leu Leu Trp Trp
                485                 490                 495

Thr Ser Glu Tyr Ala Pro Ile Lys Ala Asn Asp Tyr Asp Tyr Trp Gly
                500                 505                 510

Gln Gly Thr Leu Val Thr Val Ser Gly Gly Gly Ser Gly Gly
            515                 520                 525

Gly Ser Glu Val Gln Leu Val Glu Ser Gly Gly Val Val Gln Pro
            530                 535                 540

Gly Asn Ser Leu Arg Leu Ser Cys Ala Ala Ser Gly Phe Thr Phe Ser
545                 550                 555                 560

Ser Phe Gly Met Ser Trp Val Arg Gln Ala Pro Gly Lys Gly Leu Glu
                565                 570                 575

Trp Val Ser Ser Ile Ser Gly Ser Gly Ser Asp Thr Leu Tyr Ala Asp
                580                 585                 590

Ser Val Lys Gly Arg Phe Thr Ile Ser Arg Asp Asn Ala Lys Thr Thr
                595                 600                 605

Leu Tyr Leu Gln Met Asn Ser Leu Arg Pro Glu Asp Thr Ala Leu Tyr
                610                 615                 620

Tyr Cys Thr Ile Gly Gly Ser Leu Ser Arg Ser Ser Gln Gly Thr Leu
625                 630                 635                 640

Val Thr Val Ser Ser Ala
                645

<210> SEQ ID NO 119
<211> LENGTH: 433
<212> TYPE: PRT
<213> ORGANISM: Artificial Sequence
<220> FEATURE:
<223> OTHER INFORMATION: humanized Lama

<400> SEQUENCE: 119

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
            35                  40                  45

Ala Val Ile Thr Val Ser Gly Ile Thr Tyr Tyr Ala Asp Ser Val
        50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
```

```
                130                 135                 140
Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Arg Thr Phe Ser Asp Tyr Val Met Gly Trp Phe Arg
                180                 185                 190

Gln Ala Pro Gly Lys Glu Arg Glu Phe Val Ala Ala Ile Ser Glu Ser
                195                 200                 205

Gly Gly Arg Thr His Tyr Ala Asp Ser Val Lys Gly Arg Phe Thr Ile
                210                 215                 220

Ser Arg Asp Asn Ser Lys Asn Thr Leu Tyr Leu Gln Met Asn Ser Leu
225                 230                 235                 240

Arg Pro Glu Asp Thr Ala Leu Tyr Tyr Cys Ala Thr Thr Leu Leu Trp
                245                 250                 255

Trp Thr Ser Glu Tyr Ala Pro Ile Lys Ala Asn Asp Tyr Asp Tyr Trp
                260                 265                 270

Gly Gln Gly Thr Leu Val Thr Val Ser Ser Gly Gly Gly Gly Ser Gly
                275                 280                 285

Gly Gly Gly Ser Gly Gly Gly Gly Ser Gly Gly Gly Gly Ser Gly Gly
                290                 295                 300

Gly Gly Ser Gly Gly Gly Ser Gly Gly Gly Ser Glu Val Gln
305                 310                 315                 320

Leu Val Glu Ser Gly Gly Gly Val Val Gln Pro Gly Asn Ser Leu Arg
                325                 330                 335

Leu Ser Cys Ala Ala Ser Gly Phe Thr Phe Ser Ser Phe Gly Met Ser
                340                 345                 350

Trp Val Arg Gln Ala Pro Gly Lys Gly Leu Glu Trp Val Ser Ser Ile
                355                 360                 365

Ser Gly Ser Gly Ser Asp Thr Leu Tyr Ala Asp Ser Val Lys Gly Arg
                370                 375                 380

Phe Thr Ile Ser Arg Asp Asn Ala Lys Thr Thr Leu Tyr Leu Gln Met
385                 390                 395                 400

Asn Ser Leu Arg Pro Glu Asp Thr Ala Leu Tyr Tyr Cys Thr Ile Gly
                405                 410                 415

Gly Ser Leu Ser Arg Ser Ser Gln Gly Thr Leu Val Thr Val Ser Ser
                420                 425                 430

Ala

<210> SEQ ID NO 120
<211> LENGTH: 381
<212> TYPE: PRT
<213> ORGANISM: Artificial Sequence
<220> FEATURE:
<223> OTHER INFORMATION: humanized Lama

<400> SEQUENCE: 120

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Val Ser Gly Gly Ile Thr Tyr Tyr Ala Asp Ser Val
                50                  55                  60
```

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
            85                  90                  95

Ala Gly Asp Lys His Gln Ser Ser Phe Tyr Asp Tyr Trp Gly Gln Gly
        100                 105                 110

Thr Leu Val Thr Val Ser Ser Gly Gly Gly Ser Gly Gly Gly Ser
        115                 120                 125

Glu Val Gln Leu Val Glu Ser Gly Gly Val Val Gln Pro Gly Gly
        130                 135                 140

Ser Leu Arg Leu Ser Cys Ala Ala Ser Gly Arg Thr Phe Ser Asp Tyr
145                 150                 155                 160

Val Met Gly Trp Phe Arg Gln Ala Pro Gly Lys Glu Arg Glu Phe Val
                165                 170                 175

Ala Ala Ile Ser Glu Ser Gly Gly Arg Thr His Tyr Ala Asp Ser Val
                180                 185                 190

Lys Gly Arg Phe Thr Ile Ser Arg Asp Asn Ser Lys Asn Thr Leu Tyr
            195                 200                 205

Leu Gln Met Asn Ser Leu Arg Pro Glu Asp Thr Ala Leu Tyr Tyr Cys
        210                 215                 220

Ala Thr Thr Leu Leu Trp Trp Thr Ser Glu Tyr Ala Pro Ile Lys Ala
225                 230                 235                 240

Asn Asp Tyr Asp Tyr Trp Gly Gln Gly Thr Leu Val Thr Val Ser Ser
                245                 250                 255

Gly Gly Gly Gly Ser Gly Gly Gly Ser Glu Val Gln Leu Val Glu Ser
                260                 265                 270

Gly Gly Gly Val Val Gln Pro Gly Asn Ser Leu Arg Leu Ser Cys Ala
            275                 280                 285

Ala Ser Gly Phe Thr Phe Ser Ser Phe Gly Met Ser Trp Val Arg Gln
        290                 295                 300

Ala Pro Gly Lys Gly Leu Glu Trp Val Ser Ser Ile Ser Gly Ser Gly
305                 310                 315                 320

Ser Asp Thr Leu Tyr Ala Asp Ser Val Lys Gly Arg Phe Thr Ile Ser
                325                 330                 335

Arg Asp Asn Ala Lys Thr Thr Leu Tyr Leu Gln Met Asn Ser Leu Arg
            340                 345                 350

Pro Glu Asp Thr Ala Leu Tyr Tyr Cys Thr Ile Gly Gly Ser Leu Ser
        355                 360                 365

Arg Ser Ser Gln Gly Thr Leu Val Thr Val Ser Ser Ala
            370                 375                 380

<210> SEQ ID NO 121
<211> LENGTH: 750
<212> TYPE: PRT
<213> ORGANISM: Artificial Sequence
<220> FEATURE:
<223> OTHER INFORMATION: humanized Lama

<400> SEQUENCE: 121

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

```
Ala Val Ile Thr Val Ser Gly Ile Thr Tyr Tyr Ala Asp Ser Val
 50                  55                  60
Lys Gly Arg Phe Thr Ile Ser Arg Asp Ser Lys Asn Thr Val Tyr
 65                  70                  75                  80
Leu Gln Met Asn Ser Leu Arg Pro Glu Asp Thr Ala Leu Tyr Tyr Cys
                 85                  90                  95
Ala Gly Asp Lys His Gln Ser Ser Phe Tyr Asp Tyr Trp Gly Gln Gly
            100                 105                 110
Thr Leu Val Thr Val Ser Ser Gly Gly Gly Ser Gly Gly Gly Gly
            115                 120                 125
Ser Gly Gly Gly Ser Gly Gly Gly Ser Gly Gly Gly Ser
        130                 135                 140
Gly Gly Gly Ser Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Val Ser
        195                 200                 205
Gly Gly Ile Thr Tyr Tyr Ala Asp Ser Val Lys Gly Arg Phe Thr Ile
        210                 215                 220
Ser Arg Asp Ser Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
Ser Ser Phe Tyr Asp Tyr Trp Gly Gln Gly Thr Leu Val Thr Val Ser
            260                 265                 270
Ser Gly Gly Gly Gly Ser Gly Gly Gly Gly Ser Gly Gly Gly Gly Ser
        275                 280                 285
Gly Gly Gly Gly Ser Gly Gly Gly Gly Ser Gly Gly Gly Ser Gly
        290                 295                 300
Gly Gly Gly Ser Glu Val Gln Leu Val Glu Ser Gly Gly Gly Val Val
305                 310                 315                 320
Gln Pro Gly Gly Ser Leu Arg Leu Ser Cys Ala Ala Ser Gly Arg Thr
                325                 330                 335
Phe Ser Asp Tyr Val Met Gly Trp Phe Arg Gln Ala Pro Gly Lys Glu
            340                 345                 350
Arg Glu Phe Val Ala Ala Ile Ser Glu Ser Gly Gly Arg Thr His Tyr
        355                 360                 365
Ala Asp Ser Val Lys Gly Arg Phe Thr Ile Ser Arg Asp Asn Ser Lys
        370                 375                 380
Asn Thr Leu Tyr Leu Gln Met Asn Ser Leu Arg Pro Glu Asp Thr Ala
385                 390                 395                 400
Leu Tyr Tyr Cys Ala Thr Thr Leu Leu Trp Trp Thr Ser Glu Tyr Ala
                405                 410                 415
Pro Ile Lys Ala Asn Asp Tyr Asp Tyr Trp Gly Gln Gly Thr Leu Val
            420                 425                 430
Thr Val Ser Ser Gly Gly Gly Gly Ser Gly Gly Gly Ser Gly Gly
            435                 440                 445
Gly Gly Ser Gly Gly Gly Gly Ser Gly Gly Gly Gly Ser Gly Gly Gly
        450                 455                 460
```

```
Gly Ser Gly Gly Gly Gly Ser Glu Val Gln Leu Val Glu Ser Gly Gly
465                 470                 475                 480

Gly Val Val Gln Pro Gly Gly Ser Leu Arg Leu Ser Cys Ala Ala Ser
            485                 490                 495

Gly Arg Thr Phe Ser Asp Tyr Val Met Gly Trp Phe Arg Gln Ala Pro
        500                 505                 510

Gly Lys Glu Arg Glu Phe Val Ala Ala Ile Ser Glu Ser Gly Gly Arg
    515                 520                 525

Thr His Tyr Ala Asp Ser Val Lys Gly Arg Phe Thr Ile Ser Arg Asp
530                 535                 540

Asn Ser Lys Asn Thr Leu Tyr Leu Gln Met Asn Ser Leu Arg Pro Glu
545                 550                 555                 560

Asp Thr Ala Leu Tyr Tyr Cys Ala Thr Thr Leu Leu Trp Trp Thr Ser
            565                 570                 575

Glu Tyr Ala Pro Ile Lys Ala Asn Asp Tyr Asp Tyr Trp Gly Gln Gly
        580                 585                 590

Thr Leu Val Thr Val Ser Ser Gly Gly Gly Gly Ser Gly Gly Gly Gly
    595                 600                 605

Ser Gly Gly Gly Gly Ser Gly Gly Gly Gly Ser Gly Gly Gly Gly Ser
610                 615                 620

Gly Gly Gly Gly Ser Gly Gly Gly Ser Glu Val Gln Leu Val Glu
625                 630                 635                 640

Ser Gly Gly Gly Val Val Gln Pro Gly Asn Ser Leu Arg Leu Ser Cys
            645                 650                 655

Ala Ala Ser Gly Phe Thr Phe Ser Ser Phe Gly Met Ser Trp Val Arg
            660                 665                 670

Gln Ala Pro Gly Lys Gly Leu Glu Trp Val Ser Ser Ile Ser Gly Ser
            675                 680                 685

Gly Ser Asp Thr Leu Tyr Ala Asp Ser Val Lys Gly Arg Phe Thr Ile
        690                 695                 700

Ser Arg Asp Asn Ala Lys Thr Thr Leu Tyr Leu Gln Met Asn Ser Leu
705                 710                 715                 720

Arg Pro Glu Asp Thr Ala Leu Tyr Tyr Cys Thr Ile Gly Gly Ser Leu
            725                 730                 735

Ser Arg Ser Ser Gln Gly Thr Leu Val Thr Val Ser Ser Ala
        740                 745                 750

<210> SEQ ID NO 122
<211> LENGTH: 646
<212> TYPE: PRT
<213> ORGANISM: Artificial Sequence
<220> FEATURE:
<223> OTHER INFORMATION: humanized Lama

<400> SEQUENCE: 122

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Ser Ser Lys Asn Thr Val Tyr
65                  70                  75                  80
```

-continued

```
Leu Gln Met Asn Ser Leu Arg Pro Glu Asp Thr Ala Leu Tyr Tyr Cys
                 85                  90                  95
Ala Gly Asp Lys His Gln Ser Ser Phe Tyr Asp Tyr Trp Gly Gln Gly
            100                 105                 110
Thr Leu Val Thr Val Ser Ser Gly Gly Gly Ser Gly Gly Gly Ser
        115                 120                 125
Glu Val Gln Leu Val Glu Ser Gly Gly Val Val Gln Pro Gly Gly
        130                 135                 140
Ser Leu Arg Leu Ser Cys Ala Ala Ser Gly Ile Ala Ser Ile His
145                 150                 155                 160
Ala Met Gly Trp Phe Arg Gln Ala Pro Gly Lys Glu Arg Glu Phe Val
                165                 170                 175
Ala Val Ile Thr Val Ser Gly Gly Ile Thr Tyr Tyr Ala Asp Ser Val
            180                 185                 190
Lys Gly Arg Phe Thr Ile Ser Arg Asp Ser Ser Lys Asn Thr Val Tyr
            195                 200                 205
Leu Gln Met Asn Ser Leu Arg Pro Glu Asp Thr Ala Leu Tyr Tyr Cys
            210                 215                 220
Ala Gly Asp Lys His Gln Ser Ser Phe Tyr Asp Tyr Trp Gly Gln Gly
225                 230                 235                 240
Thr Leu Val Thr Val Ser Ser Gly Gly Gly Ser Gly Gly Gly Ser
                245                 250                 255
Glu Val Gln Leu Val Glu Ser Gly Gly Val Val Gln Pro Gly Gly
            260                 265                 270
Ser Leu Arg Leu Ser Cys Ala Ala Ser Gly Arg Thr Phe Ser Asp Tyr
            275                 280                 285
Val Met Gly Trp Phe Arg Gln Ala Pro Gly Lys Glu Arg Glu Phe Val
        290                 295                 300
Ala Ala Ile Ser Glu Ser Gly Gly Arg Thr His Tyr Ala Asp Ser Val
305                 310                 315                 320
Lys Gly Arg Phe Thr Ile Ser Arg Asp Asn Ser Lys Asn Thr Leu Tyr
                325                 330                 335
Leu Gln Met Asn Ser Leu Arg Pro Glu Asp Thr Ala Leu Tyr Tyr Cys
            340                 345                 350
Ala Thr Thr Leu Leu Trp Trp Thr Ser Glu Tyr Ala Pro Ile Lys Ala
            355                 360                 365
Asn Asp Tyr Asp Tyr Trp Gly Gln Gly Thr Leu Val Thr Val Ser Ser
        370                 375                 380
Gly Gly Gly Gly Ser Gly Gly Gly Ser Glu Val Gln Leu Val Glu Ser
385                 390                 395                 400
Gly Gly Gly Val Val Gln Pro Gly Gly Ser Leu Arg Leu Ser Cys Ala
                405                 410                 415
Ala Ser Gly Arg Thr Phe Ser Asp Tyr Val Met Gly Trp Phe Arg Gln
            420                 425                 430
Ala Pro Gly Lys Glu Arg Glu Phe Val Ala Ala Ile Ser Glu Ser Gly
            435                 440                 445
Gly Arg Thr His Tyr Ala Asp Ser Val Lys Gly Arg Phe Thr Ile Ser
        450                 455                 460
Arg Asp Asn Ser Lys Asn Thr Leu Tyr Leu Gln Met Asn Ser Leu Arg
465                 470                 475                 480
Pro Glu Asp Thr Ala Leu Tyr Tyr Cys Ala Thr Thr Leu Leu Trp Trp
                485                 490                 495
Thr Ser Glu Tyr Ala Pro Ile Lys Ala Asn Asp Tyr Asp Tyr Trp Gly
```

```
                500                 505                 510
Gln Gly Thr Leu Val Thr Val Ser Ser Gly Gly Gly Ser Gly Gly
            515                 520                 525

Gly Ser Glu Val Gln Leu Val Glu Ser Gly Gly Val Val Gln Pro
            530                 535                 540

Gly Asn Ser Leu Arg Leu Ser Cys Ala Ala Ser Gly Phe Thr Phe Ser
545                 550                 555                 560

Ser Phe Gly Met Ser Trp Val Arg Gln Ala Pro Gly Lys Gly Leu Glu
                565                 570                 575

Trp Val Ser Ser Ile Ser Gly Ser Gly Ser Asp Thr Leu Tyr Ala Asp
                580                 585                 590

Ser Val Lys Gly Arg Phe Thr Ile Ser Arg Asp Asn Ala Lys Thr Thr
            595                 600                 605

Leu Tyr Leu Gln Met Asn Ser Leu Arg Pro Glu Asp Thr Ala Leu Tyr
            610                 615                 620

Tyr Cys Thr Ile Gly Gly Ser Leu Ser Arg Ser Ser Gln Gly Thr Leu
625                 630                 635                 640

Val Thr Val Ser Ser Ala
                645

<210> SEQ ID NO 123
<211> LENGTH: 433
<212> TYPE: PRT
<213> ORGANISM: Artificial Sequence
<220> FEATURE:
<223> OTHER INFORMATION: humanized Lama

<400> SEQUENCE: 123

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Val Ser Gly Gly Ile Thr Tyr Tyr Ala Asp Ser Val
                50                  55                  60

Lys Gly Arg Phe Thr Ile Ser Arg Asp Ser Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Arg Thr Phe Ser Asp Tyr Val Met Gly Trp Phe Arg
            180                 185                 190

Gln Ala Pro Gly Lys Glu Arg Glu Phe Val Ala Ala Ile Ser Glu Ser
            195                 200                 205

Gly Gly Arg Thr His Tyr Ala Asp Ser Val Lys Gly Arg Phe Thr Ile
```

```
                    210                 215                 220
Ser Arg Asp Asn Ser Lys Asn Thr Leu Tyr Leu Gln Met Asn Ser Leu
225                 230                 235                 240

Arg Pro Glu Asp Thr Ala Leu Tyr Tyr Cys Ala Thr Thr Leu Leu Trp
                245                 250                 255

Trp Thr Ser Glu Tyr Ala Pro Ile Lys Ala Asn Asp Tyr Asp Tyr Trp
                260                 265                 270

Gly Gln Gly Thr Leu Val Thr Val Ser Ser Gly Gly Gly Gly Ser Gly
                275                 280                 285

Gly Gly Gly Ser Gly Gly Gly Ser Gly Gly Gly Gly Ser Gly Gly
            290                 295                 300

Gly Gly Ser Gly Gly Gly Ser Gly Gly Gly Ser Glu Val Gln
305                 310                 315                 320

Leu Val Glu Ser Gly Gly Val Val Gln Pro Gly Asn Ser Leu Arg
                325                 330                 335

Leu Ser Cys Ala Ala Ser Gly Phe Thr Phe Ser Ser Phe Gly Met Ser
                340                 345                 350

Trp Val Arg Gln Ala Pro Gly Lys Gly Leu Glu Trp Val Ser Ser Ile
                355                 360                 365

Ser Gly Ser Gly Ser Asp Thr Leu Tyr Ala Asp Ser Val Lys Gly Arg
                370                 375                 380

Phe Thr Ile Ser Arg Asp Asn Ala Lys Thr Thr Leu Tyr Leu Gln Met
385                 390                 395                 400

Asn Ser Leu Arg Pro Glu Asp Thr Ala Leu Tyr Tyr Cys Thr Ile Gly
                405                 410                 415

Gly Ser Leu Ser Arg Ser Ser Gln Gly Thr Leu Val Thr Val Ser Ser
                420                 425                 430

Ala

<210> SEQ ID NO 124
<211> LENGTH: 381
<212> TYPE: PRT
<213> ORGANISM: Artificial Sequence
<220> FEATURE:
<223> OTHER INFORMATION: humanized Lama

<400> SEQUENCE: 124

Asp Val Gln Leu Val Glu Ser Gly Gly Gly Val Val Gln Pro Gly Gly
1               5                  10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
            35                  40                  45

Ala Val Ile Thr Val Ser Gly Gly Ile Thr Tyr Tyr Ala Asp Ser Val
        50                  55                  60

Lys Gly Arg Phe Thr Ile Ser Arg Asp Ser Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Gly Gly Gly Gly Ser Gly Gly Gly Ser
        115                 120                 125

Glu Val Gln Leu Val Glu Ser Gly Gly Gly Val Val Gln Pro Gly Gly
    130                 135                 140
```

```
Ser Leu Arg Leu Ser Cys Ala Ala Ser Gly Arg Thr Phe Ser Asp Tyr
145                 150                 155                 160

Val Met Gly Trp Phe Arg Gln Ala Pro Gly Lys Glu Arg Glu Phe Val
                165                 170                 175

Ala Ala Ile Ser Glu Ser Gly Gly Arg Thr His Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Pro Glu Asp Thr Ala Leu Tyr Tyr Cys
    210                 215                 220

Ala Thr Thr Leu Leu Trp Trp Thr Ser Glu Tyr Ala Pro Ile Lys Ala
225                 230                 235                 240

Asn Asp Tyr Asp Tyr Trp Gly Gln Gly Thr Leu Val Thr Val Ser Ser
                245                 250                 255

Gly Gly Gly Gly Ser Gly Gly Gly Ser Glu Val Gln Leu Val Glu Ser
                260                 265                 270

Gly Gly Gly Val Val Gln Pro Gly Asn Ser Leu Arg Leu Ser Cys Ala
            275                 280                 285

Ala Ser Gly Phe Thr Phe Ser Ser Phe Gly Met Ser Trp Val Arg Gln
    290                 295                 300

Ala Pro Gly Lys Gly Leu Glu Trp Val Ser Ser Ile Ser Gly Ser Gly
305                 310                 315                 320

Ser Asp Thr Leu Tyr Ala Asp Ser Val Lys Gly Arg Phe Thr Ile Ser
                325                 330                 335

Arg Asp Asn Ala Lys Thr Thr Leu Tyr Leu Gln Met Asn Ser Leu Arg
            340                 345                 350

Pro Glu Asp Thr Ala Leu Tyr Tyr Cys Thr Ile Gly Gly Ser Leu Ser
    355                 360                 365

Arg Ser Ser Gln Gly Thr Leu Val Thr Val Ser Ser Ala
370                 375                 380

<210> SEQ ID NO 125
<211> LENGTH: 9
<212> TYPE: PRT
<213> ORGANISM: Artificial Sequence
<220> FEATURE:
<223> OTHER INFORMATION: 9GS linker

<400> SEQUENCE: 125

Gly Gly Gly Gly Ser Gly Gly Gly Ser
1               5

<210> SEQ ID NO 126
<211> LENGTH: 423
<212> TYPE: PRT
<213> ORGANISM: Artificial Sequence
<220> FEATURE:
<223> OTHER INFORMATION: Humanized lama

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
```

```
            50                  55                  60
Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Ile Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Gly Gly Gly Gly Ser Gly Gly Gly Ser
            130                 135                 140

Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
210                 215                 220

Ser Arg Asp Asn Ser Lys Asn Thr Val Tyr Leu Gln Met Asn Ser Leu
225                 230                 235                 240

Arg Pro Glu Asp Thr Ala Ile Tyr Tyr Cys Ala Gly Asp Lys His Gln
                245                 250                 255

Ser Ser Trp Tyr Asp Tyr Trp Gly Gln Gly Thr Leu Val Thr Val Ser
                260                 265                 270

Ser Gly Gly Gly Ser Gly Gly Gly Gly Ser Gly Gly Gly Gly Ser
            275                 280                 285

Gly Gly Gly Ser Gly Gly Gly Ser Gly Gly Gly Ser Gly
            290                 295                 300

Gly Gly Ser Glu Val Gln Leu Val Glu Ser Gly Gly Gly Leu Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ala Lys
            370                 375                 380

Thr Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
                405                 410                 415

Thr Leu Val Thr Val Ser Ser
            420

<210> SEQ ID NO 127
<211> LENGTH: 441
<212> TYPE: PRT
<213> ORGANISM: Artificial Sequence
<220> FEATURE:
<223> OTHER INFORMATION: Humanized lama
```

```
<400> SEQUENCE: 127

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Arg Gly Asn Glu Arg Glu Phe Val
        35                  40                  45

Ala Ala Ile Ser Glu Ser Gly Gly Arg Thr His Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Ser Gly Gly
145                 150                 155                 160

Gly Gly Ser Glu Val Gln Leu Val Glu Ser Gly Gly Leu Val Gln
                165                 170                 175

Ala Gly Gly Ser Leu Arg Leu Ser Cys Ala Ala Ser Gly Arg Thr Phe
            180                 185                 190

Ser Asp Tyr Val Met Gly Trp Phe Arg Gln Ala Arg Gly Asn Glu Arg
        195                 200                 205

Glu Phe Val Ala Ala Ile Ser Glu Ser Gly Gly Arg Thr His Tyr Ala
    210                 215                 220

Asp Ala Val Lys Gly Arg Phe Thr Ile Ser Arg Asp Asn Ala Lys Asn
225                 230                 235                 240

Thr Leu Tyr Leu Gln Met Asn Ser Leu Lys Pro Glu Asp Thr Ala Val
                245                 250                 255

Tyr Tyr Cys Ala Thr Thr Leu Leu Trp Trp Thr Ser Glu Tyr Ala Pro
            260                 265                 270

Ile Lys Ala Asn Asp Tyr Asp Tyr Trp Gly Gln Gly Thr Leu Val Thr
        275                 280                 285

Val Ser Ser Gly Gly Gly Gly Ser Gly Gly Gly Gly Ser Gly Gly Gly
    290                 295                 300

Gly Ser Gly Gly Gly Gly Ser Gly Gly Gly Gly Ser Gly Gly Gly Gly
305                 310                 315                 320

Ser Gly Gly Gly Gly Ser Glu Val Gln Leu Val Glu Ser Gly Gly Gly
                325                 330                 335

Leu Val Gln Pro Gly Asn Ser Leu Arg Leu Ser Cys Ala Ala Ser Gly
            340                 345                 350

Phe Thr Phe Ser Ser Phe Gly Met Ser Trp Val Arg Gln Ala Pro Gly
        355                 360                 365

Lys Gly Leu Glu Trp Val Ser Ser Ile Ser Gly Ser Gly Ser Asp Thr
    370                 375                 380

Leu Tyr Ala Asp Ser Val Lys Gly Arg Phe Thr Ile Ser Arg Asp Asn
385                 390                 395                 400

Ala Lys Thr Thr Leu Tyr Leu Gln Met Asn Ser Leu Arg Pro Glu Asp
                405                 410                 415
```

```
Thr Ala Val Tyr Tyr Cys Thr Ile Gly Gly Ser Leu Ser Arg Ser Ser
            420                 425                 430

Gln Gly Thr Leu Val Thr Val Ser Ser
        435                 440

<210> SEQ ID NO 128
<211> LENGTH: 162
<212> TYPE: PRT
<213> ORGANISM: Artificial Sequence
<220> FEATURE:
<223> OTHER INFORMATION: Humanized lama

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Arg Gly Asn Glu Arg Glu Phe Val
        35                  40                  45

Ala Ala Ile Ser Glu Ser Gly Gly Arg Thr His Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
        115                 120                 125

Ala Ala Ala Asp Tyr Lys Asp His Asp Gly Asp Tyr Lys Asp His Asp
    130                 135                 140

Ile Asp Tyr Lys Asp Asp Asp Lys Gly Ala Ala His His His His
145                 150                 155                 160

His His

<210> SEQ ID NO 129
<211> LENGTH: 137
<212> TYPE: PRT
<213> ORGANISM: Artificial Sequence
<220> FEATURE:
<223> OTHER INFORMATION: Humanized lama

<400> SEQUENCE: 129

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Arg Gly Asn Glu Arg Glu Phe Val
        35                  40                  45

Ala Ala Ile Ser Glu Ser Gly Gly Arg Thr His Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr Leu Leu Trp Trp Thr Ser Glu Tyr Ala Pro Ile Lys Ala
            100                 105                 110
```

```
Asn Asp Tyr Asp Tyr Trp Gly Gln Gly Thr Leu Val Thr Val Ser Ser
        115                 120                 125

Ala Ala Ala His His His His His
    130                 135

<210> SEQ ID NO 130
<211> LENGTH: 162
<212> TYPE: PRT
<213> ORGANISM: Artificial Sequence
<220> FEATURE:
<223> OTHER INFORMATION: Humanized lama

<400> SEQUENCE: 130

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asp Tyr
            20                  25                  30

Val Met Gly Trp Phe Arg Gln Ala Pro Gly Lys Glu Arg Glu Phe Val
        35                  40                  45

Ala Ala Ile Ser Glu Ser Gly Gly Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Thr Thr Leu Leu Trp Trp Thr Ser Glu Tyr Ala Pro Ile Lys Ala
            100                 105                 110

Asn Asp Tyr Asp Tyr Trp Gly Gln Gly Thr Leu Val Thr Val Ser Ser
        115                 120                 125

Ala Ala Ala Asp Tyr Lys Asp His Asp Gly Asp Tyr Lys Asp His Asp
    130                 135                 140

Ile Asp Tyr Lys Asp Asp Asp Lys Gly Ala Ala His His His His
145                 150                 155                 160

His His

<210> SEQ ID NO 131
<211> LENGTH: 153
<212> TYPE: PRT
<213> ORGANISM: Artificial Sequence
<220> FEATURE:
<223> OTHER INFORMATION: Humanized lama

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110
```

```
Thr Leu Val Thr Val Ser Ser Ala Ala Asp Tyr Lys Asp His Asp
        115                 120                 125
Gly Asp Tyr Lys Asp His Asp Ile Asp Tyr Lys Asp Asp Asp Lys
        130                 135                 140
Gly Ala Ala His His His His His His
145                 150
```

<210> SEQ ID NO 132
<211> LENGTH: 153
<212> TYPE: PRT
<213> ORGANISM: Artificial Sequence
<220> FEATURE:
<223> OTHER INFORMATION: Humanized lama

<400> SEQUENCE: 132

```
Glu Val Gln Leu Val Glu Ser Gly Gly Gly Val Val Gln Pro Gly Gly
1               5                   10                  15
Ser Leu Arg Leu Ser Cys Ala Ala Ser Gly Ser Ile Ala Ser Ile His
            20                  25                  30
Ala Met Gly Trp Phe Arg Gln Ala Pro Gly Lys Glu Arg Glu Phe Val
        35                  40                  45
Ala Val Ile Thr Trp Ser Gly Gly Ile Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Gly Asp Lys His Gln Ser Ser Trp Tyr Asp Tyr Trp Gly Gln Gly
            100                 105                 110
Thr Leu Val Thr Val Ser Ser Ala Ala Ala Asp Tyr Lys Asp His Asp
        115                 120                 125
Gly Asp Tyr Lys Asp His Asp Ile Asp Tyr Lys Asp Asp Asp Lys
        130                 135                 140
Gly Ala Ala His His His His His His
145                 150
```

<210> SEQ ID NO 133
<211> LENGTH: 125
<212> TYPE: PRT
<213> ORGANISM: Artificial Sequence
<220> FEATURE:
<223> OTHER INFORMATION: Humanized Lama

<400> SEQUENCE: 133

```
Glu Val Gln Leu Val Glu Ser Gly Gly Gly Val Val Gln Pro Gly Gly
1               5                   10                  15
Ser Leu Arg Leu Ser Cys Ala Ala Ser Gly Ser Ile Ala Ser Ile His
            20                  25                  30
Ala Met Gly Trp Phe Arg Gln Ala Pro Gly Lys Glu Arg Glu Phe Val
        35                  40                  45
Ala Val Ile Thr Trp Ser Gly Gly Ile Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Gly Asp Lys His Gln Ser Ser Trp Tyr Asp Tyr Trp Gly Gln Gly
```

100                 105                 110
Thr Leu Val Thr Val Ser Ser His His His His His His
        115                 120                 125

<210> SEQ ID NO 134
<211> LENGTH: 128
<212> TYPE: PRT
<213> ORGANISM: Artificial Sequence
<220> FEATURE:
<223> OTHER INFORMATION: Humanized Lama

<400> SEQUENCE: 134

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Ala Ala Ala His His His His His His
        115                 120                 125

<210> SEQ ID NO 135
<211> LENGTH: 128
<212> TYPE: PRT
<213> ORGANISM: Artificial Sequence
<220> FEATURE:
<223> OTHER INFORMATION: Humanized Lama

<400> SEQUENCE: 135

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Ala Ala Ala His His His His His His
        115                 120                 125

<210> SEQ ID NO 136
<211> LENGTH: 128
<212> TYPE: PRT
<213> ORGANISM: Artificial Sequence
<220> FEATURE:

<223> OTHER INFORMATION: Humanized Lama

<400> SEQUENCE: 136

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser Ala Ala Ala His His His His His His
        115                 120                 125

<210> SEQ ID NO 137
<211> LENGTH: 288
<212> TYPE: PRT
<213> ORGANISM: Homo sapiens

<400> SEQUENCE: 137

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
        180                 185                 190

Ser Arg Ala Ala Arg Gly Thr Ile Gly Ala Arg Arg Thr Gly Gln Pro
    195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro

```
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 138
<211> LENGTH: 525
<212> TYPE: PRT
<213> ORGANISM: Homo sapiens

<400> SEQUENCE: 138

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
                35                  40                  45

Pro Leu Gln Asp Leu Ser Leu Leu Arg Arg Ala Gly Val Thr Trp Gln
                50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
                115                 120                 125

Arg Gly Asp Phe Ser Leu Trp Leu Arg Pro Ala Arg Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
                195                 200                 205

Gly Arg Val Pro Val Arg Glu Ser Pro His His His Leu Ala Glu Ser
            210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
                275                 280                 285

Gly Thr Arg Ser Phe Leu Thr Ala Lys Trp Thr Pro Pro Gly Gly Gly
                290                 295                 300

Pro Asp Leu Leu Val Thr Gly Asp Asn Gly Asp Phe Thr Leu Arg Leu
305                 310                 315                 320
```

```
Glu Asp Val Ser Gln Ala Gln Ala Gly Thr Tyr Thr Cys His Ile His
            325                 330                 335

Leu Gln Glu Gln Gln Leu Asn Ala Thr Val Thr Leu Ala Ile Ile Thr
        340                 345                 350

Val Thr Pro Lys Ser Phe Gly Ser Pro Gly Ser Leu Gly Lys Leu Leu
    355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 139
<211> LENGTH: 10
<212> TYPE: PRT
<213> ORGANISM: Artificial
<220> FEATURE:
<223> OTHER INFORMATION: 11B09 LAG3 CDR2 variant of SEQ ID NO:66

<400> SEQUENCE: 139

Ala Ile Ser Glu Ser Gly Gly Arg Thr His
1               5                   10

<210> SEQ ID NO 140
<211> LENGTH: 17
<212> TYPE: PRT
<213> ORGANISM: Artificial
<220> FEATURE:
<223> OTHER INFORMATION: 11B09 LAG3 CDR2 variant of SEQ ID NO:66

<400> SEQUENCE: 140

Ala Ile Ser Glu Ser Gly Gly Arg Thr His Tyr Ala Asp Ala Val Lys
1               5                   10                  15

Gly

<210> SEQ ID NO 141
<211> LENGTH: 17
<212> TYPE: PRT
<213> ORGANISM: Artificial
<220> FEATURE:
<223> OTHER INFORMATION: 11B09 LAG3 CDR2 variant of SEQ ID NO:66

<400> SEQUENCE: 141

Ala Ile Ser Glu Ser Gly Gly Arg Thr His Tyr Ala Asp Ser Val Lys
1               5                   10                  15
```

Gly

<210> SEQ ID NO 142
<211> LENGTH: 115
<212> TYPE: PRT
<213> ORGANISM: Artificial sequence
<220> FEATURE:
<223> OTHER INFORMATION: Variant of ALB11002 SEQ ID NO: 59

<400> SEQUENCE: 142

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 143
<211> LENGTH: 17
<212> TYPE: PRT
<213> ORGANISM: Artificial sequence
<220> FEATURE:
<223> OTHER INFORMATION: 102C12 PD1 CDR2 variant

<400> SEQUENCE: 143

Val Ile Thr Trp Ser Gly Gly Ile Thr Tyr Tyr Ala Asp Ser Val Lys
1               5                   10                  15

Gly

<210> SEQ ID NO 144
<211> LENGTH: 17
<212> TYPE: PRT
<213> ORGANISM: Artificial sequence
<220> FEATURE:
<223> OTHER INFORMATION: 102C12 PD1 CDR2 variant

<400> SEQUENCE: 144

Val Ile Thr Val Ser Gly Gly Ile Thr Tyr Tyr Ala Asp Ser Val Lys
1               5                   10                  15

Gly

<210> SEQ ID NO 145
<211> LENGTH: 10
<212> TYPE: PRT
<213> ORGANISM: Artificial sequence
<220> FEATURE:
<223> OTHER INFORMATION: 102C12 PD1 CDR3 variant

<400> SEQUENCE: 145

Asp Lys His Gln Ser Ser Trp Tyr Asp Tyr
1               5                   10

```
<210> SEQ ID NO 146
<211> LENGTH: 10
<212> TYPE: PRT
<213> ORGANISM: Artificial sequence
<220> FEATURE:
<223> OTHER INFORMATION: 102C12 PD1 CDR3 variant

<400> SEQUENCE: 146

Asp Lys His Gln Ser Ser Phe Tyr Asp Tyr
1               5                   10

<210> SEQ ID NO 147
<211> LENGTH: 10
<212> TYPE: PRT
<213> ORGANISM: Artificial sequence
<220> FEATURE:
<223> OTHER INFORMATION: 102C12 PD1 CDR2 variant

<400> SEQUENCE: 147

Val Ile Thr Trp Ser Gly Gly Ile Thr Tyr
1               5                   10

<210> SEQ ID NO 148
<211> LENGTH: 10
<212> TYPE: PRT
<213> ORGANISM: Artificial sequence
<220> FEATURE:
<223> OTHER INFORMATION: 102C12 PD1 CDR2 variant

<400> SEQUENCE: 148

Val Ile Thr Val Ser Gly Gly Ile Thr Tyr
1               5                   10

<210> SEQ ID NO 149
<211> LENGTH: 10
<212> TYPE: PRT
<213> ORGANISM: Artificial sequence
<220> FEATURE:
<223> OTHER INFORMATION: 102C12 PD1 CDR3 variant

<400> SEQUENCE: 149

Asp Lys His Gln Ser Ser Trp Tyr Asp Tyr
1               5                   10

<210> SEQ ID NO 150
<211> LENGTH: 10
<212> TYPE: PRT
<213> ORGANISM: Artificial sequence
<220> FEATURE:
<223> OTHER INFORMATION: 102C12 PD1 CDR3 variant

<400> SEQUENCE: 150

Asp Lys His Gln Ser Ser Phe Tyr Asp Tyr
1               5                   10

<210> SEQ ID NO 151
<211> LENGTH: 5
<212> TYPE: PRT
<213> ORGANISM: Artificial sequence
<220> FEATURE:
<223> OTHER INFORMATION: ALB11002 CDR1 variant

<400> SEQUENCE: 151

Ser Phe Gly Met Ser
1               5
```

```
<210> SEQ ID NO 152
<211> LENGTH: 10
<212> TYPE: PRT
<213> ORGANISM: Artificial sequence
<220> FEATURE:
<223> OTHER INFORMATION: ALB11002 CDR2 variant

<400> SEQUENCE: 152

Ser Ile Ser Gly Ser Gly Ser Asp Thr Leu
1               5                   10

<210> SEQ ID NO 153
<211> LENGTH: 115
<212> TYPE: PRT
<213> ORGANISM: Artificial sequence
<220> FEATURE:
<223> OTHER INFORMATION: ALB11002 with E1D, V11L, L93V, lackd C-terminal
      Alanine

<400> SEQUENCE: 153

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 154
<211> LENGTH: 5
<212> TYPE: PRT
<213> ORGANISM: Artificial sequence
<220> FEATURE:
<223> OTHER INFORMATION: LAG3 CDR1 variant

<400> SEQUENCE: 154

Asp Tyr Val Met Gly
1               5
```

PD1 AND/OR LAG3 BINDERS

REFERENCE TO CROSS-RELATED APPLICATIONS

This application is a divisional application of U.S. application Ser. No. 15/353,919, filed Nov. 17, 2016, and which claims the benefit of U.S. Provisional Patent Application No. 62/257,009, filed Nov. 18, 2015; each of which is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "24238_US_DIV_4_SEQTXT.txt", creation date of May 10, 2019, and a size of 204 Kb. This sequence listing submitted via EFS-Web is part of the specification and is herein incorporated by reference in its entirety.

FIELD OF THE INVENTION

The present invention relates, in part, to amino acid sequences binding to programmed cell death protein 1 ("PD1"), e.g., human PD1 and lymphocyte activation gene 3 (LAG3). In particular, the present invention relates, in part, to improved heavy-chain immunoglobulin single variable domains (also referred to herein as "ISVs" or "ISVDs") binding to PD1 and LAG3, as well as to polypeptides and other compounds that comprise such ISVDs. Other aspects, embodiments, features, uses and advantages of the invention will be clear to the skilled person based on the disclosure herein.

BACKGROUND OF THE INVENTION

Programmed death receptor 1 (PD-1) is an immunoinhibitory receptor that is primarily expressed on activated T and B cells. Interaction with its ligands has been shown to attenuate T-cell responses both in vitro and in vivo. Blockade of the interaction between PD-1 and one of its ligands, PD-L1, has been shown to enhance tumor-specific CD8$^+$ T-cell immunity and may therefore be helpful in clearance of tumor cells by the immune system.

PD-1 (encoded by the gene Pdcd1) is an Immunoglobulin superfamily member related to CD28, and CTLA-4. PD-1 has been shown to negatively regulate antigen receptor signaling upon engagement of its ligands (PD-L1 and/or PD-L2) The structure of murine PD-1 has been solved as well as the co-crystal structure of mouse PD-1 with human PD-L1 (Zhang, X. et al., Immunity 20: 337-347 (2004); Lin et al., Proc. Natl. Acad. Sci. USA 105: 3011-6 (2008)). PD-1 and like family members are type I transmembrane glycoproteins containing an Ig Variable-type (V-type) domain responsible for ligand binding and a cytoplasmic tail that is responsible for the binding of signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

Following T cell stimulation, PD-1 recruits the tyrosine phosphatase SHP-2 to the ITSM motif within its cytoplasmic tail, leading to the dephosphorylation of effector molecules such as CD3 zeta, PKC theta and ZAP70 that are involved in the CD3 T cell signaling cascade. The mechanism by which PD-1 downmodulates T cell responses is similar to, but distinct from that of CTLA-4, as both molecules regulate an overlapping set of signaling proteins (Parry et al., Mol. Cell. Biol. 25: 9543-9553 (2005)). Bennett and coworkers have shown that PD-1-mediated inhibition of T-cell signaling is only effective when both activating and inhibitory signals are on the same surface, indicating that the PD-1 signaling mechanism is spatiotemporally determined (Bennett F. et al., J Immunol. 170:711-8 (2003)). PD-1 was shown to be expressed on activated lymphocytes (peripheral CD4$^+$ and CD8$^+$ T cells, B cells and monocytes) and has also been shown to be expressed during thymic development on CD4$^-$ CD8" (double negative) T cells as well as NK-T cells.

The ligands for PD-1 (PD-L1 and PD-L2) are constitutively expressed or can be induced in a variety of cell types, including non-hematopoietic tissues as well as various tumor types. PD-L1 is expressed on B, T, myeloid and dendritic cells (DCs), but also on peripheral cells, like microvascular endothelial cells and non-lymphoid organs like heart, lung etc. In contrast, PD-L2 is only found on macrophages and DCs. The expression pattern of PD-1 ligands is suggestive of a role for PD-1 in maintaining peripheral tolerance and may serve to regulate self-reactive T- and B-cell responses in the periphery. Both ligands are type I transmembrane receptors containing both IgV- and IgC-like domains in the extracellular region. Both ligands contain short cytoplasmic regions with no known signaling motifs.

Interaction of PD-1 with its ligands leads to the inhibition of lymphocyte proliferation in vitro and in vivo. Disruption of the PD-1/PD-L1 interaction has been shown to increase T cell proliferation and cytokine production and block progression of the cell cycle. Initial analysis of Pdcd1$^{-/-}$ mice did not identify any drastic immunological phenotype. However aged mice developed spontaneous autoimmune diseases which differ according to the strain onto which the Pdcd1 deficiency was backcrossed. These include lupus-like proliferative arthritis (C57BL/6) (Nishimura H. et al., Int. Immunol. 10: 1563-1572 (1998)), fatal cardiomyopathy (BALB/c) (Nishimura H. et al., Science 291: 319-322 (2001)) and type I diabetes (NOD) (Wang J. et al., Proc. Natl. Acad. Sci. USA 102: 11823-11828 (2005)). Overall, analysis of the knockout animals has led to the understanding that PD-1 functions mainly in inducing and regulating peripheral tolerance. Thus, therapeutic blockade of the PD-1 pathway may be helpful in overcoming immune tolerance. Such selective blockade may be of use in the treatment of cancer or infection as well as in boosting immunity during vaccination (either prophylactic or therapeutic).

The role of PD-1 in cancer is established in the literature. It is known that tumor microenvironment can protect tumor cells from efficient immune destruction. PD-L1 has recently been shown to be expressed on a number of mouse and human tumors (and is inducible by IFN gamma on the majority of PD-L1 negative tumor cell lines) and is postulated to mediate immune evasion (Iwai Y. et al., Proc. Natl. Acad. Sci. U.S.A. 99: 12293-12297 (2002); Strome S. E. et al., Cancer Res., 63: 6501-6505 (2003).

In humans, expression of PD-1 (on tumor infiltrating lymphocytes) and/or PD-L1 (on tumor cells) has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown J. A. et al., J. Immunol. 170: 1257-1266 (2003);

Dong H. et al., Nat. Med. 8: 793-800 (2002); Wintterle et al., Cancer Res. 63: 7462-7467 (2003); Strome S. E. et al., Cancer Res., 63: 6501-6505 (2003); Thompson R. H. et al., Cancer Res. 66: 3381-5 (2006); Thompson et al., Clin. Cancer Res. 13: 1757-61 (2007); Nomi T. et al., Clin. Cancer Res. 13: 2151-7. (2007)). More strikingly, PD-ligand expression on tumor cells has been correlated to poor prognosis of cancer patients across multiple tumor types (reviewed in Okazaki and Honjo, Int. Immunol. 19: 813-824 (2007)).

Blockade of the PD-1/PD-L1 interaction could lead to enhanced tumor-specific T-cell immunity and therefore be helpful in clearance of tumor cells by the immune system. To address this issue, a number of studies were performed. In a murine model of aggressive pancreatic cancer, T. Nomi et al. (Clin. Cancer Res. 13: 2151-2157 (2007)) demonstrated the therapeutic efficacy of PD-1/PD-L1 blockade. Administration of either PD-1 or PD-L1 directed antibody significantly inhibited tumor growth. Antibody blockade effectively promoted tumor reactive CD8+ T cell infiltration into the tumor resulting in the up-regulation of anti-tumor effectors including IFN gamma, granzyme B and perforin. Additionally, the authors showed that PD-1 blockade can be effectively combined with chemotherapy to yield a synergistic effect. In another study, using a model of squamous cell carcinoma in mice, antibody blockade of PD-1 or PD-L1 significantly inhibited tumor growth (Tsushima F. et al., Oral Oncol. 42: 268-274 (2006)).

In other studies, transfection of a murine mastocytoma line with PD-L1 led to decreased lysis of the tumor cells when co-cultured with a tumor-specific CTL clone. Lysis was restored when anti-PD-L1 mAb was added (Iwai Y. et al., Proc. Natl. Acad. Sci. U.S.A. 99: 12293-12297 (2002)). In vivo, blocking the PD1/PD-L1 interaction was shown to increase the efficacy of adoptive T cell transfer therapy in a mouse tumor model (Strome S. E. et al., Cancer Res. 63: 6501-6505 (2003)). Further evidence for the role of PD-1 in cancer treatment comes from experiments performed with PD-1 knockout mice. PD-L1 expressing myeloma cells grew only in wild-type animals (resulting in tumor growth and associated animal death), but not in PD-1 deficient mice (Iwai Y. et al., Proc. Natl. Acad. Sci. U.S.A. 99: 12293-12297 (2002)).

In human studies, R. M. Wong et al. (Int. Immunol. 19: 1223-1234 (2007)) showed that PD-1 blockade using a fully human anti-PD-1 antibody augmented the absolute numbers of tumor-specific CD8+ T cells (CTLs) in ex vivo stimulation assays using vaccine antigens and cells from vaccinated individuals. In a similar study, antibody blockade of PD-L1 resulted in enhanced cytolytic activity of tumor-associated antigen-specific cytotoxic T cells and increased cytokine production by tumor specific $T_H$ cells (Blank C. et al., Int. J. Cancer 119: 317-327 (2006)). The same authors showed that PD-L1 blockade augments tumor-specific T cell responses in vitro when used in combination with anti-CTLA-4 blockade.

Overall, the PD-1/PD-L1 pathway is a well-validated target for the development of antibody therapeutics for cancer treatment. Anti-PD-1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (Barber et al., Nature 439: 682-687 (2006)) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

Recently, it has been shown that PD-1 is highly expressed on T cells from HIV infected individuals and that receptor expression correlates with impaired T cell function and disease progression (Day et al., Nature 443:350-4 (2006); Trautmann L. et al., Nat. Med. 12: 1198-202 (2006)). In both studies, blockade of the ligand PD-L1 significantly increased the expansion of HIV-specific, IFN-gamma producing cells in vitro.

Other studies also implicate the importance of the PD-1 pathway in controlling viral infection. PD-1 knockout mice exhibit better control of adenovirus infection than wild-type mice (Iwai et al., J. Exp. Med. 198:39-50 (2003)). Also, adoptive transfer of HBV-specific T cells into HBV transgenic animals initiated hepatitis (Isogawa M. et al., Immunity 23:53-63 (2005)). The disease state of these animals oscillates as a consequence of antigen recognition in the liver and PD-1 upregulation by liver cells.

In addition, LAG3 (CD223) is a cell surface molecule expressed on activated T cells (Huard et al. Immunogenetics 39:213-217, 1994), NK cells (Triebel et al. J Exp Med 171:1393-1405, 1990), B cells (Kisielow et al. Eur J Immunol 35:2081-2088, 2005), and plasmacytoid dendritic cells (Workman et al. J Immunol 182:1885-1891, 2009) that plays an important role in the function of these lymphocyte subsets. In addition, the interaction between LAG3 and its major ligand, Class II MHC, is thought to play a role in modulating dendritic cell function (Andreae et al. J Immunol 168:3874-3880, 2002). Recent preclinical studies have documented a role for LAG-3 in CD8 T-cell exhaustion (Blackburn et al. Nat Immunol 10:29-37, 2009).

As with chronic viral infection, tumor antigen-specific CD4+ and CD8+ T cells display impaired effector function and an exhausted phenotype characterized by decreased production of pro-inflammatory cytokines and hyporesponsiveness to antigenic re-stimulation. This is mediated by cell extrinsic mechanisms, such as regulatory T-cells (Treg), and cell intrinsic mechanisms, such as inhibitory molecules that are upregulated on exhausted, tumor-infiltrating lymphocytes (TIL). These inhibitory mechanisms represent a formidable barrier to effective antitumor immunity.

LAG—is expressed on tolerized TILs suggesting that they contribute to tumor-mediated immune suppression. Inhibition of LAG3 may lead to enhanced activation of antigen-specific T cells from which a therapeutic benefit may be gained.

SUMMARY OF THE INVENTION

The present invention encompasses a PD1 binder (e.g., an immunoglobulin single variable domain (ISVD) or a Nanobody that binds to PD1 (e.g., human PD1) comprising the amino acid sequence set forth in SEQ ID NO: 1 or 2; but which comprises a mutation at one or more of positions 1, 11, 14, 52a, 73, 74, 83, 89, 100a, 110 and 112 wherein said positions are numbered according to Kabat (e.g., L11V, A14P, A74S, K83R, I89L and, optionally, E1D; or L11V, A14P, W52aV, N73P, A74S, K83R, I89L, W100a and, optionally, E1D), comprising CDR1 that comprises the amino acid sequence: IHAMG (SEQ ID NO: 3) or GSIASI-HAMG (SEQ ID NO: 6); CDR2 that comprises the amino acid sequence: VITXSGGITYYADSVKG (SEQ ID NO: 4; wherein X is W or V) or VITXSGGITY (SEQ ID NO: 7; wherein X is W or V); and CDR3 that comprises the amino acid sequence: DKHQSSXYDY (SEQ ID NO: 5, wherein X is W or F) or DKHQSSXYDY (SEQ ID NO: 8, wherein X is W or F). In an embodiment of the invention, the PD1 binder (e.g., an ISVD such as a Nanobody) comprises an amino acid residue at position 11 that is chosen from L or V; an amino acid residue at position 89 chosen from T, V or L; an amino acid residue at position 110 chosen from T, K or Q; and/or an amino acid residue at position 112 chosen from S, K or Q. In an embodiment of the invention, the PD1 binder (e.g., an ISVD such as a Nanobody) comprises one or more mutations described is a member selected from the group consisting of: 89T; 89L in combination with 11V; 89L in combination with 110K or 110Q; 89L in combination with 112K or 112Q; 89L in combination with 11V and 110K or 110Q; 89L in combination with 11V and 112K or 112Q; 11V in combination with 110K or 110Q; 11V in combination with 112K or 112Q. In an embodiment of the invention, the amino acid at positions 11, 89, 110 and 112 are as any of those set forth in the Table B herein. In an embodiment of the invention, the PD1 binder (e.g., an ISVD such as a Nanobody) comprises one or more mutations at a position selected from the group consisting of 1, 14, 41, 74, 83, 87 and 108 and/or one or more humanizing substitutions known per se (for which reference is made to the prior art cited herein, such as WO 08/020079 or WO 09/138519. In an embodiment of the invention, the PD1 binder (e.g., an ISVD such as a Nanobody) comprises a C-terminal extension of 1, 2, 3, 4, 5, 6, 7, 8, 9 or 10 amino acids. For example, in an embodiment of the invention, the PD1 binder (e.g., an ISVD such as a Nanobody) comprises a C-terminal extension according to the formula –X(n), wherein X and n are as follows: (a) n=1 and X=Ala; (b) n=2 and each X=Ala; (c) n=3 and each X=Ala; (d) n=2 and at least one X=Ala and wherein the remaining amino acid residue(s) X are independently chosen from any naturally occurring amino acid; (e) n=3 and at least one X=Ala and wherein the remaining amino acid residue(s) X are independently chosen from any naturally occurring amino acid; (f) n=3 and at least two X=Ala and wherein the remaining amino acid residue(s) X are independently chosen from any naturally occurring amino acid; (g) n=1 and X=Gly; (h) n=2 and each X=Gly; (i) n=3 and each X=Gly; (j) n=2 and at least one X=Gly wherein the remaining amino acid residue(s) X are independently chosen from any naturally occurring amino acid; (k) n=3 and at least one X=Gly wherein the remaining amino acid residue(s) X are independently chosen from any naturally occurring amino acid; (l) n=3 and at least two X=Gly wherein the remaining amino acid residue(s) X are independently chosen from any naturally occurring amino acid; (m) n=2 and each X=Ala or Gly; (n) n=3 and each X=Ala or Gly; (o) n=3 and at least one X=Ala or Gly wherein remaining amino acid residue(s) X are independently chosen from any naturally occurring amino acid; or (p) n=3 and at least two X=Ala or Gly wherein the remaining amino acid residue(s) X are independently chosen from any naturally occurring amino acid, e.g., A, AA, AAA, G, GG, GGG, AG, GA, AAG, AGG, AGA, GGA, GAA or GAG. The present invention also provides a PD1 binder (e.g., an ISVD such as a Nanobody) comprising one or mutations at position 11, 89, 110 and 112 and an amino acid sequence having at least 85% (e.g., 85, 86, 87, 88, 89, 90, 91, 92, 93, 94, 95, 96, 97, 98, 99, 99.5, 99.9 or 100%) sequence identity with the amino acid sequence set forth in a member selected from the group consisting of SEQ ID NOs: 9-40 (in which any C-terminal extension that may be present as well as any CDRs are not taken into account for determining the degree of sequence identity). The present invention also provides a multispecific immunoglobulin comprising a PD1 binder (e.g., an ISVD such as a Nanobody) that binds to PD1 linked to one or more molecules that bind to an epitope that is not the epitope to which the PD1 binder binds (e.g., PD1, CTLA4, LAG3, BTLA and/or CD27), e.g., comprising a PD1 binding moiety and a CTLA4 binding moiety; a PD1 binding moiety and a BTLA binding moiety; a PD1 binding moiety and a LAG3 binding moiety; or a PD1 binding moiety, a LAG3 binding moiety and a BTLA binding moiety, optionally linked via one or more linkers, e.g., peptide linkers. In one embodiment of the invention, the multispecific immunoglobulin comprises a first PD1 Nanobody linked to one or more molecules selected from the group consisting of an CTLA4 Nanobody, an LAG3 Nanobody, an BTLA Nanobody, an CD27 Nanobody and an PD1 Nanobody that binds to the same or a different epitope as that of the first PD1 Nanobody; e.g., comprising a PD1 binding moiety and a CTLA4 binding moiety; a PD1 binding moiety and a BTLA binding moiety; a PD1 binding moiety and a LAG3 binding moiety; or a PD1 binding moiety, a LAG3 binding moiety and a BTLA binding moiety.

The present invention includes a polypeptide, ISVD or Nanobody comprising an amino acid sequence that is described herein, e.g., which is selected from SEQ ID NOs: 9-40.

The present invention also provides a PD1 binder of the present invention (e.g., an immunoglobulin single variable domain (ISVD) or multispecific ISVD such as a Nanobody) in association with a further therapeutic agent.

Injection devices and vessels comprising PD1 binder (e.g., immunoglobulin single variable domain (ISVD) or multispecific ISVD such as a Nanobody) optionally in association with a further therapeutic agent are provided by the present invention.

The present invention provides a polynucleotide encoding a PD1 binder (e.g., immunoglobulin single variable domain (ISVD) or multispecific ISVD such as a Nanobody); or a vector comprising the polynucleotide or a host cell comprising the polynucleotide or vector.

The present invention provides a method for making an PD1 binder (e.g., immunoglobulin single variable domain (ISVD) or multispecific ISVD such as a Nanobody) comprising introducing a polynucleotide encoding the immunoglobulins into a host cell and culturing the host cell in a medium under conditions favorable to expression of said immunoglobulin from said polynucleotide and, optionally, purifying the immunoglobulin from said host cell and/or said medium. PD1 binders (e.g., an ISVDs such as a Nanobodies) produced by such methods are part of the present invention.

The present invention also provides a method for preventing PD1 from binding to PD-L1 and/or PD-L2 comprising contacting said PD1 with a PD1 binder (e.g., immunoglobulin single variable domain (ISVD) or multispecific ISVD such as a Nanobody) optionally in association with a further therapeutic agent.

The present invention also provides a method for enhancing an immune response in the body of a subject comprising administering an effective amount of a PD1 binder of the present invention (e.g., immunoglobulin single variable domain (ISVD) or multispecific ISVD such as a Nanobody)

to the subject optionally in association with a further therapeutic agent. In addition, the present invention also provides a method for treating or preventing cancer (e.g., metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelofibrosis, soft tissue sarcoma, thyroid cancer, endometrial cancer, carcinoid cancer or liver cancer, breast cancer or gastric cancer) or an infectious disease (bacterial infection, a viral infection or a fungal infection) in the body of a subject comprising administering an effective amount of PD1 binder (e.g., immunoglobulin single variable domain (ISVD) or multispecific ISVD such as a Nanobody) optionally in association with a further therapeutic agent to the subject. In an embodiment of the invention, the subject is also administered a further therapeutic agent or a therapeutic procedure in association with the PD1 binder.

The present invent invention provides PD1 binders (e.g., ISVDs such as Nanobodies) that bind to PD1 comprising: CDR1 comprising the amino acid sequence IHAMG (SEQ ID NO: 3) or GSIASIHAMG (SEQ ID NO: 6); CDR2 comprising the amino acid sequence VITXSGGITYYADSVKG (SEQ ID NO: 4; wherein X is W or V) or VITXSGGITY (SEQ ID NO: 7; wherein X is W or V); and CDR3 comprising the amino acid sequence DKHQSSXYDY (SEQ ID NO: 5, wherein X is W or F), which comprise one or more mutations at position 11 (e.g., L11V) and 89 (e.g., I89L) or one or more mutations selected from E1D, L11V, A14P, W52aV, N73 (Q, P or S), A74S, K83R, I89L, W100aF with respect to SEQ ID NO: 1 or 2. In an embodiment of the invention, the mutations are E1D, L11V, A14P, K83R and I89L; or L11V, A14P, K83R and I89L. In an embodiment of the invention, the mutations are E1D, L11V, A14P, W52aV, N73 (Q, P or S), A74S, K83R, I89L, W100aF or L11V, A14P, W52aV, N73 (Q, P or S), A74S, K83R, I89L, W100aF. In an embodiment of the invention, the PD1 binder comprises the amino acid sequence: DVQLVESGGG VVQPGGSLRL SCAASGSIAS IHAMGWFRQA PGKEREFVAV ITWSGGITYY ADSVKGRFTI SRDNSKNTVY LQMNSLRPED TALYYCAGDK HQSSWYDYWG QGTLVTVSS (SEQ ID NO: 57).

The present invention also provides LAG3 binders that bind to LAG3 comprising CDR1 comprising the amino acid sequence GRTFSDYVMG (SEQ ID NO: 65); CDR2 comprising the amino acid sequence AISESGGRTHYADXKG (SEQ ID NO:66; wherein X is A or S) or AISESGGRTH (SEQ ID NO: 139, amino acids 1-10 of SEQ ID NO: 66); and CDR3 comprising the amino acid sequence TLLWWTSEYAPIKANDYDY (SEQ ID NO: 67), e.g., comprising the amino acid sequence:

(SEQ ID NO: 64)
EVQLVE SGGGVVQPGG SLRLSCAASG RTFSDYVMGW

FRQAPGKERE FVAAISESGG RTHYADSVKG RFTISRDNSK

-continued
NTLYLQMNSL RPEDTALYYC ATTLLWWTSE YAPIKANDYD

YWGQGTLVTV SS.

The PD1 and LAG3 binders may be in a single molecule such as a PD1/LAG3 binder, which is part of the present invention, that binds to PD1 and LAG3 that comprises: a PD1 binder comprising: CDR1 comprising the amino acid sequence IHAMG (SEQ ID NO: 3) or GSIASIHAMG (SEQ ID NO: 6); CDR2 comprising the amino acid sequence VITXSGGITYYADSVKG (SEQ ID NO: 4; wherein X is W or V) or VITXSGGITY (SEQ ID NO: 7; wherein X is W or V); and CDR3 comprising the amino acid sequence DKHQSSXYDY (SEQ ID NO: 5, wherein X is W or F); and a LAG3 binder comprising: CDR1 comprising the amino acid sequence GRTFSDYVMG (SEQ ID NO: 65); CDR2 comprising the amino acid sequence AISESGGRTHYADXKG (SEQ ID NO:66; wherein X is A or S) or AISESGGRTH (SEQ ID NO: 139, amino acids 1-10 of SEQ ID NO: 66); and CDR3 comprising the amino acid sequence TLLWWTSEYAPIKANDYDY (SEQ ID NO: 67); and, optionally, a half-life extender, e.g., wherein the PD1 binder comprises the amino acid sequence: DVQLVESGGG VVQPGGSLRL SCAASGSIAS IHAMGWFRQA PGKEREFVAV ITWSGGITYY ADSVKGRFTI SRDNSKNTVY LQMNSLRPED TALYYCAGDK HQSSWYDYWG QGTLVTVSS; and (SEQ ID NO: 57); and the LAG3 binder comprises the amino acid sequence: EVQLVE SGGGVVQPGG SLRLSCAASG RTFSDYVMGW FRQAPGKERE FVAAISESGG RTHYADSVKG RFTISRDNSK NTLYLQMNSL RPEDTALYYC ATTLLWWTSE YAPIKANDYD YWGQGTLVTV SS (SEQ ID NO: 64); and, optionally, a half-life extender. For example, in an embodiment of the invention, the PD1/LAG3 binder comprises the moieties, e.g., in the order shown:

the PD1 binder 102C12 (E1D, L11V, A14P, A74S, K83R, I89L) or 1PD102C12 (E1D, L11V, A14P, W52aV, N73X (e.g., N73P or N73Q or N73S), A74S, K83R, I89L, W100aF);

a peptide linker such as 9GS, 20GS or 35 GS (e.g.,

GGGGSGGGGSGGGGSGGGGSGGGGSGGGGSGGGGS (SEQ ID NO: 70));

the LAG3 binder 11B09 or 11B09 (L11V, A14P, R41P, N43K, A62S, A74S, K83R, V89L);

a peptide linker such as 9GS, 20GS or 35 GS (e.g.,

GGGGSGGGGSGGGGSGGGGSGGGGSGGGGSGGGGS (SEQ ID NO: 70));

a half-life extender such as ALB11002; and, optionally, a C-terminal extension such as an alanine;

or the PD1 binder 102C12 (E1D, L11V, A14P, A74S, K83R, I89L) or 1PD102C12 (E1D, L11V, A14P, W52aV, N73X (e.g., N73P or N73Q or N73S), A74S, K83R, I89L, W100aF);

a peptide linker such as 9GS, 20GS or 35 GS (e.g.,

GGGGSGGGGSGGGGSGGGGSGGGGSGGGGSGGGGS (SEQ ID NO: 70));

the PD1 binder 102C12 (L11V, A14P, A74S, K83R, I89L) or 1PD102C12 (L11V, A14P, W52aV, N73X (e.g., N73P or N73Q or N73S), A74S, K83R, I89L, W100aF);
a peptide linker such as 9GS, 20GS or 35 GS (e.g.,

GGGGSGGGGSGGGGSGGGGSGGGGSGGGGSGGGGS (SEQ ID NO: 70));

the LAG3 binder 11B09 (L11V, A14P, R41P, N43K, A62S, A74S, K83R, V89L);
a peptide linker such as 9GS, 20GS or 35 GS (e.g.,

GGGGSGGGGSGGGGSGGGGSGGGGSGGGGSGGGGS (SEQ ID NO: 70));

the LAG3 binder 11B09 (L11V, A14P, R41P, N43K, A62S, A74S, K83R, V89L);
a peptide linker such as 9GS, 20GS or 35 GS (e.g.,

GGGGSGGGGSGGGGSGGGGSGGGGSGGGGSGGGGS (SEQ ID NO: 70));

a half-life extender such as ALB11002; and, optionally, a C-terminal extension such as an alanine.

The half-life extender is, in an embodiment of the invention, a human serum albumin (HSA) binder such as ALB11002. In an embodiment of the invention, the HSA binder comprises CDR1 comprising the amino acid sequence GFTFSSFGMS (SEQ ID NO: 60); CDR2 comprising the amino acid sequence SISGSGSDTL (SEQ ID NO: 152; amino acids 1-10 of SEQ ID NO: 61); and CDR3 comprising the amino acid sequence GGSLSR (SEQ ID NO: 62), e.g., comprising the amino acid sequence EVQLVESGGG VVQPGNSLRL SCAASGFTFS SFGMSWVRQA PGKGLEWVSS ISGSGSDTLYADSVKGRFTI SRDNAKTTLY LQMNSLRPED TALYYCTIGG SLSRSSQGTL VTVSSA (SEQ ID NO: 142). Such half-life extenders themselves are part of the present invention.

In an embodiment of the invention, the PD1 binder, LAG3 binder, HSA binder and/or PD1/LAG3 binder is in an injection device or vessel optionally in association with a further therapeutic agent. Such a device or vessel is part of the present invention.

The present invention also provides a polynucleotide encoding any of the binders set forth herein as well as any vector (e.g., plasmid) comprising the polynucleotide as well as any host cell (e.g., CHO or fungal cell such as *Pichia*, e.g., *P. pastoris*) comprising the polynucleotide or vector, e.g., ectopic or integrated into one or more host cell chromosomes.

The present invention also provides a method for making any of the binders set forth herein comprising introducing a polynucleotide encoding the binder into a host cell (e.g., CHO or fungal cell such as *Pichia*, e.g., *P. pastoris*) and culturing the host cell in a medium under conditions favorable to expression of said binder from said polynucleotide and, optionally, purifying the binder from said host cell and/or said medium. Optionally, the vector or polynucleotide is integrated into one or more host cell chromosomes. Any binder produced by such a method is also part of the present invention.

The present invention also provides a method for preventing PD1 from binding to PD-L1 and/or PD-L2 or for inhibiting any PD1 activity, e.g., as discussed herein, comprising contacting said PD1 with a PD1 binder of the present invention (e.g., a PD1/LAG3 binder) optionally in association with a further therapeutic agent. The present invention also provides a method for preventing LAG3 from binding to MHC class II or for inhibiting any PD1 activity, e.g., as discussed herein comprising contacting said LAG3 with a LAG3 binder of the present invention (e.g., a PD1/LAG3 binder) optionally in association with a further therapeutic agent. The present invention also provides a method for enhancing an immune response in the body of a subject (e.g., a human) comprising administering an effective amount of binder of the present invention (e.g., PD1/LAG3 binder) to the subject optionally in association with a further therapeutic agent. The present invention also provides a method for treating or preventing cancer (e.g., metastatic cancer, a solid tumor or a hematologic cancer) or an infectious disease (e.g., bacterial infection, a viral infection or a fungal infection) in the body of a subject (e.g., a human) comprising administering an effective amount of binder of the present invention (e.g., a PD1/LAG3 binder) optionally in association with a further therapeutic agent to the subject. When administered to a subject, a PD1 and/or LAG3 binder of the present invention (e.g., a PD1/LAG3 binder) is optionally administered in association with a further therapeutic agent or a therapeutic procedure e.g., surgical tumorectomy.

DESCRIPTION OF THE FIGURES

FIG. 1. A table listing some of the amino acid positions that will be specifically referred to herein and their numbering according to some alternative numbering systems (such as Aho and IMGT)

FIG. 2 (1-5). PD1 binder sequences.

FIG. 3 (A-B). Alignment of 102C12 sequence with that of the SEQ ID NOs: 9-40 (see WO 2008/071447, SEQ ID NO: 348).

FIG. 18 (A-P). Sequences of the present invention.

DETAILED DESCRIPTION OF THE INVENTION

Figure 4:
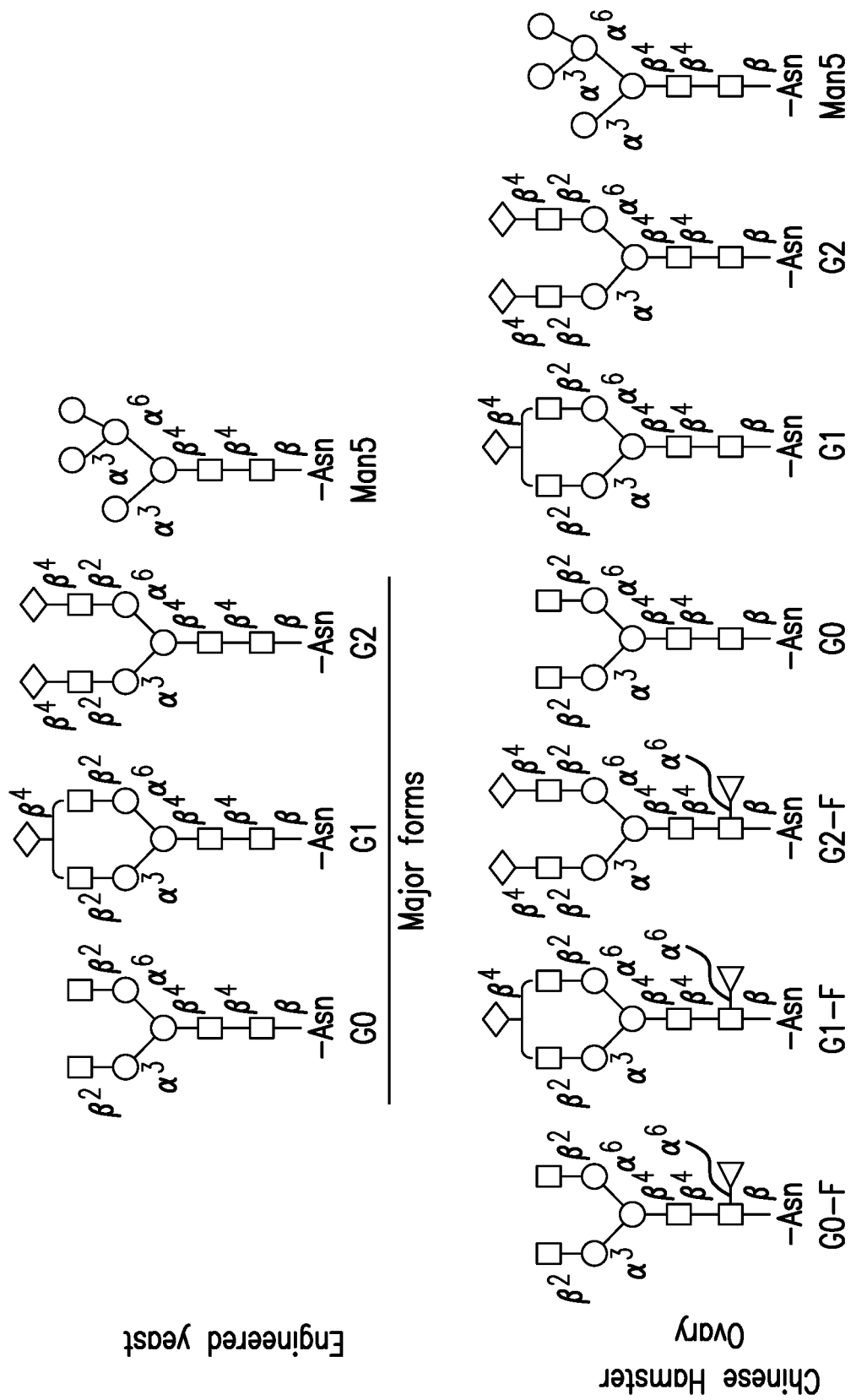
FIG. 4. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).
Figure 5:
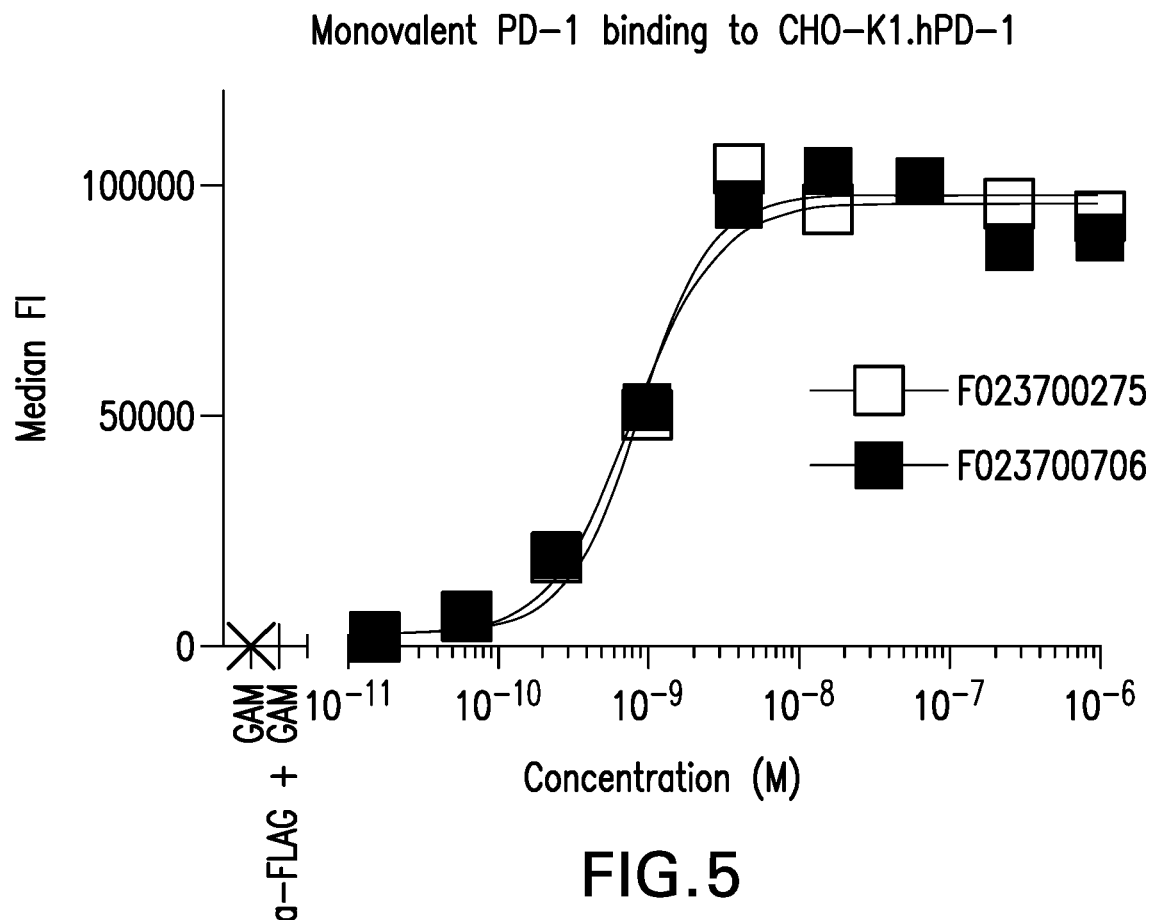
FIG. 5. Monovalent binding of CHO-K1 expressing human PD1 by F023700275 (1PD102C12(A14P, A74S, K83R)-FLAG3-HIS6) or F023700706 (1PD102C12 (L11V, A14P, A74S, K83R, I89L)-FLAG3-HIS6). GAM=goat anti-mouse secondary antibody use to detect mouse antibody that binds to FLAG epitope; α-FLAG+GAM=goat anti-mouse secondary antibody used plus mouse antibody that binds to FLAG epitope that is at C-terminus of the construct.
Figure 6:
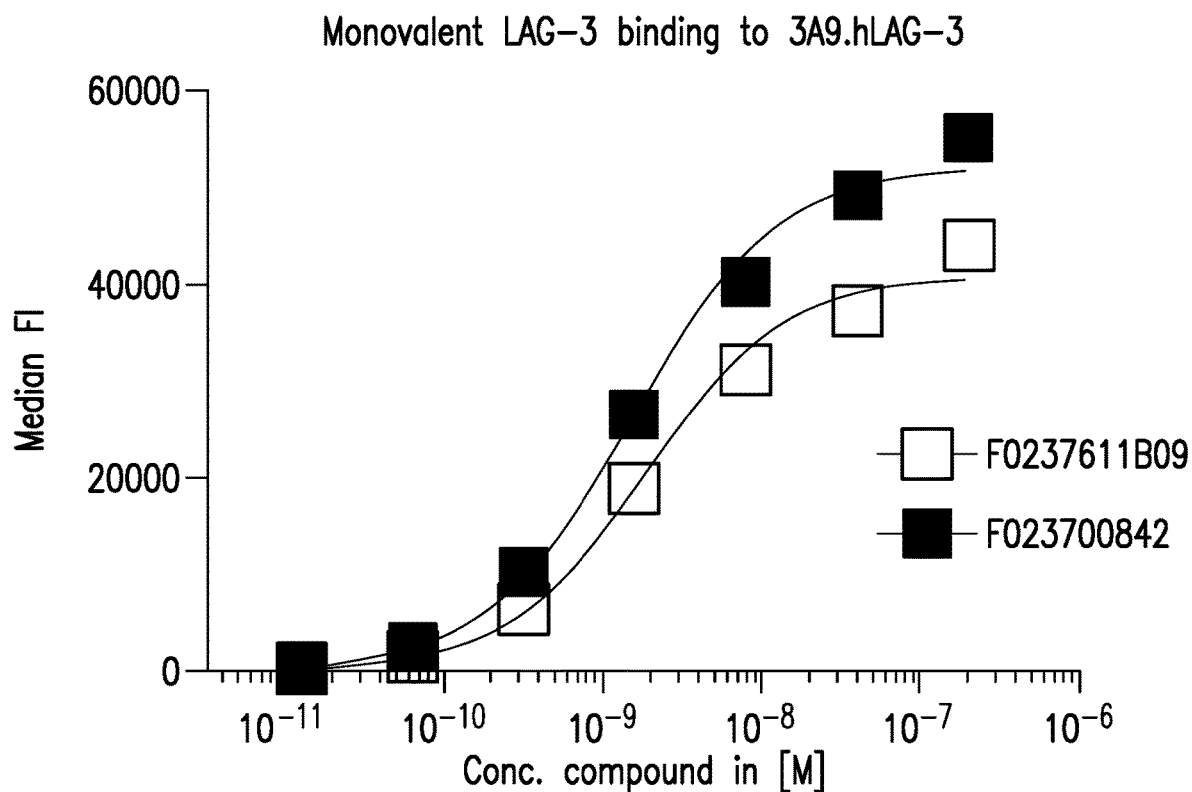
FIG. 6. Monovalent binding of 3A9 cells expressing human LAG3 by F0237611B09-FLAG-His6 or F023700842 (F0237611B09(L11V, A14P, R41P, N43K, A62S, A74S, K83R, V89L)-FLAG3-HIS6.
Figure 7A:
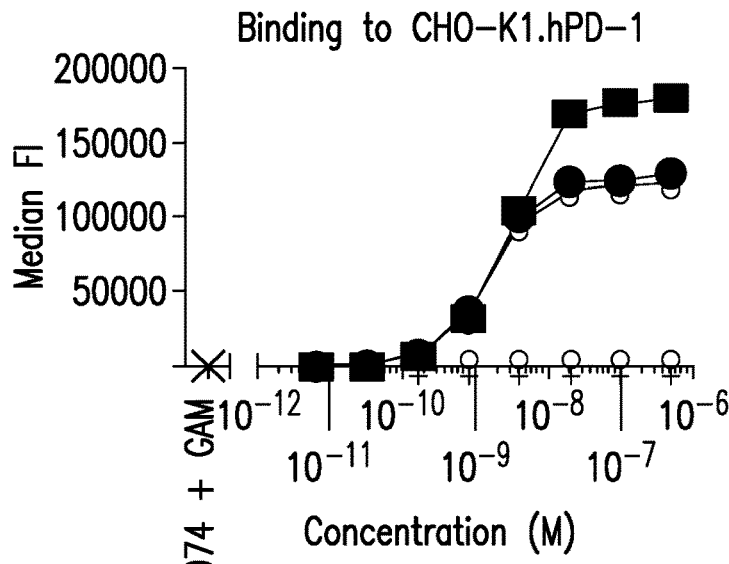
FIG. 7 (A-B). Binding of (A) CHO expressing human PD-1 by F023700931, F023700924, F023700933 or F023700962 or (B) 3A9 expressing rhesus PD-1 by F023700931 (*Pichia* or CHO expressed), F023700924 (*Pichia* or CHO expressed), F023700933, F023700962, F023700678 (1PD102C12 (A14P, A74S, K83R)-35GS-ALB11002) or F023701127. ABH0074+GAM=goat anti-mouse secondary antibody used plus mouse antibody ABH0074 that binds to nanobody frameworks.
Figure 7B:
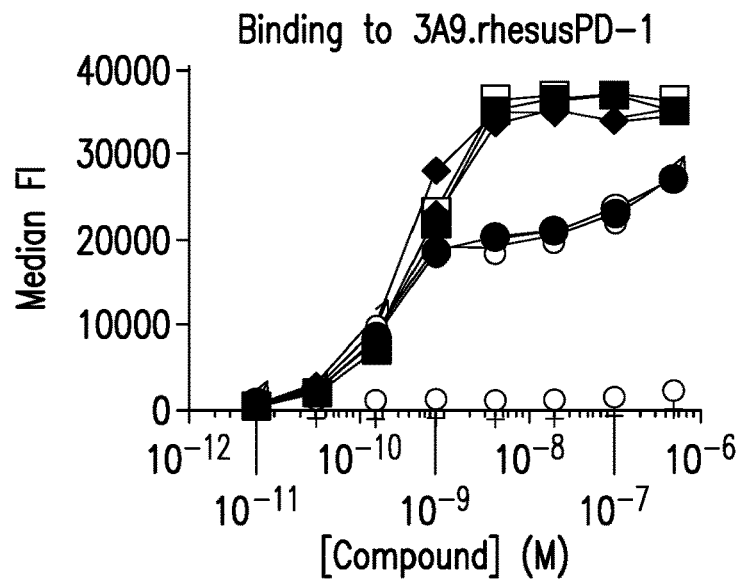

The present invention provides ISVDs that comprise mutations which block reactivity of pre-existing antibodies (pre-antibodies) to neo-epitopes within the ISVDs. Neoepitopes are epitopes within a protein which are revealed when the protein is mutated (e.g., truncated) or its folding is altered. Pre-existing antibodies are antibodies existing in the body of a patient prior to receipt of an ISVD. The ISVDs of the present invention are based, in part, in llama antibodies whose C-terminal constant domains have been removed; thus, exposing the neo-epitopes in the C-terminus of the resulting VHH to pre-antibody binding. It has been discovered that the combination of mutations of residues 11 and 89 (e.g., L11V and I89L or V89L) led to a surprising lack of pre-antibody binding. Mutations in residue 112 have also been shown to remarkably reduce pre-antibody binding. Buyse & Boutton (WO2015/173325) included data showing that the combination of an L11V and V89L mutation provided a remarkable improvement in reducing pre-antibody binding compared to an L11V mutation alone or a V89L mutation alone. For example, Table H of Buyse & Boutton on page 97 showed comparative data for an ISVD with a V89L mutation alone (with or without C-terminal extension) and the same ISVD with a V89L mutation in combination with an L11V mutation (again, with or without a C-terminal extension). Also, although generated in two separate experiments, the data shown in Table H for the L11V/V89L combination as compared to the data given in Table B for an L11V mutation alone (in the same ISVD) showed that the pre-antibody binding reduction that is obtained by the L11V/V89L combination was greater than that for the L11V mutation alone. Since the llama antibody scaffold structure is known to be very highly conserved, the effect of the mutations at positions 11 and 89 is very likely to exist for any ISVD. Indeed, the effect was demonstrated, in FIG. 19, with the instant binders, F023700924 and F023700931, which were shown to exhibit very low levels of pre-antibody binding in healthy subjects and subjects suffering from cancer.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT). This point is also further discussed herein.

With regards to the CDRs, as is well-known in the art, there are multiple conventions to define and describe the CDRs of a VH or VHH fragment, such as the Kabat definition (which is based on sequence variability and is the most commonly used) and the Chothia definition (which is based on the location of the structural loop regions). Reference is for example made to the website www.bioinf.org.uk/abs/. For the purposes of the present specification and claims, even though the CDRs according to Kabat may also be mentioned, the CDRs are most preferably defined on the basis of the Abm definition (which is based on Oxford Molecular's AbM antibody modelling software), as this is considered to be an optimal compromise between the Kabat and Chotia definitions. Reference is again made to the website www.bioinforg.uk/abs/). See Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883; Chothia & Lesk (1987) J. Mol. Biol. 196: 901-917; Elvin A. Kabat, Tai Te Wu, Carl Foeller, Harold M. Perry, Kay S. Gottesman (1991) Sequences of Proteins of Immunological Interest; Protein Sequence and Structure Analysis of Antibody Variable Domains. In: Antibody Engineering Lab Manual (Ed.: Duebel, S. and Kontermann, R., Springer-Verlag, Heidelberg). In an embodiment of the invention, CDR determination is according to Kabat, e.g., wherein FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In an embodiment of the invention, CDRs are determined according to Kontermann and Dübel (Eds., Antibody Engineering, vol 2, Springer Verlag Heidelberg Berlin, Martin, Chapter 3, pp. 33-51, 2010).

The term "immunoglobulin single variable domain" (also referred to as "ISV" or ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VHs), IgNAR, domains, (single domain) antibodies (such as dAbs™) that are VH domains or that are derived from a VH domain and (single domain) antibodies (such as dAbs™) that are VL domains or that are derived from a VL domain. ISVDs that are based on and/or derived from heavy chain variable domains (such as VH or VHH domains) are generally preferred. Most preferably, an ISVD will be a Nanobody.

The term "Nanobody" is generally as defined in WO 08/020079 or WO 09/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®). An example of an ISVD is 102C12 (E1D, L11V, A14P, A74S, K83R, I89L). Other ISVDs also appear in Tables A and C herein.

A multispecific binder (e.g., multispecific ISVD) is a molecule that comprises, for example, a first PD1 or LAG3 binding moiety (e.g., an ISVD or a Nanobody) and one or more (e.g., 1, 2, 3, 4, 5) additional binding moieties (e.g., an ISVD or a Nanobody) that bind to an epitope other than that of the first PD1 or LAG3 binding moiety (e.g., to CTLA4, CD27 and/or BTLA); e.g., comprising a PD1 or LAG3 binding moiety and a CTLA4 binding moiety; a PD1 or LAG3 binding moiety and a BTLA binding moiety; one or two PD1 binding moieties and one or two LAG3 binding moieties and a human serum albumin binding moiety; or a PD1 binding moiety, a LAG3 binding moiety and a BTLA binding moiety. A multispecific binder is, for example, F023700931 or F023700899.

A binding moiety or binding domain or binding unit is a molecule such as an ISVD or Nanobody that binds to an antigen. A binding moiety or binding domain or binding unit may be part of a larger molecule such as a multivalent or multispecific immunoglobulin that includes more than one moiety, domain or unit and/or that comprises another functional element, such as, for example, a half-life extender (HLE), targeting unit and/or a small molecule such a polyethyleneglycol (PEG).

A monovalent PD1 or LAG3 binder (e.g., ISVD such as a Nanobody) is a molecule that comprises a single antigen binding domain. A bivalent PD1 or LAG3 binder comprises two antigen binding domains (e.g., conventional antibodies including bispecific antibodies). A multivalent PD1 or LAG3 binder comprises more than one antigen-binding domain.

A monospecific PD1 or LAG3 binder binds a single antigen; a bispecific PD1 or LAG3 binder binds to two different antigens and a multispecific PD1 or LAG3 binder binds to more than one antigen.

A biparatopic PD1 or LAG3 binder is monospecific but binds to two different epitopes of the same antigen. A multiparatopic PD1 or LAG3 binder binds the same antigen but to more than one epitope in the antigen.

The term "half-life" as used herein relation to a PD1 and/or LAG3 binder or ISVD, Nanobody, ISVD-based biological, Nanobody-based biological or any other polypeptide referred to herein can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). In this respect it should be noted that the term "half-life" as used herein in particular refers to the t½-beta or terminal half-life (in which the t½-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" as also as defined in paragraph o) on page 57 of WO 08/020079 and in particular refer to an increase in the t½-beta, either with or without an increase in the t½-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, N.Y. (2005), as well as to the general background art cited herein.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

"Isolated" PD1 and/or LAG3 binders (e.g., an ISVD such as a Nanobody), polypeptides, polynucleotides and vectors, are at least partially free of other biological molecules from the cells or cell culture from which they are produced. Such biological molecules include nucleic acids, proteins, lipids, carbohydrates, or other material such as cellular debris and growth medium. An "isolated" PD1 and/or LAG3 binder may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The phrase "control sequences" refers to polynucleotides necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another polynucleotide. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The present invention includes polynucleotides encoding the PD1 and/or LAG3 binders which, optionally, are operably linked to one or more control sequences such as a promoter.

A "PD1 and/or LAG3" binder refers to a binder that includes
  a PD1 binder; or
  a LAG3 binder; or
  both a PD1 binder and a LAG3 binder (i.e., a "PD1/LAG3 binder") and, optionally, to another binder that binds, for example, human serum albumin. In an embodiment of the invention, a PD1/LAG binder is
102C12 (E1D, L11V, A14P, A74S, K83R, I89L)-35GS-11B09 (L11V, A14P, R41P, N43K, A62S, A74S, K83R, V89L)-35GS-ALB11002-A; or
102C12 (E1D, L11V, A14P, A74S, K83R, I89L)-35GS-102C12 (L11V, A14P, A74S, K83R, I89L)-35GS-11B09 (L11V, A14P, R41P, N43K, A62S, A74S, K83R, V89L)-35GS-11B09 (L11V, A14P, R41P, N43K, A62S, A74S, K83R, V89L)-35GS-ALB11002-A;
  as set forth herein.
  See F023700924 or F023700931 herein. A PD1/LAG3 binder includes a PD1 binder and a LAG3 binder.

The scope of the present invention includes any PD1 binder set forth in FIG. 18 (A-P) (or any PD1 binder comprising CDR1, CDR2 and CDR3 of such a PD1 binder), any LAG3 binder set forth in FIG. 18 (A-P) (or any LAG3 binder comprising CDR1, CDR2 and CDR3 of such a LAG3 binder) or any PD1/LAG3 binder set forth in FIG. 18 (A-P) or any PD1/LAG3 binder comprising CDR1, CDR2 and CDR3 of the PD1 binding moiety and/or LAG3 binding moiety thereof. The binders set forth in FIG. 18 (A-P), in an embodiment of the invention, do not include the C-terminal extender (e.g., A), FLAG and/or HIS tags therein (e.g., HHHHHH (amino acids 29-34 or SEQ ID NO: 68); AAAHHHHHH (SEQ ID NO: 69); or AAADYKDHDGDYKDHDIDYKDDDDK-GAAHHHHHH (SEQ ID NO: 68)). Any such binder or CDR may, in an embodiment may be a variant of what is set forth in FIG. 18 (A-P), e.g., comprising 1, 2, 3, 4, 5, 6, 7, 8, 9 or 10 point mutations (e.g., conservative substitutions or deletions).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

Examples of antigen-binding fragments include, but are not limited to, Fab, Fab', F(ab')2, and Fv fragments, and single-chain Fv molecules.

A "PD1 binder" or "PD1 ISVD" or "PD1 nanobody" refers to a binder or ISVD or Nanobody, respectively, that binds to PD1. A similar convention may be applied with respect to molecules that bind to LAG3 or CTLA4 or another antigen.

The following properties are associated with the indicated mutations in the PD1 binder 102C12:
E1D: Prevent pyroglutamic acid formation in the first amino acid of the construct E1
L11V: Decrease pre-antibody binding
A14P: Humanization
W52aV: Prevent oxidation of W52a
N73P: Prevent N73 deamidation
N73Q: Prevent N73 deamidation
N73S: Prevent N73 deamidation
A74S: Humanization
K83R: Humanization
I89L: Decrease pre-antibody binding
W100aF: Prevent oxidation of W100a
or the LAG3 binder 11B09:
L11V: Decrease pre-antibody binding
A14P: Humanization
R41P: Humanization
N43K: Humanization
A62S: Humanization
A74S: Humanization
K83R: Humanization
V89L: Decrease pre-antibody binding In an embodiment of the invention, PD1 is human PD1. In an embodiment of the invention, human PD1 comprises the amino acid sequence:

```
                                                (SEQ ID NO: 137)
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

In an embodiment of the invention, LAG3 is human LAG3. In an embodiment of the invention, human LAG3 comprises the amino acid sequence:

```
                                                (SEQ ID NO: 138)
MWEAQFLGLL FLQPLWVAPV KPLQPGAEVP VVWAQEGAPA

QLPCSPTIPL QDLSLLRRAG VTWQHQPDSG PPAAAPGHPL

APGPHPAAPS SWGPRPRRYT VLSVGPGGLR SGRLPLQPRV

QLDERGRQRG DFSLWLRPAR RADAGEYRAA VHLRDRALSC

RLRLRLGQAS MTASPPGSLR ASDWVILNCS FSRPDRPASV

HWFRNRGQGR VPVRESPHHH LAESFLFLPQ VSPMDSGPWG

CILTYRDGFN VSIMYNLTVL GLEPPTPLTV YAGAGSRVGL

PCRLPAGVGT RSFLTAKWTP PGGGPDLLVT GDNGDFTLRL

EDVSQAQAGT YTCHIHLQEQ QLNATVTLAI ITVTPKSFGS

PGSLGKLLCE VTPVSGQERF VWSSLDTPSQ RSFSGPWLEA

QEAQLLSQPW QCQLYQGERL LGAAVYFTEL SSPGAQRSGR

APGALPAGHL LLFLILGVLS LLLLVTGAFG FHLWRRQWRP

RRFSALEQGI HPPQAQSKIE ELEQEPEPEP EPEPEPEPEP EPEQL
```

PD1 Binders

The present invention provides improved PD1 binders, for example, improved PD1 ISVDs and more in particular improved PD1 Nanobodies. The improved PD1 binders provided by the invention are also referred to herein as the "PD1 binders of the invention" or "PD1 binders".

When discussed herein, monovalent PD1 binders of the present invention will include the amino acid sequence of SEQ ID NO: 1 or 2, but including one or more mutations at position 1, 11, 14, 52a, 73, 74, 83, 89, 100a, 110 or 112 (or at any of the mutational positions set forth herein with regard to PD1 binders of the invention).

When discussed herein, multispecific PD1 binders, for example, that include a LAG3, will include PD1 binding moieties including CDR1, CDR2 and CDR3 that are in the PD1 binders set forth below in Table A-1 and A-2 (e.g., in 102C12 or reference A). Optionally, the PD1 binding moiety of the multispecific binder comprises the amino acid of SEQ ID NO: 1 or 2 but including one or more mutations at position 1, 11, 14, 52a, 73, 74, 83, 89, 100a, 110 or 112.

The present invention provides improved PD1 binders, for example, improved PD1 ISVDs and more in particular improved PD1 Nanobodies. PD1 binders of the present invention include polypeptides which are variants of polypeptides comprising the amino acid sequence of SEQ ID NO: 1 or 2 which is mutated at position 1, 11, 14, 52a, 73, 74, 83, 89, 100a, 110 and/or 112. The improved PD1 binders provided by the invention are also referred to herein as the "PD1 binders of the invention" or "PD1 binders". These terms encompass any molecule that binds to PD1 and includes any of the molecules that bind to PD1 which are set forth herein. For example, the terms include an ISVD that comprises an amino acid sequence set forth in a member selected from the group consisting of SEQ ID NOs: 9-40 and 57 as well as any conventional antibody or antigen-binding fragment thereof that includes an amino acid sequence set forth in a members selected from the group consisting of SEQ ID NOs: 9-40 and 57; a multispecific immunoglobulin, such as a bispecific immunoglobulin (e.g., ISVD) that comprises an amino acid sequence set forth in a member selected from the group consisting of SEQ ID NOs: 9-40 and 57, binds to PD1 and also binds to another antigen such as a different epitope of PD1, CD27, LAG3, CTLA4, BTLA, TIM3, ICOS, B7-H3, B7-H4, CD137, GITR, PD-L1, PD-L2, ILT1, ILT2 CEACAM1, CEACAMS, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP, e.g., comprising a PD1 binding moiety and a CTLA4 binding moiety; a PD1 binding moiety and a BTLA binding moiety; a PD1 binding moiety and a LAG3 binding moiety; or a PD1 binding moiety, a LAG3 binding moiety and a BTLA binding moiety. A multivalent PD1 binder comprises more than one antigen-binding domain, for example more than one ISVD (one or more of which bind to PD1). A monospecific PD1 binder binds a single antigen (PD1); a bispecific PD1 binder binds to two different antigens (one of which is PD1) and a multispecific PD binder binds to more than one antigen (one or more of which is PD1 and one or more of which is a different antigen). For example, in an embodiment of the invention, a PD1 binder comprises an amino acid sequence selected from SEQ ID NOs: 106-124.

More in particular, the invention aims to provide improved PD1 binders that are variants of 102C12 and Reference A and that have reduced binding by interfering factors (generally referred to as "pre-existing antibodies") that may be present in the sera from some healthy human subjects as well as from patients. See WO 12/175741, WO 2013/024059 and also for example by Holland et al. (J. Clin. Immunol. 2013, 33(7):1192-203) as well the PCT application PCT/EP2015/060643 (WO2015/173325).

As further described herein, the PD1 binders of the invention preferably have the same combination of CDRs (i.e. CDR1, CDR2 and CDR3) as are present in 102C12 or in Reference A. WO 2008/071447 describes Nanobodies that can bind to PD1 and uses thereof. SEQ ID NO: 348 of WO 2008/071447 disclosed a PD-1 specific Nanobody called 102C12, the sequence of which is given herein as SEQ ID NO: 1. Also, a variant of 102C12 with a humanizing Q108L substitution (also referred to herein as "Reference A") is used herein as a reference compound and its sequence is given herein as SEQ ID NO: 2. The present invention includes PD1 binders that include a mutation at position 108, e.g., Q108L.

The present invention includes PD1 binders which are variants of 102C12 and PD1/LAG3 binders comprising such variants of 102C12 which are set forth below in Table A-2 below. The scope of the present invention includes PD1 binders that include CDR1, CDR2 and CDR3 of said varaints set forth below in Table A-2 as well as PD1/LAG3 binders comprising a PD1 binding moiety that includes CDR1, CDR2 and CDR3 of said varaints set forth below in Table A-2.

TABLE A-1

PD1 Binder 102C12.

| SEQ ID NO | Description | Sequence |
|---|---|---|
| 1 | WO 2008/071447, SEQ ID NO: 348 (102C12) (may be referred to herein as "1PD102C12") | EVQLVESGGGLVQAGGSLRLSCAASGSIAS IHAMGWFRQAPGKEREFVAVITWSGGITYY ADSVKGRFTISRDNAKNTVYLQMNSLKPED TAIYYCAGDKHQSSWYDYWGQGTQVTVSS |
| 2 | reference A | EVQLVESGGGLVQAGGSLRLSCAASGSIAS IHAMGWFRQAPGKEREFVAVITWSGGITYY ADSVKGRFTISRDNAKNTVYLQMNSLKPED TAIYYCAGDKHQSSWYDYWGQGTLVTVSS |

TABLE A-2

Sequence Optimized Variant 102C12 PD1 Binders (optionally fused to an HSA binder)

| | | |
|---|---|---|
| SO 1PD102C12 monomer 102C12 (E1D, L11V, A14P, A74S, K83R, I89L) Target: hPD-1 SEQ ID NO: 57 | | DVQLVESGGG VVQPGGSLRL SCAASGSIAS IHAMGWFRQA PGKEREFVAV ITWSGGITYY ADSVKGRFTI SRDNSKNTVY LQMNSLRPED TALYYCAGDK HQSSWYDYWG QGTLVTVSS |
| SEQ ID NO: 3 | PD1 binder CDR1 (Kabat) | IHAMG |
| SEQ ID NO: 4 | PD1 binder CDR2 (Kabat) | VITXSGGITYYADSVKG wherein X is W or V (e.g., VITwSGGITYYADSVKG (SEQ ID NO: 143) or VITvSGGITYYADSVKG (SEQ ID NO: 144)) |
| SEQ ID NO: 5 | PD1 binder CDR3 (Kabat/Abm) | DKHQSSXYDY wherein X is W or F (e.g., DKHQSSwYDY SEQ ID NO: 145) or DKHQSSfYDY (SEQ ID NO: 146)) |

TABLE A-2-continued

Sequence Optimized Variant 102C12 PD1 Binders (optionally fused to an HSA binder)

| | | |
|---|---|---|
| SEQ ID NO: 6 | PD1 binder CDR1 (Abm) | GSIASIHAMG |
| SEQ ID NO: 7 | PD1 binder CDR2 (Abm) | VITXSGGITY<br>wherein X is W or V<br>(e.g., VITwSGGITY (SEQ ID NO: 147) or VITvSGGITY (SEQ ID NO: 148)) |
| SEQ ID NO: 8 | PD1 binder CDR3 (Kabat/Abm) | DKHQSSXYDY<br>wherein X is W or F<br>(e.g., DKHQSSwYDY (SEQ ID NO: 149) or DKHQSSfYDY SEQ ID NO:150)) |
| Name: F023700275<br>Description: 1PD102C12<br>(A14P, A74S, K83R)<br>Target: hPD-1<br>SEQ ID NO: 98 | EVQLVESGGGLVQPGGSLRLSCAASGSIASIHAMGWFRQAPGKEREFVAVITW<br>SGGITYYADSVKGRFTISRDNSKNTVYLQMNSLRPEDTAIYYCAGDKHQSSWY<br>DYWGQGTLVTVSS | |
| SO 1PD102C12 monomer<br>Name: F023700706 or F023700929<br>Description: 1PD102C12 (L11V, A14P, A74S, K83R, I89L)<br>Target: hPD-1<br>SEQ ID NO: 99 | EVQLVESGGGVVQPGGSLRLSCAASGSIASIHAMGWFRQAPGKEREFVAVITW<br>SGGITYYADSVKGRFTISRDNSKNTVYLQMNSLRPEDTALYYCAGDKHQSSWY<br>DYWGQGTLVTVSS | |
| Monovalent SO<br>1PD102C12 + ALB11002<br>Name: F023701127<br>Description: 1PD102C12 (E1D, L11V, A14P, A74S, K83R, I89L)-35GS-ALB11002-A<br>Target: hPD-1<br>SEQ ID NO: 101 | DVQLVESGGGVVQPGGSLRLSCAASGSIASIHAMGWFRQAPGKEREFVAVITW<br>SGGITYYADSVKGRFTISRDNSKNTVYLQMNSLRPEDTALYYCAGDKHQSSWY<br>DYWGQGTLVTVSSGGGGSGGGGSGGGGSGGGGSGGGGSGGGGSGGGGSEVQLV<br>ESGGGVVQPGNSLRLSCAASGETFSSFGMSWVRQAPGKGLEWVSSISGSGSDT<br>LYADSVKGRFTISRDNAKTTLYLQMNSLRPEDTALYYCTIGGSLSRSSQGTLV<br>TVSSA | |
| Bivalent SO 1PD102C12 + ALB11002<br>Name: F023700933<br>Description: 1PD102C12 (E1D, L11V, A14P, A74S, K83R, I89L)-35G-5-<br>1PD102C12(L11V, A14P, A74S, K83R, I89L)-35GS-ALB11002-A<br>Target: hPD-1<br>SEQ ID NO: 102 | DVQLVESGGGVVQPGGSLRLSCAASGSIASIHAMGWFRQAPGKEREFVAVITW<br>SGGITYYADSVKGRFTISRDNSKNTVYLQMNSLRPEDTALYYCAGDKHQSSWY<br>DYWGQGTLVTVSSGGGGSGGGGSGGGGSGGGGSGGGGSGGGGSGGGGSEVQLV<br>ESGGGVVQPGGSLRLSCAASGSIASIHAMGWFRQAPGKEREFVAVITWSGGIT<br>YYADSVKGRFTISRDNSKNTVYLQMNSLRPEDTALYYCAGDKHQSSWYDYWGQ<br>GTLVTVSSGGGGSGGGGSGGGGSGGGGSGGGGSGGGGSGGGGSEVQLVESGGG<br>VVQPGNSLRLSCAASGETFSSFGMSWVRQAPGKGLEWVSSISGSGSDTLYADS<br>VKGRFTISRDNAKTTLYLQMNSLRPEDTALYYCTIGGSLSRSSQGTLVTVSSA | |
| Enhanced SO 1PD102C12 monomer<br>Name: F023701190<br>Description: 1PD102C12(E1D, L11V, A14P, W52aV, A74S, K83R, I89L, W100aF)<br>Target: hPD-1<br>SEQ ID NO: 103<br>*Optionally, F023701190 comprises an N73X mutation such as N73S | DVQLVESGGGVVQPGGSLRLSCAASGSIASIHAMGWERQAPGKEREFVAVITV<br>SGGITYYADSVKGRFTISRDNSKNTVYLQMNSLRPEDTALYYCAGDKHQSSFY<br>DYWGQGTLVTVSS | |
| Enhanced SO 1PD102C12 monomer<br>Name: F023701192<br>Description: 1PD102C12(E1D, L11V, A14P, W52aV, N73Q, A74S, K83R, I89L, W100aF)<br>Target: hPD-1<br>SEQ ID NO: 104 | DVQLVESGGGVVQPGGSLRLSCAASGSIASIHAMGWERQAPGKEREFVAVITV<br>SGGITYYADSVKGRFTISRDQSKNTVYLQMNSLRPEDTALYYCAGDKHQSSFY<br>DYWGQGTLVTVSS | |

TABLE A-2-continued

Sequence Optimized Variant 102C12 PD1 Binders (optionally fused to an HSA binder)

| | |
|---|---|
| Enhanced SO 1PD102C12 monomer<br>Name: F023701193<br>Description: 1PD102C12 (E1D, L11V, A14P, W52aV, N73P, A74S, K83R, I89L, W100aF)<br>Target: hPD-1<br>SEQ ID NO: 105 | DVQLVESGGGVVQPGGSLRLSCAASGSIASIHAMGWERQAPGKEREFVAVITV<br>SGGITYYADSVKGRFTISRDPSKNTVYLQMNSLRPEDTALYYCAGDKHQSSFY<br>DYWGQGTLVTVSS |
| F023700641<br>Description:<br>1PD102C12(A14P, A74S, K83R)-35GS-<br>1PD102C12(A14P, A74S, K83R)-35GS-ALB11002<br>Target: hPD-1<br>SEQ ID NO: 126 | EVQLVESGGGLVQPGGSLRLSCAASGSIASIHAMGWERQAPGKEREFVAVITW<br>SGGITYYADSVKGRFTISRDNSKNTVYLQMNSLRPEDTAIYYCAGDKHQSSWY<br>DYWGQGTLVTVSSGGGGSGGGGSGGGGSGGGGSGGGGSGGGGSGGGGSEVQLV<br>ESGGGLVQPGGSLRLSCAASGSIASIHAMGWERQAPGKEREFVAVITWSGGIT<br>YYADSVKGRFTISRDNSKNTVYLQMNSLRPEDTAIYYCAGDKHQSSWYDYWGQ<br>GTLVTVSSGGGGSGGGGSGGGGSGGGGSGGGGSGGGGSGGGGSEVQLVESGGG<br>LVQPGNSLRLSCAASGETFSSFGMSWVRQAPGKGLEWVSSISGSGSDTLYADS<br>VKGRFTISRDNAKTTLYLQMNSLRPEDTAVYYCTIGGSLSRSSQGTLVTVSS |
| 1PD102C12 (E1D, L11V, A14P, W52aV, N73P, A74S, K83R, I89L, W100aF)<br>amino acids 1-119 of SEQ ID NO: 113 | DVQLVESGGGVVQPGGSLRLSCAASGSIASIHAMGWERQAPGKEREFVAVITV<br>SGGITYYADSVKGRFTISRDPSKNTVYLQMNSLRPEDTALYYCAGDKHQSSFY<br>DYWGQGTLVTVSS |
| 1PD102C12 (E1D, L11V, A14P, W52aV, N73Q, A74S, K83R, I89L, W100aF)<br>amino acids 1-119 of SEQ ID NO: 117 | DVQLVESGGGVVQPGGSLRLSCAASGSIASIHAMGWERQAPGKEREFVAVITV<br>SGGITYYADSVKGRFTISRDQSKNTVYLQMNSLRPEDTALYYCAGDKHQSSFY<br>DYWGQGTLVTVSS |
| 1PD102C12 (E1D, L11V, A14P, W52aV, N73S, A74S, K83R, I89L, W100aF)<br>amino acids 1-119 of SEQ ID NO: 121 | DVQLVESGGGVVQPGGSLRLSCAASGSIASIHAMGWERQAPGKEREFVAVITV<br>SGGITYYADSVKGRFTISRDSSKNTVYLQMNSLRPEDTALYYCAGDKHQSSFY<br>DYWGQGTLVTVSS |

*PD1 binder CDRs underscored and/or bold

The present invention includes embodiments wherein a PD1 binder comprises one, two or three of the CDRs that are in a PD1 binder which is set forth above in Table A-1 or A-2 (e.g., SEQ ID NO: 57, 98, 99, 103, 104 or 105) but which comprises 0, 1, 2, 3, 4, or 5 amino acid substitutions, e.g., conservative substitutions, and/or comprises 100, 99, 98, 97, 96 or 95% sequence identity relative to the CDR sequences set forth in Table A-1 or A-2 wherein a PD1 binder having such CDRs retains the ability to bind to PD1. In an embodiment of the invention, the first amino acid of a PD1 binder of the present invention is E. In an embodiment of the invention, the first amino acid of a PD1 binder of the present invention is D. PD1/LAG3 binders comprising such a PD1/LAG3 binder are part of the present invention.

The present invention includes any PD1 binder comprising the amino acid sequence of SEQ ID NO: 57, 98, 99, 103, 104 or 105 or an amino acid sequence comprising 80% or more (e.g., 85%, 90%, 95%, 96%, 97%, 98% or 99%) amino acid sequence identity (i.e., comparing the full amino acid sequences) wherein the PD1 binder retains the ability to bind to PD1 and, optionally, includes an HSA binder. PD1/LAG3 binders comprising such a PD1/LAG3 binder are part of the present invention.

A PD1 binder described as "102C12 (E1D, L11V, A14P, A74S, K83R, I89L)" refers to a binder having the sequence of 102C12 (SEQ ID NO: 1) or reference A (SEQ ID NO: 2), but wherein the sequence comprises the mutations E1D, L11V, A14P, A74S, K83R and I89L. This notation is used through out the specification with regard to several different binders. For example, "11B09 (L11V, A14P, R41P, N43K, A62S, A74S, K83R, V89L)" refers to a LAG3 binder comprising the amino acid sequence of 11B09 (SEQ ID NO: 64), but wherein the sequence comprises mutations L11V, A14P, R41P, N43K, A62S, A74S, K83R and V89L.

The Kabat residue numbers for certain residues of the PD1 binders set forth in Table A are shown in the sequence below:

(SEQ ID NO: 2)
$E_1$VQLVESGGGL$_{11}$V$_{12}$Q$_{13}$A$_{14}$GGSLRLSCAASG$_{26}$S$_{27}$I$_{28}$A$_{29}$S$_{30}$I

HAMGW$_{36}$F$_{37}$R$_{38}$Q$_{39}$AP$_{41}$GKERE$_{46}$F$_{47}$V$_{48}$A$_{49}$VITW$_{52a}$SGGITYY

ADSVKGR$_{66}$F$_{67}$T$_{68}$I$_{69}$S$_{70}$RDN$_{73}$A$_{74}$KNTVYLQM$_{82}$N$_{82a}$S$_{82b}$

-continued $L_{82c}K_{83}P_{84}EDT_{87}A_{88}I_{89}Y_{90}Y_{91}CAGDKHQSSW_{100a}YDYW_{103}$ $G_{104}Q_{105}G_{106}T_{107}L_{108}V_{109}T_{110}V_{111}S_{112}S_{113}$.

The Kabat residue numbers for certain residues of 102C12 (E1D, L11V, A14P, A74S, K83R, I89L) are shown in the sequence below:

(SEQ ID NO: 57)
$D_1$VQLVESGGG $V_{11}$VQP$_{14}$GGSLRL SCAASGSIAS IHAMGWFRQA

PGKEREFVAV ITWSGGITYY ADSVKGRFTI SRDNS$_{74}$KNTVY

LQMNSLR$_{83}$PED TAL$_{89}$YYCAGDK HQSSWYDYWG QGTLVTVSS.

Optionally, residue 1 is an E.

Mutations may be referred to herein and are designated by their Kabat number as shown above.

Some preferred, but non-limiting PD1 binders of the invention are 102C12 (E1D (optionally), L11V, A14P, A74S, K83R, I89L), comprise the amino acid sequence set forth in SEQ ID NO: 9-40, 57, 98, 99 or 101-105 or are listed in FIG. 2, FIG. 3 or FIG. 18 (A-P). PD1 binders of SEQ ID NOs: 24 to 40, 101 or 102 are examples of PD1 binders of the invention having a C-terminal alanine extension, i.e. an alanine residue at the C-terminal end of the ISVD-sequence (also sometimes referred to as "position 114") compared to the usual C-terminal sequence VTVSS (SEQ ID NO: 52, as present in Reference A). This C-terminal alanine extension can prevent the binding of so-called "pre-existing antibodies" (assumed to be IgGs) to a putative epitope that is situated at the C-terminal region of the ISV. This epitope is assumed to include, among other residues, the surface-exposed amino acid residues of the C-terminal sequence VTVSS (SEQ ID NO: 52) as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (or, in some cases, essentially fully prevent) the binding of the "pre-existing antibodies" that can be found in the sera from a range of subjects (both healthy subjects and subjects with a medical condition or disease), it has been found that the sera from some subjects (such as the sera from patients with some immune diseases such as SLE) can contain pre-existing antibodies that can bind to the C-terminal region of an ISV (when such region is exposed) even when the ISV contains such a C-terminal alanine (or more generally, such C-terminal extension).

Accordingly, one specific objective of the invention is to provide PD1 binders that are improved variants of the PD1 Nanobody referred to herein as "Reference A" and that have reduced binding by so-called "pre-existing antibodies", and in particular of the kind described in PCT/EP2015/060643 (WO2015/173325)(i.e. those pre-existing antibodies that can bind to an exposed C-terminal region of an ISV even in the presence of a C-terminal extension).

The invention provides PD1 binders comprising amino acid sequences that are variants of the sequence of SEQ ID NO: 1 or 2 which comprise one or more of the following mutations compared to the sequence of SEQ ID NO: 1 or 2:

1D or 1E;
11V;
14P;
52aV
73Q, 73P or 73S
74S;
83R;
89T or 89L;
100aF
1D or 1E in combination with 11V, 14P, 74S, 83R and 89L;
1D in combination with 11V, 14P, 52aV, 73Q 73S or 73P, 74S, 83R, 89L and 100aF;
1E in combination with 11V, 14P, 52aV, 73S or 73Q or 73P, 74S, 83R, 89L and 100aF;
89L in combination with 11V, 14P, 52aV, 73S or 73Q or 73P, 74S, 83R and 100aF, and optionally, 1D;
89L in combination with 11V;
89L in combination with 110K or 110Q;
89L in combination with 112K or 112Q;
89L in combination with 11V, 14P, 74S, 83R, and, optionally, 1D;
110K or 110Q in combination with 11V, 14P, 52aV, 73S or 73Q or 73P, 74S, 83R, 89L and 100aF and optionally, 1D;
112K or 112Q in combination with 11V, 14P, 52aV, 73S or 73Q or 73P, 74S, 83R, 89L and 100aF and optionally, 1D;
89L in combination with 11V and 110K or 110Q;
89L in combination with 11V and 112K or 112Q;
11V in combination with 110K or 110Q; or
11V in combination with 112K or 112Q.

In particular, the PD1 binders (e.g., an ISVD such as a Nanobody) provided by the invention comprise a variant of SEQ ID NO: 1 or 2 wherein, in an embodiment of the invention:

the amino acid residue at position 1 is selected from E and D;
the amino acid residue at position 11 is selected from L and V;
the amino acid residue at position 14 is selected from A and P;
the amino acid residue at position 52a is selected from W and V;
the amino acid residue at position 73 is selected from N, S, P and Q;
the amino acid residue at position 74 is selected from A or S;
the amino acid residue at position 83 is selected from K or R;
the amino acid residue at position 89 is selected from T, V, I or L;
the amino acid residue at position 100a is selected from W and F;
the amino acid residue at position 110 is selected from T, K or Q; and/or
the amino acid residue at position 112 is selected from S, K or Q;

for example, wherein the PD1 binder comprises one or more of the following mutations:
(i) position 1 is D or E;
(ii) position 11 is V;
(iii) position 14 is P;
(iv) position 52a is V;
(v) position 73 is P, S or Q;
(vi) position 74 is S;
(vii) position 83 is R;

(viii) position 89 is T or L;
(ix) position 100a is F;
for example, comprising a set of mutations as follows:
a. position 1 is D or E, position 11 is V, position 14 is P, position 74 is S, position 83 is R; and position 89 is L;
b. position 1 is D or E, position 11 is V, position 14 is P, position 52a is V; position 73 is S, P or Q; position 74 is S, position 83 is R; position 89 is L; and position 100a is F;
c. position 89 is L and position 11 is V;
d. position 89 is L and position 110 is K or Q;
e. position 89 is L and position 112 is K or Q;
f. position 1 is D or E, position 11 is V, position 14 is P, position 52a is V; position 73 is S, P or Q; position 74 is S, position 83 is R; position 89 is L; position 100a is F and position 110 is K or Q;
g. position 1 is D or E, position 11 is V, position 14 is P, position 52a is V; position 73 is S, P or Q; position 74 is S, position 83 is R; position 89 is L; position 100a is F and position 112 is K or Q;
h. position 89 is L and position 11 is V and position 110 is K or Q;
i. position 89 is L and position 11 is V and position 112 is K or Q;
j. position 11 is V and position 110 is K or Q; and/or
k. position 11 is V and position 112 is K or Q;
relative to the amino acid sequence of SEQ ID NO: 1 or 2

In particular embodiments, the PD1 binders (e.g., an ISVD such as a Nanobody) of the invention comprise amino acid sequences that are variants of SEQ ID NO: 1 or SEQ ID NO: 2 in which position 89 is T or L, or in which 1 is D or E, 11 is V, 14 is P, 74 is S, 83 is R and 89 is L or in which position 11 is V and position 89 is L (optionally in suitable combination with a 110K or 110Q mutation and/or a 112K or 112Q mutation, and in particular in combination with a 110K or 110Q mutation) are also part of the present invention. The present invention includes amino acid sequences in which position 11 is V and position 89 is L, optionally with a 110K or 110Q mutation.

As mentioned, the PD1 binders provided by the invention described herein can bind (and in particular, can specifically bind) to PD-1. In an embodiment of the invention, they can bind to PD1 and inhibit binding between PD1 and PD-L1 and/or PD-L2. For example, in an embodiment of the invention, the PD1 binders of the present invention, binds to PD-1 and releases T-cells from PD-1 pathway-mediated inhibition of the T-cell mediated immune response (e.g., by releasing the T-cells from PD1 mediated inhibition of proliferation and cytokine production)

Table B lists some non-limiting possible combinations of the amino acid residues that can be present at positions 11, 89, 110 and 112 in the PD1 binders of the invention.

TABLE B

Possible Combinations of Mutations at Amino Acid Positions 11, 89, 110 and 112 in PD1 Binder Variants of SEQ ID NOs: 1 or 2.

| COM-BINATION | POSITION | | | | COM-BINATION | POSITION | | | |
|---|---|---|---|---|---|---|---|---|---|
| | 11 | 89 | 110 | 112 | | 11 | 89 | 110 | 112 |
| | L | T | T | S | | V | T | T | S |
| | L | T | T | K | | V | T | T | K |
| | L | T | T | Q | | V | T | T | Q |
| | L | T | K | S | | V | T | K | S |
| | L | T | Q | S | | V | T | Q | S |
| | L | V | T | K | | V | V | T | K |
| | L | V | T | Q | | V | V | T | Q |
| | L | V | K | S | | V | V | K | S |

TABLE B-continued

Possible Combinations of Mutations at Amino Acid Positions 11, 89, 110 and 112 in PD1 Binder Variants of SEQ ID NOs: 1 or 2.

| L | V | Q | S | V | V | Q | S |
|---|---|---|---|---|---|---|---|
| L | I | T | K | V | I | T | K |
| L | I | T | Q | V | I | T | Q |
| L | I | K | S | V | I | K | S |
| L | I | Q | S | v | I | Q | S |
| | | | | V | L | T | S |
| L | L | T | K | V | L | T | K |
| L | L | T | Q | V | L | T | Q |
| L | L | K | S | V | L | K | S |
| L | L | Q | S | V | L | Q | S |

These positions may be combined with the mutations such as E1D, A14P, A74S and/or K83R (and/or others).

The PD1 binders provided by the invention are further as described in the description, examples and figures herein, i.e. they have CDRs that are as described herein and have an overall degree of sequence identity (as defined herein) with the sequence of SEQ ID NO: 1 or 2 that is as disclosed herein and/or may have a limited number of "amino acid differences" (as described herein) with (one of) these reference sequences.

The PD1 binders (e.g., ISVDs such as Nanobodies) of the invention that comprise the amino acid sequence of SEQ ID NO:1 or 2 and one or more mutations at position 1, 11, 14, 52a, 73, 74, 83, 89, 100a, 110 and/or 112 preferably include the following CDRs (according to the Kabat convention):

a CDR1 (according to Kabat) that is the amino acid sequence IHAMG (SEQ ID NO: 3); and a CDR2 (according to Kabat) that is the amino acid sequence VITXSGGITYYADSVKG (SEQ ID NO: 4; wherein X is W or V); and a CDR3 (according to Kabat) that is the amino acid sequence DKHQSSXYDY (SEQ ID NO: 5, wherein X is W or F); optionally, wherein CDR1, CDR2 and/or CDR3 has 1, 2, 3, 4, 5, 6, 7, 8, 9 or 10 substitutions, e.g., conservative substitutions.

Alternatively, when the CDRs are given according to the Abm convention, the PD1 binders (e.g., ISVDs such as Nanobodies) of the invention preferably comprise the following CDRs:

a CDR1 (according to Abm) that is the amino acid sequence GSIASIHAMG (SEQ ID NO: 6); and a CDR2 (according to Abm) that is the amino acid sequence VITXSGGITY (SEQ ID NO: 7, wherein X is W or V); and a CDR3 (according to Abm) that is the amino acid sequence DKHQSSXYDY (SEQ ID NO: 8, which is the same as SEQ ID NO: 5; wherein X is W or F); optionally, wherein CDR1, CDR2 and/or CDR3 has 1, 2, 3, 4, 5, 6, 7, 8, 9 or 10 substitutions, e.g., conservative substitutions.

A PD1 binder (e.g., ISVDs such as Nanobodies) of the invention, in addition to the CDR1, CDR2 and CDR3 set forth above, preferably also has:

a degree of sequence identity with the amino acid sequence of SEQ ID NO: 1 or 2 of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or no more than 7, such as no more than 5, preferably no more than 3, such as only 3, 2 or 1 "amino acid differences" with the amino acid sequence of SEQ ID NO: 1 or 2 (in which said amino acid differences, if present, may be present in the frameworks and/or the CDRs but are preferably present only in the frameworks and not in the CDRs; not taking into account any C-terminal extension that may be present and not taking into account the mutations at positions 1, 11, 14, 52a, 73, 74, 83, 89, 100a, 110 and/or 112 required by the specific aspect involved).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

With regards to the various aspects and preferred aspects of the PD1 binders (e.g., ISVD such as a Nanobody) of the invention provided by the invention, when it comes to the degree of overall sequence identity with respect to SEQ ID NO: 1 or 2 and/or the number and kind of "amino acid differences" that may be present in such a binder of the invention (i.e. compared to the sequence of SEQ ID NO: 1 or 2), it should be noted that, unless otherwise stated, when it is said that (i) an amino acid sequence of the invention has a degree of sequence identity with the sequence of SEQ ID NO: 1 or 2 of at least 85%, preferably at least 90%, more preferably at least 95% (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity); and/or when it is said that (ii) an amino acid sequence of the invention has no more than 7, preferably no more than 5, such as only 3, 2 or 1 "amino acid differences" with the sequence of SEQ ID NO: 1 or 2 (again, not taking into account any C-terminal extension that may be present and not taking into account the mutations at positions 1, 11, 14, 52a, 73, 74, 83, 89, 100a, 110 and/or 112 required by the specific aspect involved), then this also includes sequences that have no amino acid differences with the sequence of SEQ ID NO: 1 or 2 other than the mutations at positions 1, 11, 14, 52a, 73, 74, 83, 89, 100a, 110 and/or 112 (as required by the specific aspect involved) and any C-terminal extension that may be present.

Thus, in one specific aspect of the invention, the PD1 binders of the invention comprising the amino acid sequence of SEQ ID NO: 1 or 2, but with at least one amino acid mutation at position 1, 11, 14, 52a, 73, 74, 83, 89, 100a, 110 and/or 112, may have 100% sequence identity with SEQ ID NO: 1 or 2 (including a CDR1, CDR2 and CDR3 thereof optionally comprising a W52aV and/or W100aF mutation, but not taking into account the mutation(s) or combination of mutations at positions 1, 11, 14, 52a, 73, 74, 83, 89, 100a, 110 and/or 112 disclosed herein and/or any C-terminal extension that may be present) and/or may have no amino acid differences with SEQ ID NO: 1 or 2 (i.e. other than the mutation(s) or combination of mutations at positions 1, 11, 14, 52a, 73, 74, 83, 89, 100a, 110 and/or 112 disclosed herein and any C-terminal extension that may be present).

When any amino acid differences are present (i.e. besides any C-terminal extension and the mutations at positions 1, 11, 14, 52a, 73, 74, 83, 89, 100a, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the PD1 binders of the invention have the same CDRs (defined according to the Abm convention) as are present in SEQ ID NO: 1, 2, 9-40, 57, 98, 99, 101, 102, 103, 104 or 105.

Also, when a PD1 binder of the invention according to any aspect of the invention has one or more amino acid differences with the sequence of SEQ ID NO: 1 or 2 (besides the mutations at positions 1, 11, 14, 52a, 73, 74, 83, 89, 100a, 110 and/or 112 that are required by the specific aspect involved), then some specific, but non-limiting examples of such mutations/amino acid differences that may be present (i.e. compared to the sequences of SEQ ID NO: 1 or 2) are for example "humanizing" substitutions; reference is for example made to WO 09/138519 (or in the prior art cited in WO 09/138519) and WO 08/020079 (or in the prior art cited in WO 08/020079), as well as Tables A-3 to A-8 from WO 08/020079 (which are lists showing possible humanizing substitutions).

Also, when the PD-1 binders of the invention are present at and/or form the N-terminal part of the polypeptide in which they are present, then they preferably contain a D at position 1 (i.e. an E1D mutation compared to Reference A). A preferred but non-limiting example of such an N-terminal PD-1 binder is given as SEQ ID NOs: 24 or 57. Accordingly, in a further aspect, the invention relates to a polypeptide (which is as further described herein) that has a PD-1 binder (which is as further described herein) at its N-terminal end, wherein said PD-1 binder has a D at position 1, and is for example SEQ ID NOs: 24, 25, 57 or 101-105.

Similarly, when a PD-1 binder of the invention is used in monovalent format, it preferably has both a C-terminal extension X(n) as described herein and a D at position 1. A preferred but non-limiting example of such a monovalent PD-1 binder is given as SEQ ID NO: 40. Accordingly, in a further aspect, the invention relates to a monovalent PD-1 binder of the invention (which is as further described herein) that has a D at position 1 and a C-terminal extension X(n) (which is preferably a single Ala residue). In one specific aspect, said monovalent PD-1 binder is SEQ ID NO: 40, 101 or 102.

By means of preferred, but non-limiting examples, SEQ ID NOs: 23, 24, 39, 40 and 57 are examples of PD-1 binders of the invention having amino acid differences with SEQ ID NO: 1 or 2 such as A14P, A74S and/or K83R (in addition, as indicated in the previous paragraphs, SEQ ID NOs: 24 and 40 and 57 also have a E1D mutation). Thus, in a specific aspect, the invention relates to PD-1 binders of the invention (i.e. having mutations at positions 11, 89, 110 and/or 112 as described herein and also further being as described herein) that at least have a suitable combination of an optional E1D mutation, an A14P mutation, an A74S mutation, a K83R mutation and/or I89L mutation and, preferably, a suitable combination of any two of these mutations, such as all of these mutations.

The PD1 binders of the invention, when they are used in a monovalent format and/or when they are present at and/or form the C-terminal end of the polypeptide in which they are present (or when they otherwise have an "exposed" C-terminal end in such polypeptide by which is generally meant that the C-terminal end of the ISVD is not associated with or linked to a constant domain (such as a CH1 domain)); (see WO 12/175741 and PCT/EP2015/060643 (WO2015/173325)), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as follows:
(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);
with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a PD1 binder of the invention does not contain a (free) cysteine residue (unless said cysteine residue is used or intended for further functionalization, for example for PEGylation).

Some specific, but non-limiting examples of useful C-terminal extensions are the following amino acid sequences: A, AA, AAA, G, GG, GGG, AG, GA, AAG, AGG, AGA, GGA, GAA or GAG.

When the PD1 binders of the invention contain mutations at positions 110 or 112 (optionally in combination with mutations at position 1, 11, 14, 52a, 73, 74, 83, 89 and/or 100a as described herein), the C-terminal amino acid residues of framework 4 (starting from position 109) can, in an embodiment of the invention be as set forth in SEQ ID NO: 1, 2, 9-40, 57, 100, 101, 103, 104, 105, 106 or 107 but wherein the 5 C-terminal residues can be substituted as follows:
(i) if no C-terminal extension is present: VTVKS (SEQ ID NO: 42), VTVQS (SEQ ID NO: 43), VKVKS (SEQ ID NO: 44) or VQVSS (SEQ ID NO: 45); or
(ii) if a C-terminal extension is present: VTVKSX$_{(n)}$ (SEQ ID NO: 46), VTVQSX(n) (SEQ ID NO: 47), VKVSSX(n) (SEQ ID NO: 48) or VQVSSX$_{(n)}$ (SEQ ID NO: 49), such as VTVKSA (SEQ ID NO: 50), VTVQSA (SEQ ID NO: 51), VKVSSA (SEQ ID NO: 52) or VQVSSA (SEQ ID NO: 53).

When the PD1 binders of the invention contain or, alternatively, do not contain mutations at positions 110 or 112 (but only mutations at position 1, 11, 14, 52a, 73, 74, 83, 89 and/or 100a as described herein), the C-terminal amino acid residues of framework 4 (starting from position 109) can, in an embodiment of the invention be as set forth in SEQ ID NO: 1, 2, 9-40, 57, 98, 99, 101, 102, 103, 104 or 105 but wherein the 5 C-terminal residues can be substituted as follows:
(i) when no C-terminal extension is present: VTVSS (SEQ ID NO: 54) (as in the sequence of SEQ ID NO: 1 or 2); or
(ii) when a C-terminal extension is present: VTVSSX$_{(n)}$ (SEQ ID NO: 55) such as VTVSSA (SEQ ID NO: 56). In these C-terminal sequences, X and n are as defined herein for the C-terminal extensions.

Some preferred but non-limiting examples of PD1 binders of the invention are given in SEQ ID NOs: 9-40, 57, 98, 99, 101, 102, 103, 104 or 105 and each of these sequences forms a further aspect of the invention. Of these, the PD1 binders of SEQ ID NOs: 9-24, 57, 98, 99, 103, 104 and 105 do not have a C-terminal extension, and the PD1 binders of SEQ ID NOs: 25-40, 101 and 102 contain a C-terminal alanine (which is a preferred but non-limiting example of a C-terminal extension as described herein).

Examples of PD1 binders of the present invention comprise the amino acid sequence set forth in SEQ ID NO: 23, 24, 39, 40, 57, 98, 99, 101, 102, 103, 104 or 105.

Thus, in an embodiment of the invention, a PD1 binder (e.g., an ISVD such as a Nanobody) comprises:
- a CDR1 (according to Kabat) that is the amino acid sequence IHAMG (SEQ ID NO: 3); and
- a CDR2 (according to Kabat) that is the amino acid sequence VITXSGGITYYADSVKG (SEQ ID NO: 4; wherein X is W or V); and
- a CDR3 (according to Kabat) that is the amino acid sequence DKHQSSXYDY (SEQ ID NO: 5, wherein X is W or F);

and also has:
- a degree of sequence identity with the amino acid sequence of SEQ ID NO: 1 or 2 of at least 85%, preferably at least 90%, more preferably at least 95% (e.g., 100%) (in which the CDRs thereof, optionally comprising a W52aV and/or W100aF mutation, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);

and/or
- no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and optionally has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which, in an embodiment of the invention:
- the amino acid residue at position 1 is E or D;
- the amino acid residue at position 11 is L or V;
- the amino acid residue at position 14 is A or P;
- the amino acid residue at position 52a is W or V;
- the amino acid residue at position 73 is N, S, P or Q;
- the amino acid residue at position 74 is A or S;
- the amino acid residue at position 83 is K or R;
- the amino acid residue at position 89 is T, V, I or L;
- the amino acid residue at position 100a is W or F;
- the amino acid residue at position 110 is T, K or Q; and
- the amino acid residue at position 112 is S, K or Q;

for example, wherein the PD1 binder comprises one or more of the following mutations:
  (i) position 1 is E or D;
  (ii) position 11 is V;
  (iii) position 14 is P;
  (iv) position 52a is V;
  (v) position 73 is S, P or Q;
  (vi) position 74 is S;
  (vii) position 83 is R;
  (viii) position 89 is L;
  (ix) position 100a is F;

for example, comprising a set of mutations as follows:
a. position 1 is D or E, position 11 is V, position 14 is P, position 74 is S, position 83 is R and position 89 is L;
b. position 1 is D or E, position 11 is V, position 14 is P, position 52a is V; position 73 is S, P or Q; position 74 is S, position 83 is R, position 89 is L and position 100a is F;
c. position 1 is D or E, position 11 is V, position 14 is P, position 74 is S, position 83 is R and position 89 is L;
d. position 89 is L and position 11 is V;
e. position 89 is L and position 110 is K or Q;
f. position 89 is L and position 112 is K or Q;
g. position 89 is L and position 11 is V and position 110 is K or Q;
h. position 89 is L and position 11 is V and position 112 is K or Q;
i. 110K or 110Q in combination with 11V, 14P, 52aV, 73S or 73Q or 73P, 74S, 83R, 89L and 100aF, and optionally, 1D or 1E; or in combination with 11V, 14P, 74S, 83R, 89L and optionally, 1D or 1E;
j. 112K or 112Q in combination with 11V, 14P, 52aV, 73S or 73Q or 73P, 74S, 83R, 89L and 100a F and, optionally, 1D or 1E; or in combination with 11V, 14P, 74S, 83R, 89L and optionally, 1D or 1E;
k. position 11 is V and position 110 is K or Q; or
l. position 11 is V and position 112 is K or Q.

In a further aspect, the invention relates to a PD1 binder (e.g., an ISVD such as a Nanobody) having:
- a CDR1 (according to Kabat) that is the amino acid sequence IHAMG (SEQ ID NO: 3); and
- a CDR2 (according to Kabat) that is the amino acid sequence VITXSGGITYYADSVKG (SEQ ID NO: 4; wherein X is W or V); and
- a CDR3 (according to Kabat) that is the amino acid sequence DKHQSSXYDY (SEQ ID NO: 5, wherein X is W or F);

and also having:
- a degree of sequence identity with the amino acid sequence of SEQ ID NO: 1 or 2 (in which any C-terminal extension that may be present as well as the CDRs thereof, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);

and/or
- no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and optionally having:
  a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

which PD1 binder (e.g., an ISVD such as a Nanobody) comprises, in an embodiment of the invention, one or more of the following amino acid residues (i.e. mutations compared to the amino acid sequence of SEQ ID NO: 1 or 2) at the positions mentioned (numbering according to Kabat):
  1D or 1E;
  11V;
  14P;
  52aV;
  73Q, 73P or 73S;
  74S;
  83R;
  89T or 89L; or
  100aF;

for example, comprising a set of mutations as follows:
  1D or 1E in combination with 11V, 14P, 52aV, 73S or 73Q or 73P, 74S, 83R, 89L and/or 100aF;
  1D or 1E in combination with 11V, 14P, 74S, 83R and/or 89L;
  89L in combination with 11V;
  89L in combination with 110K or 110Q;
  89L in combination with 112K or 112Q;
  89L in combination with 11V, 14P, 74S, 83R and 1D and 1E;
  110K or 110Q in combination with 11V, 14P, 52aV, 73S or 73Q or 73P, 74S, 83R, 89L and/or 100aF and 1D or 1E;
  112K or 112Q in combination with 11V, 14P, 52aV, 73S or 73Q or 73P, 74S, 83R, 89L and/or 100aF and 1D or 1E;
  110K or 110Q in combination with 11V, 14P, 74S, 83R, 89L and/or 1D or 1E;
  112K or 112Q in combination with 11V, 14P, 74S, 83R, 89L and/or 1D or 1E;
  89L in combination with 11V and 110K or 110Q;
  89L in combination with 11V and 112K or 112Q;
  11V in combination with 110K or 110Q; or
  11V in combination with 112K or 112Q.

As mentioned, when a PD1 binder (e.g., an ISVD such as a Nanobody) of the invention is used in a monovalent format and/or is present at the C-terminal end of a polypeptide (as defined herein), the PD1 binder preferably has a C-terminal extension X(n), which C-terminal extension may be as described herein for the PD1 binders of the invention and/or as described in WO 12/175741 or PCT/EP2015/060643 (WO2015/173325).

Some preferred, but non-limiting examples of PD1 binders (e.g., an ISVD such as a Nanobody) of the invention are given in SEQ ID NOs: 9-40, 57, 98, 99, 101, 102, 103, 104 and 105 and each of these amino acid sequences individually forms a further aspect of the invention.

As mentioned, the invention includes PD1 binders comprising amino acid sequences of SEQ ID NO: 1 or 2 but wherein position 89 is T; or in which position 1 is E or D, position 11 is V, position 14 is P, position 52a is V, position 73 is P, S or Q, position 74 is S, position 83 is R, position 89 is L and/or positon 100a is F; or in which position 11 is V and position 89 is L (optionally in suitable combination with a 110K or 110Q mutation and/or a 112K or 112Q mutation, and in particular in combination with a 110K or 110Q mutation). In an embodiment of the invention, the amino acid sequences in which position 11 is V and position 89 is L, optionally with a 110K or 110Q mutation.

Thus, in one preferred aspect, the invention relates to a PD1 binder (e.g., an immunoglobulin single variable domain (ISVD) such as a Nanobody) having:
  a CDR1 (according to Kabat) that is the amino acid sequence IHAMG (SEQ ID NO: 3); and
  a CDR2 (according to Kabat) that is the amino acid sequence VITXSGGITYYADSVKG (SEQ ID NO: 4; wherein X is W or V); and
  a CDR3 (according to Kabat) that is the amino acid sequence DKHQSSXYDY (SEQ ID NO: 5, wherein X is W or F);

and also having:
  a degree of sequence identity with the amino acid sequence of SEQ ID NO: 1 or 2 (in which any C-terminal extension that may be present as well as the CDRs thereof, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);

and/or
  no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and optionally having:
  a C-terminal extension (X) n, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

wherein, in an embodiment of the invention:
  the amino acid at position 1 is E or D;
  the amino acid at position 11 is L or V;
  the amino acid at position 14 is A or P;
  the amino acid at position 52a is W or V;
  the amino acid at position 73 is N, S, P or Q;
  the amino acid at position 74 is A or S;
  the amino acid at position 83 is K or R;
  the amino acid at position 89 is I, T or L;
  the amino acid at position 100a is W or F;

the amino acid residue at position 110 is T, K or Q (and is preferably T); and the amino acid residue at position 112 is S, K or Q (and is preferably S).

In another preferred aspect, the invention relates to a PD1 binder (e.g., an immunoglobulin single variable domain (ISVD) such as a Nanobody) having:

a CDR1 (according to Kabat) that is the amino acid sequence IHAMG (SEQ ID NO: 3); and a CDR2 (according to Kabat) that is the amino acid sequence VITXSGGITYYADSVKG (SEQ ID NO: 4; wherein X is W or V); and a CDR3 (according to Kabat) that is the amino acid sequence DKHQSSXYDY (SEQ ID NO: 5, wherein X is W or F);

and having:

a degree of sequence identity with the amino acid sequence of SEQ ID NO: 1 or 2 (in which any C-terminal extension that may be present as well as the CDRs thereof, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);

and/or no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which one or more of the following is true:
the amino acid at position 1 is E or D;
the amino acid at position 11 is L or V;
the amino acid at position 14 is A or P;
the amino acid at position 52a is W or V;
the amino acid at position 73 is S, P, N or Q;
the amino acid at position 74 is A or S;
the amino acid at position 83 is K or R;
the amino acid at position 89 is I, T or L;
the amino acid at position 100a is W or F;
the amino acid residue at position 110 is T, K or Q (and is preferably T); or
the amino acid residue at position 112 is S, K or Q (and is preferably S).

In one specific, but non-limiting aspect, the PD1 binders (e.g., an ISVD such as a Nanobody) of the invention comprise one or more of the following amino acid residues (i.e. mutations compared to the sequence of SEQ ID NO: 1 or 2) at the positions mentioned (numbering according to Kabat):

11V in combination with 89L;
11V in combination with 14P, 52aV, 73S or 73Q or 73P, 74S, 83R, 89L and/or 100aF and, optionally, 1D;
11V in combination with 14P, 74S, 83R, 89L and 1D or 1E;
11V in combination with 110K or 110Q;
11V in combination with 112K or 112Q;
11V in combination with 14P, 52aV, 73S or 73Q or 73P, 74S, 83R, 89L, 100aF, 110K or 110Q and/or 1D or 1E;
11V in combination with 14P, 52aV, 73S or 73Q or 73P, 74S, 83R, 89L, 100aF, 112K or 112Q and/or 1D or 1E;
11V in combination with 89L and 110K or 110Q;
11V in combination with 89L and 112K or 112Q; or
11V in combination with 1D or 1E, 14P, 52aV, 73S or 73Q or 73P, 74S, 83R, 89L and/or 100aF;

and have CDRs that are the same as the CDRs that are present in the sequence of SEQ ID NO: 9-40, 57, 98, 99, 101, 102, 103, 104 or 105 (e.g., according to Kabat) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one or more of the following amino acid residues (i.e. mutations compared to the sequence of SEQ ID NO: 1 or 2) at the positions mentioned (numbering according to Kabat):

89L in combination with 11V;
89L in combination with 11V, 14P, 52aV, 73S or 73Q or 73P, 74S, 83R, 100aF and/or 1D or 1E;
89L in combination with 11V, 14P, 74S, 83R, and/or 1D or 1E;
89L in combination with 110K or 110Q;
89L in combination with 112K or 112Q;
89L in combination with 11V, 14P, 52aV, 73S or 73Q or 73P, 74S, 83R, 100aF, 110K or 110Q and/or 1D or 1E;
89L in combination with 11V, 14P, 52aV, 73S or 73Q or 73P, 74S, 83R, 100aF, 112K or 112Q and/or 1D or 1E;
89L in combination with 11V, 14P, 74S, 83R, 110K or 110Q and/or 1D or 1E;
89L in combination with 11V, 14P, 74S, 83R, 112K or 112Q and/or 1D or 1E;
89L in combination with 11V and 110K or 110Q; or
89L in combination with 11V and 112K or 112Q;

and have CDRs that are the same as the CDRs that are present in the sequence of SEQ ID NO: 9-40, 57, 98, 99, 101, 102, 103, 104 or 105 (e.g., according to Kabat) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one or more of the following amino acid residues (i.e. mutations compared to the sequence of SEQ ID NO: 1 or 2) at the positions mentioned (numbering according to Kabat):

110K or 110Q in combination with 1D;
110K or 110Q in combination with 1E;
110K or 110Q in combination with 11V;
110K or 110Q in combination with 14P;
110K or 110Q in combination with 52aV;
110K or 110Q in combination with 73S or 73Q or 73P;
110K or 110Q in combination with 74S;
110K or 110Q in combination with 83R;

110K or 110Q in combination with 89L;
110K or 110Q in combination with 100aF;
110K or 110Q in combination with 11V, 14P, 52aV, 73S or 73Q or 73P, 74S, 83R, 89L, 100aF and/or 1D or 1E;
110K or 110Q in combination with 11V, 14P, 74S, 83R, 89L and/or 1D or 1E;
110K or 110Q in combination with 89L; or
110K or 110Q in combination with 11V and 89L;

and have CDRs that are the same as the CDRs that are present in the sequence of SEQ ID NO: 9-40, 57, 98, 99, 101, 102, 103, 104 or 105 (e.g., according to Kabat) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one or more of the following amino acid residues (i.e. mutations compared to the sequence of SEQ ID NO: 1 or 2) at the positions mentioned (numbering according to Kabat):
112K or 112Q in combination with 1D or 1E;
112K or 112Q in combination with 11V;
112K or 112Q in combination with 14P;
112K or 112Q in combination with 52aV;
112K or 112Q in combination with 73S or 73Q or 73P;
112K or 112Q in combination with 74S;
112K or 112Q in combination with 83R;
112K or 112Q in combination with 89L;
112K or 112Q in combination with 100aF;
112K or 112Q in combination with 11V, 14P, 52aV, 73S or 73Q or 73P, 74S, 83R, 89L, 100aF and/or 1D or 1E;
112K or 112Q in combination with 11V, 14P, 74S, 83R, 89L and/or 1D or 1E; or
112K or 112Q in combination with 11V and 89L;

and have CDRs that are the same as the CDRs that are present in the sequence of SEQ ID NO: 9-40, 57, 98, 99, 101, 102, 103, 104 or 105 (e.g., according to Kabat) and have an overall degree of sequence identity with the amino acid sequence of SEQ ID NO: 1 or 2 that are as described herein.

In another aspect, the PD1 binders (e.g., an ISVD such as a Nanobody) of the invention comprise a T at position 89 and have CDRs that are the same as the CDRs that are present in the sequence of SEQ ID NO: 9-40, 57, 98, 99, 101, 102, 103, 104 or 105 (e.g., according to Kabat) and have an overall degree of sequence identity with the amino acid sequence of SEQ ID NO: 1 or 2 that are as described herein.

In another aspect, the PD1 binders (e.g., an ISVD such as a Nanobody) of the invention comprise a V at position 11 and an L at position 89 and have CDRs that are the same as the CDRs that are present in the sequence of SEQ ID NO: 9-40, 57, 100, 101, 102 103, 104 or 105 (e.g., according to Kabat) and have an overall degree of sequence identity with the amino acid sequence of SEQ ID NO: 1 or 2 that are as described herein.

As mentioned, the PD1 binders (e.g., an ISVD such as a Nanobody) of the invention according to the above aspects are preferably further such that they contain a suitable combination of an A14P mutation, an A74S mutation and/or a K83R mutation, and preferably a suitable combination of any two of these mutations, such as all three of these mutations (e.g., E1D (optionally), L11V, A14P, W52aV, N73S or N73Q or N73P, A74S, K83R, I89L and W100aF). When a LAG3 or HSA binder is present at the N-terminal end of a PD1 binder of the present invention, the N-terminal binding moiety preferably has an E1D mutation.

In another aspect, the invention relates to a PD1 binder (e.g., an immunoglobulin single variable domain (ISVD) such as a Nanobody) having:
a CDR1 (according to Abm) that is the amino acid sequence GSIASIHAMG (SEQ ID NO: 6); and
a CDR2 (according to Abm) that is the amino acid sequence VITXSGGITY (SEQ ID NO: 7, wherein X is W or V); and
a CDR3 (according to Abm) that is the amino acid sequence DKHQSSXYDY (SEQ ID NO: 5, wherein X is W or F);

and also having:
a degree of sequence identity with the amino acid sequence of SEQ ID NO: 1 or 2 (in which any C-terminal extension that may be present as well as the CDRs, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);

and/or
no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and optionally having:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

wherein, in an embodiment of the invention:
the amino acid at position 1 is E or D;
the amino acid at position 11 is L or V;
the amino acid at position 14 is A or P;
the amino acid at position 52a is W or V;
the amino acid at position 73 is N, S, P or Q;
the amino acid at position 74 is A or S;
the amino acid at position 83 is K or R;
the amino acid at position 89 is V, I, T or L;
the amino acid residue at position 89 is T;
the amino acid at position 100a is W and F;
the amino acid residue at position 110 is T, K or Q (and is preferably T); and
the amino acid residue at position 112 is S, K or Q (and is preferably S) for example, in an embodiment of the invention, the PD1 binder comprises one or more of the following mutations:
(i) position 1 is D or E;
(ii) position 11 is V;
(iii) position 14 is P;
(iv) position 52a is V;
(v) position 73 is Q, P or S;

(vi) position 74 is S;
(vii) position 83 is R;
(viii) position 89 is L or T;
(ix) position 100a is F;
for example, comprising a set of mutations as follows:
  a. position 11 is V; position 14 is P; position 52a is V; position 73 is P, S or Q; position 74 is S; position 83 is R; position 89 is L; position 100a is F; and, optionally, position 1 is E or D;
  b. position 11 is V; position 14 is P; position 74 is S; position 83 is R; position 89 is L; and, optionally, position 1 is E or D;
  c. position 89 is L and position 11 is V;
  d. position 89 is L and position 110 is K or Q;
  e. position 89 is L and position 112 is K or Q;
  f. position 11 is V; position 14 is P; position 52a is V; position 73 is P, S or Q; position 74 is S; position 83 is R; position 89 is L; position 100a is F; position 110 is K or Q and, optionally, position 1 is E or D;
  g. position 11 is V; position 14 is P; position 52a is V; position 73 is S, P or Q; position 74 is S; position 83 is R; position 89 is L; position 100a is F; position 112 is K or Q and, optionally, position 1 is E or D;
  h. position 11 is V; position 14 is P; position 74 is S; position 83 is R; position 89 is L; position 110 is K or Q and, optionally, position 1 is E or D;
  i. position 11 is V; position 14 is P; position 74 is S; position 83 is R; position 89 is L; position 112 is K or Q and, optionally, position 1 is E or D;
  j. position 89 is L and position 11 is V and position 110 is K or Q;
  k. position 89 is L and position 11 is V and position 112 is K or Q;
  l. position 11 is V and position 110 is K or Q; or
  m. position 11 is V and position 112 is K or Q.

In a further aspect, the invention relates to a PD1 binder (e.g., an immunoglobulin single variable domain (ISVD) such as a Nanobody) having:
  a CDR1 (according to Abm) that is the amino acid sequence GSIASIHAMG (SEQ ID NO: 6); and
  a CDR2 (according to Abm) that is the amino acid sequence VITXSGGITY (SEQ ID NO: 7, wherein X is W or V); and
  a CDR3 (according to Abm) that is the amino acid sequence DKHQSSXYDY (SEQ ID NO: 5, wherein X is W or F);
and also having:
  a degree of sequence identity with the amino acid sequence of SEQ ID NO: 1 or 2 (in which any C-terminal extension that may be present as well as the CDRs, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);
and/or
  no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);
and optionally having:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
which immunoglobulin single variable domain comprises one or more of the following amino acid residues (i.e. mutations compared to the amino acid sequence of SEQ ID NO: 1 or 2) at the positions mentioned (numbering according to Kabat):
  1D or 1E;
  11V;
  14P;
  52aV;
  73Q, 73S or 73P;
  74S;
  83R;
  89L or 89T; or
  100aF;
for example, comprising a set of mutations as follows:
  89T or 89L in combination with 11V, 14P, 52aV, 73S or 73Q or 73P, 74S, 83R, 100aF or 1E or 1D;
  89T or 89L in combination with 11V, 14P, 74S, 83R, or 1E or 1D;
  89L in combination with 11V;
  89L in combination with 110K or 110Q;
  89L in combination with 112K or 112Q;
  89L in combination with 11V, 14P, 74S, 83R, 110K or 110Q or 1E or 1D;
  89L in combination with 11V, 14P, 74S, 83R, 112K or 112Q or 1E or 1D;
  89L in combination with 11V, 14P, 52aV, 73S or 73Q or 73P, 74S, 83R, 100aF, 110K or 110Q or 1E or 1D;
  89L in combination with 11V, 14P, 52aV, 73S or 73Q or 73P, 74S, 83R, 100aF, 112K or 112Q or 1E or 1D;
  89L in combination with 11V and 110K or 110Q;
  89L in combination with 11V and 112K or 112Q;
  11V in combination with 110K or 110Q; or
  11V in combination with 112K or 112Q.

As mentioned, when a PD1 binder (e.g., an ISVD such as a Nanobody) of the invention is used in a monovalent format and/or wherein the moiety that binds to PD1 is present at the C-terminal end of a polypeptide (as defined herein), the PD1 binding moiety preferably has a C-terminal extension X(n), which C-terminal extension may be as described herein for the PD1 binders of the invention and/or as described in WO 12/175741 or PCT/EP2015/060643 (WO2015/173325).

Some preferred, but non-limiting examples of PD1 binders (e.g., an ISVD such as a Nanobody) of the invention are given in SEQ ID NOs: 9 to 40, 57, 98, 99, 101, 102, 103, 104 or 105 and each of these amino acid sequences individually forms a further aspect of the invention.

As mentioned, in the invention, amino acid sequences in which position 89 is T; or in which in which position 1 is E or D, position 11 is V, position 14 is P, position 52a is V, position 73 is P, S or Q, position 74 is S, position 83 is R, position 89 is L and/or position 100a is F; or in which position 11 is V and position 89 is L (optionally in suitable combination with a 110K or 110Q mutation and/or a 112K or 112Q mutation, and in particular in combination with a 110K or 110Q mutation) are part of the present invention. In an embodiment of the invention, the amino acid sequence at position 11 is V and position 89 is L, optionally with a 110K or 110Q mutation.

Thus, in one preferred aspect, the invention relates to a PD1 binder (e.g., an immunoglobulin single variable domain (ISVD) such as a Nanobody) having:
  a CDR1 (according to Abm) that is the amino acid sequence GSIASIHAMG (SEQ ID NO: 6); and
  a CDR2 (according to Abm) that is the amino acid sequence VITXSGGITY (SEQ ID NO: 7, wherein X is W or V); and
  a CDR3 (according to Abm) that is the amino acid sequence DKHQSSXYDY (SEQ ID NO: 5, wherein X is W or F);
and also having:
  a degree of sequence identity with the amino acid sequence of SEQ ID NO: 1 or 2 (in which any C-terminal extension that may be present as well as the CDRs, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);
and/or
  no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);
and optionally having:
  a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
in which, in an embodiment of the invention:
  the amino acid residue at position 1 is E or D;
  the amino acid residue at position 11 is L or V;
  the amino acid residue at position 14 is A or P;
  the amino acid residue at position 52a is W or V;
  the amino acid residue at position 73 is S, P, N or Q;
  the amino acid residue at position 74 is A or S;
  the amino acid residue at position 83 is K or R;
  the amino acid residue at position 89 is T, L or I;
  the amino acid residue at position 100a is W or F;
  the amino acid residue at position 110 is T, K or Q (and is preferably T); and
  the amino acid residue at position 112 is S, K or Q (and in preferably S).

In another preferred aspect, the invention relates to a PD1 binder (e.g., an immunoglobulin single variable domain (ISVD) such as a Nanobody) having:
  a CDR1 (according to Abm) that is the amino acid sequence GSIASIHAMG (SEQ ID NO: 6); and
  a CDR2 (according to Abm) that is the amino acid sequence VITXSGGITY (SEQ ID NO: 7, wherein X is W or V); and
  a CDR3 (according to Abm) that is the amino acid sequence DKHQSSXYDY (SEQ ID NO: 5, wherein X is W or F);
and also having:
  a degree of sequence identity with the amino acid sequence of SEQ ID NO: 1 or 2 (in which any C-terminal extension that may be present as well as the CDRs, optionally comprising a W52aV and/or W100aF mutation, are not taken into account for determining the degree of sequence identity) of at least 85%, preferably at least 90%, more preferably at least 95% (e.g., 100%) (in which the CDRs, any C-terminal extension that may be present, as well as the mutations at positions 1, 11, 14, 52a, 73, 74, 83, 89, 100a, 110 and/or 112 required by the specific aspect involved are not taken into account for determining the degree of sequence identity);
and/or
  no more than 7, such as no more than 5, preferably no more than 3, such as only 3, 2 or 1 "amino acid differences" (as defined herein, and not taking into account any of the mutations set forth herein at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);
and optionally having:
  a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
in which, for example, one or more of the following is true:
  the amino acid residue at position 1 is E or D;
  the amino acid residue at position 11 is V;
  the amino acid residue at position 14 is P;
  the amino acid residue at position 52a is V;
  the amino acid residue at position 73 is S, P or Q;
  the amino acid residue at position 74 is S;
  the amino acid residue at position 83 is R;
  the amino acid residue at position 89 is L;
  the amino acid residue at position 100a is F;
  the amino acid residue at position 110 is T, K or Q; or
  the amino acid residue at position 112 is S, K or Q.

In one specific, but non-limiting aspect, the PD1 binders (e.g., an ISVD such as a Nanobody) of the invention comprise one of the following sets of mutations (i.e. mutations compared to the sequence of SEQ ID NO: 1 or 2) at the positions mentioned (numbering according to Kabat):
  11V in combination with 89L;
  11V in combination with 14P, 52aV, 73S or 73Q or 73P, 74S, 83R, 89L, 100aF and 1E or 1D;
  11V in combination with 14P, 74S, 83R, 89L and 1E or 1D;
  11V in combination with 110K or 110Q;
  11V in combination with 112K or 112Q;

11V in combination with 14P, 52aV, 73S or 73Q or 73P, 74S, 83R, 89L, 100aF, 110K or 110Q and 1E or 1D;
11V in combination with 14P, 52aV, 73S or 73Q or 73P, 74S, 83R, 89L, 100aF, 112K or 112Q and 1E or 1D;
11V in combination with 14P, 74S, 83R, 89L, 110K or 110Q and 1E or 1D;
11V in combination with 14P, 74S, 83R, 89L, 112K or 112Q and 1E or 1D;
11V in combination with 89L and 110K or 110Q; or
11V in combination with 89L and 112K or 112Q;

and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one of the following sets of mutations (i.e. mutations compared to the sequence of SEQ ID NO: 1 or 2) at the positions mentioned (numbering according to Kabat):
89L in combination with 11V;
89L in combination with 11V, 14P, 52aV, 73S or 73Q or 73P, 74S, 83R, 100aF and 1E or 1D;
89L in combination with 11V, 14P, 74S, 83R and 1E or 1D;
89L in combination with 110K or 110Q;
89L in combination with 112K or 112Q;
89L in combination with 11V, 14P, 52aV, 73S or 73Q or 73P, 74S, 83R, 100aF, 110K or 110Q and 1E or 1D;
89L in combination with 11V, 14P, 52aV, 73S or 73Q or 73P, 74S, 83R, 100aF, 112K or 112Q and 1E or 1D;
89L in combination with 11V, 14P, 74S, 83R, 110K or 110Q and 1E or 1D;
89L in combination with 11V, 14P, 74S, 83R, 112K or 112Q and 1E or 1D;
89L in combination with 11V and 110K or 110Q; or
89L in combination with 11V and 112K or 112Q;

and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one of the following sets of mutations (i.e. mutations compared to the sequence of SEQ ID NO: 1 or 2) at the positions mentioned (numbering according to Kabat):
110K or 110Q in combination with 11V;
110K or 110Q in combination with 89L;
110K or 110Q in combination with 11V and 89L;
110K or 110Q in combination with 11V, 14P, 52aV, 73S or 73Q or 73P, 74S, 83R, 89L and 100aF, and 1E or 1D;
110K or 110Q in combination with 11V, 14P, 74S, 83R, 89L and 1D; or
110K or 110Q in combination with 11V, 14P, 74S, 83R, 89L, and 1E, and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

In another specific, but non-limiting aspect, the PD1 binders (e.g., an ISVD such as a Nanobody) of the invention comprise one or more of the following sets of mutations (i.e. mutations compared to the sequence of SEQ ID NO: 1 or 2) at the positions mentioned (numbering according to Kabat):
112K or 112Q in combination with 11V;
112K or 112Q in combination with 89L;
112K or 112Q in combination with 11V and 89L;
112K or 112Q in combination with 11V, 14P, 52aV, 73S or 73Q or 73P, 74S, 83R, 89L and 100aF, and 1E or 1D; or
112K or 112Q in combination with 11V, 14P, 74S, 83R, 89L, and 1E or 1D;

and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

In another aspect, the PD1 binders (e.g., an ISVD such as a Nanobody) of the invention comprise a T or L at position 89 and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

In another aspect, the PD1 binders (e.g., an ISVD such as a Nanobody) of the invention comprise a V at position 11 and an L at position 89 and have CDRs that are the same as the CDRs that are present in the sequence of SEQ ID NO: 1, 2, 9-40, 57, 98, 99, 101, 102, 103, 104 or 105 (e.g., according to Abm) and have an overall degree of sequence identity with the amino acid sequence of SEQ ID NO: 1 or 2 that are as described herein.

As mentioned, the PD-1 binders of the invention according to the above aspects are preferably further such that they contain a suitable combination of an E1D mutation, an L11V mutation, an A14P mutation, a W52aV mutation, an N73S or N73Q or N73P mutation, an A74S mutation, a K83R mutation, an I89L mutation and/or a W100aF mutation, and preferably a suitable combination of any two of these mutations, such as all of these mutations. When a PD-1 binder is monovalent or wherein the PD1 binding moiety thereof is present at the N-terminal end of a polypeptide, it preferably also has an E1D mutation.

In another specific, but non-limiting aspect, the invention relates to an immunoglobulin single variable domain that comprises or consists essentially of an amino acid sequence chosen from one of the following amino acid sequences: SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38, SEQ ID NO: 39, SEQ ID NO: 40, SEQ ID NO: 57, SEQ ID NO: 98, SEQ ID NO: 99, SEQ ID NO: 101, SEQ ID NO: 102, SEQ ID NO: 103, SEQ ID NO: 104 or SEQ ID NO: 105.

In another specific, but non-limiting aspect, the invention relates to an immunoglobulin single variable domain that is or essentially consists of an amino acid sequence chosen from one of the following amino acid sequences: SEQ ID NO: 23, SEQ ID NO: 24, SEQ ID NO: 39, SEQ ID NO: 40, SEQ ID NO: 57, SEQ ID NO: 98, SEQ ID NO: 99, SEQ ID NO: 101, SEQ ID NO: 102, SEQ ID NO:103, SEQ ID NO: 104 and SEQ ID NO: 105.

Also, as already indicated herein, the amino acid residues of a PD1 binder (e.g., an ISVD such as a Nanobody) are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. It should be noted that, as is well known in the art for VH domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, according to the numbering of Kabat and irrespective of the number of amino acid residues in the CDRs, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

These and other aspects, embodiments, advantages, applications and uses of the invention will become clear from the further description herein.

Accordingly, in a further aspect, the invention relates to polypeptides or other chemical entities that comprise or essentially consist of at least one (such as one, two or three) PD1 binding moieties described herein.

PD1 binders (e.g., an ISVD such as a Nanobody) of the invention can be fused to one or more other amino acid sequences, chemical entities or moieties. These other amino acid sequences, chemical entities or moieties can confer one or more desired properties to the resulting PD1 binders of the invention and/or can alter the properties of the resulting PD1 binders of the invention in a desired manner, for example to provide the resulting PD1 binders of the invention with a desired biological and/or therapeutic activity (for example, to provide the resulting PD1 binders of the invention with affinity and preferably potency against another therapeutically relevant target such that the resulting polypeptide becomes "bispecific" with respect to PD1 and that other therapeutically relevant target such as CTLA4, LAG3, BTLA or CD27), to provide a desired half-life and/or to otherwise modify or improve pharmacokinetic and/or pharmacodynamic properties, to target the PD1 binder to specific cells, tissues or organs (including cancer cells and cancer tissues), to provide a cytotoxic effect and/or to serve as a detectable tag or label. Some non-limiting examples of such other amino acid sequences, chemical entities or moieties are:

one or more suitable linkers (such as a 9GS, 15GS or 35GS linker (any combination of 9, 15, 20 or 35 G and S amino acids such as, for example, GGGGSGGGS (9GS linker; SEQ ID NO: 125), GGGGSGGGGSGGGGSGGGGS (20GS linker; SEQ ID NO: 100) or GGGGSGGGGSGGGGSGGGGSGGGGSGGGGSGGGS (35GS linker; SEQ ID NO: 58)) or (GGGS)n wherein n is 1, 2, 3, 4, 5, 6, 7, 8, 9 or 10); and/or one or more binding moieties, binding domains or binding units that are directed against a therapeutically relevant target other than PD1 (i.e. so as to provide a PD1 binder (e.g., an ISVD such as a Nanobody) of the invention that is bispecific for both PD1 and the other therapeutically relevant target, for example, against a different epitope of PD1, CD27, LAG3, CTLA4, BTLA, TIM3, ICOS, B7-H3, B7-H4, CD137, GITR, PD-L1, PD-L2, ILT1, ILT2 CEACAM1, CEACAMS, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP); and/or one or more binding domains or binding units that provide for an increase in half-life (for example, a binding domain or binding unit that can bind against a serum protein such as serum albumin, e.g., human serum albumin), e.g., ALB11002; and/or one or more binding domains or binding units that target the PD1 binder (e.g., an ISVD such as a Nanobody) to a desired cell, tissue or organ (such as a cancer cell); and/or one or more binding domains or binding units that provide for increased specificity against PD1 (usually, these will be able to bind to PD1 but will generally by themselves essentially not be functional against PD1); and/or a binding domain, binding unit or other chemical entity that allows for the PD1 binder (e.g., an ISVD such as a Nanobody) to be internalized into a desired cell (for example, an internalizing anti-EGFR Nanobody as described in WO 05/044858); and/or a moiety that improves half-life such as a suitable polyethyleneglycol group (i.e. PEGylation) or an amino acid sequence that provides for increased half-life such as human serum albumin or a suitable fragment thereof (i.e. albumin fusion) or for example a serum albumin binding peptide as described in WO 2008/068280; and/or a payload such as a cytotoxic payload; and/or a detectable label or tag, such as a radiolabel or fluorescent label; and/or a tag that can help with immobilization, detection and/or purification of the PD1 binder (e.g., an ISVD such as a Nanobody), such as a HIS (e.g., HHHHHH; SEQ ID NO: 93 or HHHHHHHHHHHHHHHHHH; SEQ ID NO: 94) or FLAG tag (DYKDDDK (SEQ ID NO: 95)) (e.g., FLAG3); and/or a tag that can be functionalized, such as a C-terminal GGC or GGGC tag; and/or a C-terminal extension X(n) (e.g., -Ala), which may be as further described herein for the PD1 binders (e.g., an ISVD such as a Nanobody) of the invention and/or as described in WO 12/175741 or PCT/EP2015/060643 (WO2015/173325).

The scope of the invention includes PD1 binder (e.g., an ISVD such as a Nanobody) that include one or more parts or fragments of a (preferably human) antibody (such as an Fc part or a functional fragment thereof or one or more constant domains) and/or from a Camelid heavy-chain only antibody (such as one or more constant domains).

LAG3 Binders

The present invention provides improved LAG3 binders, for example, improved anti-LAG3 ISVDs and more in particular improved LAG3 Nanobodies, e.g., 11B09 (L11V, A14P, R41P, N43K, A62S, A74S, K83R, V89L); F0237611B09 (L11V, A14P, R41P, N43K, A62S, A74S, K83R, V89L); F0237611B09 (E1D, L11V, A14P, R41P, N43K, A62S, A74S, K83R, V89L)-35GS-ALB11002-A; or F0237611B09(E1D, L11V, A14P, R41P, N43K, A62S, A74S, K83R, V89L)-35GS-F0237611B09(L11V, A14P, R41P, N43K, A62S, A74S, K83R, V89L)-35GS-ALB11002-A.

As discussed the "LAG3 binders" of the present invention are any of the molecules described herein that bind to LAG3 (e.g., an ISVD such as a Nanobody) as well as any multi-valent or multispecific binder (e.g., PD1/LAG3 binder) which includes such a molecule that is fused to another binder. For example, a LAG3 binder may include a LAG3 binding moiety fused to a moiety that binds to PD1, CD27, CTLA4, HSA, BTLA, TIM3, ICOS, B7-H3, B7-H4, CD137, GITR, PD-L1, PD-L2, ILT1, ILT2 CEACAM1, CEACAMS, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP. An individual LAG3 binder may be referred to as a LAG3 binding moiety if it is part of a larger molecule, e.g., a multivalent molecule, wherein the LAG3 binding moiety is fused to another binding moiety, such as F023700924 or F023700931.

LAG3 binders of the present invention include polypeptides which are variants of polypeptides comprising the amino acid sequence of SEQ ID NO: 63 but which is mutated at position 1, 11, 14, 41 43, 62, 74, 83 and/or 89.

As further described herein, the LAG3 binders of the invention preferably have the same combination of CDRs (i.e. CDR1, CDR2 and CDR3) as are present in 11B09 or in a binder comprising the sequence of 11B09 (SEQ ID NO: 63). See Table B-1.

The present invention also includes LAG3 binders which are variants of 11B09 which comprise an amino acid sequence as set forth below in Table B-2 below. The scope of the present invention includes LAG3 binders that include CDR1, CDR2 and CDR3 of said varaints set forth below in Table B-2.

In addition, the present invention includes PD1/LAG3 binders comprising a LAG3 binding moiety that includes CDR1, CDR2 and CDR3 or the amino acid sequence of 11B09 or of one of its varaints set forth below in Table B-2.

TABLE B-1

| LAG3 Binder 11B09. | |
|---|---|
| Description | Sequence |
| 11B09 (may be referred to herein as "F0237611B09" or "611B09") SEQ ID NO: 63 | EVQLVESGGGLVQAGGSLRLSCAASGRTFSDYVMGWERQARGNEREFVAAISESGGRTHYADAVKGRFTISRDNAKNTLYLQMNSLKPEDTAVYYCATTLLWWTSEYAPIKANDYDYWGQGTLVTVSS |

TABLE B-2

| Sequence Optimized 11B09 LAG3 Binders. | |
|---|---|
| Description | Sequence |
| 11B09 (L11V, A14P, R41P, N43K, A62S, A74S, K83R, V89L) Name: F023700842 SEQ ID NO: 64 | EVQLVE SGGGVVQPGG SLRLSCAASG RTFSDYVMGW FRQAPGKERE FVAAISESGG RTHYADSVKG RFTISRDNSK NTLYLQMNSL RPEDTALYYC ATTLLWWTSE YAPIKANDYD YWGQGTLVTV SS |
| CDR1 (SEQ ID NO: 65) | GRTFSDYVMG or DYVMG (SEQ ID NO: 154; amino acids 6-10 of SEQ ID NO: 65) |
| CDR2 (SEQ ID NO: 66) | AISESGGRTHYADXVKG; wherein X is A or S (e.g., AISESGGRTHYADAVKG (SEQ ID NO: 140) or AISESGGRTHYADSVKG (SEQ ID NO: 141)) or AISESGGRTH (SEQ ID NO: 139, amino acids 1-10 of SEQ ID NO: 66) |
| CDR3 (SEQ ID NO: 67) | TLLWWTSEYAPIKANDYDY |
| Monovalent SO (sequence optimized) 611B09 + ALB11002 Name: F023701128 Description: F0237611B09 (E1D, L11V, A14P, R41P, N43K, A62S, A74S, K83R, V89L)-35GS-ALB11002-A Target: hLAG-3 SEQ ID NO: 96 | DVQLVESGGGVVQPGGSLRLSCAASGRTFSDYVMGWFRQAPGKEREFV AAISESGGRTHYADSVKGRFTISRDNSKNTLYLQMNSLRPEDTALYYC ATTLLWWTSEYAPIKANDYDYWGQGTLVTVSSGGGGSGGGGSGGGGSG GGGSGGGGSGGGGSGGGGSEVQLVESGGGVVQPGNSLRLSCAASGFTF SSFGMSWVRQAPGKGLEWVSSISGSGSDTLYADSVKGRFTISRDNAKT TLYLQMNSLRPEDTALYYCTIGGSLSRSSQGTLVTVSSA |
| Bivalent SO (sequence optimized) 611B09 + ALB11002 | DVQLVESGGGVVQPGGSLRLSCAASGRTFSDYVMGWERQAPGKEREFV AAISESGGRTHYADSVKGRFTISRDNSKNTLYLQMNSLRPEDTALYYC |

TABLE B-2-continued

Sequence Optimized 11B09 LAG3 Binders.

| Description | Sequence |
|---|---|
| Name: F023700962<br>Description: F0237611B09<br>(E1D, L11V, A14P, R41P, N43K,<br>A62S, A74S, K83R, V89L)-35GS-<br>F0237611B09<br>(L11V, A14P, R41P, N43K, A62S,<br>A74S, K83R, V89L)-35GS-<br>ALB11002-A<br>Target: hLAG-3<br>SEQ ID NO: 97 | ATTLLWWTSEYAPIKANDYDYWGQGTLVTVSSGGGGSGGGGSGGGGSG<br>GGGSGGGGSGGGGSGGGGSEVQLVESGGGVVQPGGSLRLSCAASGRTF<br>SDYVMGWFRQAPGKEREFVAAISESGGRTHYADSVKGRFTISRDNSKN<br>TLYLQMNSLRPEDTALYYCATTLLWWTSEYAPIKANDYDYWGQGTLVT<br>VSSGGGGSGGGGSGGGGSGGGGSGGGGSGGGGSGGGGSEVQLVESGGG<br>VVQPGNSLRLSCAASGETFSSFGMSWVRQAPGKGLEWVSSISGSGSDT<br>LYADSVKGRFTISRDNAKTTLYLQMNSLRPEDTALYYCTIGGSLSRSS<br>QGTLVTVSSA |
| Name: F023700594<br>Description: F0237611B09-<br>35GS-F0237611B09-35GS-<br>ALB11002<br>Target: hLAG-3<br>SEQ ID NO: 127 | EVQLVESGGGLVQAGGSLRLSCAASGRTFSDYVMGWFRQARGNEREFV<br>AAISESGGRTHYADAVKGRFTISRDNAKNTLYLQMNSLKPEDTAVYYC<br>ATTLLWWTSEYAPIKANDYDYWGQGTLVTVSSGGGGSGGGGSGGGGSG<br>GGGSGGGGSGGGGSGGGGSEVQLVESGGGLVQAGGSLRLSCAASGRTF<br>SDYVMGWFRQARGNEREEVAAISESGGRTHYADAVKGRFTISRDNAKN<br>TLYLQMNSLKPEDTAVYYCATTLLWWTSEYAPIKANDYDYWGQGTLVT<br>VSSGGGGSGGGGSGGGGSGGGGSGGGGSGGGGSGGGGSEVQLVESGGG<br>LVQPGNSLRLSCAASGETFSSFGMSWVRQAPGKGLEWVSSISGSGSDT<br>LYADSVKGRFTISRDNAKTTLYLQMNSLRPEDTAVYYCTIGGSLSRSS<br>QGTLVTVSS |

*CDRs of LAG3 binders underscored and/or bold.

The present invention includes embodiments wherein the LAG3 binder of the invention (e.g., in a PD1/LAG3 binder) includes one, two or three of the CDRs of a LAG3 binder set forth above in Table B-1 or B-2 (e.g., SEQ ID NO: 63, 64, 95, 96 or 97) wherein each comprises 0, 1, 2, 3, 4, or 5 amino acid substitutions, e.g., conservative substitutions, and/or comprises 100, 99, 98, 97, 96 or 95% sequence identity relative to the CDR sequences set forth in Table B-1 or B-2 wherein the LAG3 binder of the invention having such CDRs retains the ability to bind to LAG3. In an embodiment of the invention, the first amino acid of a LAG3 binder of the present invention is E. In an embodiment of the invention, the first amino acid of a LAG3 binder of the present invention is E or D.

The present invention includes the LAG3 binder F023700656 (11B09 (E1D); SEQ ID NO: 63 (E1D)).

The Kabat residue numbers for certain residues of the LAG3 binders set forth in Table B-1 or B-2 are shown in the sequence below:

(SEQ ID NO: 64)
EVQLVESGGGV$_{11}$VQP$_{14}$GGSLRLSCAASGRTFSDYVMGWFRQAP$_{41}$GK$_{43}$ERE
FVAAISESGGRTHYADS$_{62}$VKGRFTISRDNS$_{74}$KNTLYLQMNSL
R$_{83}$PEDTAL$_{89}$YYC ATTLLWWTSE YAPIKANDYD YWGQGTLVTV SS.

Optionally, residue 1 is a D.

The present invention includes any LAG3 binder comprising the amino acid sequence of SEQ ID NO: 63, 64 or 127 (or having the LAG3 binder moiety of SEQ ID NO: 96 or 97) (as well as LAG3 binders having an E1D or D1E mutation) or an amino acid sequence comprising 80% or more (e.g., 85%, 90%, 95%, 96%, 97%, 98% or 99%) amino acid sequence identity (i.e., comparing the full amino acid sequences) wherein the LAG3 binder retains the ability to bind to LAG3 and, optionally, includes an HSA binder.

The present invention includes LAG3 binders, such as LAG3 ISVDs (e.g., a Nanobodies), having CDR1, CDR2 and CDR3 of a binder comprising the amino acid sequence set forth in SEQ ID NO: 63, 64, 96, 97 or 127 (or a variant thereof as described herein), e.g., comprising the following CDRs:

a CDR1 that comprises the amino acid sequence GRTFSDYVMG (SEQ ID NO: 65); and a CDR2 that comprises the amino acid sequence AISESGGRTH (SEQ ID NO: 139; amino acids 1-10 of SEQ ID NO: 66); and a CDR3 that comprises the amino acid sequence TLLWWTSEYAPIKANDYDY (SEQ ID NO: 67);

and, optionally, having:

a degree of sequence identity with the amino acid sequence of SEQ ID NO: 63, 64, 96, 97 or 127 (in which any C-terminal extension that may be present as well as the CDRs are not taken into account for determining the degree of sequence identity) of at least 85%, preferably at least 90%, more preferably at least 95% (in which the CDRs, any C-terminal extension that may be present, as well as the mutations at positions 1, 11, 14, 41 43, 62, 74, 76, 83, 89, 100 and/or 105 are not taken into account for determining the degree of sequence identity);

and/or no more than 7, such as no more than 5, preferably no more than 3, such as only 3, 2 or 1 "amino acid differences" (as defined herein, and not taking into account any of the mutations set forth herein at position(s) 1, 11, 14, 41 43, 62, 74, 76, 83, 89, 100 and/or 105 that may be present and not taking into account any C-terminal extension that may be present) with the amino acid sequence of SEQ ID NO: 63, 64, 96, 97 or 127 (in which said amino acid differences, if present, may be present in the frameworks and/or the CDRs but are preferably present only in the frameworks and not in the CDRs);

and optionally having:

a C-terminal extension as discussed herein, e.g., (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

The present invention also includes LAG3 binders fused to one or more half-life extenders, such as an ISVD that binds human serum albumin, e.g., ALB11002.

Multispecific Binders

The present invention includes PD1 binders and LAG3 binders that may be fused in a single multivalent, multispecific molecule that binds to PD1 and LAG3 (a PD1/LAG3 binder) and, in an embodiment of the invention, such binders are linked to one or more half-life extenders that increases the half-life of the binders in the body of a subject. In an embodiment of the invention, the half-life extender is an ISVD (e.g., a Nanobody) that specifically binds to human serum albumin (HSA), e.g., ALB11002. In an embodiment of the invention, the multispecific binder is F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177 as described herein.

In an embodiment of the invention, the PD1/LAG3 binder comprises
(1) a PD1 binder comprising CDR1, CDR2 and CDR3 of any of the PD1 binders set forth in Table A-1 or A-2, optionally, each independently comprising 1, 2, 3, 4, 5, 6, 7, 8, 9 or 10 amino acid substitutions (e.g., conservative mutations) or:
a CDR1 comprising the amino acid sequence IHAMG (SEQ ID NO: 3) or GSIASIHAMG (SEQ ID NO: 6);
a CDR2 comprising the amino acid sequence VITXSGGITYY-ADSVKG (SEQ ID NO: 4; wherein X is W or V, e.g., W) or VITXSGGITY (SEQ ID NO: 7; wherein X is W or V, e.g., W); and
a CDR3 comprising the amino acid sequence DKHQSSXYDY (SEQ ID NO: 5, wherein X is W or F, e.g., W);
and
(2) a LAG3 binder comprising CDR1, CDR2 and CDR3 of any of the LAG3 binders set forth in Table B-1 or B-2, optionally, each independently comprising 1, 2, 3, 4, 5, 6, 7, 8, 9 or 10 amino acid substitutions (e.g., conservative mutations) or:
a CDR1 comprising the amino acid sequence GRTFSDYVMG (SEQ ID NO: 65);
a CDR2 comprising the amino acid sequence AISESGGRTH (SEQ ID NO: 139; amino acids 1-10 of SEQ ID NO: 66); and
a CDR3 comprising the amino acid sequence TLLWWTSEYAPI-KANDYDY (SEQ ID NO: 67),
and, optionally, a half-life extender and/or a C-terminal extender, for example, an HSA binder as set forth herein and/or, optionally a C-terminal extender such as Alanine.

In an embodiment of the invention, the PD1 binder is as set forth above under "PD1 Binders", e.g., comprising the amino acid sequence of SEQ ID NO: 57, 98, 99, 103, 104 or 105 (optionally wherein residue 1 is E or D). In an embodiment of the invention, the LAG3 binder is as set forth above under "LAG3 Binders", e.g., comprising the amino acid sequence of SEQ ID NO: 63, 64 or 95 (optionally wherein residue 1 is E or D).

Multispecific binders may include a PD1 and LAG3 and, optionally, an HSA binder as well as one or more binders that bind to an additional antigen such as, CD27, CTLA4, BTLA, TIM3, ICOS, B7-H3, B7-H4, CD137, GITR, PD-L1, PD-L2, ILT1, ILT2 CEACAM1, CEACAMS, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 or TSLP.

When the PD1 and/or LAG3 binders (e.g., an ISVD such as a Nanobody) contain one or more further binding domains or binding units (e.g. a further essentially non-functional binding domain or binding unit against PD1 and/or LAG3 that provides for increased specificity against PD1 and/or LAG3, a binding domain or binding unit against a therapeutic target other than PD1 and/or LAG3 (e.g., CTLA4, BTLA or CD27), a binding domain or binding unit against a target such as human serum albumin that provides for increased half-life, and/or a binding domain or binding unit that targets the PD1 and/or LAG3 binder to a specific cell, tissue or organ and/or that allows for the PD1 and/or LAG3 binder to be internalized into a cell), these other binding domains or binding units preferably comprise one or more ISVDs (e.g., Nanobodies), and more preferably are all ISVDs. For example and without limitation, these one or more further binding domains or binding units can be one or more Nanobodies (including a VHH, a humanized VHH and/or a camelized VHs such as camelized human VHs), a (single domain) antibody is a VH domain or that is derived from a VH domain, a dAb that is or essentially consists of a VH domain or that is derived from a VH domain, or even a (single) domain antibody or a dAb that is or essentially consists of VL domain. In particular, these one or more binding domains or binding units, when present, may comprise one or more Nanobodies, and more in particular are all Nanobodies. In an embodiment of the invention, the ISVD (e.g., Nanobody) that binds a target other than PD1 and/or LAG3 binds to another target such as HSA, CTLA-4, BTLA or CD27.

When a PD1 and/or LAG3 binder (e.g., an ISVD such as a Nanobody) of the invention has an ISVD (e.g., Nanobody) at its C-terminal end (e.g., which C-terminal ISVD binds to PD1 and/or LAG3 or may for example be, if present in the polypeptide, a further essentially non-functional ISVD against PD1 and/or LAG3 that provides for increased specificity against PD1 and/or LAG3, an ISVD against a therapeutic target other than PD1 and/or LAG3, an ISVD against a target such as human serum albumin that provides for increased half-life, or an ISVD that targets the PD1 and/or LAG3 binder to a specific cell, tissue or organ and/or that allows for the PD1 and/or LAG3 binder to be internalized into a cell), then the PD1 and/or LAG3 binder (i.e. comprising said C-terminal ISVD) preferably has a C-terminal extension X(n) (e.g., -Ala), which C-terminal extension may be as described herein for the PD1 and/or LAG3 binders of the invention and/or as described in WO 12/175741 or PCT/EP2015/060643 (WO2015/173325).

When a PD1 and/or LAG3 binder contains, in addition to the one or more moieties that bind to PD1 and/or LAG3, any further ISVDs (e.g., Nanobodies) (which one or more further ISVDs may, as mentioned, be a further essentially non-functional ISVD against PD1 and/or LAG3 that provides for increased specificity against PD1 and/or LAG3, an ISVD against a therapeutic target other than PD1 and/or LAG3, an ISVD against a target such as human serum albumin that provides for increased half-life, and/or an ISVD that targets the polypeptide of the invention to a specific cell, tissue or organ and/or that allows for the polypeptide of the invention to be internalized into a cell), and where such further ISVDs are Nanobodies or are ISVDs that are, or that essentially consist of and/or that are derived from VH sequences, then according to a preferred aspect of the invention said one or more (and preferably all) of such ISVDs present in the PD1 and/or LAG3 binder will contain within their sequence one or more framework mutations that reduce binding by pre-existing antibodies. In particular, according to this aspect of the invention, such further ISVDs may contain a suitable combination of amino acid residues/mutations at positions 1, 11, 14, 74, 83, 89, 110 and/or 112 that are as described in PCT/EP2015/060643 (WO2015/173325) and/or that essentially are as described herein for the PD1 and/or LAG3 binders of the invention. In one specific aspect, when the PD1 and/or LAG3 binder has such an ISVD at its C-terminal end, then said ISVD that is present at and/or forms the C-terminus has such framework mutations that reduce binding by pre-existing antibodies; and said C-terminal ISVD will preferably also have a C-terminal extension X(n) (e.g., -Ala) as described herein.

When a PD1 and/or LAG3 binder is to have an increased half-life (i.e. compared to a monovalent binder of the invention that lacks a half-life extender such as ALB11002), the PD1 and/or LAG3 binder preferably contains at least one (e.g., one) ISVD (e.g., a Nanobody) that provides for such increased half-life (e.g., ALB11002). Such an ISVD is, in an embodiment of the invention, directed against a suitable serum protein such as transferrin or against (human) serum HSA binder may be referred to as a HSA binding moiety if it is part of a larger molecule, e.g., a multivalent molecule, wherein the HSA binding moiety is fused to another binding moiety.

In an embodiment of the invention, the half-life extender is an ISVD (e.g., Nanobody) that binds to human serum albumin, e.g., ALB11002 as summarized below in Table C.

As further described herein, the HSA binders of the invention preferably have the same combination of CDRs (i.e. CDR1, CDR2 and CDR3) as are present in ALB11002 or comprising the sequence of ALB11002 (SEQ ID NO: 59). See Table C.

The present invention also includes HSA binders which are variants of ALB11002 which comprise an amino acid sequence as set forth below in Table C below. The scope of the present invention includes HSA binders that include CDR1, CDR2 and CDR3 of said varaints set forth below in Table C.

In addition, the present invention includes PD1/LAG3 binders comprising an HSA binding moiety that includes CDR1, CDR2 and CDR3 or the amino acid sequence of ALB11002 or of one of its varaints set forth below in Table C.

TABLE C

Human Serum Albumin (HSA) Nanobody ALB11002

| SEQ ID NO | Description | Sequence |
|---|---|---|
| 59 | ALB11002 (may be referred to herein as "ALB201") | EVQLVESGGG XVQPGNSLRL SCAASGFTFS SFGMSWVRQA PGKGLEWVSS ISGSGSDTLY ADSVKGRFTI SRDNAKTTLY LQMNSLRPED TAXYYCTIGG SLSRSSQGTL VTVSSA; wherein X at residues 11 and 93 are L or V |
| 60 | CDR1 | GFTFSSFGMS or SFGMS (SEQ ID NO: 151; amino acids 6-10 of SEQ ID NO: 60) |
| 61 | CDR2 | SISGSGSDTLYADSVKG or SISGSGSDTL (SEQ ID NO: 152; amino acids 1-10 of SEQ ID NO: 61) |
| 62 | CDR3 | GGSLSR |

*Optionally, ALB11002 lacks the C-terminal Alanine. Optionally, the HSA binder comprises the amino acid sequence set forth in SEQ ID NO: 59 but which comprises an E1D, V11L and/or an L93V mutation, e.g., comprising the amino acid sequence:
EVQLVESGGGVVQPGNSLRLSCAASGFTESSEGMSWVRQAPGKGLEWVSSISGSGSDTLY-
ADSVKGRETISRDNAKTTLYLQMNSLRPEDTALYYCTIGGSLSRSSQGTLVTVSSA (SEQ ID NO: 142).

albumin. In particular, such an ISVD or Nanobody may be a (single) domain antibody or dAb against human serum albumin as described in for example EP 2 139 918, WO 2011/006915, WO 2012/175400, WO 2014/111550 and may in particular be a serum albumin binding Nanobody as described in WO 2004/041865, WO 2006/122787, WO 2012/175400 or PCT/EP2015/060643 (WO2015/173325). Particularly preferred serum albumin binding ISVDs are the Nanobody Alb-1 (see WO 2006/122787) or its humanized variants such as Alb-8 (WO 2006/122787, SEQ ID NO: 62), Alb-23 (WO 2012/175400, SEQ ID NO: 1) and other humanized (and preferably also sequence-optimized) variants of Alb-1 and/or variants of Alb-8 or Alb-23 (or more generally ISVDs that have essentially the same CDRs as Alb-1, Alb-8 and Alb-23).

As discussed the "HSA binders" of the present invention any of the molecules, such as those described herein, that bind to HSA (e.g., an ISVD such as a Nanobody) as well as any multivalent or multispecific binder which includes such a molecule that is fused to another binder. An individual In an embodiment of the invention, the first amino acid of a HSA binder of the present invention is E. In an embodiment of the invention, the first amino acid of a HSA binder of the present invention is D.

The present invention includes embodiments wherein one, two or three of the CDRs of a HSA binder each comprises 0, 1, 2, 3, 4, or 5 amino acid substitutions, e.g., conservative substitutions, and/or comprises 99, 98, 97, 96 or 95% sequence identity relative to the CDR sequences set forth in Table C, wherein the HSA binder having such CDRs retain the ability to bind to HSA.

In an embodiment of the invention, the half-life extender is an HSA ISVD (e.g., a Nanobody) comprising:
 a CDR1 that comprises the amino acid sequence GFTFSSFGMS (SEQ ID NO: 60); and
 a CDR2 that comprises the amino acid sequence SIS-GSGSDTL (SEQ ID NO: 152; amino acids 1-10 of SEQ ID NO: 61); and
 a CDR3 that comprises the amino acid sequence GGSLSR (SEQ ID NO: 62);

and, optionally, having:
- a degree of sequence identity with the amino acid sequence of SEQ ID NO: 59 (in which any C-terminal extension that may be present as well as the CDRs are not taken into account for determining the degree of sequence identity) of at least 85%, preferably at least 90%, more preferably at least 95% (in which the CDRs, any C-terminal extension that may be present are not taken into account for determining the degree of sequence identity);

and/or
- no more than 7, such as no more than 5, preferably no more than 3, such as only 3, 2 or 1 "amino acid differences" (not taking into account any C-terminal extension that may be present) with the amino acid sequence of SEQ ID NO: 59 (in which said amino acid differences, if present, may be present in the frameworks and/or the CDRs but are preferably present only in the frameworks and not in the CDRs);

and optionally having:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

Such a human serum albumin binding ISVD (e.g., Nanobody), when present, may contain within its sequence one or more framework mutations that reduce binding by pre-existing antibodies. In particular, when such a serum albumin binding ISVD is a Nanobody or a (single) domain antibody that is, essentially consist of and/or is derived from a VH domain, the serum albumin binding ISVD may contain (a suitable combination of) amino acid residues/mutations at positions 11, 89, 110 and/or 112 that are as described in PCT/EP2015/060643 (WO2015/173325) and/or that essentially are as described herein for the PD1 binders of the invention. For example, PCT/EP2015/060643 (WO2015/173325) describes a number of variants of Alb-1, Alb-8 and Alb-23 that contain amino acid residues/mutations at positions 11, 89, 110 and/or 112 that reduce binding by pre-existing antibodies that can be used in the polypeptides of the invention.

When such a serum albumin binding ISVD (e.g., Nanobody) is present at the C-terminal end of a PD1 and/or LAG3 binder, the serum albumin binding ISVD (and as a result, the PD1 and/or LAG3 binder of the invention) preferably has a C-terminal extension X(n), which C-terminal extension may be as described herein for the PD1 and/or LAG3 binders of the invention and/or as described in WO 12/175741 or PCT/EP2015/060643 (WO2015/173325). For example, the C-terminal extension may be a single Alanine residue. It also preferably has mutations that reduce the binding of pre-existing antibodies, like (a suitable combination of) the amino acid residues/mutations at positions 11, 89, 110 and/or 112 described in PCT/EP2015/060643 (WO2015/173325).

However, as mentioned, other means of increasing the half-life of a polypeptide of the invention (such as PEGylation, fusion to human albumin or a suitable fragment thereof, or the use of a suitable serum albumin-binding peptide), are also included in the scope of the invention.

Generally, when a PD1 and/or LAG3 binder of the invention has increased half-life (e.g. through the presence of a half-life increasing ISVD (e.g., Nanobody) or any other suitable way of increasing half-life), the resulting PD1 and/or LAG3 binder of the invention preferably has a half-life (as defined herein) that is at least 2 times, preferably at least 5 times, for example at least 10 times or more than 20 times, greater than the half-life of a PD1 and/or LAG3 binder of the invention lacking the a half-life extender (as measured in either in man and/or a suitable animal model, such as mouse or cynomolgus monkey). In particular, a PD1 and/or LAG3 binder of the invention preferably has a half-life (as defined herein) in human subjects of at least 1 day, preferably at least 3 days, more preferably at least 7 days, such as at least 10 days.

It will be clear from the disclosure herein that PD1 binders and LAG3 binders that are based on one or more ISVDs (e.g., Nanobodies) can have different "formats", i.e. essentially be monovalent, bivalent or trivalent, can be monospecific, bispecific, trispecific etc., and can be biparatopic (as defined herein and in for example WO2009/68625). For example, a PD1 binder or LAG3 binder of the invention can be:
- monovalent, i.e. comprising a single PD1 or LAG3 binding moiety (e.g., an ISVD such as a Nanobody). As mentioned, when used in monovalent format, a PD1 binder or LAG3 binder of the invention preferably has a C-terminal extension X(n) as further described herein. Such a PD1 binder or LAG3 binder of the invention may also be half-life extended;
- can be bivalent or trivalent and monospecific. For example, in an embodiment of the invention, such a PD1 binder or LAG3 binder of the invention comprises two or more ISVDs (e.g., Nanobodies) against PD1 or against LAG3, respectively, which may be the same or different; and when different, may be directed against the same epitope of PD1 or LAG3, or against different epitopes on PD1 or LAG3 (in the latter case, so as to provide a biparatopic or multiparatopic PD1 binder or LAG3 binder of the invention). Such a PD1 binder or LAG3 binder of the invention may also be half-life extended;
- can be bivalent, trivalent (or multivalent) and bispecific or trispecific (or multispecific). For example, in an embodiment of the invention, such a PD1 binder of the invention will be directed against PD1 and at least one other target such as, for example, CTLA-4, LAG-3, BTLA and/or CD27; e.g., comprising a PD1 binding moiety and a CTLA4 binding moiety; a PD1 binding moiety and a BTLA binding moiety; a PD1 binding moiety and a LAG3 binding moiety (i.e., a PD1/LAG3 binder); or a PD1 binding moiety, a LAG3 binding moiety and a BTLA binding moiety. As described herein, said other target may for example be another therapeutically relevant target (i.e. other than PD1) so as to provide a PD1 binder of the invention that is bispecific with regards to PD1 and said other therapeutic target. Said other target may also be a target that provides for increased half-life (such as human serum albumin), so as to provide a PD1 binder of the invention that has increased half-life. As also mentioned herein, such other target may allow also for the PD1 binder of the invention to be targeted to specific cells, tissues or organs or may allow for the PD1 binder of the invention to be internalized into a cell. It is also possible to combine these approaches/ISVDs, for example to provide a PD1 binder of the invention that is bispecific for PD1 and for at least one other therapeutically relevant target and that is half-life extended.

Again, preferably, when these PD1 binders and LAG3 binders include one or more ISVDs (e.g., Nanobodies) other than a PD1 binding moiety or LAG3 binding moiety, at least one and preferably all of these other ISVDs will contain within its sequence one or more framework mutations that reduce binding by pre-existing antibodies (such as, in particular, a combination of amino acid residues/mutations at positions 1, 11, 14, 52a, 73, 74, 83, 89, 100a, 110 and/or 112 that is as described herein for the PD1 binders and LAG3 binders of the invention and/or as generally described in PCT/EP2015/060643 (WO2015/173325)). Also, when such PD1 binders or LAG3 binders of the invention have a PD1 binding moiety or LAG3 binding moiety, respectively, at their C-terminal end, then said C-terminal PD1 binding moiety or LAG3 binding moiety (and as a result, the PD1 binder or LAG3 binder of the invention) will preferably have a C-terminal extension X(n) as described herein. Similarly, when such PD1 binders LAG3 binders of the invention have another ISVD at their C-terminal end (i.e. not a PD1 binding moiety or LAG3 binding moiety, but for example a half-life extending ISVD), then said C-terminal ISVD (and, as a result, the PD1 binder or LAG3 binder of the invention will preferably has a C-terminal extension X(n) as described herein and/or will contain within its sequence one or more framework mutations that reduce binding by pre-existing antibodies (again, as further described herein and in PCT/EP2015/060643 (WO2015/173325)).

As will be clear to the skilled person, when a PD1 binder or LAG3 binder (e.g., an ISVD such as a Nanobody) of the invention is intended for topical use (i.e. on the skin or in the eye) or is for example meant to have a (localized) therapeutic action somewhere in for example the GI tract (i.e. after oral administration or administration by suppository) or in the lungs (i.e. after administration by inhalation) or is otherwise meant to be directly applied to its intended place of action (for example, by direct injection), a PD1 binder or LAG3 binder of the invention will usually not require half-life extension. Also, for treatment of certain acute conditions or indications, it may be preferable not to have a prolonged half-life. In these cases, the use of a monovalent PD1 binder or LAG3 binder of the invention or of another PD1 binder or LAG3 binder of the invention (comprising a PD1 binder or LAG3 binder) without half-life extension, for example, a PD1 binder or LAG3 binder of the invention that is bivalent or biparatopic with respect to PD1 or LAG3, is preferred.

Some preferred, but non-limiting examples of such PD1 binders and or LAG3 binder of the invention are schematically represented in Table D-1a and D-1b below, and each of these forms a further aspect of the invention. Other examples of suitable polypeptides of the invention without half-life extension will be clear to the skilled person based on the disclosure herein.

TABLE D-1a

Schematic Representation of Some PD1 and/or LAG3 Binders of the Invention Without a Half-Life Extending ISVD.

[PD-1 binder of the invention]
[PD-1 binder of the invention]-X(n)
[PD-1 binder of the invention]-[PD-1 binder of the invention]- [Other]-[Other]
[PD-1 binder of the invention]-[PD-1 binder of the invention]- [Other]-[Other]
[PD-1 binder of the invention]-[PD-1 binder of the invention]- [Other]-[Other]-X(n)
[PD-1 binder of the invention]-[PD-1 binder of the invention]- [Other]-[Other]-X(n)
[PD-1 binder of the invention]-[PD-1 binder of the invention]-X(n)
[PD-1 binder of the invention]-[Other]

TABLE D-1a-continued

Schematic Representation of Some PD1 and/or LAG3 Binders of the Invention Without a Half-Life Extending ISVD.

[PD-1 binder of the invention]-[Other]-X(n)
[Other]-[PD-1 binder of the invention]
[Other]-[PD-1 binder of the invention]-X(n)
[PD-1 binder of the invention]-[Targeting unit]
[Targeting unit]-[PD-1 binder of the invention]
[PD-1 binder of the invention]-[Targeting unit]-X(n)
[Targeting unit]-[PD-1 binder of the invention]-X(n)
[PD-1 binder of the invention]- [PD-1 binder of the invention]-[Targeting unit]
[PD-1 binder of the invention]- [PD-1 binder of the invention]-[Targeting unit]-X(n)
[Targeting unit]-[PD-1 binder of the invention]-[PD-1 binder of the invention]
[Targeting unit]-[PD-1 binder of the invention]-[PD-1 binder of the invention]-X(n)
[PD-1 binder of the invention]
[PD-1 binder of the invention]-X(n)
[PD-1 binder of the invention]-[PD-1 binder of the invention]
[PD-1 binder of the invention]-[PD-1 binder of the invention]-X(n)
[PD-1 binder of the invention]-[Other]
[PD-1 binder of the invention]-[Other]-X(n)
[Other]-[PD-1 binder of the invention]
[Other]-[PD-1 binder of the invention]-X(n)
[PD-1 binder of the invention]-[Targeting unit]
[Targeting unit]-[PD-1 binder of the invention]
[PD-1 binder of the invention]-[Targeting unit]-X(n)
[Targeting unit]-[PD-1 binder of the invention]-X(n)

Legend:
"[PD1 binder of the invention]" represents a PD1 binding domain or moiety or unit such as the ISVD 102C12 (E1D, L11V, A14P, A74S, K83R, I89L) as described herein
"-" represents either a direct covalent linkage or a suitable linker, such as a 9GS, 15GS or 35GS linker
"X(n)" represents a C-terminal extension as defined herein such as a single alanine residue.
"[Other]" represents a binding domain or binding unit (e.g., an ISVD such as a Nanobody) against an epitope that is different from the PD1 binder, e.g., one or more CTLA4, BTLA, LAG3 and/or CD27 ISVDs such as the LAG3 ISVD 11B09 (L11V, A14P, R41P, N43K, A62S, A74S, K83R, V89L) as described herein
"[Targeting unit]" represents a binding domain or binding unit (and in particular ISVD such as a Nanobody) that targets the polypeptide of the invention to a specific cell, tissue or organ TABLE D-1b Schematic Representation of Some PD1 and/or LAG3 Binders of the Invention Without a Half-Life Extending ISVD.

[LAG3 binder of the invention]
[LAG3 binder of the invention]-X(n)
[LAG3 binder of the invention]-[LAG3 binder of the invention]- [Other]-[Other]
[LAG3 binder of the invention]-[LAG3 binder of the invention]- [Other]-[Other]
[LAG3 binder of the invention]-[LAG3 binder of the invention]- [Other]-[Other]-X(n)
[LAG3 binder of the invention]-[LAG3 binder of the invention]- [Other]-[Other]-X(n)
[LAG3 binder of the invention]-[LAG3 binder of the invention]-X(n)
[LAG3 binder of the invention]-[Other]
[LAG3 binder of the invention]-[Other]-X(n)
[Other]-[LAG3 binder of the invention]
[Other]-[LAG3 binder of the invention]-X(n)
[LAG3 binder of the invention]-[Targeting unit]
[Targeting unit]-[LAG3 binder of the invention]
[LAG3 binder of the invention]-[Targeting unit]-X(n)
[Targeting unit]-[LAG3 binder of the invention]-X(n)
[LAG3 binder of the invention]- [LAG3 binder of the invention]-[Targeting unit]
[LAG3 binder of the invention]- [LAG3 binder of the invention]-[Targeting unit]-X(n)
[Targeting unit]-[LAG3 binder of the invention]-[LAG3 binder of the invention]
[Targeting unit]-[LAG3 binder of the invention]-[LAG3 binder of the invention]-X(n)
[LAG3 binder of the invention]
[LAG3 binder of the invention]-X(n)
[LAG3 binder of the invention]-[LAG3 binder of the invention]
[LAG3 binder of the invention]-[LAG3 binder of the invention]-X(n)

TABLE D-1b-continued

Schematic Representation of Some PD1 and/or LAG3 Binders
of the Invention Without a Half-Life Extending ISVD.

[LAG3 binder of the invention]-[Other]
[LAG3 binder of the invention]-[Other]-X(n)
[Other]-[LAG3 binder of the invention]
[Other]-[LAG3 binder of the invention]-X(n)
[LAG3 binder of the invention]-[Targeting unit]
[Targeting unit]-[LAG3 binder of the invention]
[LAG3 binder of the invention]-[Targeting unit]-X(n)
[Targeting unit]-[LAG3 binder of the invention]-X(n)

Legend:
"[LAG3 binder of the invention]" represents a LAG3 binding domain or moiety or unit such as the ISVD 11B09 (L11V, A14P, R41P, N43K, A62S, A74S, K83R, V89L) as described herein
"-" represents either a direct covalent linkage or a suitable linker, such as a 9GS, 15GS or 35GS linker
"X(n)" represents a C-terminal extension as defined herein such as a single alanine residue.
"[Other]" represents a binding domain or binding unit (e.g., an ISVD such as a Nanobody) against an epitope that is different from the PD1 binder, e.g., one or more CTLA4, BTLA, LAG3 and/or CD27 ISVDs such as the PD1 ISVD 102C12 (E1D, L11V, A14P, A74S, K83R, I89L) as described herein
"[Targeting unit]" represents a binding domain or binding unit (and in particular ISVD such as a Nanobody) that targets the polypeptide of the invention to a specific cell, tissue or organ As will be clear to the skilled person, when a PD1 binder or LAG3 binder (e.g., comprising an ISVD such as a Nanobody) of the invention is intended for systemic administration and/or for prevention and/or treatment of a chronic disease or disorder, it will usually be preferred that said PD1 binder or LAG3 binder of the invention has increased half-life (as defined herein). More preferably, such a PD1 binder or LAG3 binder of the invention will contain a half-life extending ISVD (e.g., Nanobody) such as, preferably, an ISVD and in particular a Nanobody binding to human serum albumin (as described herein).

Some preferred, but non-limiting examples of such PD1 binder or LAG3 binder of the invention are schematically represented in Table D-2a and D-2b below, and each of these forms a further aspect of the invention. Other examples of a suitable PD1 binder or LAG3 binder of the invention with half-life extension will be clear to the skilled person based on the disclosure herein. Generally, for polypeptides of the invention with half-life extension, the presence of a C-terminal extension is much preferred.

TABLE D-2a

Schematic Representation of Some PD1 and/or LAG3 Binders
of the Invention with a Half-Life Extending ISVD.

[PD-1 binder of the invention]-[HLE]
[HLE]-[PD-1 binder of the invention]
[PD-1 binder of the invention]-[HLE]-X(n)
[HLE]-[PD-1 binder of the invention]-X(n)
[PD-1 binder of the invention]-[PD-1 binder of the invention]-[HLE]
[PD-1 binder of the invention]-[HLE]-[PD-1 binder of the invention]
[HLE]-[PD-1 binder of the invention]-[PD-1 binder of the invention]
[PD-1 binder of the invention]-[PD-1 binder of the invention]-[HLE]-X(n)
[PD-1 binder of the invention]-[HLE]-[PD-1 binder of the invention]-X(n)
[HLE]-[PD-1 binder of the invention]-[PD-1 binder of the invention]-X(n)
[PD-1 binder of the invention]-[Other]-[HLE]
[PD-1 binder of the invention]- [PD-1 binder of the invention]-[Other]- [Other]-[HLE]
[PD-1 binder of the invention]-[Other]-[HLE] -X(n)
[PD-1 binder of the invention]- [PD-1 binder of the invention]-[Other]- [Other]-[HLE] -X(n)
[PD-1 binder of the invention]-[HLE]-[Other]
[HLE]-[PD-1 binder of the invention]-[Other]
[HLE] -[Other]-[PD-1 binder of the invention]
[Other]-[PD-1 binder of the invention]-[HLE]
[Other] -[HLE] -[PD-1 binder of the invention]
[PD-1 binder of the invention]-[Other]-[HLE]-X(n)
[PD-1 binder of the invention]-[HLE]-[Other]-X(n)
[HLE]-[PD-1 binder of the invention]-[Other]-X(n)
[HLE] -[Other]-[PD-1 binder of the invention]-X(n)
[Other]-[PD-1 binder of the invention]-[HLE]-X(n)
[Other] -[HLE] -[PD-1 binder of the invention]-X(n)
[PD-1 binder of the invention]-[Targeting unit]-[HLE]
[PD-1 binder of the invention]-[HLE]-[Targeting unit]
[HLE]-[PD-1 binder of the invention]-[Targeting unit]
[Targeting unit]-[PD-1 binder of the invention]-[HLE]
[Targeting unit]-[HLE]-[PD-1 binder of the invention]
[HLE]-[Targeting unit]-[PD-1 binder of the invention]
[PD-1 binder of the invention]-[Targeting unit]-[HLE]-X(n)
[PD-1 binder of the invention]-[HLE]-[Targeting unit]-X(n)
[HLE]-[PD-1 binder of the invention]-[Targeting unit]-X(n)
[Targeting unit]-[PD-1 binder of the invention]-[HLE]-X(n)
[Targeting unit]-[HLE]-[PD-1 binder of the invention]-X(n)
[HLE]-[Targeting unit]-[PD-1 binder of the invention]-X(n)
[PD-1 binder of the invention]-[PD-1 binder of the invention]-[Targeting unit]-[HLE]
[PD-1 binder of the invention]-[PD-1 binder of the invention]-[HLE]-[Targeting unit]
[PD-1 binder of the invention]-[HLE]-[PD-1 binder of the invention]-[Targeting unit]
[HLE]-[PD-1 binder of the invention]-[PD-1 binder of the invention]-[Targeting unit]
[PD-1 binder of the invention]-[PD-1 binder of the invention]-[Targeting unit]-[HLE]-X(n)
[PD-1 binder of the invention]-[PD-1 binder of the invention]-[HLE]-[Targeting unit]-X(n)
[PD-1 binder of the invention]-[HLE]-[PD-1 binder of the invention]-[Targeting unit]-X(n)
[HLE]-[PD-1 binder of the invention]-[PD-1 binder of the invention]-[Targeting unit]-X(n)
[Targeting unit]-[PD-1 binder of the invention]-[PD-1 binder of the invention]-[HLE]
[Targeting unit]-[PD-1 binder of the invention]-[HLE]-[PD-1 binder of the invention]
[Targeting unit]-[HLE]-[PD-1 binder of the invention]-[PD-1 binder of the invention]
[HLE]-[Targeting unit]-[PD-1 binder of the invention]-[PD-1 binder of the invention]

TABLE D-2a-continued

Schematic Representation of Some PD1 and/or LAG3 Binders
of the Invention with a Half-Life Extending ISVD.

[Targeting unit]-[PD-1 binder of the invention]-[PD-1 binder of the invention]-[HLE]-X(n)
[Targeting unit]-[PD-1 binder of the invention]-[HLE]-[PD-1 binder of the invention]-X(n)
[Targeting unit]-[HLE]-[PD-1 binder of the invention]-[PD-1 binder of the invention]-X(n)
[HLE]-[Targeting unit]-[PD-1 binder of the invention]-[PD-1 binder of the invention]-X(n)
[PD-1 binder of the invention]-[HLE]
[HLE]-[PD-1 binder of the invention]
[PD-1 binder of the invention]-[HLE]-X(n)
[HLE]-[PD-1 binder of the invention]-X(n)
[PD-1 binder of the invention]-[PD-1 binder of the invention]-[HLE]
[PD-1 binder of the invention]-[HLE]-[PD-1 binder of the invention]
[HLE]-[PD-1 binder of the invention]-[PD-1 binder of the invention]
[PD-1 binder of the invention]-[PD-1 binder of the invention]-[HLE]-X(n)
[PD-1 binder of the invention]-[HLE]-[PD-1 binder of the invention]-X(n)
[HLE]-[PD-1 binder of the invention]-[PD-1 binder of the invention]-X(n)
[PD-1 binder of the invention]-[Other]-[HLE]

Legend:
"[PD1 binder of the invention]" represents a PD1 binding domain or binding unit such as the PD1 ISVD 102C12 (E1D, L11V, A14P, A74S, K83R, I89L) as described herein
"-" represents either a direct covalent linkage or a suitable linker, such as a 9GS, 15GS or 35GS linker
"X(n)" represents a C-terminal extension as defined herein such as a single alanine residue.
"[HLE]" represents a half-life extending binding domain or binding unit (and in particular a half-life extending ISVD, such as a Nanobody), such as an ISVD (and in particular Nanobody) against (human) serum albumin such as the anti-HSA ISVD ALB11002 as described herein;
"[Other]" represents a binding domain or binding unit (e.g., an ISVD such as a Nanobody) against an epitope that is different from the PD1 binder, e.g., one or more CTLA4, BTLA, LAG3 and/or CD27 ISVDs, such as the LAG3 the ISVD 11B09 (L11V, A14P, R41P, N43K, A62S, A74S, K83R, V89L) as described herein
"[Targeting unit]" represents a binding domain or binding unit (and in particular an ISVD such as a Nanobody) that targets the polypeptide of the invention to a specific cell, tissue or organ

TABLE D-2b

Schematic Representation of Some PD1 and/or LAG3 Binders
of the Invention with a Half-Life Extending ISVD.

[LAG3 binder of the invention]-[HLE]
[HLE]-[LAG3 binder of the invention]
[LAG3 binder of the invention]-[HLE]-X(n)
[HLE]-[LAG3 binder of the invention]-X(n)
[LAG3 binder of the invention]-[LAG3 binder of the invention]-[HLE]
[LAG3 binder of the invention]-[HLE]-[LAG3 binder of the invention]
[HLE]-[LAG3 binder of the invention]-[LAG3 binder of the invention]
[LAG3 binder of the invention]-[LAG3 binder of the invention]-[HLE]-X(n)
[LAG3 binder of the invention]-[HLE]-[LAG3 binder of the invention]-X(n)
[HLE]-[LAG3 binder of the invention]-[LAG3 binder of the invention]-X(n)
[LAG3 binder of the invention]-[Other]-[HLE]
[LAG3 binder of the invention]- [LAG3 binder of the invention]-[Other]- [Other]-[HLE]
[LAG3 binder of the invention]-[Other]-[HLE] -X(n)
[LAG3 binder of the invention]- [LAG3 binder of the invention]-[Other]- [Other]-[HLE] -X(n)
[LAG3 binder of the invention]-[HLE]-[Other]
[HLE]-[LAG3 binder of the invention]-[Other]
[HLE] -[Other]-[LAG3 binder of the invention]
[Other]-[LAG3 binder of the invention]-[HLE]
[Other] -[HLE] -[LAG3 binder of the invention]
[LAG3 binder of the invention]-[Other]-[HLE]-X(n)
[LAG3 binder of the invention]-[HLE]-[Other]-X(n)
[HLE]-[LAG3 binder of the invention]-[Other]-X(n)
[HLE] -[Other]-[LAG3 binder of the invention]-X(n)
[Other]-[LAG3 binder of the invention]-[HLE]-X(n)
[Other] -[HLE] -[LAG3 binder of the invention]-X(n)
[LAG3 binder of the invention]-[Targeting unit]-[HLE]
[LAG3 binder of the invention]-[HLE]-[Targeting unit]
[HLE]-[LAG3 binder of the invention]-[Targeting unit]
[Targeting unit]-[LAG3 binder of the invention]-[HLE]
[Targeting unit]-[HLE]-[LAG3 binder of the invention]
[HLE]-[Targeting unit]-[LAG3 binder of the invention]
[LAG3 binder of the invention]-[Targeting unit]-[HLE]-X(n)
[LAG3 binder of the invention]-[HLE]-[Targeting unit]-X(n)
[HLE]-[LAG3 binder of the invention]-[Targeting unit]-X(n)
[Targeting unit]-[LAG3 binder of the invention]-[HLE]-X(n)
[Targeting unit]-[HLE]-[LAG3 binder of the invention]-X(n)
[HLE]-[Targeting unit]-[LAG3 binder of the invention]-X(n)
[LAG3 binder of the invention]-[LAG3 binder of the invention]-[Targeting unit]-[HLE]
[LAG3 binder of the invention]-[LAG3 binder of the invention]-[HLE]-[Targeting unit]
[LAG3 binder of the invention]-[HLE]-[LAG3 binder of the invention]-[Targeting unit]
[HLE]-[LAG3 binder of the invention]-[LAG3 binder of the invention]-[Targeting unit]
[LAG3 binder of the invention]-[PD-1binder of the invention]-[Targeting unit]-[HLE]-X(n)
[LAG3 binder of the invention]-[LAG3 binder of the invention]-[HLE]-[Targeting unit]-X(n)

TABLE D-2b-continued

Schematic Representation of Some PD1 and/or LAG3 Binders
of the Invention with a Half-Life Extending ISVD.

[LAG3 binder of the invention]-[HLE]-[LAG3 binder of the invention]-[Targeting unit]-X(n)
[HLE]-[LAG3 binder of the invention]-[LAG3 binder of the invention]-[Targeting unit]-X(n)
[Targeting unit]-[LAG3 binder of the invention]-[LAG3 binder of the invention]-[HLE]
[Targeting unit]-[LAG3 binder of the invention]-[HLE]-[LAG3 binder of the invention]
[Targeting unit]-[HLE]-[LAG3 binder of the invention]-[LAG3 binder of the invention]
[HLE]-[Targeting unit]-[LAG3 binder of the invention]-[LAG3 binder of the invention]
[Targeting unit]-[LAG3 binder of the invention]-[LAG3 binder of the invention]-[HLE]-X(n)
[Targeting unit]-[LAG3 binder of the invention]-[HLE]-[LAG3 binder of the invention]-X(n)
[Targeting unit]-[HLE]-[LAG3 binder of the invention]-[LAG3 binder of the invention]-X(n)
[HLE]-[Targeting unit]-[LAG3 binder of the invention]-[LAG3 binder of the invention]-X(n)
[LAG3 binder of the invention]-[HLE]
[HLE]-[LAG3 binder of the invention]
[LAG3 binder of the invention]-[HLE]-X(n)
[HLE]-[LAG3 binder of the invention]-X(n)
[LAG3 binder of the invention]-[LAG3 binder of the invention]-[HLE]
[LAG3 binder of the invention]-[HLE]-[LAG3 binder of the invention]
[HLE]-[LAG3 binder of the invention]-[LAG3 binder of the invention]
[LAG3 binder of the invention]-[LAG3 binder of the invention]-[HLE]-X(n)
[LAG3 binder of the invention]-[HLE]-[LAG3 binder of the invention]-X(n)
[HLE]-[LAG3 binder of the invention]-[LAG3 binder of the invention]-X(n)
[LAG3 binder of the invention]-[Other]-[HLE]

Legend:
"[LAG3 binder of the invention]" represents a LAG3 binding domain or moiety or unit such as the LAG3 ISVD the ISVD 11B09 (L11V, A14P, R41P, N43K, A62S, A74S, K83R, V89L) as described herein
"-" represents either a direct covalent linkage or a suitable linker, such as a 9GS, 15GS or 35GS linker
"X(n)" represents a C-terminal extension as defined herein such as a single alanine residue.
"[HLE]" represents a half-life extending binding domain or binding unit (and in particular Nanobody), such as an ISVD (and in particular Nanobody) against (human) serum albumin such as the anti-HSA ISVD ALB11002 as described herein;
"[Other]" represents a binding domain or binding unit (e.g., an ISVD such as a Nanobody) against an epitope that is different from the PD1 binder, e.g., one or more CTLA4, BTLA, LAG3 and/or CD27 ISVDs, such as the PD1 ISVD 102C12 (E1D, L11V, A14P, A74S, K83R, I89L) as described herein
"[Targeting unit]" represents a binding domain or binding unit (and in particular an ISVD such as a Nanobody) that targets the polypeptide of the invention to a specific cell, tissue or organ In an embodiment of the invention, the PD1/LAG3 binders of the present invention are as summarized below in Table D-3

TABLE D-3

PD1/LAG3 Binders of the Present Invention.

| Description | Sequence |
|---|---|
| Name: F023700899<br>Description:<br>1PD102C12 (A14P, A74S, K83R)-35GS-<br>1PD102C12 (A14P, A74S, K83R)-35GS-<br>F0237611B09-35GS-F0237611B09-35GS-<br>ALB11002<br>Target: hPD-1/hLAG-3<br>SEQ ID NO: 106 | EVQLVESGGGLVQPGGSLRLSCAASGSIASIHAMGWERQ<br>APGKEREFVAVITWSGGITYYADSVKGRFTISRDNSKNT<br>VYLQMNSLRPEDTAIYYCAGDKHQSSWYDYWGQGTLVTV<br>SSGGGGSGGGGSGGGGSGGGGSGGGGSGGGGSGGGGSEV<br>QLVESGGGLVQPGGSLRLSCAASGSIASIHAMGWERQAP<br>GKEREFVAVITWSGGITYYADSVKGRFTISRDNSKNTVY<br>LQMNSLRPEDTAIYYCAGDKHQSSWYDYWGQGTLVTVSS<br>GGGGSGGGGSGGGGSGGGGSGGGGSGGGGSGGGGSEVQL<br>VESGGGLVQAGGSLRLSCAASGRTFSDYVMGWFRQARGN<br>EREEVAAISESGGRTHYADAVKGRFTISRDNAKNTLYLQ<br>MNSLKPEDTAVYYCATTLLWWTSEYAPIKANDYDYWGQG<br>TLVTVSSGGGGSGGGGSGGGGSGGGGSGGGGSGGGGSGG<br>GGSEVQLVESGGGLVQAGGSLRLSCAASGRTFSDYVMGW<br>FRQARGNEREFVAAISESGGRTHYADAVKGRFTISRDNA<br>KNTLYLQMNSLKPEDTAVYYCATTLLWWTSEYAPIKAND<br>YDYWGQGTLVTVSSGGGGSGGGGSGGGGSGGGGSGGGGS<br>GGGGSGGGGSEVQLVESGGGLVQPGNSLRLSCAASGFTF<br>SSFGMSWVRQAPGKGLEWVSSISGSGSDTLYADSVKGRF<br>TISRDNAKTTLYLQMNSLRPEDTAVYYCTIGGSLSRSSQ<br>GTLVTVSS |
| Name: F023700931<br>Description: 1PD102C12<br>(E1D, L11V, A14P, A74S, K83R, I89L)-<br>35GS-1PD102C12<br>(L11V, A14P, A74S, K83R, I89L)-35GS-<br>F0237611B09<br>(L11V, A14P, R41P, N43K, A62S, A74S,<br>K83R, V89L)-35GS-F0237611B09<br>(L11V, A14P, R41P, N43K, A62S, A74S,<br>K83R, V89L)-35GS-ALB11002-A<br>Target: hPD-1/hLAG-3 | DVQLVESGGGVVQPGGSLRLSCAASGSIASIHAMGWERQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGGSGGGGSGGGGSGGGGSGGGGSGGGGSEV<br>QLVESGGGVVQPGGSLRLSCAASGSIASIHAMGWERQAP<br>GKEREFVAVITWSGGITYYADSVKGRFTISRDNSKNTVY<br>LQMNSLRPEDTALYYCAGDKHQSSWYDYWGQGTLVTVSS<br>GGGGSGGGGSGGGGSGGGGSGGGGSGGGGSGGGGSEVQL<br>VESGGGVVQPGGSLRLSCAASGRTFSDYVMGWERQAPGK<br>EREEVAAISESGGRTHYADSVKGRFTISRDNSKNTLYLQ<br>MNSLRPEDTALYYCATTLLWWTSEYAPIKANDYDYWGQG |

TABLE D-3-continued

PD1/LAG3 Binders of the Present Invention.

| Description | Sequence |
| --- | --- |
| SEQ ID NO: 107 | TLVTVSSGGGGSGGGGSGGGGSGGGGSGGGGSGGGGSGG<br>GGSEVQLVESGGGVVQPGGSLRLSCAASGRTFSDYVMGW<br>FRQAPGKEREFVAAISESGGRTHYADSVKGRFTISRDNS<br>KNTLYLQMNSLRPEDTALYYCATTLLWWTSEYAPIKAND<br>YDYWGQGTLVTVSSGGGGSGGGGSGGGGSGGGGSGGGGS<br>GGGGSGGGGSEVQLVESGGGVVQPGNSLRLSCAASGFTF<br>SSFGMSWVRQAPGKGLEWVSSISGSGSDTLYADSVKGRF<br>TISRDNAKTTLYLQMNSLRPEDTALYYCTIGGSLSRSSQ<br>GTLVTVSSA |
| Name: F023701016<br>Description:<br>102C12 (E1D, L11V, A14P, A74S, K83R,<br>I89L)-20GS-<br>102C12 (L11V, A14P, A74S, K83R, I89L)-<br>20GS-<br>F0237611B09 (L11V, A14P, R41P, N43K,<br>A62S, A74S, K83R, V89L)-20GS-<br>F0237611B09 (L11V, A14P, R41P, N43K,<br>A62S, A74S, K83R, V89L)-20GS-ALB11002-<br>A<br>Target: hPD-1/hLAG-3<br>SEQ ID NO: 108 | DVQLVESGGGVVQPGGSLRLSCAASGSIASIHAMGWERQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGGSGGGGSGGGGSEVQLVESGGGVVQPGGS<br>LRLSCAASGSIASIHAMGWFRQAPGKEREFVAVITWSGG<br>ITYYADSVKGRFTISRDNSKNTVYLQMNSLRPEDTALYY<br>CAGDKHQSSWYDYWGQGTLVTVSSGGGGSGGGGSGGGGS<br>GGGGSEVQLVESGGGVVQPGGSLRLSCAASGRTFSDYVM<br>GWERQAPGKEREEVAAISESGGRTHYADSVKGRFTISRD<br>NSKNTLYLQMNSLRPEDTALYYCATTLLWWTSEYAPIKA<br>NDYDYWGQGTLVTVSSGGGGSGGGGSGGGGSGGGGSEVQ<br>LVESGGGVVQPGGSLRLSCAASGRTFSDYVMGWFRQAPG<br>KEREFVAAISESGGRTHYADSVKGRFTISRDNSKNTLYL<br>QMNSLRPEDTALYYCATTLLWWTSEYAPIKANDYDYWGQ<br>GTLVTVSSGGGGSGGGGSGGGGSGGGGSEVQLVESGGGV<br>VQPGNSLRLSCAASGETFSSFGMSWVRQAPGKGLEWVSS<br>ISGSGSDTLYADSVKGRFTISRDNAKTTLYLQMNSLRPE<br>DTALYYCTIGGSLSRSSQGTLVTVSSA |
| Name: F023701017<br>Description:<br>102C12 (E1D, L11V, A14P, A74S, K83R,<br>I89L)-9GS-<br>102C12 (L11V, A14P, A74S, K83R, I89L)-<br>9GS-<br>F0237611B09 (L11V, A14P, R41P, N43K,<br>A62S, A74S, K83R, V89L)-9GS-<br>F0237611B09 (L11V, A14P, R41P, N43K,<br>A62S, A74S, K83R, V89L)-9GS-ALB11002-<br>A<br>Target: hPD-1/hLAG-3<br>SEQ ID NO: 109 | DVQLVESGGGVVQPGGSLRLSCAASGSIASIHAMGWFRQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGSEVQLVESGGGVVQPGGSLRLSCAASGSI<br>ASIHAMGWFRQAPGKEREFVAVITWSGGITYYADSVKGR<br>FTISRDNSKNTVYLQMNSLRPEDTALYYCAGDKHQSSWY<br>DYWGQGTLVTVSSGGGGSGGGSEVQLVESGGGVVQPGGS<br>LRLSCAASGRTFSDYVMGWERQAPGKEREFVAAISESGG<br>RTHYADSVKGRFTISRDNSKNTLYLQMNSLRPEDTALYY<br>CATTLLWWTSEYAPIKANDYDYWGQGTLVTVSSGGGGSG<br>GGSEVQLVESGGGVVQPGGSLRLSCAASGRTFSDYVMGW<br>FRQAPGKEREFVAAISESGGRTHYADSVKGRFTISRDNS<br>KNTLYLQMNSLRPEDTALYYCATTLLWWTSEYAPIKAND<br>YDYWGQGTLVTVSSGGGGSGGGSEVQLVESGGGVVQPGN<br>SLRLSCAASGETFSSFGMSWVRQAPGKGLEWVSSISGSG<br>SDTLYADSVKGRFTISRDNAKTTLYLQMNSLRPEDTALY<br>YCTIGGSLSRSSQGTLVTVSSA |
| Name: F023700924<br>Description: 1PD102C12<br>(E1D, L11V, A14P, A74S, K83R, I89L)-<br>35GS-F0237611B09<br>(L11V, A14P, R41P, N43K, A62S, A74S,<br>K83R, V89L)-35GS-ALB11002-A<br>Target: hPD-1/hLAG-3<br>SEQ ID NO: 110 | DVQLVESGGGVVQPGGSLRLSCAASGSIASIHAMGWFRQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGGSGGGGSGGGGSGGGGSGGGGSGGGGSEV<br>QLVESGGGVVQPGGSLRLSCAASGRTFSDYVMGWFRQAP<br>GKEREFVAAISESGGRTHYADSVKGRFTISRDNSKNTLY<br>LQMNSLRPEDTALYYCATTLLWWTSEYAPIKANDYDYWG<br>QGTLVTVSSGGGGSGGGGSGGGGSGGGGSGGGGSGGGGS<br>GGGGSEVQLVESGGGVVQPGNSLRLSCAASGFTFSSFGM<br>SWVRQAPGKGLEWVSSISGSGSDTLYADSVKGRFTISRD<br>NAKTTLYLQMNSLRPEDTALYYCTIGGSLSRSSQGTLVT<br>VSSA |
| Name: F023700969<br>Description:<br>102C12 (E1D, L11V, A14P, A74S, K83R,<br>I89L)-20GS-<br>F0237611B09 (L11V, A14P, R41P, N43K,<br>A62S, A74S, K83R, V89L)-20GS-ALB11002-<br>A<br>Target: hPD-1/hLAG-3<br>SEQ ID NO: 111 | DVQLVESGGGVVQPGGSLRLSCAASGSIASIHAMGWFRQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGGSGGGGSGGGGSEVQLVESGGGVVQPGGS<br>LRLSCAASGRTFSDYVMGWERQAPGKEREFVAAISESGG<br>RTHYADSVKGRFTISRDNSKNTLYLQMNSLRPEDTALYY<br>CATTLLWWTSEYAPIKANDYDYWGQGTLVTVSSGGGGGS<br>GGGGSGGGGSEVQLVESGGGVVQPGNSLRLSCAAS<br>GETFSSFGMSWVRQAPGKGLEWVSSISGSGSDTLYADSV<br>KGRFTISRDNAKTTLYLQMNSLRPEDTALYYCTIGGSLS<br>RSSQGTLVTVSSA |
| Name: F023700970<br>Description: 102C12<br>(E1D, L11V, A14P, A74S, K83R, I89L)-<br>9GS-F0237611B09 | DVQLVESGGGVVQPGGSLRLSCAASGSIASIHAMGWFRQ<br>APGKEREFVAVITWSGGITYYADSVKGRFTISRDNSKNT<br>VYLQMNSLRPEDTALYYCAGDKHQSSWYDYWGQGTLVTV<br>SSGGGGSGGGSEVQLVESGGGVVQPGGSLRLSCAASGRT |

TABLE D-3-continued

PD1/LAG3 Binders of the Present Invention.

| Description | Sequence |
|---|---|
| (L11V, A14P, R41P, N43K, A62S, A74S, K83R, V89L)-9GS-ALB11002-A<br>Target: hPD-1/hLAG-3<br>SEQ ID NO: 112 | FSDYVMGWERQAPGKEREFVAAISESGGRTHYADSVKGR FTISRDNSKNTLYLQMNSLRPEDTALYYCATTLLWWTSE YAPIKANDYDYWGQGTLVTVSSGGGGSGGGGSEVQLVESG GGVVQPGNSLRLSCAASGFTFSSFGMSWVRQAPGKGLEW VSSISGSGSDTLYADSVKGRFTISRDNAKTTLYLQMNSL RPEDTALYYCTIGGSLSRSSQGTLVTVSSA |
| Name: F023701163<br>Description: 1PD102C12 (E1D, L11V, A14P, W52aV, N73P, A74S, K83R, I89L, W100aF)-35GS-1PD102C12 (L11V, A14P, W52aV, N73P, A74S, K83R, I89L, W100aF)-35GS-F023700842-35GS-F023700842-35GS-ALB11002-A<br>Target: hPD-1/hLAG-3<br>SEQ ID NO: 113 | DVQLVESGGGVVQPGGSLRLSCAASGSIASIHAMGWFRQ APGKEREFVAVITVSGGITYYADSVKGRFTISRDPSKNT VYLQMNSLRPEDTALYYCAGDKHQSSFYDYWGQGTLVTV SSGGGGSGGGGSGGGGSGGGGSGGGGSGGGGSGGGGSEV QLVESGGGVVQPGGSLRLSCAASGSIASIHAMGWFRQAP GKEREFVAVITVSGGITYYADSVKGRFTISRDPSKNTVY LQMNSLRPEDTALYYCAGDKHQSSFYDYWGQGTLVTVSS GGGGSGGGGSGGGGSGGGGSGGGGSGGGGSGGGGSEVQL VESGGGVVQPGGSLRLSCAASGRTFSDYVMGWFRQAPGK EREFVAAISESGGRTHYADSVKGRFTISRDNSKNTLYLQ MNSLRPEDTALYYCATTLLWWTSEYAPIKANDYDYWGQG TLVTVSSGGGGSGGGGSGGGGSGGGGSGGGGSGGGGSGG GGSEVQLVESGGGVVQPGGSLRLSCAASGRTFSDYVMGW FRQAPGKEREFVAAISESGGRTHYADSVKGRFTISRDNS KNTLYLQMNSLRPEDTALYYCATTLLWWTSEYAPIKAND YDYWGQGTLVTVSSGGGGSGGGGSGGGGSGGGGSGGGGS GGGGSGGGGSEVQLVESGGGVVQPGNSLRLSCAASGFTF SSFGMSWVRQAPGKGLEWVSSISGSGSDTLYADSVKGRF TISRDNAKTTLYLQMNSLRPEDTALYYCTIGGSLSRSSQ GTLVTVSSA |
| Name: F023701168<br>Description: 1PD102C12 (E1D, L11V, A14P, W52aV, N73P, A74S, K83R, I89L, W100aF)-9GS-1PD102C12 (L11V, A14P, W52aV, N73P, A74S, K83R, I89L, W100aF)-9GS-F023700842-9GS-F023700842-9GS-ALB11002-A<br>Target: hPD-1/hLAG-3<br>SEQ ID NO: 114 | DVQLVESGGGVVQPGGSLRLSCAASGSIASIHAMGWFRQ APGKEREFVAVITVSGGITYYADSVKGRFTISRDPSKNT VYLQMNSLRPEDTALYYCAGDKHQSSFYDYWGQGTLVTV SSGGGGSGGGGSEVQLVESGGGVVQPGGSLRLSCAASGSI ASIHAMGWERQAPGKEREFVAVITVSGGITYYADSVKGR FTISRDPSKNTVYLQMNSLRPEDTALYYCAGDKHQSSFY DYWGQGTLVTVSSGGGGSGGGGSEVQLVESGGGVVQPGGS LRLSCAASGRTFSDYVMGWFRQAPGKEREFVAAISESGG RTHYADSVKGRFTISRDNSKNTLYLQMNSLRPEDTALYY CATTLLWWTSEYAPIKANDYDYWGQGTLVTVSSGGGGSG GGGSEVQLVESGGGVVQPGGSLRLSCAASGRTFSDYVMGW FRQAPGKEREFVAAISESGGRTHYADSVKGRFTISRDNS KNTLYLQMNSLRPEDTALYYCATTLLWWTSEYAPIKAND YDYWGQGTLVTVSSGGGGSGGGGSEVQLVESGGGVVQPGN SLRLSCAASGFTFSSFGMSWVRQAPGKGLEWVSSISGSG SDTLYADSVKGRFTISRDNAKTTLYLQMNSLRPEDTALY YCTIGGSLSRSSQGTLVTVSSA |
| Name: F023701173<br>Description: 1PD102C12 (E1D, L11V, A14P, W52aV, N73P, A74S, K83R, I89L, W100aF)-35GS-F023700842-35GS-ALB11002-A<br>Target: hPD-1/hLAG-3<br>SEQ ID NO: 115 | DVQLVESGGGVVQPGGSLRLSCAASGSIASIHAMGWFRQ APGKEREFVAVITVSGGITYYADSVKGRFTISRDPSKNT VYLQMNSLRPEDTALYYCAGDKHQSSFYDYWGQGTLVTV SSGGGGSGGGGSGGGGSGGGGSGGGGSGGGGSGGGGSEV QLVESGGGVVQPGGSLRLSCAASGRTFSDYVMGWFRQAP GKEREFVAAISESGGRTHYADSVKGRFTISRDNSKNTLY LQMNSLRPEDTALYYCATTLLWWTSEYAPIKANDYDYWG QGTLVTVSSGGGGSGGGGSGGGGSGGGGSGGGGSGGGGS GGGGSEVQLVESGGGVVQPGNSLRLSCAASGFTFSSFGM SWVRQAPGKGLEWVSSISGSGSDTLYADSVKGRFTISRD NAKTTLYLQMNSLRPEDTALYYCTIGGSLSRSSQGTLVT VSSA |
| Name: F023701178<br>Description: 1PD102C12 (E1D, L11V, A14P, W52aV, N73P, A74S, K83R, I89L, W100aF)-9GS-F023700842-9GS-ALB11002-A<br>Target: hPD-1/hLAG-3<br>SEQ ID NO: 116 | DVQLVESGGGVVQPGGSLRLSCAASGSIASIHAMGWERQ APGKEREFVAVITVSGGITYYADSVKGRFTISRDPSKNT VYLQMNSLRPEDTALYYCAGDKHQSSFYDYWGQGTLVTV SSGGGGSGGGGSEVQLVESGGGVVQPGGSLRLSCAASGRT FSDYVMGWERQAPGKEREFVAAISESGGRTHYADSVKGR FTISRDNSKNTLYLQMNSLRPEDTALYYCATTLLWWTSE YAPIKANDYDYWGQGTLVTVSSGGGGSGGGGSEVQLVESG GGVVQPGNSLRLSCAASGFTFSSFGMSWVRQAPGKGLEW VSSISGSGSDTLYADSVKGRFTISRDNAKTTLYLQMNSL RPEDTALYYCTIGGSLSRSSQGTLVTVSSA |
| Name: F023701161<br>Description: 1PD102C12 (E1D, L11V, A14P, W52aV, N73Q, A74S, K83R, I89L, W100aF)-35GS-1PD102C12 (L11V, A14P, W52aV, N73Q, A74S, K83R, I89L, W100aF)-35GS-F023700842-35GS- | DVQLVESGGGVVQPGGSLRLSCAASGSIASIHAMGWERQ APGKEREFVAVITVSGGITYYADSVKGRFTISRDQSKNT VYLQMNSLRPEDTALYYCAGDKHQSSFYDYWGQGTLVTV SSGGGGSGGGGSGGGGSGGGGSGGGGSGGGGSGGGGSEV QLVESGGGVVQPGGSLRLSCAASGSIASIHAMGWERQAP GKEREFVAVITVSGGITYYADSVKGRFTISRDQSKNTVY |

TABLE D-3-continued

PD1/LAG3 Binders of the Present Invention.

| Description | Sequence |
|---|---|
| F023700842-35GS-ALB11002-A<br>Target: hPD-1/hLAG-3<br>SEQ ID NO: 117 | LQMNSLRPEDTALYYCAGDKHQSSFYDYWGQGTLVTVSS<br>GGGGSGGGGSGGGGSGGGGSGGGGSGGGGSGGGGSEVQL<br>VESGGGVVQPGGSLRLSCAASGRTFSDYVMGWFRQAPGK<br>EREEVAAISESGGRTHYADSVKGRFTISRDNSKNTLYLQ<br>MNSLRPEDTALYYCATTLLWWTSEYAPIKANDYDYWGQG<br>TLVTVSSGGGGSGGGGSGGGGSGGGGSGGGGSGGGGSGG<br>GGSEVQLVESGGGVVQPGGSLRLSCAASGRTFSDYVMGW<br>FRQAPGKEREFVAAISESGGRTHYADSVKGRFTISRDNS<br>KNTLYLQMNSLRPEDTALYYCATTLLWWTSEYAPIKAND<br>YDYWGQGTLVTVSSGGGGSGGGGSGGGGSGGGGSGGGGS<br>GGGGSGGGGSEVQLVESGGGVVQPGNSLRLSCAASGFTF<br>SSFGMSWVRQAPGKGLEWVSSISGSGSDTLYADSVKGRF<br>TISRDNAKTTLYLQMNSLRPEDTALYYCTIGGSLSRSSQ<br>GTLVTVSSA |
| Name: F023701166<br>Description: 1PD102C12 (E1D, L11V,<br>A14P, W52aV, N73Q, A74S, K83R, I89L,<br>W100aF)-9GS-1PD102C12 (L11V, A14P,<br>W52aV, N73Q, A74S, K83R, I89L,<br>W100aF)-9GS-F023700842-9GS-<br>ALB11002-A<br>Target: hPD-1/hLAG-3<br>SEQ ID NO: 118 | DVQLVESGGGVVQPGGSLRLSCAASGSIASIHAMGWERQ<br>APGKEREFVAVITVSGGITYYADSVKGRFTISRDQSKNT<br>VYLQMNSLRPEDTALYYCAGDKHQSSFYDYWGQGTLVTV<br>SSGGGGSGGGSEVQLVESGGGVVQPGGSLRLSCAASGSI<br>ASIHAMGWERQAPGKEREFVAVITVSGGITYYADSVKGR<br>FTISRDQSKNTVYLQMNSLRPEDTALYYCAGDKHQSSFY<br>DYWGQGTLVTVSSGGGGSGGGSEVQLVESGGGVVQPGGS<br>LRLSCAASGRTFSDYVMGWERQAPGKEREFVAAISESGG<br>RTHYADSVKGRFTISRDNSKNTLYLQMNSLRPEDTALYY<br>CATTLLWWTSEYAPIKANDYDYWGQGTLVTVSSGGGGSG<br>GGSEVQLVESGGGVVQPGGSLRLSCAASGRTFSDYVMGW<br>FRQAPGKEREFVAAISESGGRTHYADSVKGRFTISRDNS<br>KNTLYLQMNSLRPEDTALYYCATTLLWWTSEYAPIKAND<br>YDYWGQGTLVTVSSGGGGSGGGSEVQLVESGGGVVQPGN<br>SLRLSCAASGETFSSFGMSWVRQAPGKGLEWVSSISGSG<br>SDTLYADSVKGRFTISRDNAKTTLYLQMNSLRPEDTALY<br>YCTIGGSLSRSSQGTLVTVSSA |
| Name: F023701171<br>Description: 1PD102C12 (E1D, L11V,<br>A14P, W52aV, N73Q, A74S, K83R, I89L,<br>W100aF)-35GS-F023700842-35GS-<br>ALB11002-A<br>Target: hPD-1/hLAG-3<br>SEQ ID NO: 119 | DVQLVESGGGVVQPGGSLRLSCAASGSIASIHAMGWERQ<br>APGKEREFVAVITVSGGITYYADSVKGRFTISRDQSKNT<br>VYLQMNSLRPEDTALYYCAGDKHQSSFYDYWGQGTLVTV<br>SSGGGGSGGGGSGGGGSGGGGSGGGGSGGGGSGGGGSEV<br>QLVESGGGVVQPGGSLRLSCAASGRTFSDYVMGWFRQAP<br>GKEREFVAAISESGGRTHYADSVKGRFTISRDNSKNTLY<br>LQMNSLRPEDTALYYCATTLLWWTSEYAPIKANDYDYWG<br>QGTLVTVSSGGGGSGGGGSGGGGSGGGGSGGGGSGGGGS<br>GGGGSEVQLVESGGGVVQPGNSLRLSCAASGFTFSSFGM<br>SWVRQAPGKGLEWVSSISGSGSDTLYADSVKGRFTISRD<br>NAKTTLYLQMNSLRPEDTALYYCTIGGSLSRSSQGTLVT<br>VSSA |
| Name: F023701176<br>Description: 1PD102C12 (E1D, L11V,<br>A14P, W52aV, N73Q, A74S, K83R, I89L,<br>W100aF)-9GS-F023700842-9GS-<br>ALB11002-A<br>Target: hPD-1/hLAG-3<br>SEQ ID NO: 120 | DVQLVESGGGVVQPGGSLRLSCAASGSIASIHAMGWERQ<br>APGKEREFVAVITVSGGITYYADSVKGRFTISRDQSKNT<br>VYLQMNSLRPEDTALYYCAGDKHQSSFYDYWGQGTLVTV<br>SSGGGGSGGGSEVQLVESGGGVVQPGGSLRLSCAASGRT<br>FSDYVMGWERQAPGKEREFVAAISESGGRTHYADSVKGR<br>FTISRDNSKNTLYLQMNSLRPEDTALYYCATTLLWWTSE<br>YAPIKANDYDYWGQGTLVTVSSGGGGSGGGSEVQLVESG<br>GGVVQPGNSLRLSCAASGFTFSSFGMSWVRQAPGKGLEW<br>VSSISGSGSDTLYADSVKGRFTISRDNAKTTLYLQMNSL<br>RPEDTALYYCTIGGSLSRSSQGTLVTVSSA |
| Name: F023701162<br>Description: 1PD102C12 (E1D, L11V,<br>A14P, W52aV, N73S, A74S, K83R, I89L,<br>W100aF)-35GS-1PD102C12 (L11V,<br>A14P, W52aV, N73S, A74S, K83R, I89L,<br>W100aF)-35GS-F023700842-35GS-<br>ALB11002-A<br>Target: hPD-1/hLAG-3<br>SEQ ID NO: 121 | DVQLVESGGGVVQPGGSLRLSCAASGSIASIHAMGWERQ<br>APGKEREFVAVITVSGGITYYADSVKGRFTISRDSSKNT<br>VYLQMNSLRPEDTALYYCAGDKHQSSFYDYWGQGTLVTV<br>SSGGGGSGGGGSGGGGSGGGGSGGGGSGGGGSGGGGSEV<br>QLVESGGGVVQPGGSLRLSCAASGSIASIHAMGWERQAP<br>GKEREFVAVITVSGGITYYADSVKGRFTISRDSSKNTVY<br>LQMNSLRPEDTALYYCAGDKHQSSFYDYWGQGTLVTVSS<br>GGGGSGGGGSGGGGSGGGGSGGGGSGGGGSGGGGSEVQL<br>VESGGGVVQPGGSLRLSCAASGRTFSDYVMGWFRQAPGK<br>EREEVAAISESGGRTHYADSVKGRFTISRDNSKNTLYLQ<br>MNSLRPEDTALYYCATTLLWWTSEYAPIKANDYDYWGQG<br>TLVTVSSGGGGSGGGGSGGGGSGGGGSGGGGSGGGGSGG<br>GGSEVQLVESGGGVVQPGGSLRLSCAASGRTFSDYVMGW<br>FRQAPGKEREFVAAISESGGRTHYADSVKGRFTISRDNS<br>KNTLYLQMNSLRPEDTALYYCATTLLWWTSEYAPIKAND<br>YDYWGQGTLVTVSSGGGGSGGGGSGGGGSGGGGSGGGGS<br>GGGGSGGGGSEVQLVESGGGVVQPGNSLRLSCAASGFTF<br>SSFGMSWVRQAPGKGLEWVSSISGSGSDTLYADSVKGRF<br>TISRDNAKTTLYLQMNSLRPEDTALYYCTIGGSLSRSSQ |

TABLE D-3-continued

PD1/LAG3 Binders of the Present Invention.

| Description | Sequence |
|---|---|
| | GTLVTVSSA |
| Name: F023701167<br>Description: 1PD102C12 (E1D, L11V, A14P, W52aV, N73S, A74S, K83R, I89L, W100aF)-9GS-1PD102C12 (L11V, A14P, W52aV, N73S, A74S, K83R, I89L, W100aF)-9GS-F023700842-9GS-F023700842-9GS-ALB11002-A<br>Target: hPD-1/hLAG-3<br>SEQ ID NO: 122 | DVQLVESGGGVVQPGGSLRLSCAASGSIASIHAMGWFRQ APGKEREFVAVITVSGGITYYADSVKGRFTISRDSSKNT VYLQMNSLRPEDTALYYCAGDKHQSSFYDYWGQGTLVTV SSGGGGSGGGSEVQLVESGGGVVQPGGSLRLSCAASGSI ASIHAMGWFRQAPGKEREFVAVITVSGGITYYADSVKGR FTISRDSSKNTVYLQMNSLRPEDTALYYCAGDKHQSSFY DYWGQGTLVTVSSGGGGSGGGSEVQLVESGGGVVQPGGS LRLSCAASGRTFSDYVMGWERQAPGKEREFVAAISESGG RTHYADSVKGRFTISRDNSKNTLYLQMNSLRPEDTALYY CATTLLWWTSEYAPIKANDYDYWGQGTLVTVSSGGGGSG GGSEVQLVESGGGVVQPGGSLRLSCAASGRTFSDYVMGW FRQAPGKEREFVAAISESGGRTHYADSVKGRFTISRDNS KNTLYLQMNSLRPEDTALYYCATTLLWWTSEYAPIKAND YDYWGQGTLVTVSSGGGGSGGGSEVQLVESGGGVVQPGN SLRLSCAASGETFSSFGMSWVRQAPGKGLEWVSSISGSG SDTLYADSVKGRFTISRDNAKTTLYLQMNSLRPEDTALY YCTIGGSLSRSSQGTLVTVSSA |
| Name: F023701172<br>Description: 1PD102C12 (E1D, L11V, A14P, W52aV, N73S, A74S, K83R, I89L, W100aF)-35GS-F023700842-35GS-ALB11002-A<br>Target: hPD-1/hLAG-3<br>SEQ ID NO: 123 | DVQLVESGGGVVQPGGSLRLSCAASGSIASIHAMGWFRQ APGKEREFVAVITVSGGITYYADSVKGRFTISRDSSKNT VYLQMNSLRPEDTALYYCAGDKHQSSFYDYWGQGTLVTV SSGGGGSGGGSGGGGSGGGSGGGGSGGGSGGGGSEV QLVESGGGVVQPGGSLRLSCAASGRTFSDYVMGWFRQAP GKEREFVAAISESGGRTHYADSVKGRFTISRDNSKNTLY LQMNSLRPEDTALYYCATTLLWWTSEYAPIKANDYDYWG QGTLVTVSSGGGGSGGGGSGGGGSGGGGSGGGGSGGGGS GGGGSEVQLVESGGGVVQPGNSLRLSCAASGFTFSSFGM SWVRQAPGKGLEWVSSISGSGSDTLYADSVKGRFTISRD NAKTTLYLQMNSLRPEDTALYYCTIGGSLSRSSQGTLVT VSSA |
| Name: F023701177<br>Description: 1PD102C12 (E1D, L11V, A14P, W52aV, N73S, A74S, K83R, I89L, W100aF)-9GS-F023700842-9GS-ALB11002-A<br>Target: hPD-1/hLAG-3<br>SEQ ID NO: 124 | DVQLVESGGGVVQPGGSLRLSCAASGSIASIHAMGWFRQ APGKEREFVAVITVSGGITYYADSVKGRFTISRDSSKNT VYLQMNSLRPEDTALYYCAGDKHQSSFYDYWGQGTLVTV SSGGGGSGGGSEVQLVESGGGVVQPGGSLRLSCAASGRT FSDYVMGWERQAPGKEREFVAAISESGGRTHYADSVKGR FTISRDNSKNTLYLQMNSLRPEDTALYYCATTLLWWTSE YAPIKANDYDYWGQGTLVTVSSGGGGSGGGSEVQLVESG GGVVQPGNSLRLSCAASGFTFSSFGMSWVRQAPGKGLEW VSSISGSGSDTLYADSVKGRFTISRDNAKTTLYLQMNSL RPEDTALYYCTIGGSLSRSSQGTLVTVSSA |

*PD1 binder and LAG3 binder CDRs underscored and/or bolded

Optionally, the first residue of any binder moiety in the molecule is substituted with a D or an E as appropriate.

The present invention includes any PD1/LAG3 binder comprising the amino acid sequence of SEQ ID NO: 106-124 or an amino acid sequence comprising 80% or more (e.g., 85%, 90%, 95%, 96%, 97%, 98% or 99%) amino acid sequence identity (i.e., comparing the full amino acid sequences) wherein the PD1/LAG3 binder retains the ability to bind to PD1 and LAG3 and, optionally, HSA.

The present invention includes any PD1/LAG3 binder having the following arrangement of moieties:
PD1 binder 1PD102C12 (A14P, A74S, K83R)-
Peptide linker, e.g., 35GS-
PD1 binder 1PD102C12 (A14P, A74S, K83R)-
Peptide linker, e.g., 35GS-
LAG3 binder F0237611B09-
Peptide linker, e.g., 35GS-
LAG3 binder F0237611B09-
Peptide linker, e.g., 35GS-
Human serum albumin binder, e.g., ALB11002
or
PD1 binder 1PD102C12 (E1D, L11V, A14P, A74S, K83R, I89L)-
Peptide linker, e.g., 35GS-
PD1 binder 1PD102C12 (L11V, A14P, A74S, K83R, I89L)-
Peptide linker, e.g., 35GS-
LAG3 binder F0237611B09 (L11V, A14P, R41P, N43K, A62S, A74S, K83R, V89L)-
Peptide linker, e.g., 35GS-
LAG3 binder F0237611B09 (L11V, A14P, R41P, N43K, A62S, A74S, K83R, V89L)-
Peptide linker, e.g., 35GS-
Human serum albumin binder, e.g., ALB11002-
Optional C-terminal extension alanine
or
PD1 binder 102C12 (E1D, L11V, A14P, A74S, K83R, I89L)-
Peptide linker, e.g., 20GS-
PD1 binder 102C12(L11V, A14P, A74S, K83R, 189L)-
Peptide linker, e.g., 20GS-
LAG3 binder F0237611B09 (L11V, A14P, R41P, N43K, A62S, A74S, K83R, V89L)-
Peptide linker, e.g., 20GS-
LAG3 binder F0237611B09 (L11V, A14P, R41P, N43K, A62S, A74S, K83R, V89L)-
Peptide linker, e.g., 20GS-
Human serum albumin binder, e.g., ALB11002-

Optional C-terminal extension alanine
or
PD1 binder 102C12 (E1D, L11V, A14P, A74S, K83R, I89L)-
Peptide linker, e.g., 9GS-
PD1 binder 102C12 (L11V, A14P, A74S, K83R, I89L)-
Peptide linker, e.g., 9GS-
LAG3 binder F0237611B09 (L11V, A14P, R41P, N43K, A62S, A74S, K83R, V89L)-
Peptide linker, e.g., 9GS-
LAG3 binder F0237611B09 (L11V, A14P, R41P, N43K, A62S, A74S, K83R, V89L)-
Peptide linker, e.g., 9GS-
Human serum albumin binder, e.g., ALB11002-
Optional C-terminal extension alanine
or
PD1 binder 1PD102C12 (E1D, L11V, A14P, A74S, K83R, I89L)-
Peptide linker, e.g., 35GS-
LAG3 binder F0237611B09 (L11V, A14P, R41P, N43K, A62S, A74S, K83R, V89L)-
Peptide linker, e.g., 35GS-
Human serum albumin binder, e.g., ALB11002-
Optional C-terminal extension alanine
or
PD1 binder 102C12(E1D, L11V, A14P, A74S, K83R, I89L)-
Peptide linker, e.g., 20GS-
LAG3 binder F0237611B09(L11V, A14P, R41P, N43K, A62S, A74S, K83R, V89L)-
Peptide linker, e.g., 20GS-
Human serum albumin binder, e.g., ALB11002-
Optional C-terminal extension alanine
or
PD1 binder 102C12 (E1D, L11V, A14P, A74S, K83R, I89L)-
Peptide linker, e.g., 9GS-
LAG3 binder F0237611B09 (L11V, A14P, R41P, N43K, A62S, A74S, K83R, V89L)-
Peptide linker, e.g., 9GS-
Human serum albumin binder, e.g., ALB11002-
Optional C-terminal extension alanine
or
PD1 binder 1PD102C12 (E1D, L11V, A14P, W52aV, N73P, A74S, K83R, I89L, W100aF)-
Peptide linker, e.g., 35GS-
PD1 binder 1PD102C12 (L11V, A14P, W52aV, N73P, A74S, K83R, I89L, W100aF)-
Peptide linker, e.g., 35GS-
LAG3 binder F023700842-
Peptide linker, e.g., 35GS-
LAG3 binder F023700842-
Peptide linker, e.g., 35GS-
Human serum albumin binder, e.g., ALB11002-
Optional C-terminal extension alanine
or
PD1 binder 1PD102C12 (E1D, L11V, A14P, W52aV, N73P, A74S, K83R, I89L, W100aF)-
Peptide linker, e.g., 9GS-
PD1 binder 1PD102C12 (L11V, A14P, W52aV, N73P, A74S, K83R, I89L, W100aF)-
Peptide linker, e.g., 9GS-
LAG3 binder F023700842-
Peptide linker, e.g., 9GS-
LAG3 binder F023700842-
Peptide linker, e.g., 9GS-
Human serum albumin binder, e.g., ALB11002-
Optional C-terminal extension alanine
or
PD1 binder 1PD102C12 (E1D, L11V, A14P, W52aV, N73P, A74S, K83R, I89L, W100aF)-
Peptide linker, e.g., 35GS-
LAG3 binder F023700842-
Peptide linker, e.g., 35GS-
Human serum albumin binder, e.g., ALB11002-
Optional C-terminal extension alanine
or
PD1 binder 1PD102C12 (E1D, L11V, A14P, W52aV, N73P, A74S, K83R, I89L, W100aF)-
Peptide linker, e.g., 9GS-
LAG3 binder F023700842-
Peptide linker, e.g., 9GS-
Human serum albumin binder, e.g., ALB11002-
Optional C-terminal extension alanine
or
PD1 binder 1PD102C12 (E1D, L11V, A14P, W52aV, N73Q, A74S, K83R, I89L, W100aF)-
Peptide linker, e.g., 35GS-
PD1 binder 1PD102C12 (L11V, A14P, W52aV, N73Q, A74S, K83R, I89L, W100aF)-
Peptide linker, e.g., 35GS-
LAG3 binder F023700842-
Peptide linker, e.g., 35GS-
LAG3 binder F023700842-
Peptide linker, e.g., 35GS-
Human serum albumin binder, e.g., ALB11002-
Optional C-terminal extension alanine
or
PD1 binder 1PD102C12 (E1D, L11V, A14P, W52aV, N73Q, A74S, K83R, I89L, W100aF)-
Peptide linker, e.g., 9GS-
PD1 binder 1PD102C12 (L11V, A14P, W52aV, N73Q, A74S, K83R, I89L, W100aF)-
Peptide linker, e.g., 9GS-
LAG3 binder F023700842-
Peptide linker, e.g., 9GS-
LAG3 binder F023700842-
Peptide linker, e.g., 9GS-
Human serum albumin binder, e.g., ALB11002-
Optional C-terminal extension alanine
or
PD1 binder 1PD102C12 (E1D, L11V, A14P, W52aV, N73Q, A74S, K83R, I89L, W100aF)-
Peptide linker, e.g., 35GS-
LAG3 binder F023700842-
Peptide linker, e.g., 35GS-
Human serum albumin binder, e.g., ALB11002-
Optional C-terminal extension alanine
or
PD1 binder 1PD102C12 (E1D, L11V, A14P, W52aV, N73Q, A74S, K83R, I89L, W100aF)-
Peptide linker, e.g., 9GS-
LAG3 binder F023700842-
Peptide linker, e.g., 9GS-
Human serum albumin binder, e.g., ALB11002-
Optional C-terminal extension alanine
or
PD1 binder 1PD102C12 (E1D, L11V, A14P, W52aV, N73S, A74S, K83R, I89L, W100aF)-
Peptide linker, e.g., 35GS-
PD1 binder 1PD102C12 (L11V, A14P, W52aV, N73S, A74S, K83R, I89L, W100aF)-
Peptide linker, e.g., 35GS-
LAG3 binder F023700842-

Peptide linker, e.g., 35GS-
LAG3 binder F023700842-
Peptide linker, e.g., 35GS-
Human serum albumin binder, e.g., ALB11002-
Optional C-terminal extension alanine or PD1 binder 1PD102C12 (E1D, L11V, A14P, W52aV, N73S, A74S, K83R, I89L, W100aF)-
Peptide linker, e.g., 9GS-
PD1 binder 1PD102C12 (L11V, A14P, W52aV, N73S, A74S, K83R, I89L, W100aF)-
Peptide linker, e.g., 9GS-
LAG3 binder F023700842-
Peptide linker, e.g., 9GS-
LAG3 binder F023700842-
Peptide linker, e.g., 9GS-
Human serum albumin binder, e.g., ALB11002-
Optional C-terminal extension alanine or PD1 binder 1PD102C12 (E1D, L11V, A14P, W52aV, N73S, A74S, K83R, I89L, W100aF)-
Peptide linker, e.g., 35GS-
LAG3 binder F023700842-
Peptide linker, e.g., 35GS-
Human serum albumin binder, e.g., ALB11002-
Optional C-terminal extension alanine or PD1 binder 1PD102C12 (E1D, L11V, A14P, W52aV, N73S, A74S, K83R, I89L, W100aF)-
Peptide linker, e.g., 9GS-
LAG3 binder F023700842-
Peptide linker, e.g., 9GS-
Human serum albumin binder, e.g., ALB11002-
Optional C-terminal extension alanine.

In an embodiment of the invention, the PD1/LAG3 binders of the present invention include the following arrangement of moieties:

PD1 binder SEQ ID NO: 98;
35GS linker SEQ ID NO: 58;
PD1 binder SEQ ID NO: 98;
35GS linker SEQ ID NO: 58;
LAG3 binder SEQ ID NO: 63;
35GS linker SEQ ID NO: 58;
LAG3 binder SEQ ID NO: 63;
35GS linker SEQ ID NO: 58;
HSA binder SEQ ID NO: 59;
Alanine or PD1 binder SEQ ID NO: 57;
35GS linker SEQ ID NO: 58;
PD1 binder SEQ ID NO: 99;
35GS linker SEQ ID NO: 58;
LAG3 binder SEQ ID NO: 64;
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 57;
20GS linker SEQ ID NO: 100;
PD1 binder SEQ ID NO: 99;
20GS linker SEQ ID NO: 100;
LAG3 binder SEQ ID NO: 64;
20GS linker SEQ ID NO: 100;
LAG3 binder SEQ ID NO: 64;
20GS linker SEQ ID NO: 100;
HSA binder SEQ ID NO: 59;
Alanine or PD1 binder SEQ ID NO: 57;
9GS linker SEQ ID NO: 125;
PD1 binder SEQ ID NO: 99;
9GS linker SEQ ID NO: 125;
LAG3 binder SEQ ID NO: 64;
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 57;
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 57;
20GS linker SEQ ID NO: 100;
LAG3 binder SEQ ID NO: 64;
20GS linker SEQ ID NO: 100;
HSA binder SEQ ID NO: 59;
Alanine or PD1 binder SEQ ID NO: 57;
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 105;
35GS linker SEQ ID NO: 58;
PD1 binder SEQ ID NO: 105 (D1E);
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 105;
9GS linker SEQ ID NO: 125;
PD1 binder SEQ ID NO: 105 (D1E);
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 105;
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 105;
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 104;
35GS linker SEQ ID NO: 58;
PD1 binder SEQ ID NO: 104 (D1E);
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 104;
9GS linker SEQ ID NO: 125;
PD1 binder SEQ ID NO: 104 (D1E);
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 104;
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 104;
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 103 (N73S);
35GS linker SEQ ID NO: 58;
PD1 binder SEQ ID NO:103 (D1E, N73S);
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 103 (N73S);
9GS linker SEQ ID NO: 125;
PD1 binder SEQ ID NO:103 (D1E, N73S);
9GS linker SEQ ID NO: 125;
LAG3 binder SEQ ID NO: 64;
9GS linker SEQ ID NO: 125;
HSA binder SEQ ID NO: 59;
Alanine or PD1 binder SEQ ID NO: 103 (N73S);
35GS linker SEQ ID NO: 58;
LAG3 binder SEQ ID NO: 64;
35GS linker SEQ ID NO: 58;
HSA binder SEQ ID NO: 59;
Alanine or PD1 binder SEQ ID NO: 103 (N73S);
9GS linker SEQ ID NO: 125;
LAG3 binder SEQ ID NO: 64;
9GS linker SEQ ID NO: 125;
HSA binder SEQ ID NO: 59;
Alanine Cross-Blocking Antibodies The present invention also provides cross-blocking binders that are able to cross-block binding of any of the binders disclosed herein (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177). Such cross-blocking binders may be any molecule that exhibits such cross-blocking, e.g., an ISVD, Nanobody, antibody or antigen-binding fragment thereof.

In general, a binder (e.g., ISVD such as Nanobody) or antibody or antigen-binding fragment thereof that "cross-blocks" a reference binder or "cross competes with" a reference binder refers to a binder (e.g., ISVD such as Nanobody) or antibody or antigen-binding fragment thereof that blocks binding of the reference binder to its antigen in a competition assay by 50% or more, and conversely, the reference binder blocks binding of the binder (e.g., ISVD such as Nanobody) or antibody or antigen-binding fragment thereof to its antigen in a competition assay by 50% or more. Cross-blocking or cross-competition can be determined any assay known in the art, including surface plasmon resonance (SPR), ELISA and flow cytometry.

In an embodiment of the invention, cross-blocking is determined by use of a Biacore assay. For convenience reference is made to two binders, the scope of the present invention includes antibodies and antigen binding fragments thereof, e.g., Fab fragments, that cross-block a binder of the present invention. A Biacore machine (for example the Biacore 3000) is operated in line with the manufacturer's recommendations.

Thus, in one cross-blocking assay, PD1 or LAG3 is coupled to a CM5 Biacore chip using standard amine coupling chemistry to generate a PD1 or LAG3-coated surface. For example, 200-800 resonance units of PD1 or LAG3 would be coupled to the chip (or any amount that gives easily measurable levels of binding but that is readily saturable by the concentrations of test reagent being used).

The two binders (termed A* and B*) to be assessed for their ability to cross-block each other are mixed at a one to one molar ratio of binding sites in a suitable buffer to create the test mixture.

The concentration of each binder in the test mix should be high enough to readily saturate the binding sites for that binder on the PD1 or LAG3 molecules captured on the Biacore chip. The binders in the mixture are at the same molar concentration.

Separate solutions containing binder A* alone and binder B* alone are also prepared. Binder A* and binder B* in these solutions should be in the same buffer and at the same concentration as in the test mix.

The test mixture is passed over the PD1 or LAG3-coated Biacore chip and the total amount of binding recorded. The chip is then treated in such a way as to remove the bound binders without damaging the chip-bound PD1 or LAG3. In an embodiment of the invention, this is done by treating the chip with 30 mM HCl for 60 seconds.

The solution of binder A* alone is then passed over the PD1 or LAG3-coated surface and the amount of binding recorded. The chip is again treated to remove all of the bound binder without damaging the chip-bound PD1 or LAG3.

The solution of binder B* alone is then passed over the PD1 or LAG3-coated surface and the amount of binding recorded.

The maximum theoretical binding of the mixture of binder A* and binder B* is next calculated, and is the sum of the binding of each binder when passed over the PD1 or LAG3 surface alone. If the actual recorded binding of the mixture is less than this theoretical maximum, then the two binders are cross-blocking each other.

Thus, in general, a cross-blocking binder according to the invention is one which will bind to PD1 or LAG3 in the above Biacore cross-blocking assay such that, during the assay and in the presence of a second binder, the recorded binding is between, for example, 80% and 0.1% (e.g., 80% to 4%) of the maximum theoretical binding, for example between 75% and 0.1% (e.g., 75% to 4%) of the maximum theoretical binding, for example, between 70% and 0.1% (e.g., 70% to 4%) of maximum theoretical binding (as just defined above) of the two binders in combination.

In an embodiment of the invention, an ELISA assay is used for determining whether a PD1 and/or LAG3 binder cross-blocks or is capable of cross-blocking according to the invention.

The general principal of the assay is to have an PD1 or LAG3 binder coated onto the wells of an ELISA plate. An excess amount of a second, potentially cross-blocking, anti-PD1 or LAG3 binder is added in solution (i.e., not bound to the ELISA plate). A limited amount of PD1 or LAG3 is then added to the wells. The coated binder and the binder in solution compete for binding of the limited number of PD1 or LAG3 molecules. The plate is washed to remove PD1 or LAG3 that has not been bound by the coated binder and to also remove the second, solution phase binder as well as any complexes formed between the second, solution phase binder and PD1 or LAG3. The amount of bound PD1 or LAG3 is then measured using an appropriate PD1 or LAG3 detection reagent. A binder in solution that is able to cross-block the coated binder will be able to cause a decrease in the number of PD1 or LAG3 molecules that the coated binder can bind relative to the number of PD1 or LAG3 molecules that the coated binder can bind in the absence of the second, solution phase, binder.

Expression Methods

The present invention includes recombinant methods for making PD1 and/or LAG3 binders (e.g., an ISVD such as a Nanobody) of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) comprising (i) introducing a polynucleotide encoding the amino acid sequence of said PD1 and/or LAG3 binder, for example, wherein the polynucleotide is in a vector and/or is operably linked to a promoter; (ii) culturing the host cell (e.g., CHO or *Pichia* or *Pichia pastoris*) under condition favorable to expression of the polynucleotide and, (iii) optionally, isolating the PD1 and/or LAG3 binder from the host cell and/or medium in which the host cell is grown. See e.g., WO 04/041862, WO 2006/122786, WO 2008/020079, WO 2008/142164 or WO 2009/068627.

The invention also relates to polynucleotides that encode PD1 and/or LAG3 binders of the present invention (e.g., an ISVD such as a Nanobody) as described herein (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177). The polynucleotides may, in an embodiment of the invention, be operably linked to one or more control sequences.

The polynucleotide may be in the form of a plasmid or vector. Again, such polynucleotides can be generally as described in the published patent applications of Ablynx N.V., such as for example WO 04/041862, WO 2006/122786, WO 2008/020079, WO 2008/142164 or WO 2009/068627.

The invention also relates to hosts or host cells that contain such polynucleotides encoding PD1 and/or LAG3 binders, vectors, and/or PD1 and/or LAG3 binder polypeptide described herein (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177). Again, such host cells can be generally as described in the published patent applications of Ablynx N.V., such as for example WO 04/041862, WO 2006/122786, WO 2008/020079, WO 2008/142164 or WO 2009/068627. Examples of specific host cells are discussed below.

Eukaryotic and prokaryotic host cells, including mammalian cells as hosts for expression of the PD1 and/or LAG3 binder (e.g., an ISVD such as a Nanobody) are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha,* any *Kluyveromyces* sp., *Candida albicans,* any *Aspergillus* sp., *Trichoderma reesei, Chrysosporium lucknowense,* any *Fusarium* sp., *Yarrowia lipolytica,* and *Neurospora crassa.* The present invention includes any host cell (e.g., a CHO cell or *Pichia* cell, e.g., *Pichia pastoris*) containing an PD1 and/or LAG3 binder of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) or containing a polynucleotide encoding such a binder or containing a vector that contains the polynucleotide.

Further, expression of a PD1 and/or LAG3 binder (e.g., an ISVD such as a Nanobody) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell. Such host cells containing the binder or polynucleotide or vector as discussed herein as well as expression methods, as discussed herein, for making the binder using such a host cell are part of the present invention.

The present invention includes methods for purifying a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) comprising introducing a sample (e.g., culture medium, cell lysate or cell lysate fraction, e.g., a soluble fraction of the lysate) comprising the PD1 and/or LAG3 binder to a purification medium (e.g., cation-exchange medium, anion-exchange medium and/or hydrophobic exchange medium) and either collecting purified PD1 and/or LAG3 binder from the flow-through fraction of said sample that does not bind to the medium; or, discarding the flow-through fraction and eluting bound PD1 and/or LAG3 binder from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the PD1 and/or LAG3 binder is secreted into the culture medium by the host cell and the medium or a fraction thereof is applied to the purification medium.

In general, glycoproteins produced in a particular cell line or transgenic animal will have a glycosylation pattern that is characteristic for glycoproteins produced in the cell line or transgenic animal. Therefore, the particular glycosylation pattern of a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) will depend on the particular cell line or transgenic animal used to produce the PD1 and/or LAG3 binder. PD1 and/or LAG3 binders comprising only non-fucosylated N-glycans are part of the present invention and may be advantageous, because non-fucosylated antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These PD1 and/or LAG3 binders with non-fucosylated N-glycans are not likely to be immunogenic because their carbohydrate structures are a normal component of the population that exists in human serum IgG.

The present invention includes PD1 and/or LAG3 binders (e.g., an ISVD such as a Nanobody) comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the PD1 and/or LAG3 binder comprises one or more of the "engineered yeast N-linked glycans" or "CHO N-linked glycans" that are set forth in FIG. 4 (e.g., G0 and/or G0-F and/or G1 and/or G1-F and/or and/or G2-F and/or Man5). In an embodiment of the invention, the PD1 and/or LAG3 binder comprises the engineered yeast N-linked glycans, i.e., G0 and/or G1 and/or G2, optionally, further including Man5. In an embodiment of the invention, the PD1 and/or LAG3 binders comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the PD1 and/or LAG3 binders are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Combinations

In particular embodiments, the PD1 and/or LAG3 binders (e.g., an ISVD such as a Nanobody) of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) may be used alone, or in association with other, further therapeutic agents and/or therapeutic procedures, for treating or preventing any disease such as cancer, e.g., as discussed herein, in a subject in need of such treatment or prevention. Compositions or kits, e.g., pharmaceutical compositions comprising a pharmaceutically acceptable carrier, comprising such PD1 and/or LAG3 binders in association with further therapeutic agents are also part of the present invention.

The term "in association with" indicates that the components, a PD1 and/or LAG3 binder (e.g., an ISVD such as a Nanobody) of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) along with another agent such as pembrolizumab or nivolumab, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein a PD1 and/or LAG3 binder of the present invention is administered parenterally and paclitaxel is administered orally).

In particular embodiments, the PD1 and/or LAG3 binders (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) may be used in association with an anti-cancer therapeutic agent or immunomodulatory drug such as an immunomodulatory receptor inhibitor, e.g., an antibody or antigen-binding fragment thereof that specifically binds to the receptor.

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with one or more of an inhibitors (e.g., a small organic molecule or an antibody or antigen-binding fragment thereof) such as: an MTOR (mammalian target of rapamycin) inhibitor, a cytotoxic agent, a platinum agent a BRAF inhibitor, a CDK4/6 inhibitor an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with one or more of: anti-PD1 antibody or antigen-binding fragment thereof (e.g., pembrolizumab, nivolumab, CT-011), anti-PDL1, anti-CTLA4, anti-TIM3, anti-CS1, (e.g., elotuzumab), anti-KIR2DL1/2/3 (e.g., lirilumab), anti-CD27, anti-CD137 (e.g., urelumab), anti-GITR (e.g., TRX518), anti-PD-L1 (e.g., BMS-936559, MSB0010718C or MPDL3280A), anti-PD-L2, anti-ILT1, anti-ILT2, anti-ILT3, anti-ILT4, anti-ILT5, anti-ILT6, anti-ILT7, anti-ILT8, anti-CD40, anti-OX40, anti-CD137, anti-KIR2DL1, anti-KIR2DL2/3, anti-KIR2DL4, anti-KIR2DL5A, anti-KIR2DL5B, anti-KIR3DL1, anti-KIR3DL2, anti-KIR3DL3, anti-NKG2A, anti-NKG2C, anti-NKG2E, or any small organic molecule inhibitor of such targets; IL-10, anti-IL10, anti-TSLP (thymic stromal lymphopoietin) or PEGylated IL-10.

In an embodiment of the invention, the molecular weight of the polyethylene glycol (PEG) moiety, on a PEGylated IL-10 molecule, is about 12,000 daltons or about 20,000 daltons. In an embodiment of the invention, PEGylated IL-10 (e.g., PEGylated human IL-10) comprises one or more polyethylene glycol molecules covalently attached via a linker (e.g., $C_{2-12}$ alkyl such as —$CH_2CH_2CH_2$—) to a single amino acid residue of a single subunit of IL-10, wherein said amino acid residue is the alpha amino group of the N-terminal amino acid residue or the epsilon amino group of a lysine residue. In an embodiment of the invention PEGylated IL-10 is: (PEG) b-L-NH-IL-10; wherein b is 1-9 and L is a $C_{2-12}$ alkyl linker moiety covalently attached to a nitrogen (N) of the single amino acid residue of the IL-10. In an embodiment of the invention, the IL-10 of PEGylated IL-10 has the formula: $[X—O(CH_2CH_2O)_n]_b$-L-NH-IL-10, wherein X is H or $C_{1-4}$ alkyl; n is 20 to 2300; b is 1 to 9; and L is a $C_{1-11}$ alkyl linker moiety which is covalently attached to the nitrogen (N) of the alpha amino group at the amino terminus of one IL-10 subunit; provided that when b is greater than 1, the total of n does not exceed 2300. See U.S. Pat. No. 7,052,686.

In an embodiment of the invention, the anti-IL-10 antibody or antigen-binding fragment thereof (e.g., humanized antibody) comprises the CDRs set forth below:

```
CDR-L1:
                                  (SEQ ID NO: 71)
KTSQNIFENLA

CDR-L2:
                                  (SEQ ID NO: 72)
NASPLQA

CDR-L3:
                                  (SEQ ID NO: 73)
HQYYSGYT

CDR-H1:
                                  (SEQ ID NO: 74)
GFTFSDYHMA

CDR-H2:
                                  (SEQ ID NO: 75)
SITLDATYTYYRDSVRG

CDR-H3:
                                  (SEQ ID NO: 76)
HRGFSVVAILDY
```
(See U.S. Pat. No. 7,662,379)

In an embodiment of the invention, the anti-TSLP antibody or antigen-binding fragment thereof (e.g., humanized antibody) comprises the CDRs set forth below:

```
CDR-H1:
                                  (SEQ ID NO: 77)
GYIFTDYAMH

CDR-H2:
                                  (SEQ ID NO: 78)
TFIPLLDTSDYNQNFK

CDR-H3:
                                  (SEQ ID NO: 79)
MGVTHSYVMDA

CDR-L1:
                                  (SEQ ID NO: 80)
RASQPISISVH

CDR-L2:
                                  (SEQ ID NO: 81)
FASQSIS

CDR-L3:
                                  (SEQ ID NO: 82)
QQTFSLPYT
```
(see WO2008/76321)

In an embodiment of the invention, the anti-CD27 antibody or antigen-binding fragment thereof (e.g., humanized antibody) comprises the CDRs set forth below:

```
CDR-H1:
                                    (SEQ ID NO: 83)
GFIIKATYMH

CDR-H2:
                                    (SEQ ID NO: 84)
RIDPANGETKYDPKFQV

CDR-H3:
                                    (SEQ ID NO: 85)
YAWYFDV

CDR-L1:
                                    (SEQ ID NO: 86)
RASENIYSFLA

CDR-L2:
                                    (SEQ ID NO: 87)
HAKTLAE

CDR-L3:
                                    (SEQ ID NO: 88)
QHYYGSPLT
```

(See WO2012/04367).

Thus, the present invention includes compositions comprising a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) in association with pembrolizumab; as well as methods for treating or preventing cancer in a subject comprising administering an effective amount of the PD1 and/or LAG3 binder in association with pembrolizumab (e.g., pembrolizumab dosed at 200 mg once every three weeks) to the subject. Optionally, the subject is also administered in association with a another further therapeutic agent.

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with a pembrolizumab antibody which comprises an immunoglobulin heavy chain (or CDR-H1, CDR-H2 and CDR-H3 thereof) comprising the amino acid sequence:

```
                                    (SEQ ID NO: 89)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK;
``` and an immunoglobulin light chain (or CDR-L1, CDR-L2 and CDR-L3 thereof) comprising the amino acid sequence:

```
                                    (SEQ ID NO: 90)
EIVLTQSPATLSLSPGERATLSCRASKGVSTSGYSYLHWYQQKPGQAPRLL

TYLASYLESGVPARFSGSGSGTDFTLTISSLEPEDFAVYYCQHSRDLPLTF

GGGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC.
```

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with an antibody comprising an immunoglobulin heavy chain (or CDR-H1, CDR-H2 and CDR-H3 thereof) comprising the amino acid sequence:

```
                                    (SEQ ID NO: 91)
QVQLVESGGGVVQPGRSLRLDCKASGITFSNSGMHWVRQAPGKGLEWVAVI

WYDGSKRYYADSVKGRFTISRDNSKNTLFLQMNSLRAEDTAVYYCATNDDY

WGQGTLVTVSSASTKGPSVFPLAPCSRSTSESTAALGCLVKDYFPEPVTVS

WNSGALTSGVHTFPAVLQSSGLYSLSSVVTVPSSSLGTKTYTCNVDHKPSN

TKVDKRVESKYGPPCPPCPAPEFLGGPSVFLFPPKPKDTLMISRTPEVTCV

VVDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQVS

LTCLVKGFYPSDIAVEWESNGQPENNYKTTPPVLDSDGSFFLYSRLTVDKS

RWQEGNVFSCSVMHEALHNHYTQKSLSLSLGK;
``` and an immunoglobulin light chain (or CDR-L1, CDR-L2 and CDR-L3 thereof) comprising the amino acid sequence:

```
                                    (SEQ ID NO: 92)
EIVLTQSPATLSLSPGERATLSCRASQSVSSYLAWYQQKPGQAPRLLIYDA

SNRATGIPARFSGSGSGTDFTLTISSLEPEDFAVYYCQQSSNWPRTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.
```

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, aflibercept, ALT-110, altretamine, amifostine, aminoglutethimide, amrubicin, amsacrine, anagrelide, anastrozole, angiostatin, AP-23573, ARQ-197, arzoxifene, AS-252424, AS-605240, asparaginase, ATI3387, AT-9263, atrasentan, axitinib, AZD1152, *Bacillus* Calmette-Guerin (BCG) vaccine, batabulin, BC-210, besodutox, bevacizumab, BGJ398, bicalutamide, Bio111, BI0140, BKM120, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, CEA (recombinant vaccinia-carcinoembryonic antigen vaccine), cediranib, CG-1521, CG-781, chlamydocin, chlorambucil, chlorotoxin, cilengitide, cimitidine, cisplatin, cladribine, clodronate, cobimetnib, COL-3, CP-724714, cyclophosphamide, cyproterone, cyproteroneacetate, cytarabine, cytosinearabinoside, dabrafenib, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, DNE03, docetaxel, dovitinib, doxorubicin, droloxifene, edotecarin, yttrium-90 labeled-edotreotide, edotreotide, EKB-569, EMD121974, encorafenib, endostatin, enzalutamide, enzastaurin, epirubicin, epithilone B, ERA-923, erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, fulvestrant, galeterone, ganetespib, gefitinib, gemcitabine, gimatecan, glucopyranosyl lipid A, goserelin, goserelin acetate, gossypol, GSK461364, GSK690693, EMIR-3339, hydroxyprogesteronecaproate, hydroxyurea, IC87114, idarubicin, idoxyfene, ifosfamide, IM862, imatinib, IMC-1C11, imiquimod, INC280, INCB24360, INO1001, interferon, interleukin-2, interleukin-12, ipilimumab, irinotecan, JNJ-16241199, ketoconazole, KRX-0402, lapatinib, lasofoxifene, LEE011, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, LY3009120, marimastat, mechlorethamine, medroxyprogesteroneacetate, megestrolacetate, MEK162, melphalan, mercaptopurine, mesna, methotrexate, mithramycin, mitomycin, mitotane, mitoxantrone, a suspension of heat killed *Mycobacterium obuense*, tozasertib, MLN8054, natitoclax, neovastat, Neratinib, neuradiab, nilotinib, nilutimide, nolatrexed, NVP-BEZ235, oblimersen, octreotide, ofatumumab, oregovomab, ornatuzumab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, poly-ICLC, porfimer, prednisone, procarbazine, progestins, PSK protein bound polysaccharide (derived from *Basidiomycete coriolus versicolor*), PLX8394, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, 6-thioguanine, thiotepa, ticilimumab, tipifarnib, tivozanib, TKI-258, TLK286, TNF☐ (tumor necrosis factor alpha), topotecan, toremifene citrate, trabectedin, trametinib, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vemurafenib, vinblastine, vincristine, vindesine, vinorelbine, vitaxin, vitespan, vorinostat, VX-745, wortmannin, Xr311, Z-100 hot water extract of *Bacillus* tuberculosis, zanolimumab, ZK186619, ZK-304709, ZM336372 or ZSTK474.

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with an agent which treats or prevents such a deficiency, such as, e.g., filgrastim, PEG-filgrastim, erythropoietin, epoetin alfa or darbepoetin alfa.

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is in association with a vaccine. In an embodiment of the invention, the vaccine is an anti-cancer vaccine, a peptide vaccine or a DNA vaccine. For example, in an embodiment of the invention, the vaccine is a tumor cell (e.g., an irradiated tumor cell) or a dendritic cell (e.g., a dendritic cell pulsed with a tumor peptide).

In an embodiment of the invention, a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8;

F023701161; F023701166; F023701171; F023701176; F023701162; F023701167; F023701172; or F023701177) is administered in association with a therapeutic procedure. A therapeutic procedure is one or more steps carried out by a physician or clinician in treating a subject which is intended to alleviate one or more symptoms (e.g., of cancer and/or infectious disease) in the treated subject, whether by inducing the regression or elimination of such symptoms or by inhibiting the progression of such symptom(s), e.g., cancer symptoms such as tumor growth or metastasis, by any clinically measurable degree.

In an embodiment of the invention, a therapeutic procedure is anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures.

In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with a PD1 and/or LAG3 binder (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) is surgical tumorectomy.

Therapeutic Uses

The invention includes a method for the prevention and/or treatment of at least one disease or disorder that can be prevented or treated by the use of a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) of the present invention, optionally in association with a further therapeutic agent or therapeutic procedure, which method comprises administering, to a subject in need thereof, a pharmaceutically active amount of the PD1 and/or LAG3 binder, and/or of a pharmaceutical composition comprising the same.

"Treat" or "treating" means to administer PD1 and/or LAG3 binders (e.g., an ISVD such as a Nanobody) of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177), to a subject having one or more symptoms of a disease for which the PD1 and/or LAG3 binders are effective, e.g., in the treatment of a subject having cancer or an infectious disease, or being suspected of having cancer or infectious disease, for which the agent has therapeutic activity. Typically, the PD1 and/or LAG3 binder is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the PD1 and/or LAG3 binder may vary according to factors such as the disease stage, age, and weight of the patient, and the ability of the drug to elicit a desired response in the subject.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein. Generally, the treatment regimen will be followed until the desired therapeutic effect is achieved and/or for as long as the desired therapeutic effect is to be maintained. Again, this can be determined by the clinician.

The invention also relates to a pharmaceutical composition that comprises at least one amino acid sequence, a PD1 and/or LAG3 binder (e.g., an ISVD such as a Nanobody), polypeptide or compound as described herein, such as F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177, and optionally at least one pharmaceutically acceptable carrier, diluent or excipient. Such preparations, carriers, excipients and diluents may generally be as described in the published patent applications of Ablynx N.V., such as for example WO 04/041862, WO 2006/122786, WO 2008/020079, WO 2008/142164 or WO 2009/068627.

To prepare pharmaceutical or sterile compositions of the PD1 and/or LAG3 binders (e.g., an ISVD such as a Nanobody) of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177), the PD1 and/or LAG3 binders is admixed with a pharmaceutically acceptable carrier or excipient. See, e.g., Remington's Pharmaceutical Sciences and U.S. Pharmacopeia: National Formulary, Mack Publishing Company, Easton, Pa. (1984). Such compositions are part of the present invention.

The scope of the present invention includes dessicated, e.g., freeze-dried, compositions comprising an PD1 and/or LAG3 binders (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) or a pharmaceutical composition thereof that includes a pharmaceutically acceptable carrier but substantially lacks water.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

The mode of administration of a PD1 and/or LAG3 binder (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) to a subject can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Guidance in selecting appropriate doses of PD1 and/or LAG3 binders (e.g., F023700924 or F023700931) is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

As the PD1 and/or LAG3 binders of the present invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) are capable of binding to PD1 (e.g., an ISVD such as a Nanobody), they can in particular be used for treatment or prevention of cancer, metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer and gastric cancer.

PD1 and/or LAG3 binders (e.g., an ISVD such as a Nanobody) of the present invention can be used for treatment or prevention of infectious diseases such as, for example, viral infection, bacterial infection, fungal infection or parasitic infection. In an embodiment of the invention, the viral infection is infection with a virus selected from the group consisting of human immunodeficiency virus (HIV), ebola virus, hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus. In an embodiment of the invention, the bacterial infection is infection with a bacteria selected from the group consisting of *Chlamydia*, rickettsial bacteria, mycobacteria, staphylococci, streptococci, pneumonococci, meningococci and gonococci, *kleb-* siella, proteus, serratia, pseudomonas, Legionella, Corynebacterium diphtheriae, Salmonella, bacilli, Vibrio cholerae, Clostridium tetan, Clostridium botulinum, Bacillus anthricis, Yersinia pestis, Mycobacterium leprae, Mycobacterium lepromatosis, and Borriella. In an embodiment of the invention, the fungal infection is infection with a fungus selected from the group consisting of Candida (albicans, krusei, glabrata, tropicalis, etc.), Cryptococcus neoformans, Aspergillus (fumigatus, niger, etc.), Genus Mucorales (mucor, absidia, rhizopus), Sporothrix schenkii, Blastomyces dermatitidis, Paracoccidioides brasiliensis, Coccidioides immitis and Histoplasma capsulatum. In an embodiment of the invention, the parasitic infection is infection with a parasite selected from the group consisting of Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii, Nippostrongylus brasiliensis.

The present invention also includes methods for:
inhibiting LAG3 binding to MEW class II molecules;
competing with MEW class II molecules for LAG3 binding;
binding a LAG3 binder, e.g., PD1/LAG3 binder, to native LAG3 on the surface of activated CD4+ and/or CD8+ T-cells;
inhibiting LAG3 homodimerization; and/or
stimulating antigen-specific T-cell production of IL-2
in the body of a subject by administering the PD1/LAG3 binder (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177) to the subject; or in vitro by contacting LAG3 with the PD1/LAG3 binder. Such activities can be mediated via the LAG3 binder. Thus, such methods may also be performed with any binder that includes a LAG3 binder.

The present invention also includes methods for:
blocking binding between PD1 and PD-L1 and/or PD-L2
binding a PD1 binder, e.g., a PD1/LAG3 binder, to B-cells and/or T-cells
blocking PD1 mediated T-cell inhibition, T-cell apoptosis and/or T-cell exhaustion
in the body of a subject by administering the PD1/LAG3 binder (e.g., F023700924 or F023700931) to the subject; or in vitro by contacting PD1 with the PD1/LAG3 binder. Such activities can be mediated via the PD1 binder. Thus, such methods may also be performed with any binder that includes a PD1 binder.

The present invention further includes methods for increasing the half-life of a binder, such as a PD1 and/or: LAG3 binder by fusing the binder to an anti-human serum albumin binder such as ALB11002.

The invention also relates to methods of treatment of the aforementioned diseases and disorders, which generally comprise administering to a subject in need thereof (i.e. suffering from one of the aforementioned diseases) a therapeutically effective amount of a PD1 and/or LAG3 binder (e.g., an ISVD such as a Nanobody) of the invention (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177). The invention also relates to a PD1 and/or LAG3 binder of the invention for use in the prevention or treatment of one of the aforementioned diseases or disorders.

The PD1 and/or LAG3 binders (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177), polypeptides, compounds, and polynucleotides (e.g., vectors) described herein are preferably administered to the circulation. As such, they can be administered in any suitable manner that allows the PD1 and/or LAG3 binders, polypeptides, compounds, and polynucleotides to enter the circulation, such as intravenously, via injection or infusion, or in any other suitable manner (including oral administration, subcutaneous administration, intramuscular administration, administration through the skin, intranasal administration, administration via the lungs, etc.) that allows the PD1 and/or LAG3 binders, polypeptides, compounds, and polynucleotides to enter the circulation. Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

The present invention also provides an injection device comprising any of the PD1 and/or LAG3 binders (e.g., an ISVD such as a Nanobody) (e.g., F023700899; F023700931; F023701016; F023701017; F023700924; F023700969; F023700970; F023701163; F023701168; F023701173; F02370117 F023701176; 8; F023701161; F023701166; F023701171; F023701176; F023701162; F023701167; F023701172; or F023701177), polypeptides or polynucleotides set forth herein or a pharmaceutical composition thereof. An injection device is a device that introduces a substance into the body of a patient via a parenteral route, e.g., intramuscular, subcutaneous or intravenous. For example, an injection device may be a syringe (e.g., prefilled with the pharmaceutical composition, such as an auto-injector) which, for example, includes a cylinder or barrel for holding fluid to be injected (e.g., comprising the PD1 and/or LAG3 binder or a pharmaceutical composition thereof), a needle for piecing skin and/or blood vessels for injection of the fluid; and a plunger for pushing the fluid out of the cylinder and through the needle bore. In an embodiment of the invention, an injection device that comprises an PD1 and/or LAG3 binder or a pharmaceutical composition thereof is an intravenous (IV) injection device. Such a device includes the PD1 and/or LAG3 binder or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the subject through the cannula or trocar/needle. The PD1 and/or LAG3 binder or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump.

Figure 8A:
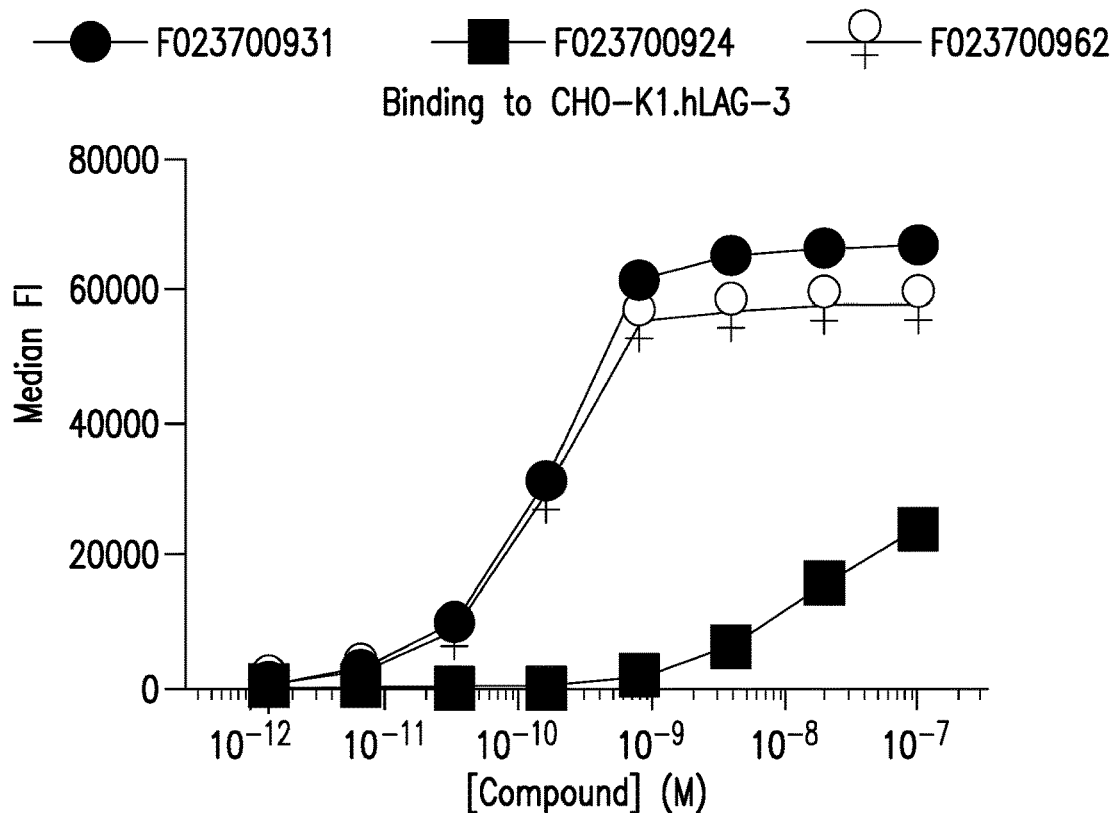
FIG. 8 (A-B). Binding of (A) CHO expressing human LAG3 by F023700931, F023700924 or F023700962 or (B) 3A9 expressing rhesus LAG3 by F023700931 (*Pichia* or CHO expressed), F023700924 (*Pichia* or CHO expressed), F023700933 or F023700962.
Figure 8B:
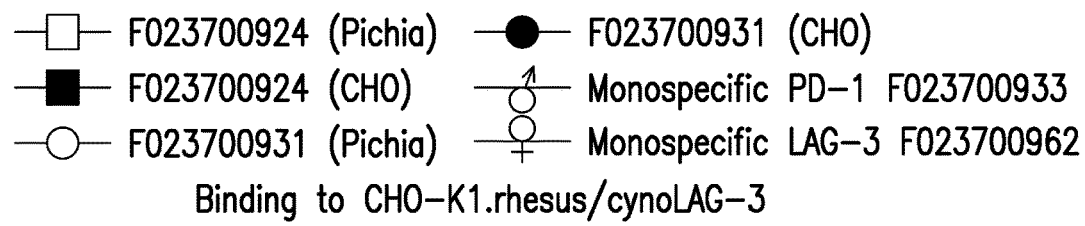
Figure 9A:
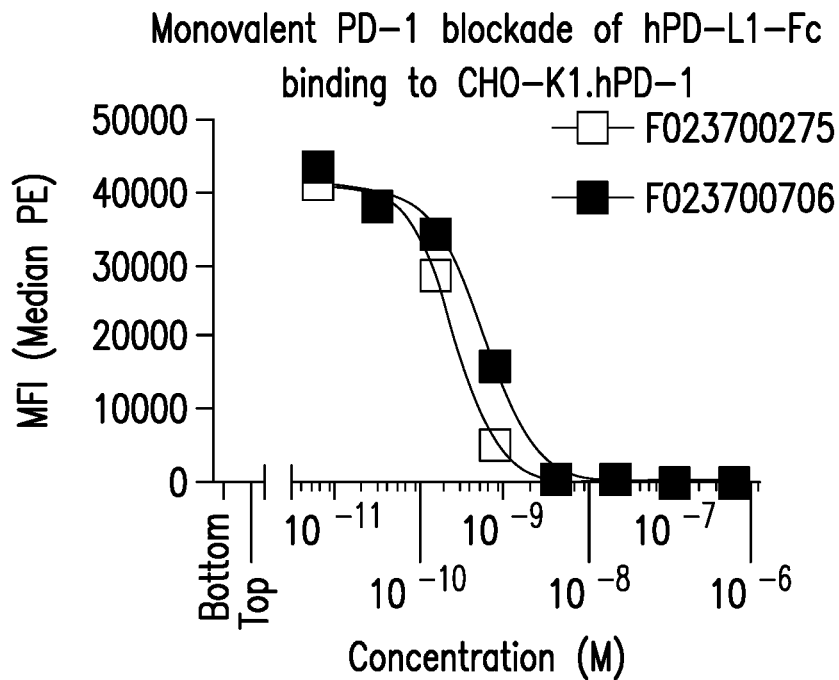
FIG. 9 (A-H). Blockage of binding between (A) human PD-L1-Fc and CHO-K1 expressing human PD1 by F023700275 or F023700706; (B) human PD-L2-Fc and CHO-K1 expressing human PD1 by F023700275 or F023700706; (C) human PD-L1-Fc and CHO-K1 expressing human PD1 by F023700931 (*Pichia* or CHO expressed), F023700924 (*Pichia* or CHO expressed), F023700933 or F023700962; (D) human PD-L2-Fc and CHO-K1 expressing human PD1 by F023700931 (*Pichia* or CHO expressed), F023700924 (*Pichia* or CHO expressed), F023700933 or F023700962; (E) human PD-L1-Fc and CHO-K1 expressing human PD1 by F023700931, F023700924, F023700933 or F023700962; (F) human PD-L2-Fc and CHO-K1 expressing human PD1 by F023700931, F023700924, F023700933 or F023700962; (G) human PD-L1-Fc and CHO-K1 expressing human PD1 by F023700929 (1PD102C12 (L11V, A14P, A74S, K83R, I89L)-HIS6), F023701190 (1PD102C12 (E1D, L11V, A14P, W52aV, A74S, K83R, I89L, W100aF)-HIS6), F023701192 (1PD102C12 (E1D, L11V, A14P, W52aV, N73Q, A74S, K83R, I89L, W100aF)-HIS6, or F023701193 (1PD102C12(E1D, L11V, A14P, W52aV, N73P, A74S, K83R, I89L, W100aF)-HIS6); (H) human PD-L2-Fc and CHO-K1 expressing human PD1 by F023700929 (1PD102C12 (L11V, A14P, A74S, K83R, I89L)-HIS6), F023701190 (1PD102C12 (E1D, L11V, A14P, W52aV, A74S, K83R, I89L, W100aF)-HIS6), F023701192 (1PD102C12 (E1D, L11V, A14P, W52aV, N73Q, A74S, K83R, I89L, W100aF)-HIS6, or F023701193 (1PD102C12 (E1D, L11V, A14P, W52aV, N73P, A74S, K83R, I89L, W100aF)-HIS6). US=Stained; hPD-L1 EC30=the staining intensity of hPD-L1-Fc that has been titrated to give 30% of the maximal staining intensity that could be obtained; GAH=goat anti-human secondary antibody used to detect the human Fc portion of hPD-L1-Fc.
Figure 9B:
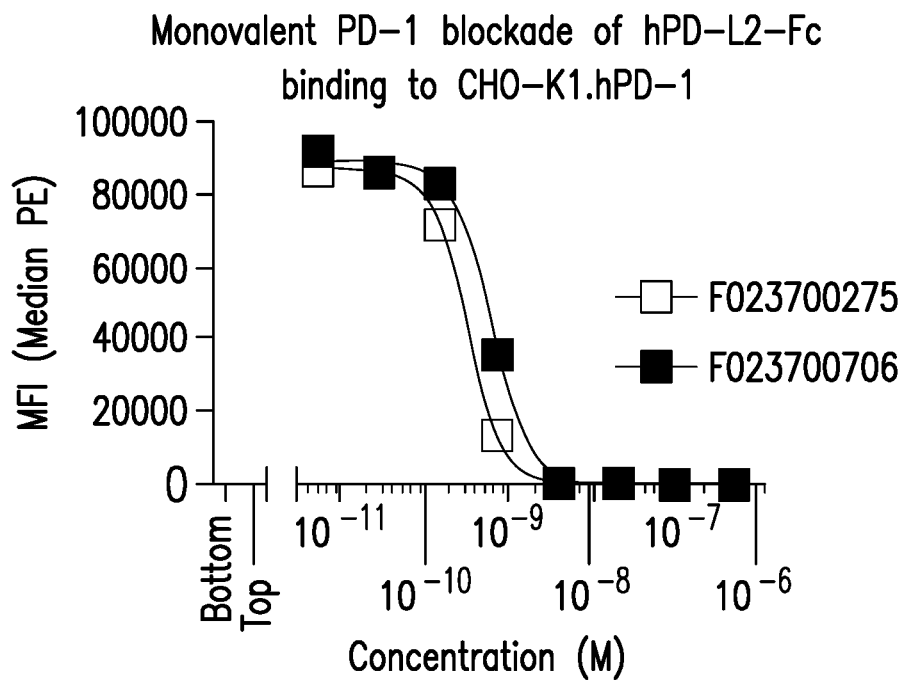
Figure 9C:
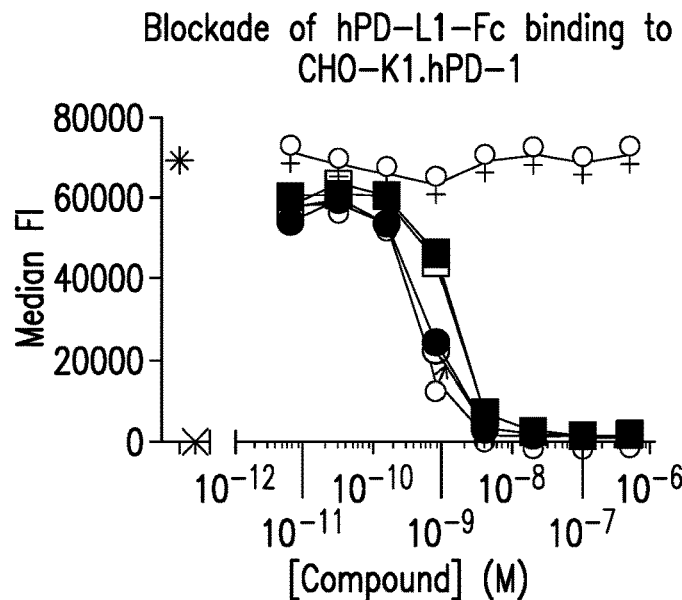
Figure 9D:
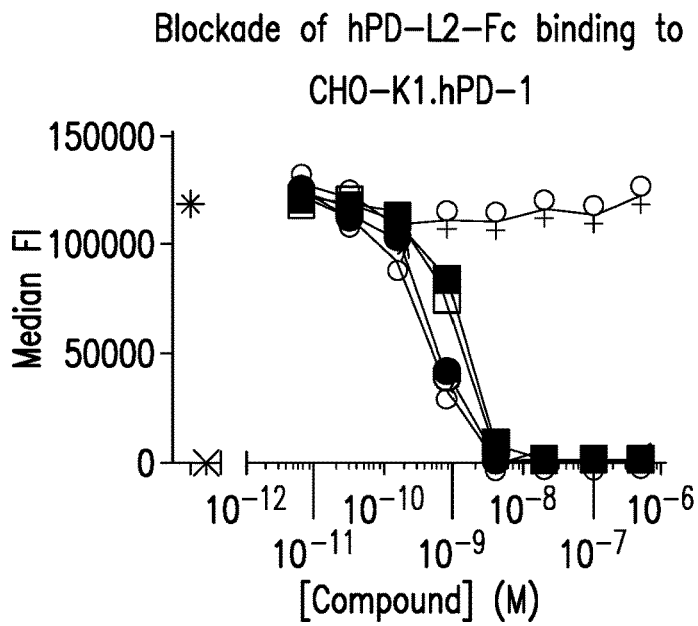
Figure 9E:
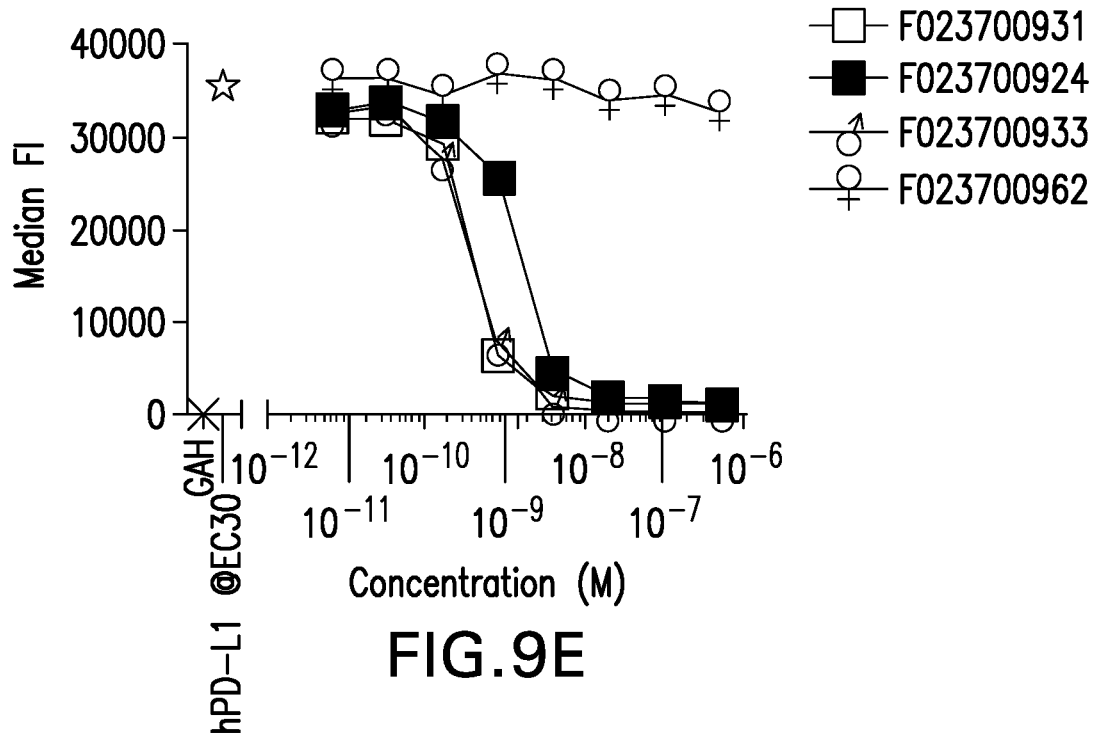
Figure 9F:
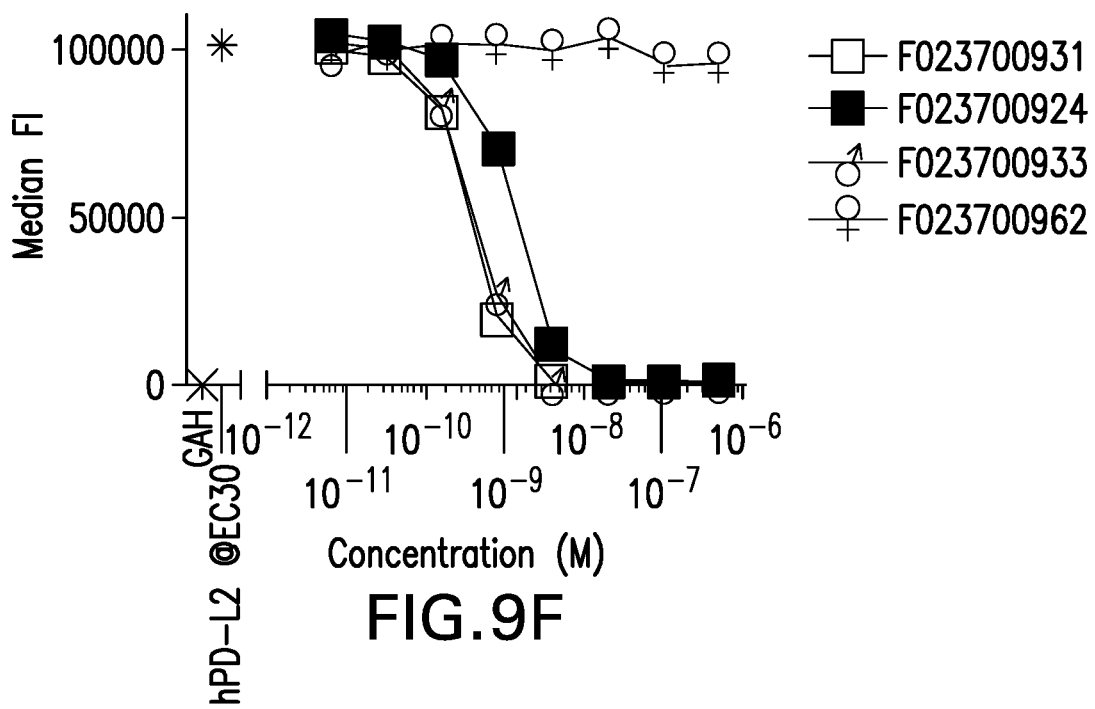
Figure 9G:
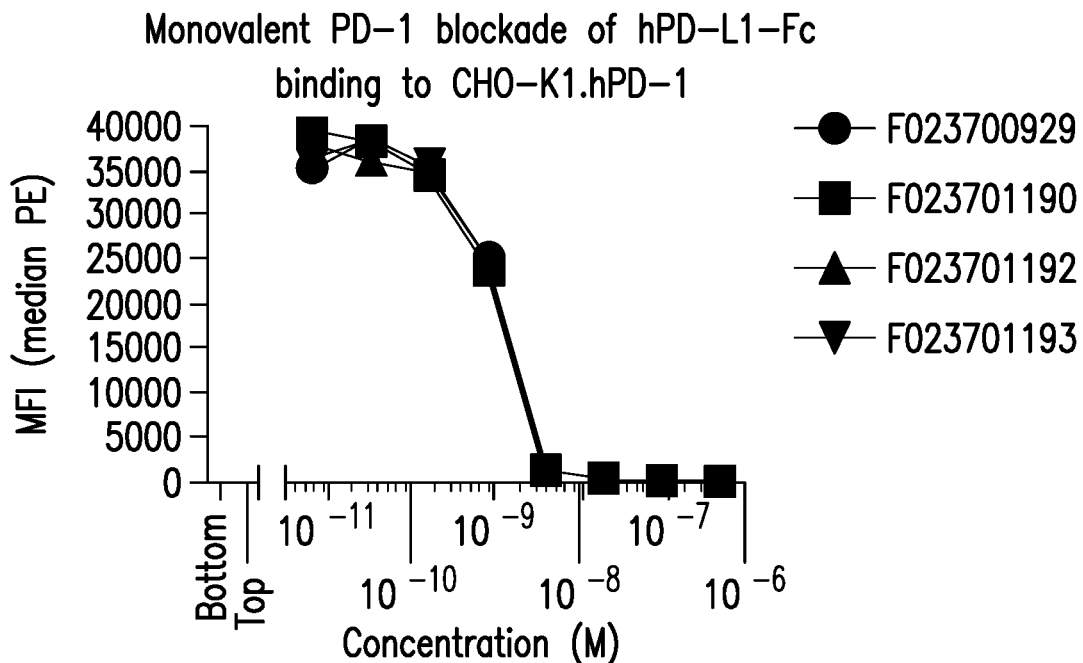
Figure 9H:
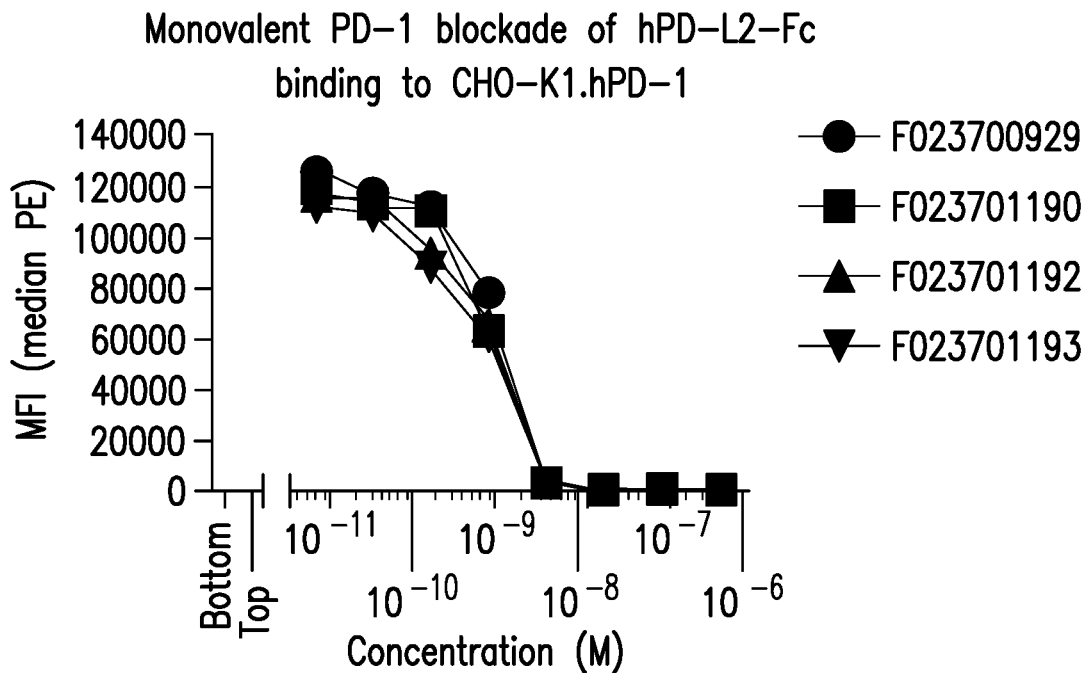

A jet injector uses a high-pressure narrow jet of liquid which penetrate the epidermis to introduce the PD1 and/or LAG3 binder or a pharmaceutical composition thereof to a patient's body. External infusion pumps are medical devices that deliver the PD1 and/or LAG3 binder or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

Other aspects, embodiments, advantages and applications of the invention will become clear from the further description herein.

Examples

These examples are intended to exemplify the present invention are not a limitation thereof. Compositions and methods set forth in the Examples form part of the present invention.

Example 1: Monovalent Human PD-1 Nanobody Binding to CHO.Hpd-1

Binding to cell-expressed human PD-1 was evaluated on human PD-1 over-expressing CHO cells. A Nanobody dilution series was prepared in assay buffer: PBS/10% FBS/0.05% sodium azide. $1\times10^5$ cells/well were transferred to a 96-well V-bottom plate and resuspended in 100 μL Nanobody dilution. After 30 minutes incubation at 4° C., the cells were washed with 100 μL/well assay buffer and resuspended in 100 μL/well of 1 μg/ml anti-FLAG (Sigma, F1804) or anti-HIS (AbD Serotec, MCA 1396). Samples were incubated for 30 minutes at 4° C., washed with 100 μL/well assay buffer, and resuspended in 100 μL/well of 5 μg/ml PE-labeled Goat anti-mouse IgG (Jackson ImmunoResearch, 115-116-071). Samples were incubated for 30 minutes at 4° C., washed, and resuspended in 100 μL/well of 5 nM TOPRO3 (LifeTechnologies, T3606) solution before analysis on FACS CANTO II (BD). The data from these experiments are set forth in FIG. 5.

This Example demonstrated that the anti-human PD-1 monovalent Nanobody F023700706 bound to human PD-1 in a manner similar to the F023700275 monovalent Nanobody from which it was derived.

Example 2: Monovalent Human LAG-3 Nanobody Binding to 3A9.hLAG-3

Binding to cell-expressed human LAG-3 was evaluated on human LAG-3 over-expressing 3A9 cells. A Nanobody dilution series was prepared in assay buffer: PBS/10% FBS/0.05% sodium azide. $1\times10^5$ cells/well were transferred to a 96-well V-bottom plate and resuspended in 100 μL Nanobody dilution. After 30 minutes incubation at 4° C., the cells were washed with 100 μL/well assay buffer and resuspended in 100 μL/well of 1 μg/ml anti-FLAG (Sigma, F1804). Samples were incubated for 30 minutes at 4° C., washed with 100 μL/well assay buffer and resuspended in 100 μL/well of 5 μg/ml PE-labeled Goat anti-mouse IgG (Jackson ImmunoResearch, 115-116-071). Samples were incubated for 30 minutes at 4° C., washed, and resuspended in 100 μL/well of 5 nM TOPRO3 (LifeTechnologies, T3606) solution before analysis on FACS CANTO II (BD). The data from these experiments are set forth in FIG. 6.

This Example demonstrated that the sequence optimized anti-human LAG-3 monovalent Nanobody F023700842 bound to human LAG-3 in a manner similar to the original F02376611B09 monovalent Nanobody from which it was derived.

Example 3: Human PD-1 Nanobody-Containing Multispecific Nanobody Binding to CHO.hPD-1 and 3A9.rhesusPD-1

Binding to cell-expressed human PD-1 and rhesus PD-1 was evaluated on human PD-1 over-expressing CHO cells and rhesus PD-1 over-expressing 3A9 cells, respectively. A Nanobody dilution series was prepared in assay buffer: PBS/10% FBS/0.05% sodium azide. $1\times10^5$ cells/well were transferred to a 96-well V-bottom plate and resuspended in 100 μL Nanobody dilution. After 30 minutes incubation at 4° C., the cells were washed with 100 μL/well assay buffer and resuspended in 100 μL/well of 3 μg/ml ABH0074, a monoclonal antibody that recognizes the albumin binding Nanobody half-life extension moiety. Samples were incubated for 30 minutes at 4° C., washed with 100 μL/well assay buffer, and resuspended in 100 μL/well of 5 μg/ml PE-labeled Goat anti-mouse IgG (Jackson ImmunoResearch, 115-116-071). Samples were incubated for 30 minutes at 4° C., washed and resuspended in 100 μL/well of 5 nM TOPRO3 (LifeTechnologies, T3606) solution before analysis on FACS CANTO II (BD). The data from these experiments were set forth in FIG. 7 (A-B).

This Example demonstrated that the bispecific anti-human PD-1/LAG-3 Nanobodies F023700931 and F023700924 bound to both human PD1 and rhesus PD-1. The monospecific, bivalent controls anti-human PD-1 F023700933 and anti-human LAG-3 F023700962 were also shown.

Example 4: Human LAG-3 Nanobody-Containing Multispecific Nanobody Binding to CHO.hLAG3 and CHO.rhesus/cynoLAG3

Binding to cell-expressed human and non-human primate LAG-3 (the extracellular domain is identical between cynomolgus and rhesus monkey; therefore, the gene will be referred to a rhesus/cynoLAG-3) was evaluated on human and rhesus/cynoLAG-3 over-expressing CHO cells. A Nanobody dilution series was prepared in assay buffer: PBS/10% FBS/0.05% sodium azide. $1\times10^5$ cells/well were transferred to a 96-well V-bottom plate and resuspended in 100 μL Nanobody dilution. After 30 minutes incubation at 4° C., the cells were washed with 100 μL/well assay buffer and resuspended in 100 μL/well of 1-3 μg/ml ABH0074, a monoclonal antibody that recognizes the albumin binding Nanobody half-life extension moiety. Samples were incubated for 30 minutes at 4° C., washed with 100 μL/well assay buffer, and resuspended in 100 μL/well of 5 μg/ml PE-labeled Goat anti-mouse IgG (Jackson ImmunoResearch, 115-116-071).

Samples were incubated for 30 minutes at 4° C., washed and resuspended in 100 μL/well of 5 nM TOPRO3 (LifeTechnologies, T3606) solution before analysis on FACSArray (BD). The data from these experiments are set forth in FIG. 8 (A-B).

This Example demonstrated that the bispecific anti-human PD-1/LAG-3 Nanobodies F023700931 and F023700924 bound to both human LAG-3 and rhesus/cynomolgus monkey LAG-3. The monospecific, bivalent controls anti-human PD-1 F023700933 and anti-human LAG-3 F023700962 were also shown.

Example 5: Biophysical PD-L1-Fc and PD-L2-Fc Blockade Assay

Ligand competition assays were performed on human PD-1 over-expressing CHO cells. A Nanobody dilution series was prepared in assay buffer: PBS/10% FBS/0.05% sodium azide. Five-fold serial dilutions of Nanobody were made starting from 1 μM (2×) and pre-diluted with 11 nM (2×) human PD-L1-hFc or 29 nM (2×) human PD-L2-hFc in a total volume of 220 μL. $2\times10^4$ cells/well were seeded in V-bottom 96-well plates and resuspended in 200 μL/well of the Nanobody/ligand dilution. After 90 minutes incubation at 4° C., the cells were washed with 100 μL/well assay buffer and resuspended in 100 μL/well PE-labeled Goat anti-human IgG (Southern Biotech, 2043-09). Samples were incubated for 30 minutes at 4° C., washed, and resuspended in 100 μL/well of 5 nM TOPRO3 (LifeTechnologies, T3606) solution before analysis on FACS CANTO II (BD). The data from these experiments are set forth in FIG. 9 (A-H).

This Example demonstrated that the anti-human PD-1 Nanobody monovalent module F023700706 bound to human PD-1 and fully blocked its interaction with PD-L1 (FIG. 9 (A)) and PD-L2 (FIG. 9 (B)) similar to the original F023700275 monovalent module from which it was derived. In addition, this example demonstrated that the bispecific anti-human PD-1/LAG-3 Nanobodies F023700931 and F023700924 bound to human PD-1 and fully blocked their interaction with PD-L1 (FIG. 9 (C)) and PD-L2 (FIG. 9 (D)). The sequence optimized, monospecific, bivalent controls, anti human PD-1 F023700933 and anti-human LAG-3 F023700962 were also shown (FIG. 9 (E-F)). Lastly, this example demonstrated that additional amino acid variants of anti-human PD-1 Nanobody monovalent module F023700929 bound to human PD-1 and fully blocked its interaction with PD-L1 (FIG. 9 (G)) and PD-L2 (FIG. 9 (H)). It should be noted that F023700706 and F023700929 were the identical anti-human PD-1 monovalent Nanobody entity either as a FLAG3-HIS6 fusion protein or as a HIS6 fusion protein, respectively.

Example 6: Biophysical LAG-3-Fc Blockade Assay

Ligand competition assays were performed on human Daudi cells which showed high endogenous expression of surface major histocompatibility complex (MHC) class II (Class II). A Nanobody dilution series was prepared in assay buffer: HBSS/2% FBS. Prior to the experiment, Fc receptors on the Daudi cells were blocked with human Fc block (BD Pharmingen, 564220) and 5 μg/mL goat IgG (Jackson ImmunoResearch, 005-000-003) for 30 minutes at 4° C. Five-fold serial dilutions of Nanobody were made starting from 2 (2×) and pre-diluted with 80 nM (2×) human LAG-3-hFc in a total volume of 120 μL. $1\times10^5$ cells/well were seeded in V-bottom 96-well plates and resuspended in 100 μL/well of the Nanobody/ligand dilution. After 30 minutes incubation at 4° C., the cells were washed and resuspended in 100 μL/well PE-labeled Goat anti-human IgG (Southern Biotech, 2043-09). Samples were incubated for 15 minutes at 4° C., washed, and resuspended in 100 μL/well of 5 nM TOPRO3 (LifeTechnologies, T3606) solution before analysis on FACS CANTO II (BD). The data from these experiments are set forth in FIG. 10 (A-C).

Figure 10A:
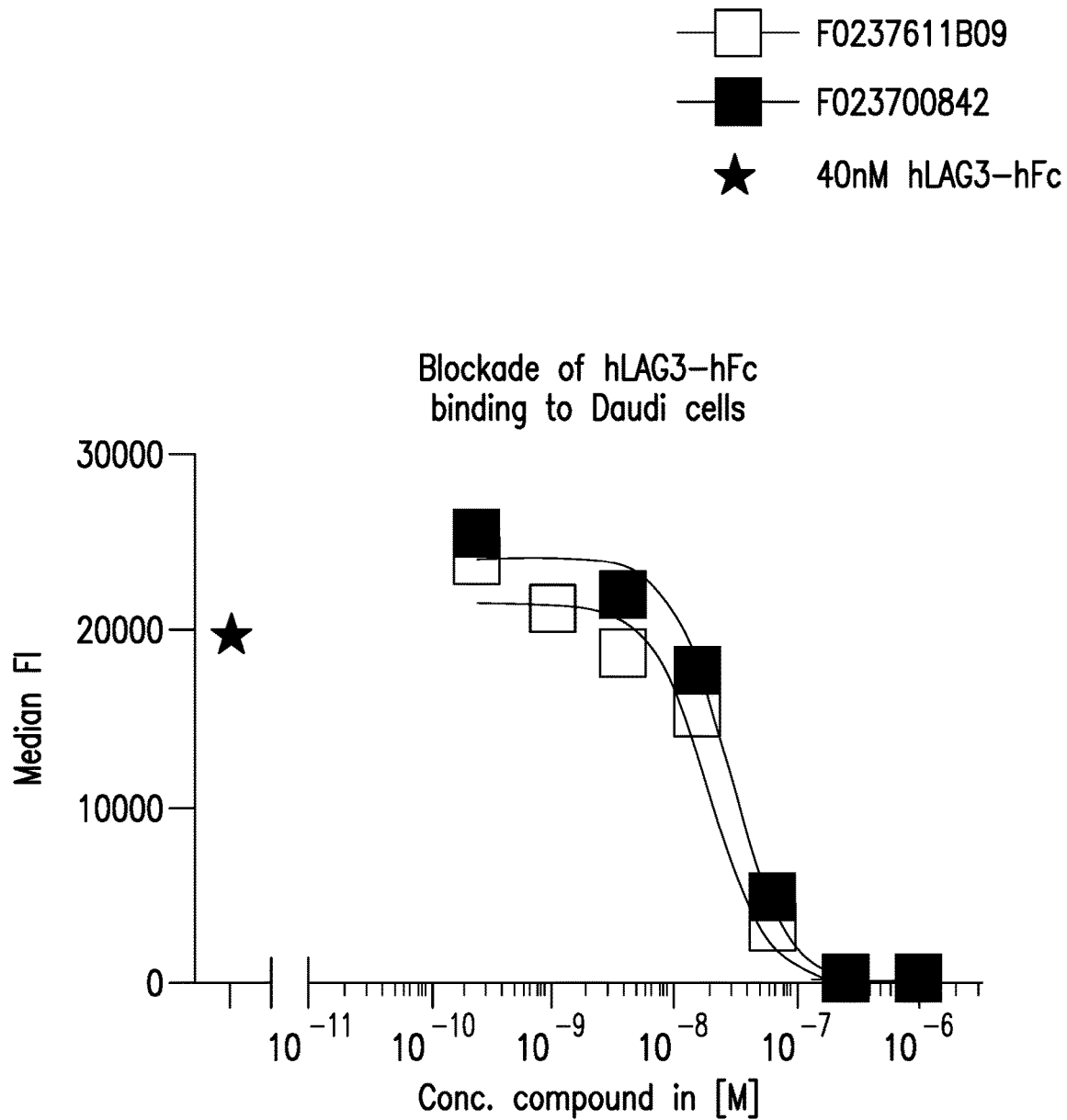
FIG. 10 (A-C). Blockade of human LAG3-Fc binding to Daudi cells by (A) F0237611B09-FLAG3-HIS6, F023700842-FLAG3-HIS6 or human LAG3-Fc; (B) F023700931 (*Pichia* or CHO expressed), F023700924 (*Pichia* or CHO expressed), F023700933 or F023700962, human LAG3-Fc; or (C) F023700924, F023700931 or F023700962 or human LAG3-Fc. Sec only=secondary antibody only (GAH/GAM).
Figure 10C:
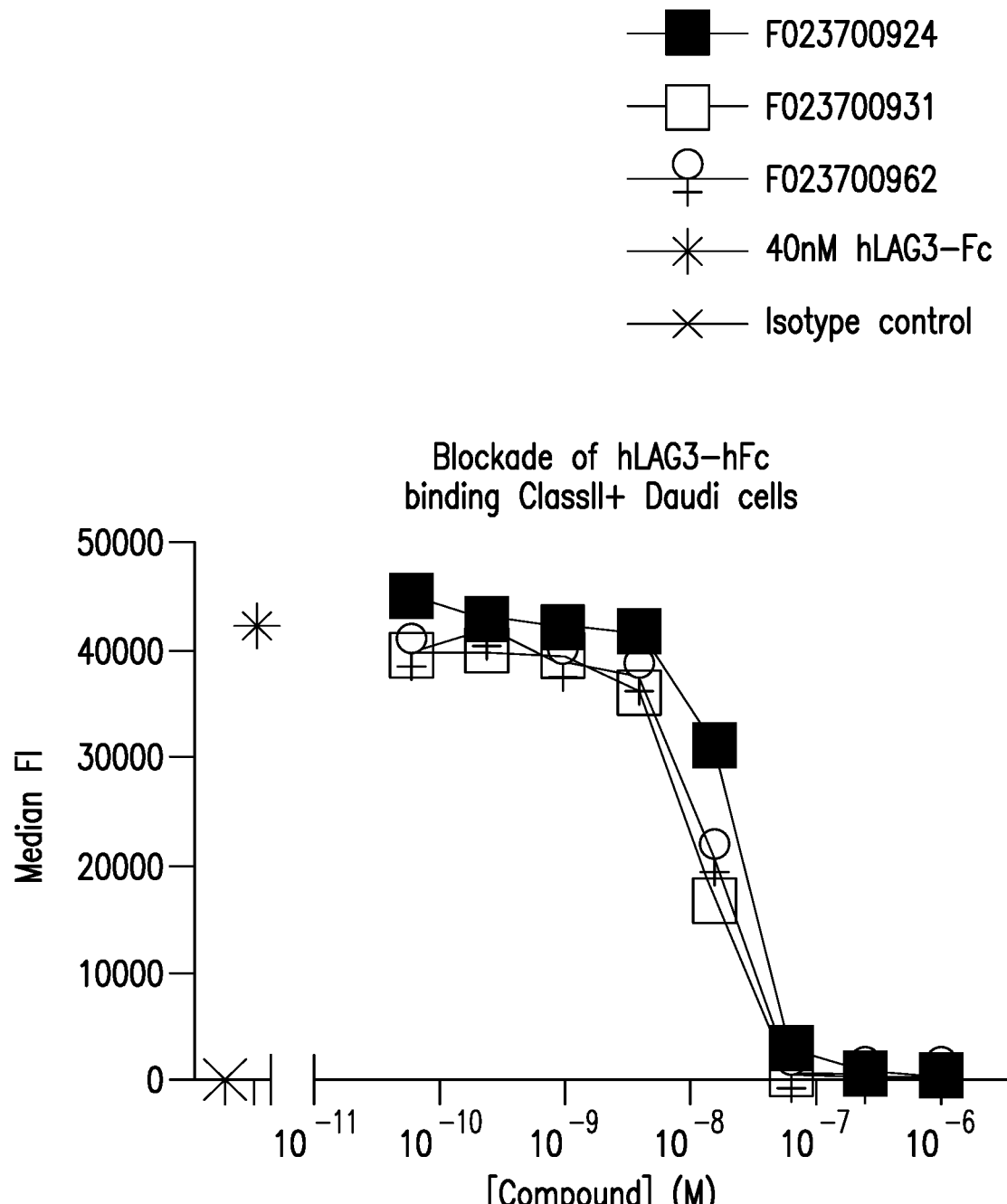

This Example demonstrated that the anti-human LAG-3 Nanobody monovalent module F023700842 bound to human LAG-3 and fully blocked its interaction with MEW Class II similar to the original F0237611B09 monovalent Nanobody from which it was derived (FIG. 10 (A)). In addition, this example demonstrated that the bispecific anti human PD-1/LAG-3 Nanobodies F023700931 and F023700924 bound to human LAG-3 and fully blocked its interaction with MEW Class II (FIG. 10 (B-C)). The monospecific, bivalent controls anti-human PD-1 F023700933 and anti human LAG-3 F023700962 were also shown.

Example 7: Proximity Dimerization Assay

A proximity dimerization assay was used that was based on a beta-Galactosidase Enzyme Fragment Complementation assay system. The assay utilizes a fusion protein generated with a tag termed ProLink (PK) and a complementation protein in which the enzyme acceptor protein (EA) is fused to a second protein. U2OS cells were stably transfected with the extracellular domain of LAG-3 (1-477) fused to the EA subunit and the extracellular domain of PD-1 (1-199) fused to the PK subunit. U2OS.LAG3(1-477)-EA.PD1(1-199)-PK cell line #9 was plated in quadruplicate at 5,000 cells/well in DiscoverX CP5 plating media on 384-well plates. Cells were allowed to attach for 4 hours at 37° C. in a 5% carbon dioxide incubator. An 11 point, 1:3 dilution series of Nanobody samples were then added to the cells and incubated overnight (16 hours) at 37° C. in a 5% carbon dioxide incubator. PathHunter detection reagent was added to the wells, incubated one hour at room temperature in the dark, and the plate was then read on an Envision luminometer. The data from these experiments are set forth in FIG. 11 (A-B).

Figure 11A:
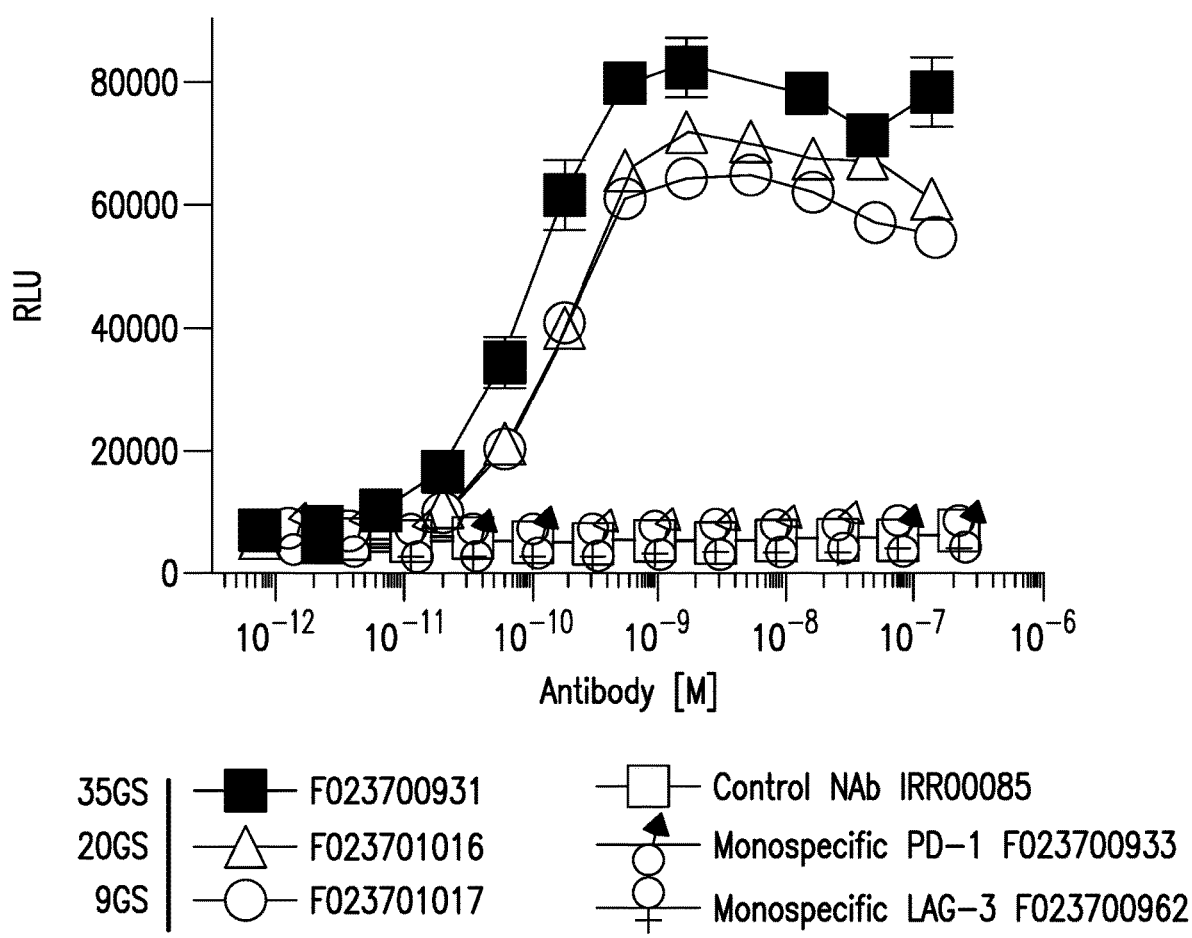
FIG. 11 (A-B). Proximity Assay (beta-galactosidase enzyme fragment complementation assay system) with (A) F023700931; F023701016, F023701017, control Nanobody (IRR00085; respiratory syncitia virus (RSV) binder), F023700933 or F023700962; or (B) F023700924; F023700969, F023700970, control Nanobody (IRR00085), F023700933 or F023700962.
Figure 11B:
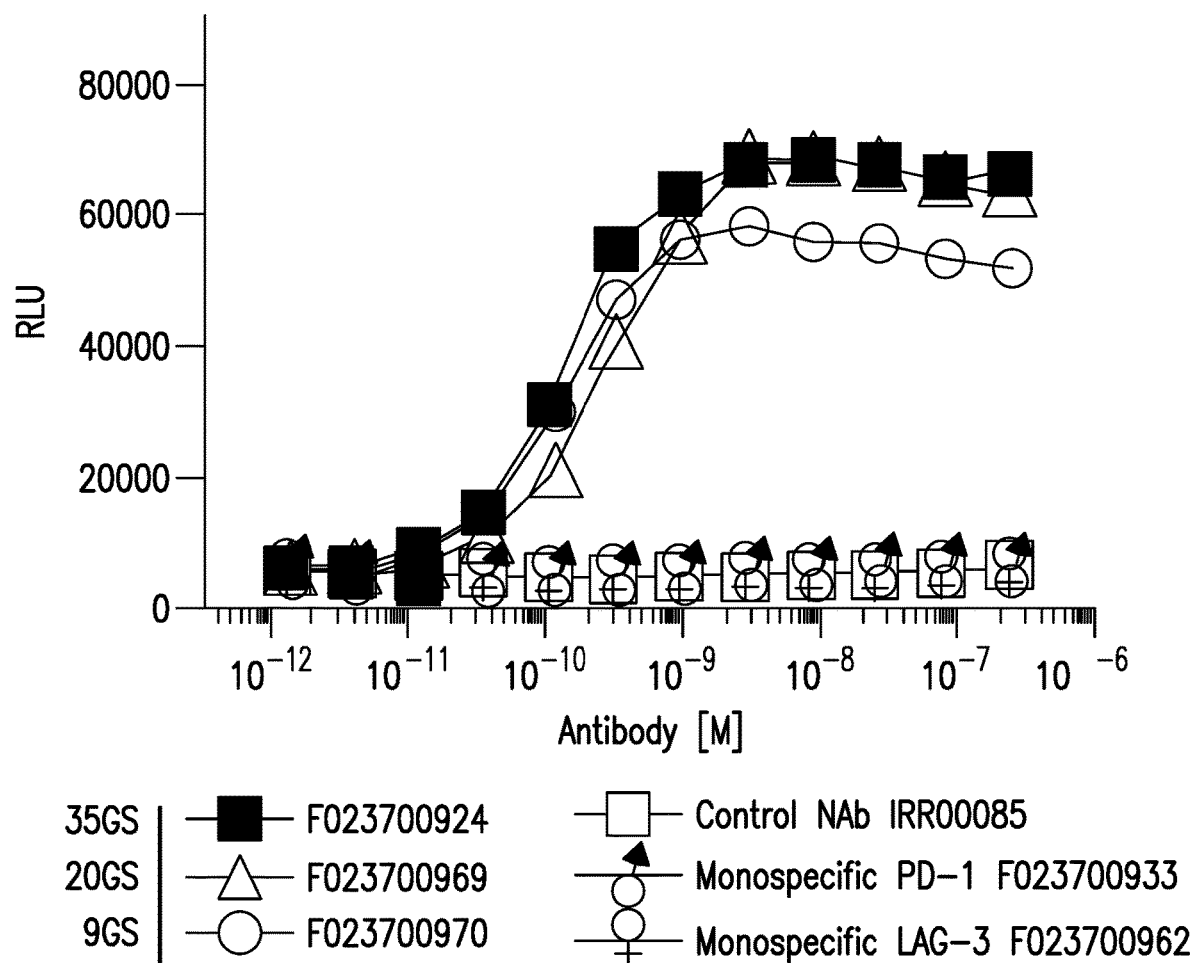
Figure 12A:
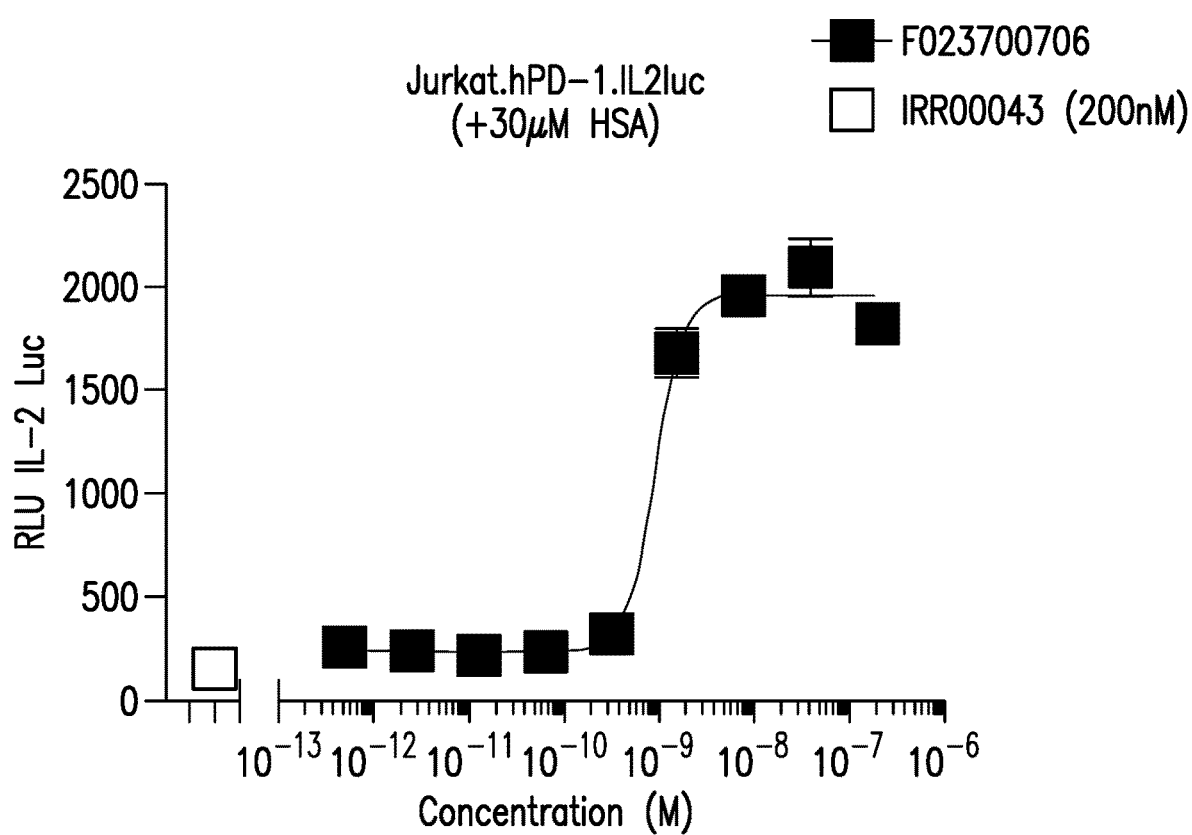
FIG. 12 (A-E). Activation of Jurkat T-cells (expression of luciferase operably linked to IL2 promoter) in presence of HSA by (A) F023700706 or control Nanobody (IRR00043; two anti-lysozyme nanobodies linked with a 35GS linker that has a C-terminal FLAG3-His6), (B) F023700931 (*Pichia* or CHO expressed), F023700924 (*Pichia* or CHO expressed), F023700933, F023700962 or control Nanobody (IRR00085 or IRR00087; RSV binder), (C) F023700924 F023700969, F023700970 or control Nanobody (IRR00043), (D) F023700931, F023701016, F023701017 or control Nanobody (IRR00043), or (E) F023700706, F023701192 (1PD102C12(E1D, L11V, A14P, W52aV, N73Q, A74S, K83R, I89L, W100aF)-HIS6, F023701193 (1PD102C12 (E1D, L11V, A14P, W52aV, N73P, A74S, K83R, I89L, W100aF)-HIS6 or control nanobody (IRR00088; RSV binder).
Figure 12B:
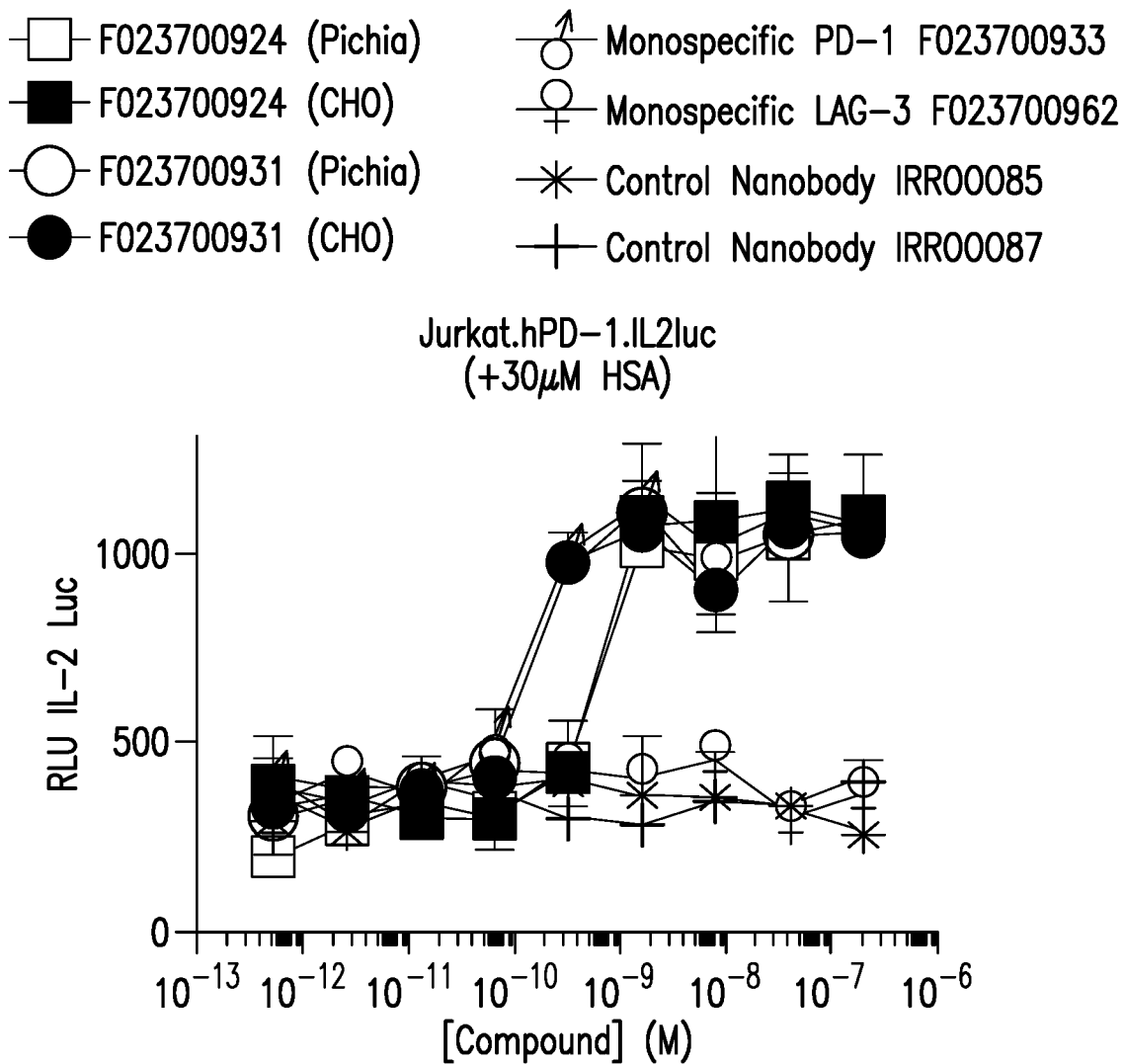
Figure 12C:
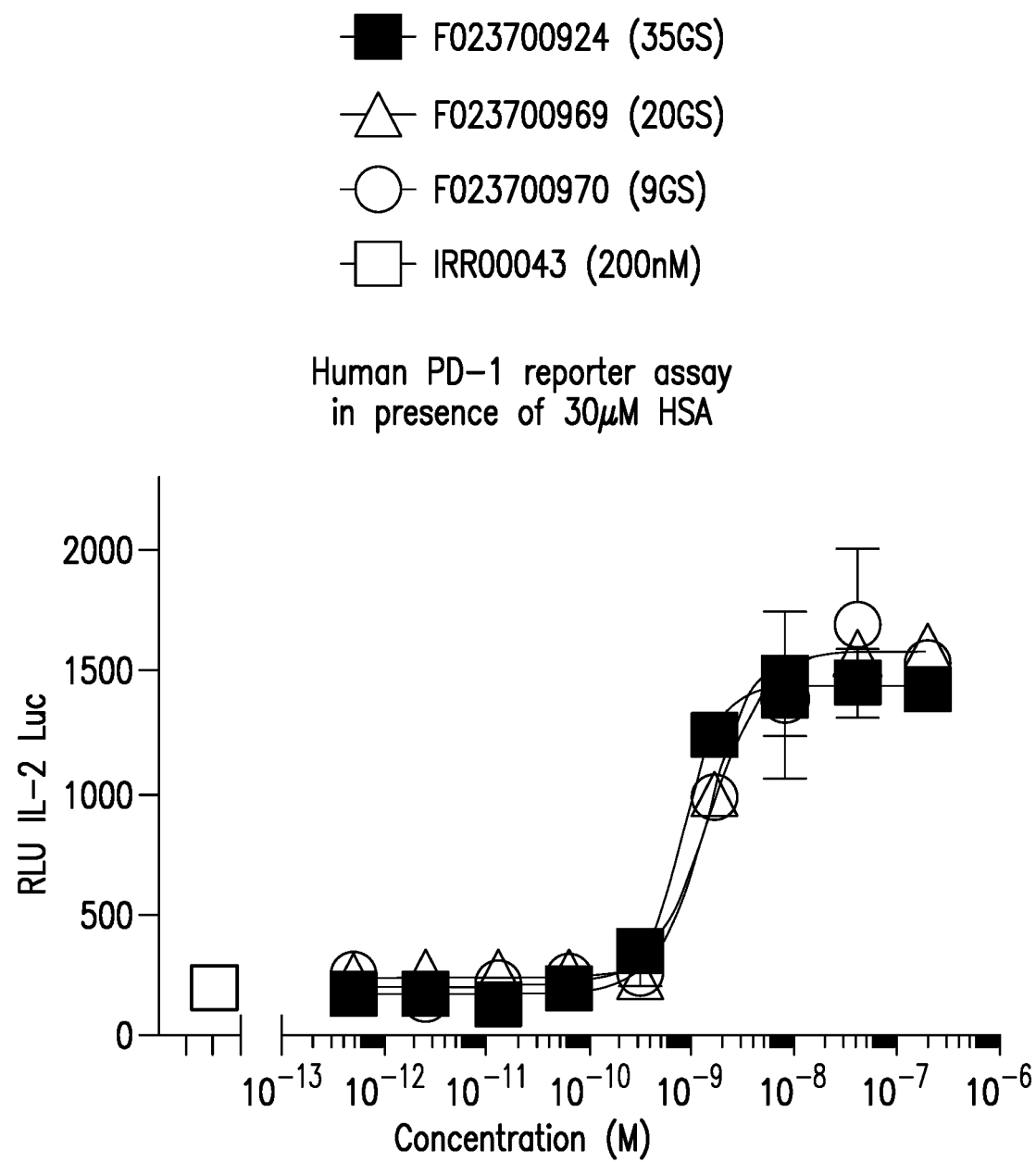
Figure 12D:
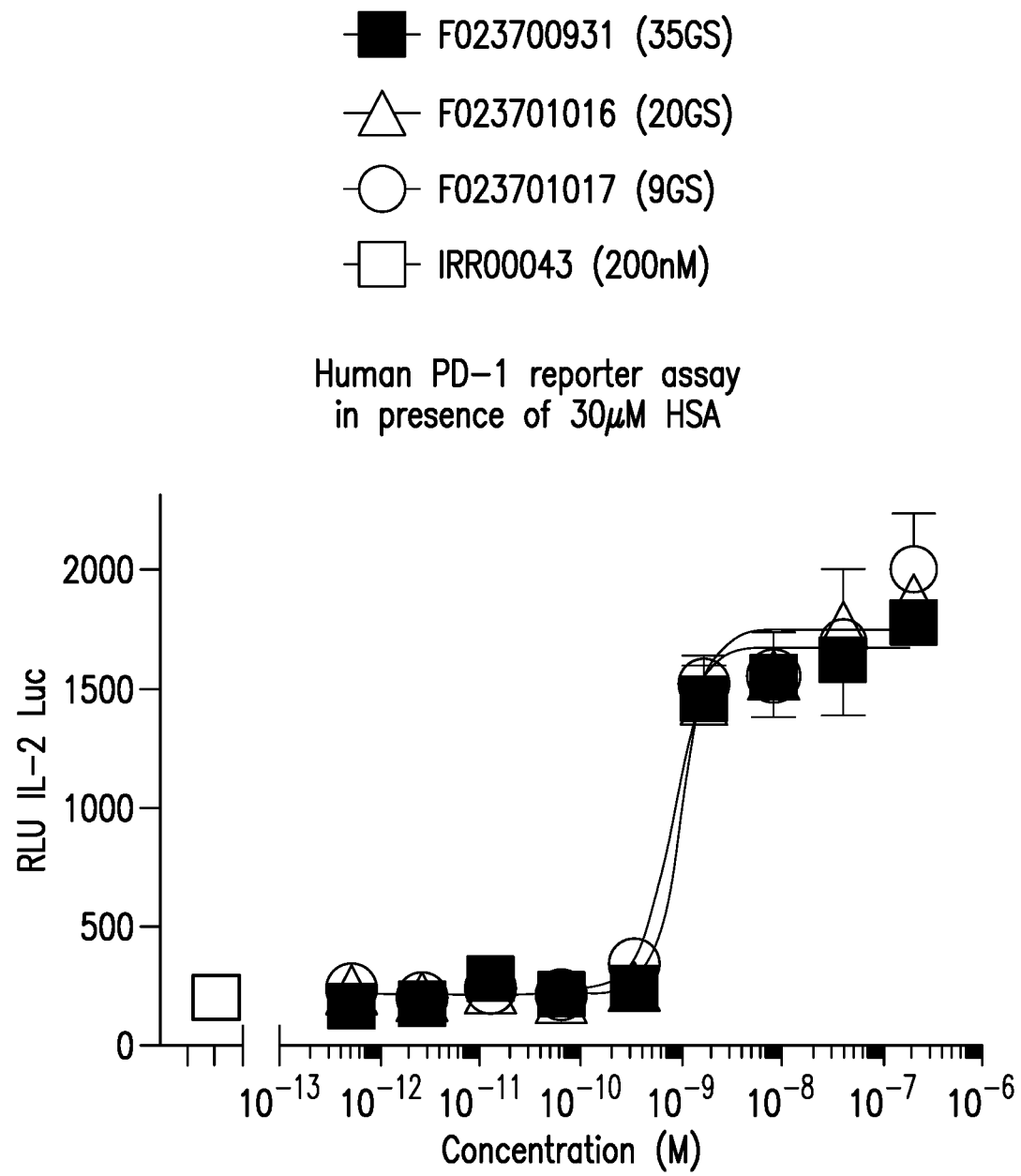
Figure 12E:
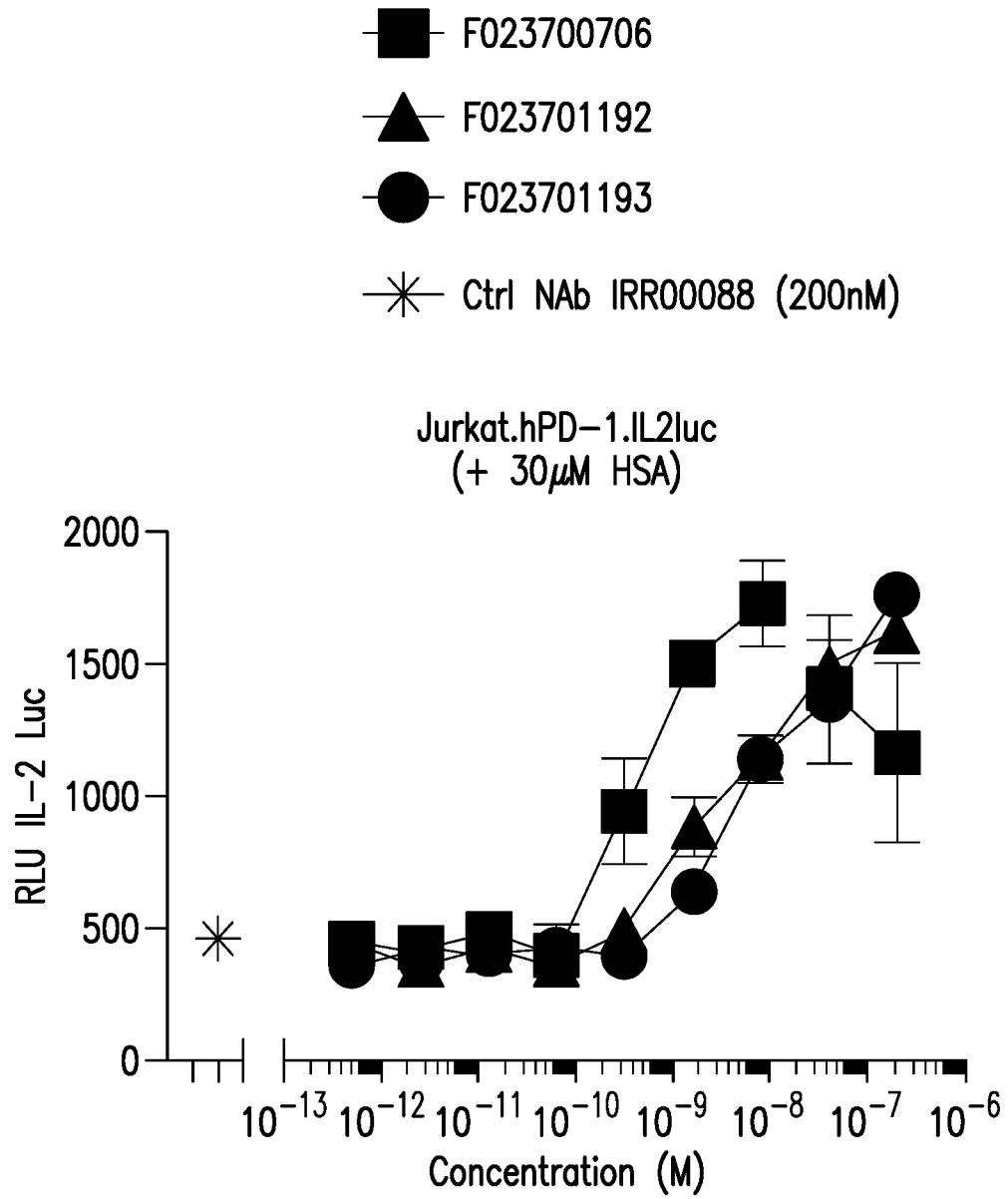
Figure 13A:
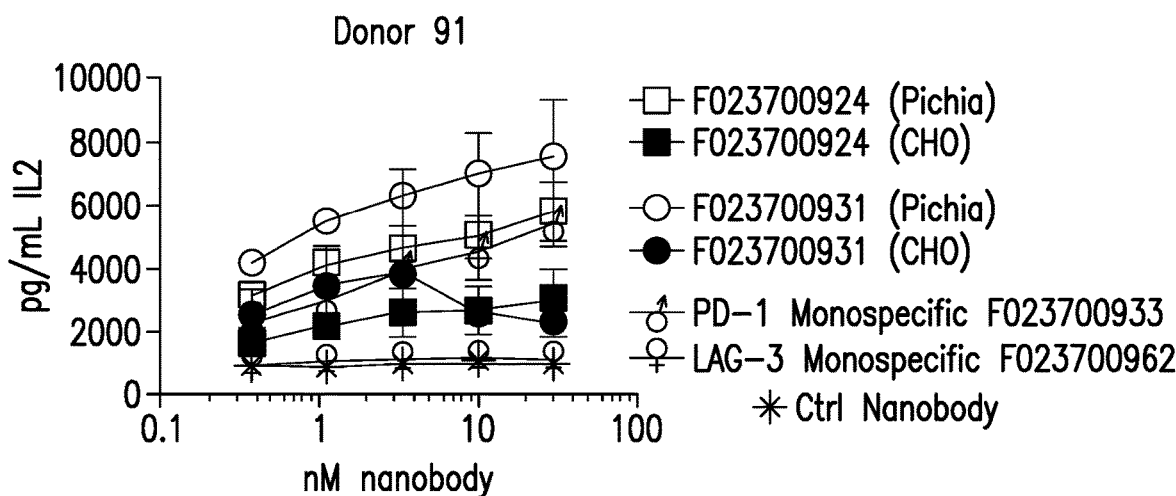
FIG. 13 (A-R). Activation of human peripheral blood monocytes (IL2 production) from donors (A) 91, (B) 985, (C) 907, (D) 91, (E) 985, (F) 907, (G) 91 (with 10 nM SEB), (H) 985 (with 10 nM SEB), (I) 907 (with 10 nM SEB), (J) 91 (with 25 nM SEB), (K) 985 (with 25 nM SEB), (L) 907 (with 25 nM SEB) with F023700931 (*Pichia* or CHO expressed), F023700924 (*Pichia* or CHO expressed), F023700933, F023700962 or control Nanobody; or (M) 91 (N) 985 (0) 907 with F023700931, F023700924 or control Nanobody; or (P) 91, (Q) 985 or (R) 907 with F023700924, F023700969, F023700970.
Figure 13B:
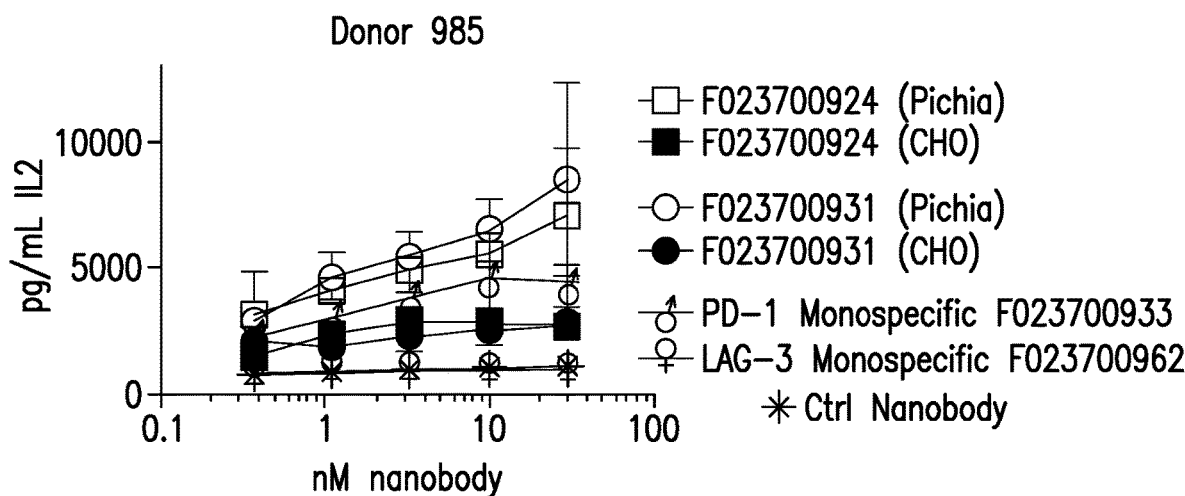
Figure 13C:
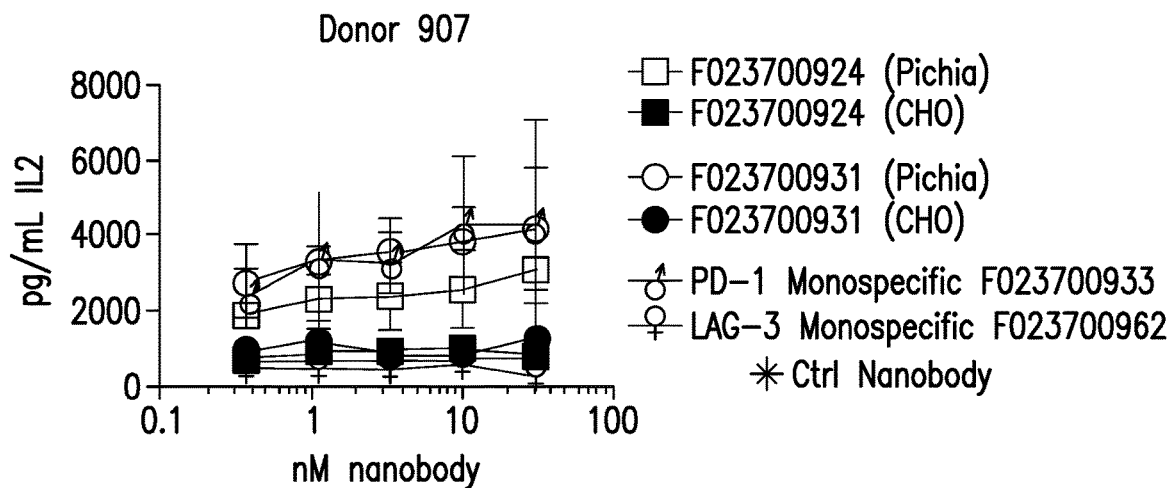
Figure 13D:
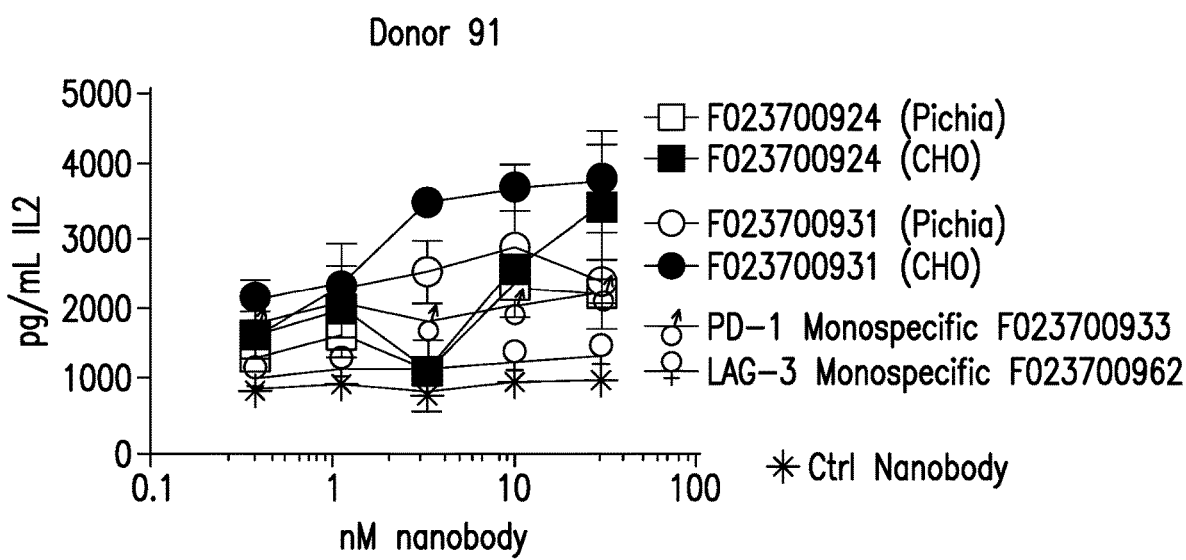
Figure 13E:
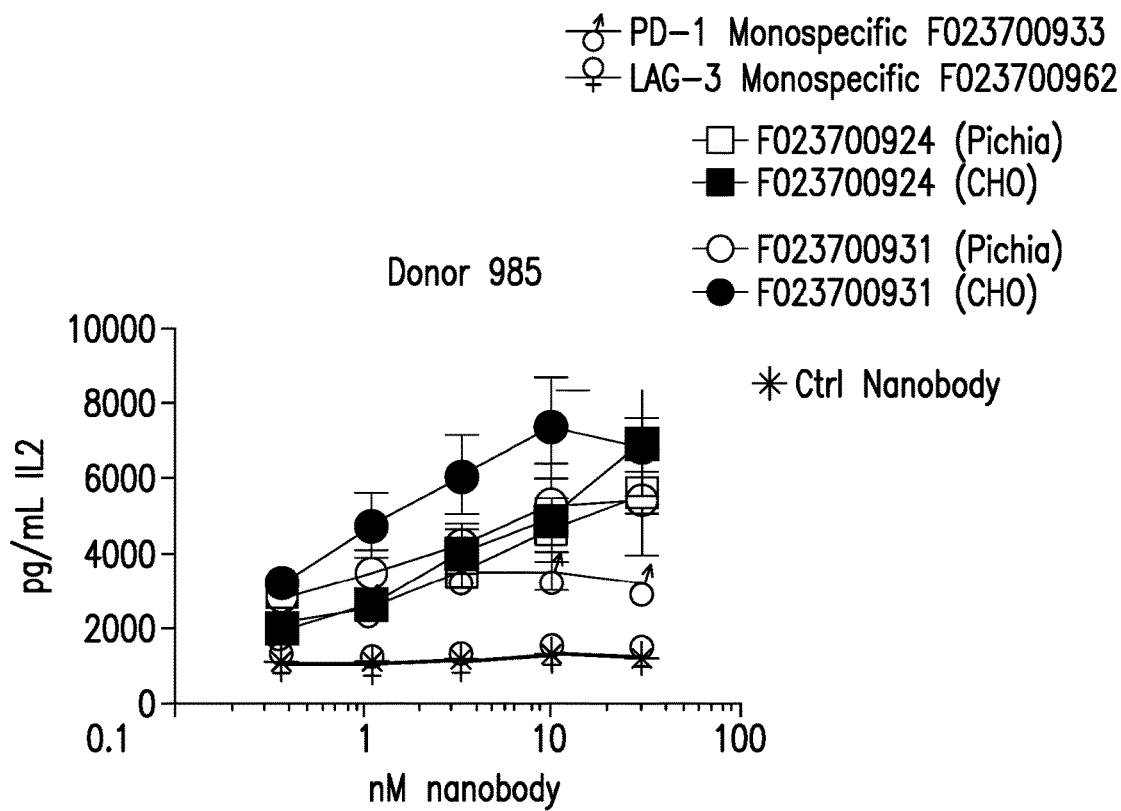
Figure 13F:
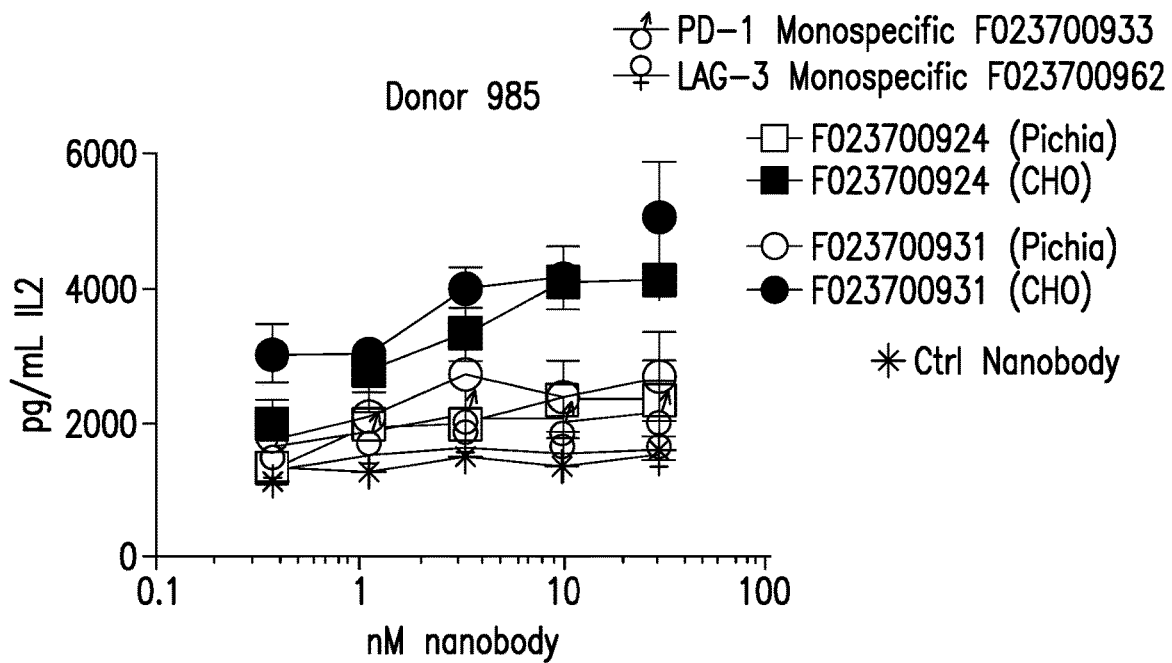
Figure 13G:
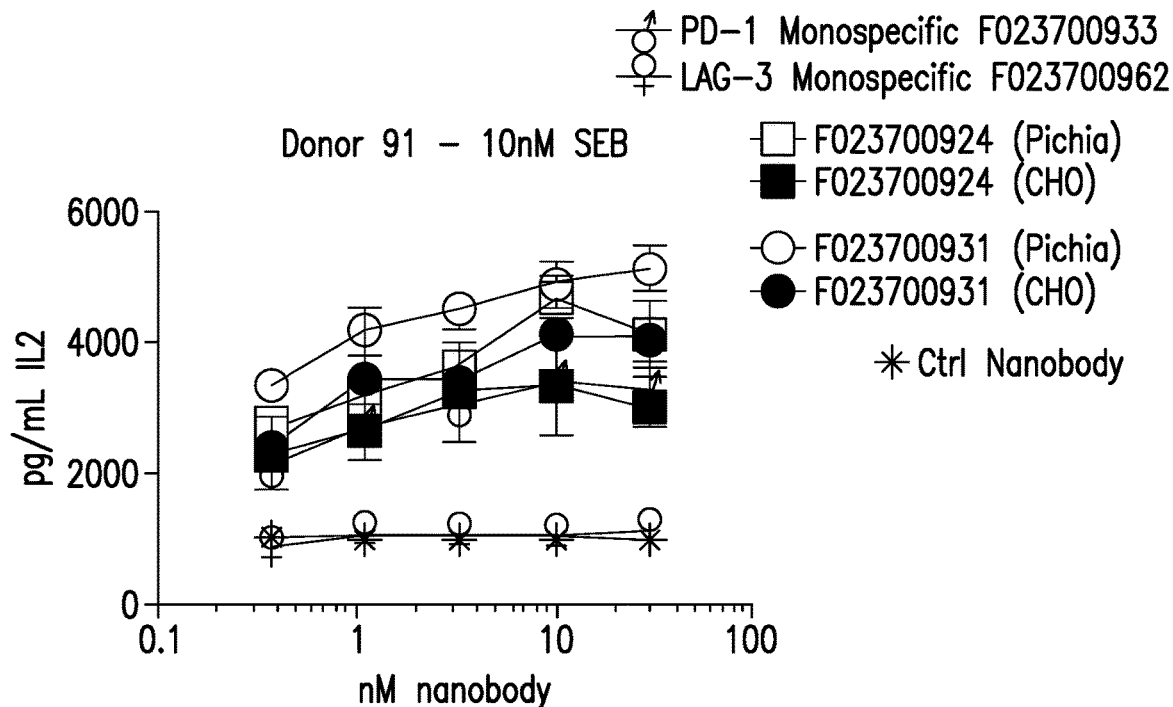
Figure 13H:
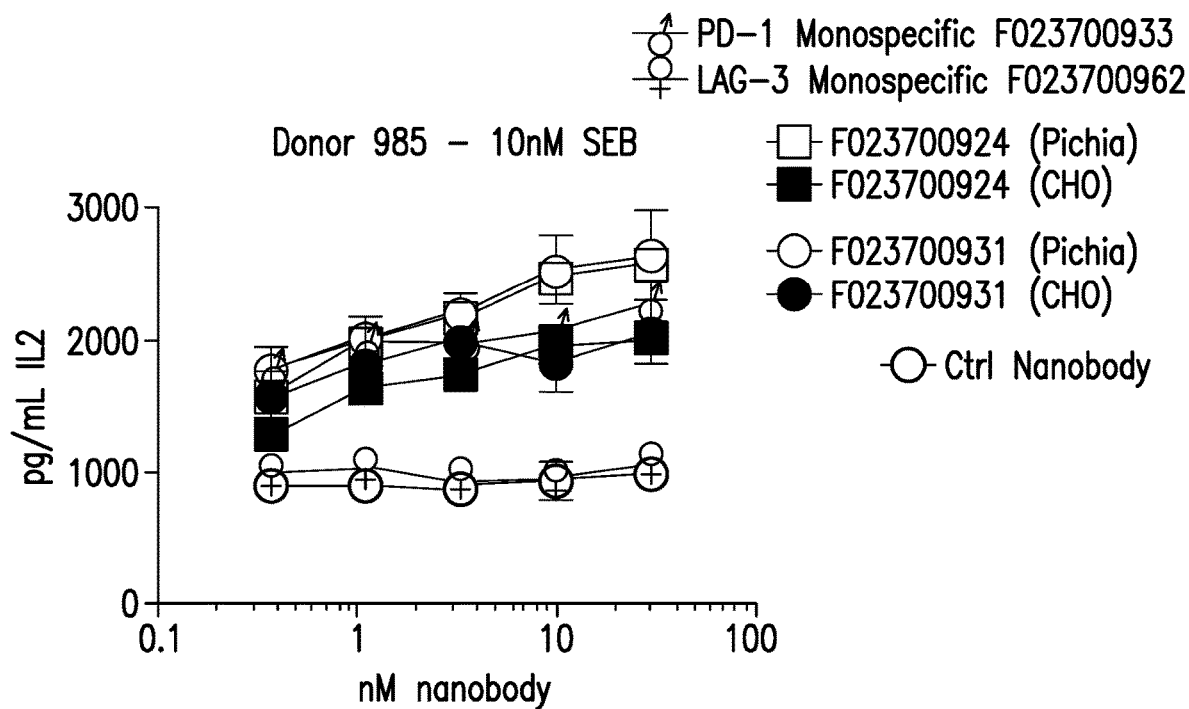
Figure 13I:
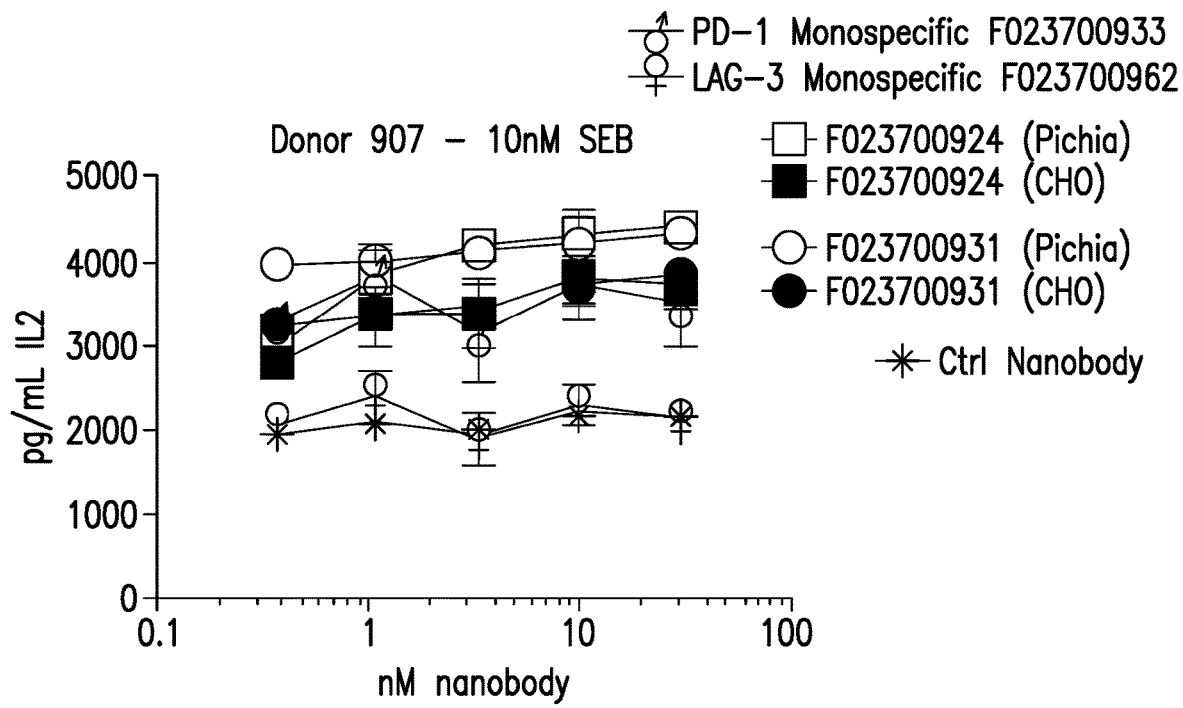
Figure 13J:
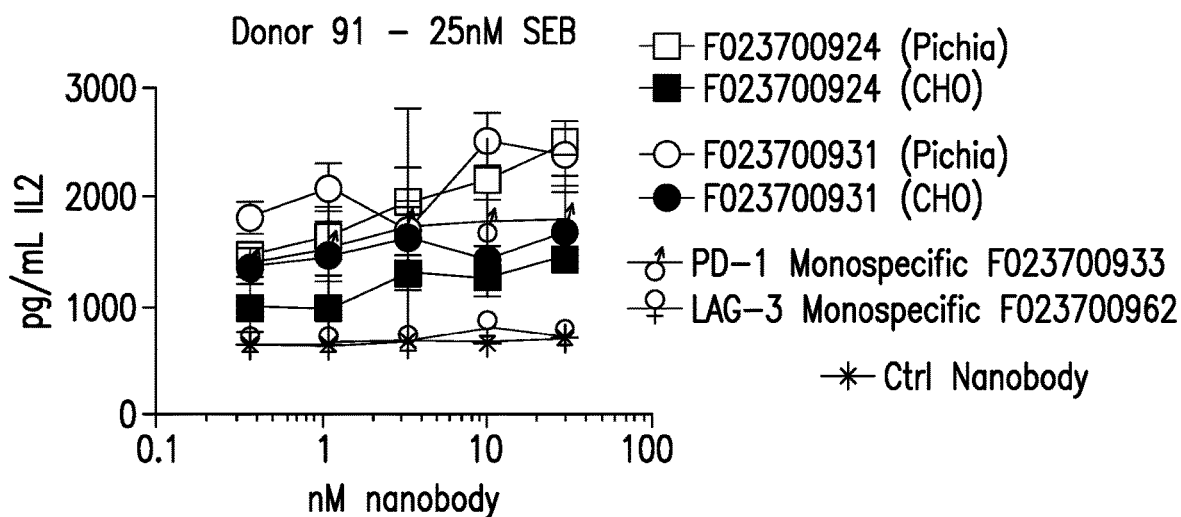
Figure 13K:
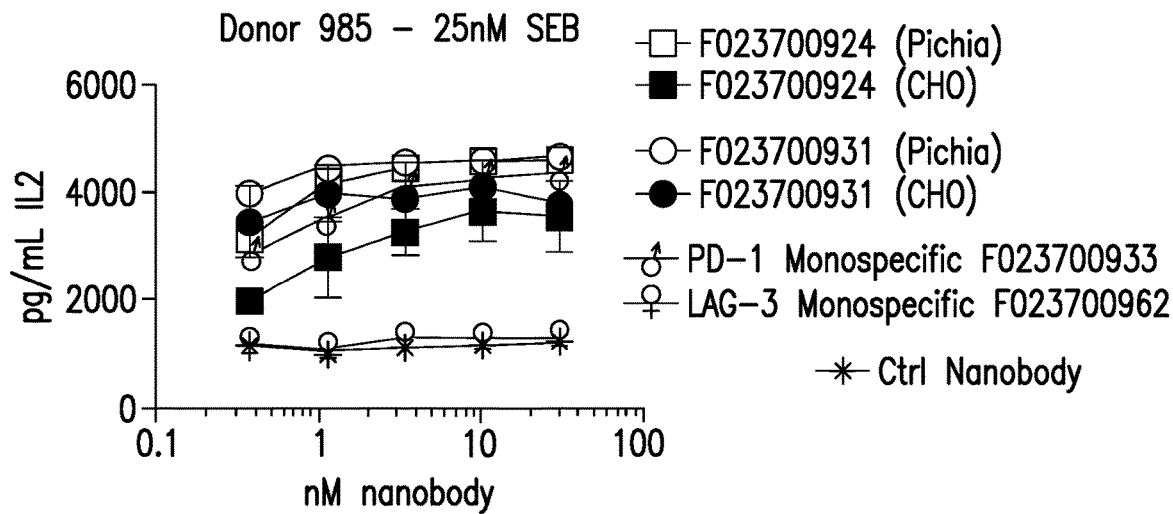
Figure 13L:
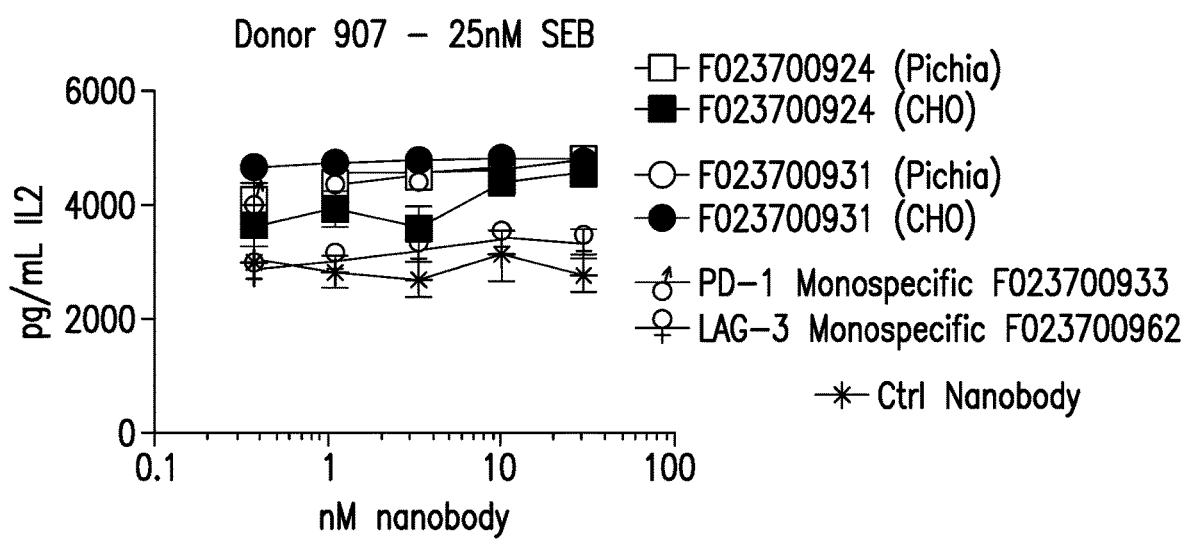
Figure 13M:
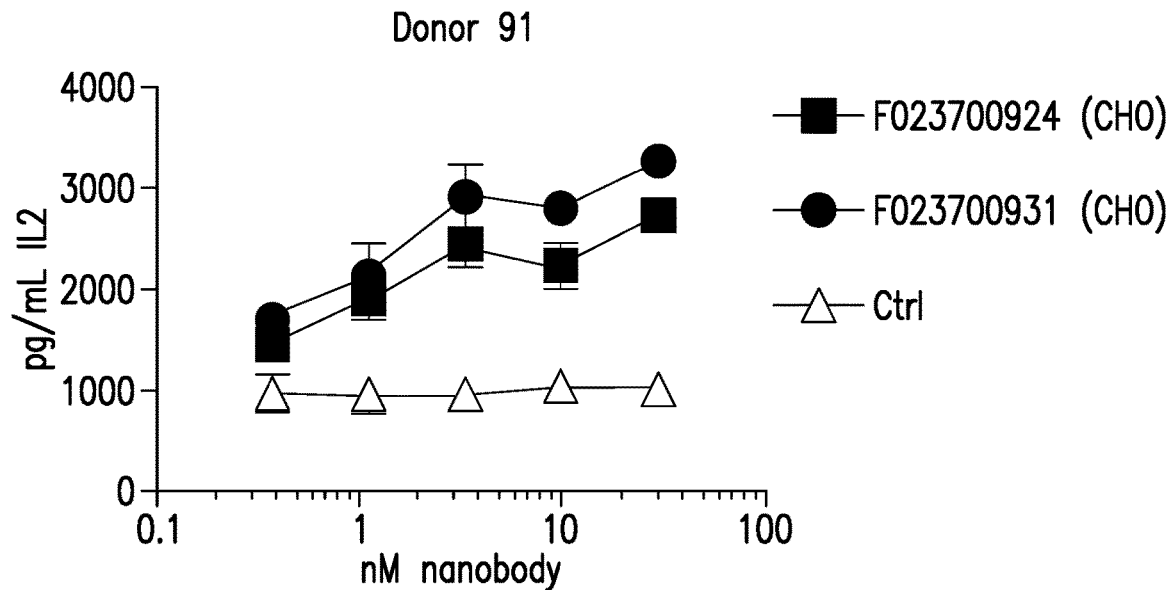
Figure 13N:
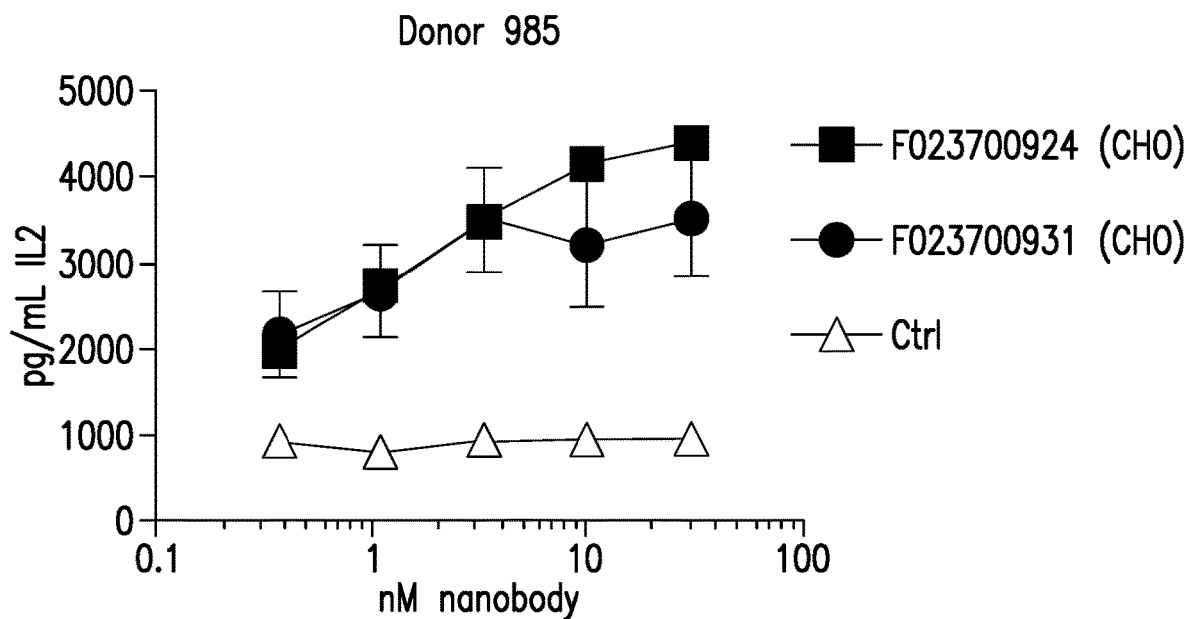
Figure 13O:
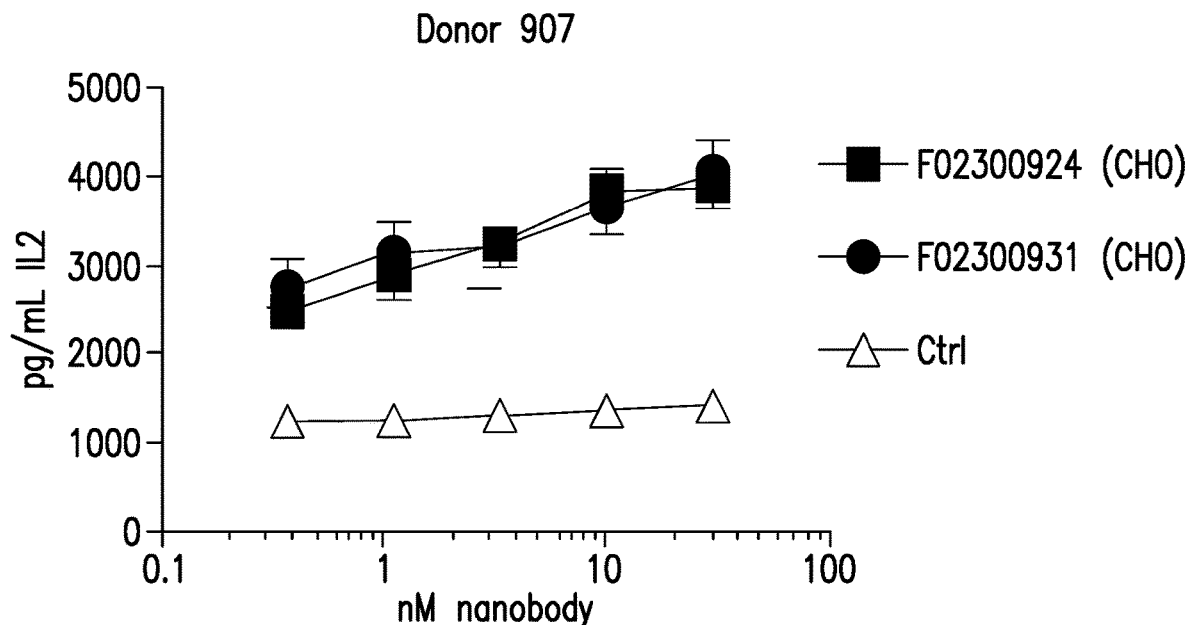
Figure 13P:
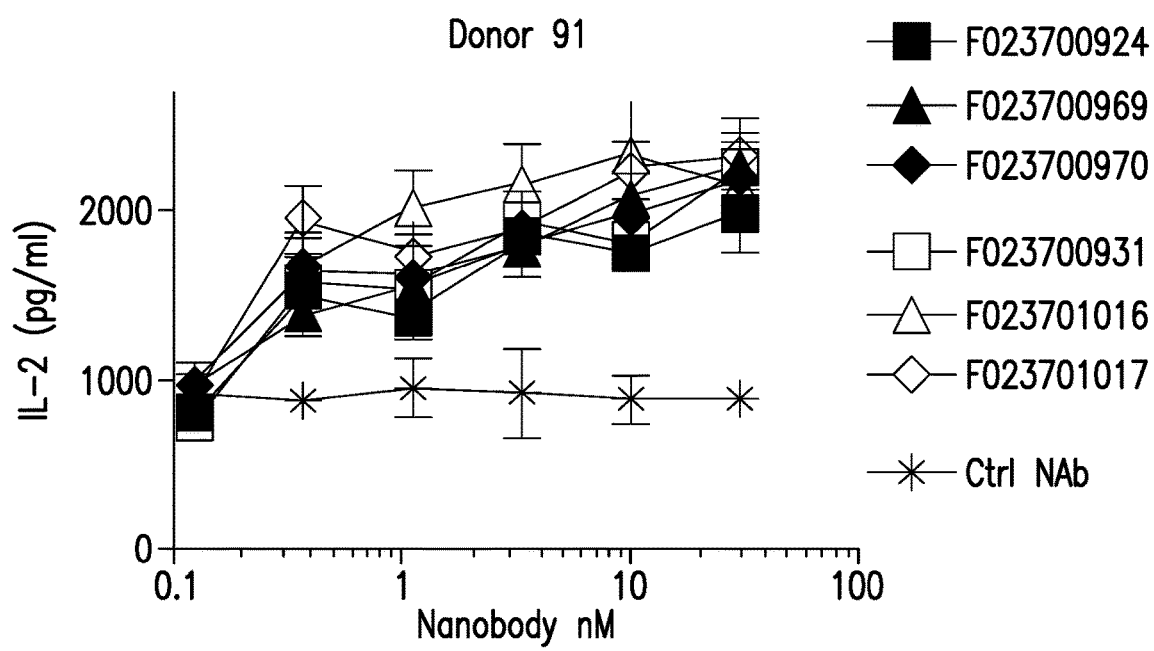
Figure 13Q:
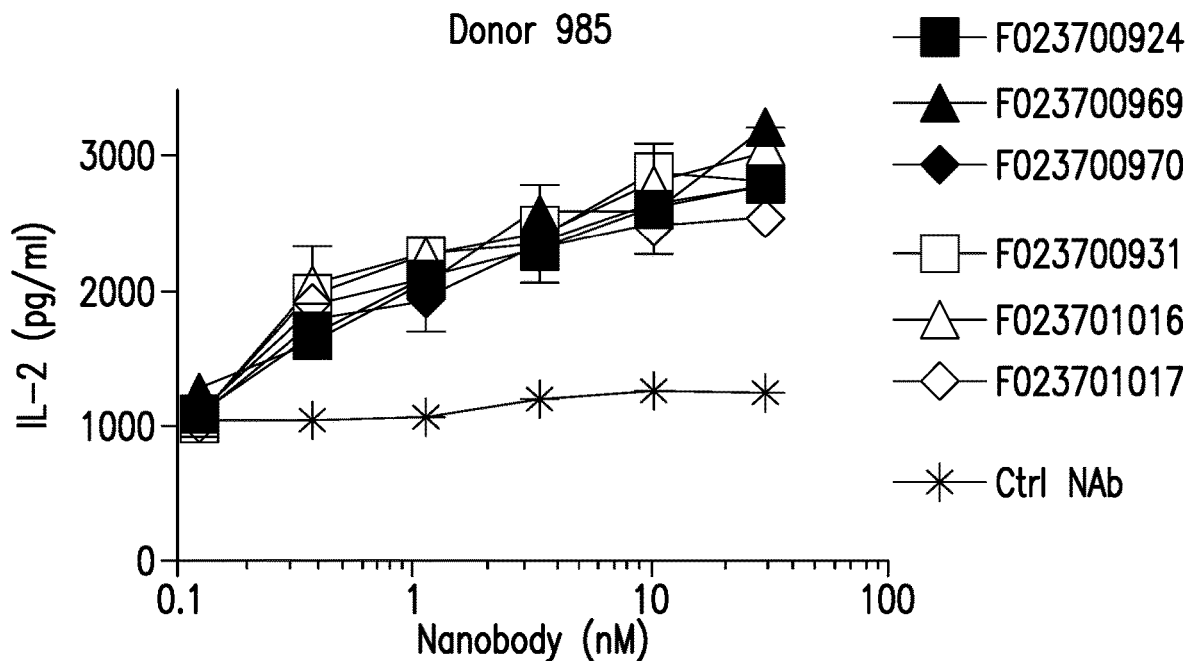
Figure 13R:
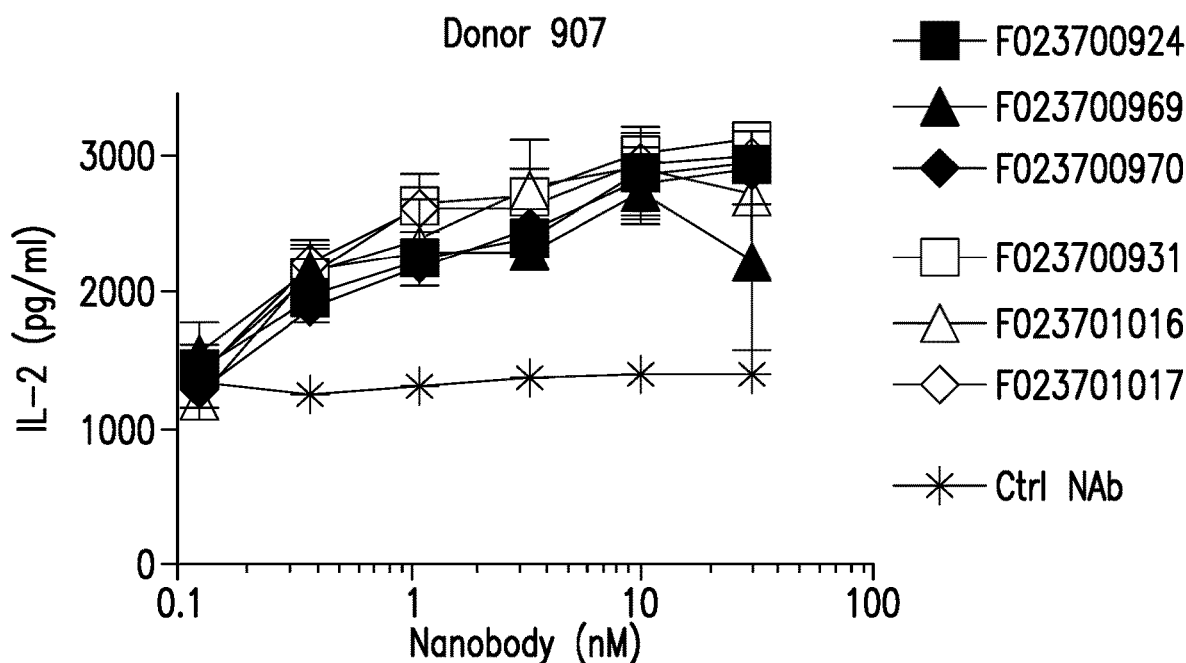
Figure 14A:
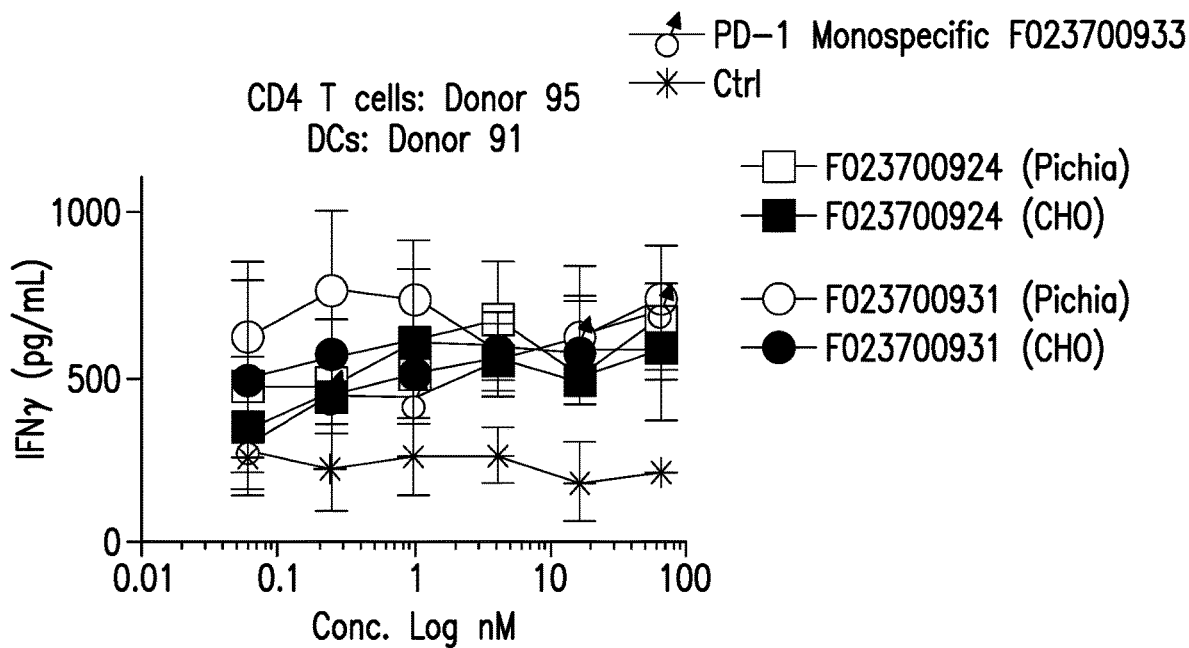
FIG. 14 (A-F). Mixed lymphocyte assay of CD4 T-cells and dendritic cells from different donors determining (A-C) interferon-gamma production at varying concentrations of Nanobody F023700931 (*Pichia* or CHO expressed), F023700924 (*Pichia* or CHO expressed) or F023700933 or a control antibody; (D-F) interferon-gamma production at varying concentrations of Nanobody F023700924, F023700969, F023700970, F023700931 F023701016 or F023701017 or control Nanobody.
Figure 14B:
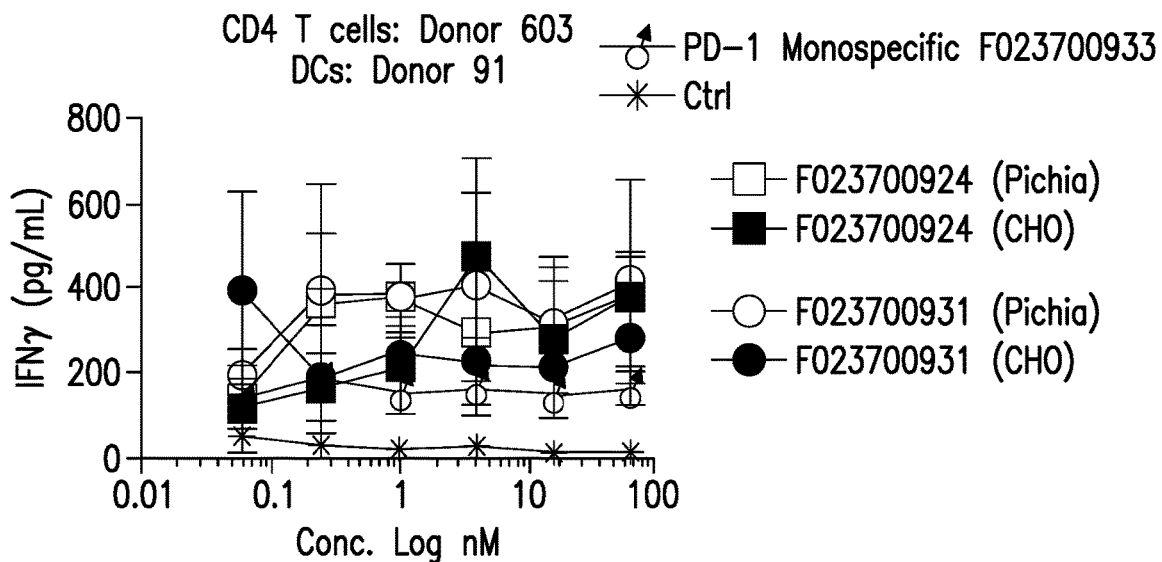
Figure 14C:
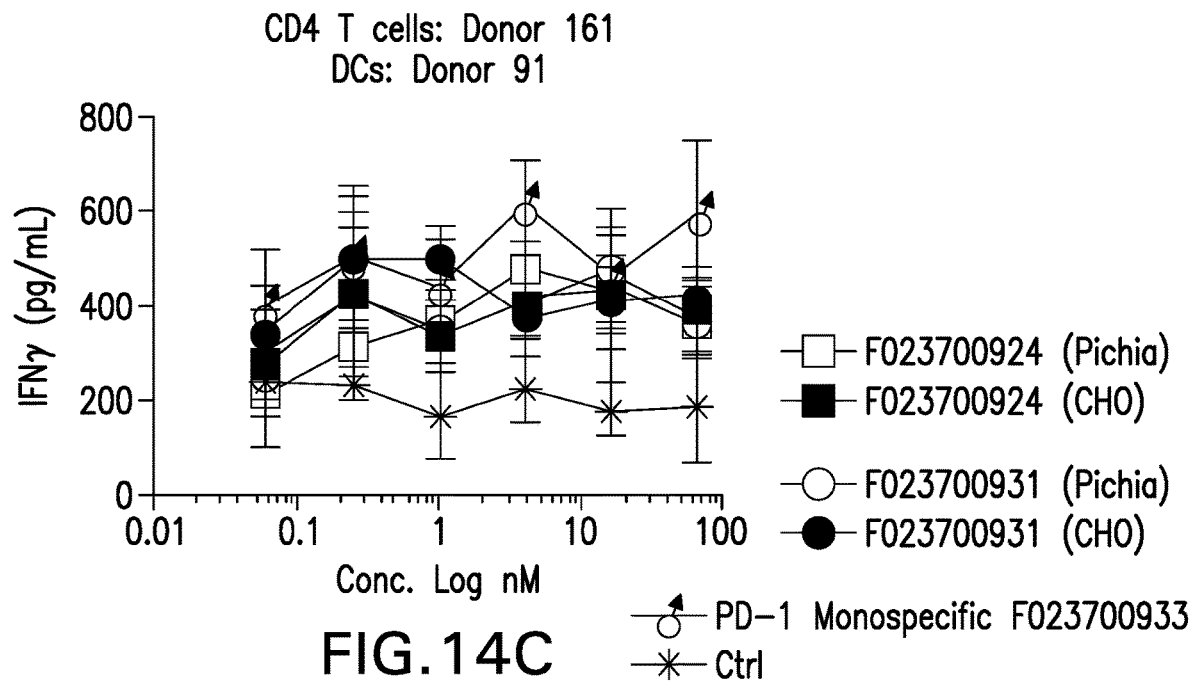
Figure 14D:
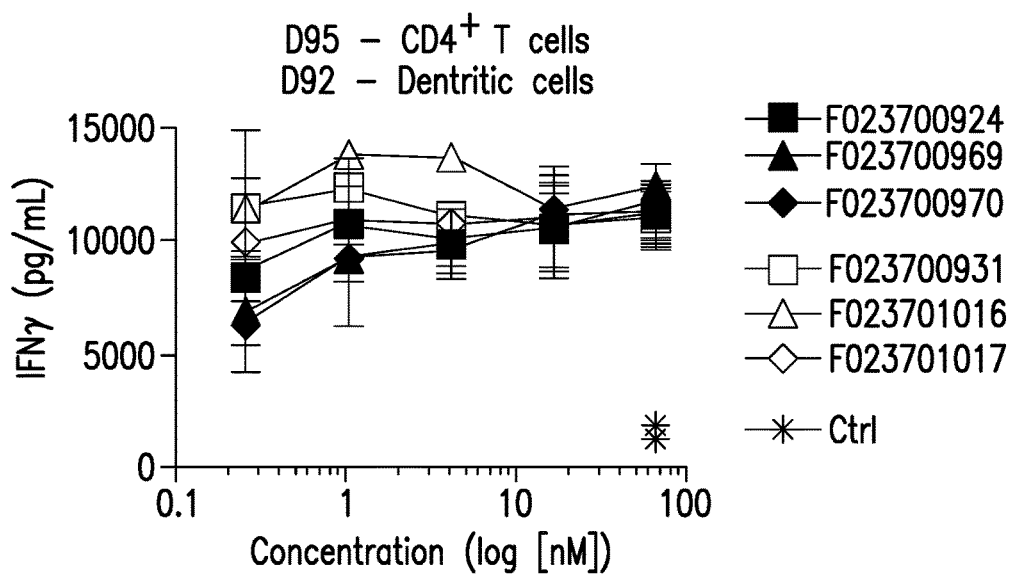
Figure 14E:
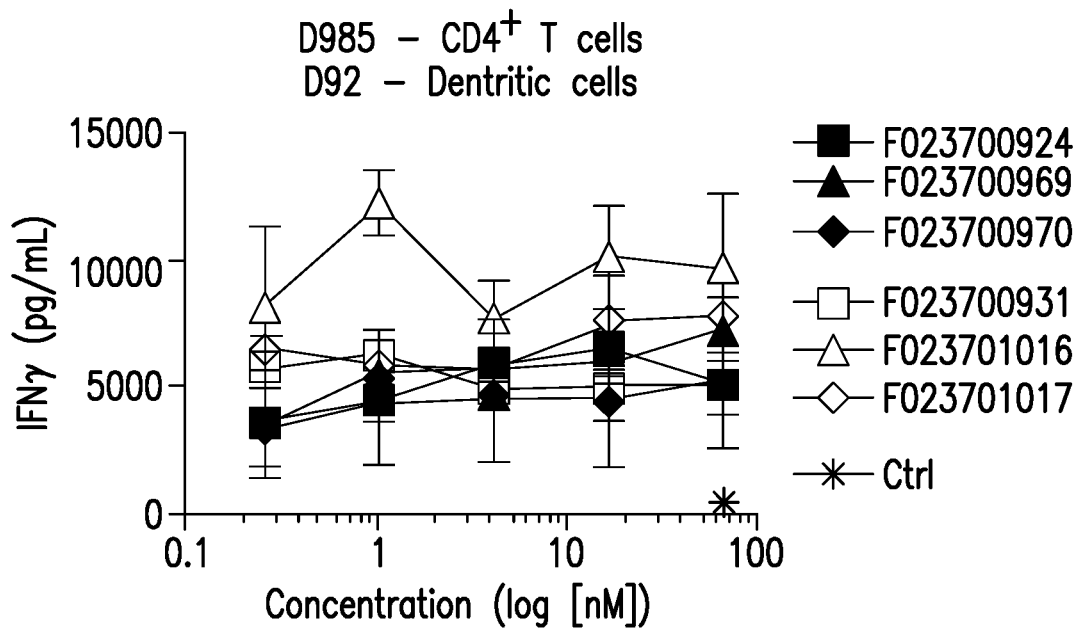
Figure 14F:
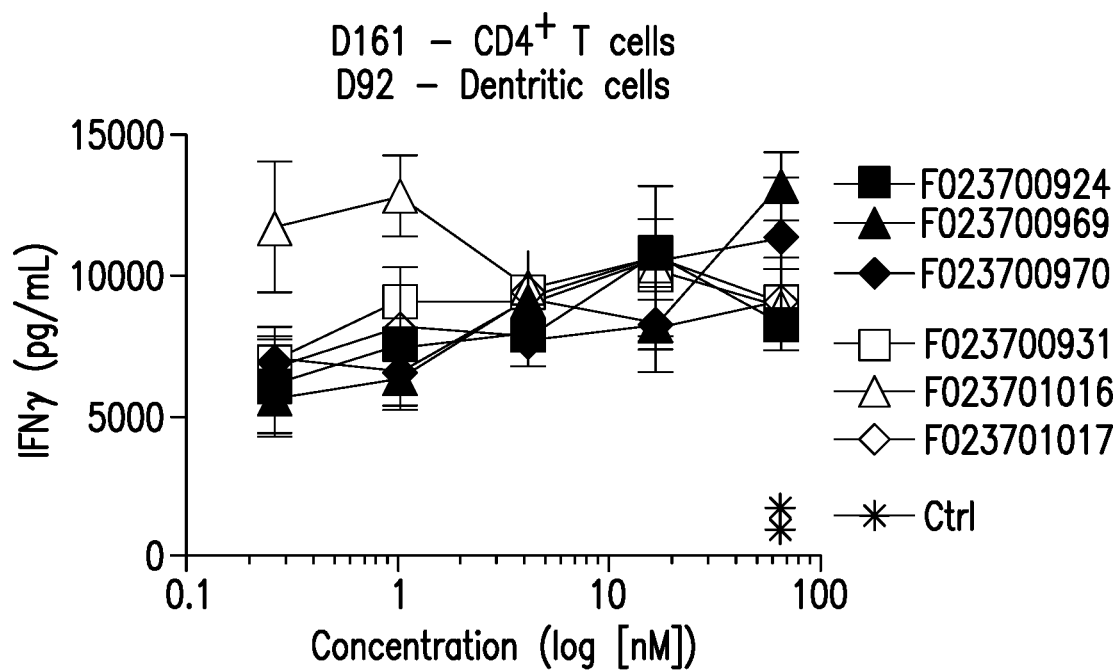

This Example demonstrated that the bispecific anti-human PD-1/LAG-3 Nanobody F023700931 simultaneously bound to human PD-1 and human LAG-3 expressed in the cell membrane due to bringing the PK and the EA subunits together to form an active enzyme complex to give a light signal (FIG. 11 (A)). The monospecific, bivalent controls anti-human PD-1 F023700933 individually and the anti-human LAG-3 F023700962 individually were unable to bind both targets simultaneously and therefore did not generate a light signal. The individual modules in the bispecific anti-human PD-1/LAG-3 Nanobody F023700931 were linked with a Glycine-Serine linker that is 35 amino acids long (35GS). The bispecific anti-human PD-1/LAG-3 Nanobody F023701016 and F023701017 contained the identical PD-1 and LAG-3 modules as F023700931 but the Glycine-Serine linker between all modules in the constructs were 20 amino acids long (20GS) or 9 amino acids long (9GS), respectively. This example showed that shortening the Glycine-Serine linker from 35GS to 9GS had minimal impact on the ability to bind both targets simulataneously on the cell membrane and give a light signal. Collectively, these data showed that the bispecific anti human PD-1/LAG-3 Nanobody F023700931 can bind both targets simultaneously, if both targets were expressed by the same cell.

This Example also demonstrated that the bispecific anti-human PD-1/LAG-3 Nanobody F023700924 simultaneously bound to human PD-1 and human LAG-3 expressed in the cell membrane (FIG. 11 (B)). The individual modules in the bispecific anti-human PD-1/LAG-3 Nanobody F023700924 are linked with a Glycine-Serine linker that is 35 amino acids long (35GS). The bispecific anti-human PD-1/LAG-3 Nanobody F023700969 and F023700970 contained the identical PD-1 and LAG-3 modules as F023700924 but the Glycine-Serine linker between all modules in the construct were 20 amino acids long (20GS) or 9 amino acids long (9GS), respectively. This example showed that shortening the Glycine-Serine linker from 35GS to 9GS had minimal impact on the ability to bind both targets simulataneously and give a light signal. Collectively, these data showed that the bispecific anti-human PD-1/LAG-3 Nanobody F023700924 could bind both targets simultaneously, if both targets were expressed by the same cell.

Example 8: Engineered
Jurkat.hPD-1.IL2luc+THP-1.PD-L1 Assay

Clone DT999A1 is a PD-1 transgene expressing Jurkat cell clone with an IL-2 mediated luciferase reporter (Jurkat.hPD-1.IL2luc). Jurkat.hPD-1.IL2luc were grown in RPMI media (Corning Cellgro 10-040-CV)+heat inactivated 10% FBS (Hyclone SH30910.03)+2 mM L-glutamine (Cellgro 25-005-CI)+2 ug/ml puromycin (Sigma P9620)+0.5 mg/ml Geneticin (Gibco 10131-027). Cells were split twice per week after seeding cells at $2\times10^5$ cells/ml and were split when the density exceeded $1\times10^6$ cells/ml. PD-L1 transgene expressing THP-1 cells (THP-1.PD-L1) were grown in RPMI media+heat inactivated 10% FBS+2 mM L-glutamine+0.5 ug/ml puromycin. Cells were split twice per week after seeding at $3\times10^5$ cells/ml and were split when they reach $1\times10^6$ cells/ml.

The bioassay was setup using Assay Media (Phenol red free RPMI media (Gibco 11835-030)+10% dialyzed FBS (Hyclone, SH30079.03). Human albumin (Sigma, A8763) was prepared as 600 uM stock. A 4× (120 uM) solution was prepared using assay media and 25 uL added to white walled tissue culture treated plates (Costar 3903). Dilute Nanobodies using assay media to get a starting 4× concentration. Make six 10-fold serial dilutions of the Nanobodies. Add 25 ul of the Nanobody titration to the white walled tissue culture treated plate containing albumin. Incubate the Nanobodies+albumin for 20-30 minutes at room temperature. Harvest a T-75 flask of THP-1.PD-L1 cells, spin the cells, and resuspend in 10 ml of assay media. Count the cell suspension and adjust to get a cell suspension of $4\times10^6$ cells/ml. Harvest a T-75 flask of Jurkat.hPD-1.IL2luc cells, centrifuge cells, and resuspend in 10 ml of assay media. Count the cell suspension and adjust to get Jurkat.hPD-1.IL2luc cells suspension of $1\times10^6$ cells/ml. Mix equal volume of THP-1.PD-L1 cells+Jurkat.hPD-1.IL2luc cells. To this mixed suspension, add 2 ng/ml LPS (2×) and 100 ng/ml IFN-g (2×). Add 50 uL cell suspension containing the stimulation conditions [IFN-g (R&D systems 285-IF/CF)+ LPS (Sigma L4391)] to the Nanobody titration. Incubate the cells with the Nanobody titration for approximately 22 hours in an incubator. At the end of 22 hours, carefully add 10 ul of 55 ng/ml anti-CD3 antibody (BD Pharmingen 555336; 11× working solution) and leave in the incubator for an additional two hours. At the end of two hours incubation, stick white tape (Perkin Elmer 6005199) to the bottom of the plate and add 100 ul of One-Glo reagent (Promega E6120). Incubate with shaking at room temperature for 3 minutes. Read the plate on a plate reader capable of reading luminescence with an integration time of 0.1 secs. Raw data in RLU (Relative light units) can be plotted directly or plotted as fold change in luciferase signal obtained by dividing the treatment wells with wells that have no Nanobody. The data from these experiments are set forth in FIG. 12 (A-E).

This Example demonstrated that the anti-human PD-1 Nanobody monovalent module, F023700706, bound to human PD-1 expressed by the T-cell line, blocks PD-1's interaction with PD-L1 expressed by the co-culture cell line to relieve the suppression that PD-L1 was providing to the T-cell; thereby, allowing the T-cell to respond, to a greater degree, to the T-cell receptor agonist based on inhibiting the PD-L1-mediated suppression (FIG. 12 (A)). Furthermore, this Example demonstrated that the bispecific anti human PD-1/LAG-3 Nanobodies F023700931 and F023700924 bound to human PD-1 expressed by the T-cell line, blocks PD-1's interaction with PD-L1; thereby, allowing the T-cell to respond to a greater degree to the T-cell receptor agonist based on inhibiting the PD-L1-mediated suppression (FIG. 12 (B)). The monospecific, bivalent controls anti human PD-1 F023700933 and anti-human LAG-3 F023700962 were also shown. Additionally, this Example showed that the bispecific anti-human PD-1/LAG-3 Nanobody F023700969 and F023700970 containing 20GS or 9GS linkers, respectively, had similar potency as the parent F023700924 molecule containing 35GS linkers (FIG. 12 (C)). Similarly, the bispecific anti-human PD-1/LAG-3 Nanobody F023701016 and F023701017 containing 20GS or 9GS linkers, respectively, had similar potency as the parent F023700931 molecule containing 35GS linkers (FIG. 12 (D)). Also, this Example demonstrated that additional amino acid variants of sequence optimized anti-human PD-1 Nanobody monovalent module F023700706 bound to human PD-1 expressed by the T-cell line, blocking PD-1's interaction with PD-L1; thereby, allowing the T-cell to respond to a greater degree to the T-cell receptor agonist based on inhibiting the PD-L1-mediated suppression (FIG. 12 (E)).

Example 9: SEB Activated Human PBMC Assay

Thawed human peripheral blood mononuclear cells (PBMCs) into complete RPMI with 10% human serum (RPMI 1640 Glutamax (Thermo Fisher Scientific, catalog 11875085), 1× Penicillin-Streptomycin (Thermo Fisher Scientific, catalog 15140148), 1× beta-mercaptoethanol (Thermo Fisher Scientific, catalog 21985023), 1×HEPES (Thermo Fisher Scientific, catalog 15630080), 1× sodium pyruvate (Thermo Fisher Scientific, catalog 11360070), 1× non-essential amino acids (Thermo Fisher Scientific, catalog 11140076), human serum (Sigma, catalog H4522-100ML lot #SLBP2783V). Suspended to 2.5E6 cells/mL and aliquot 100 uL to 96-well U-bottom plate at 2.5E5 cells/well. Nanobodies were serially diluted using a 3-fold dilution series to prepared 4× working stocks and create a 6-point dose-response curve. Added 50 uL of Nanobody solution to wells and incubated 15-30 minutes at room temperature while preparing *streptococcus* exotoxin B (SEB) solution.

Stock SEB (Toxin Technology Inc, catalog BT202) was prepared by reconstituting SEB at 1 mg/mL in distilled water and freezing at −80° C. A 2 uM working solution was made by adding 2 ul stock per mL media and the 2 uM working solution was serially diluted using a 10-fold dilution series to make a titration curve. Added 50 uL to appropriate wells to make a titration curve as an internal standard to confirm assay was performing as expected and to determine the maximum response that could be elicited from different donors. The 2 uM SEB working solution was diluted to 40 nM SEB and 50 uL added to wells to stimulate PBMC (final concentration of SEB is 10 nM). Incubate for 72 hours at 38° C. and 5% $CO_2$. Transferred top 100 uL supernatant into a fresh 96-well plate and dilute 1:2 for IL-2 analysis using MSD V-plex human IL-2 kit (MesoScale Discovery, K151QQD-1). Remainder stored at −80° C. The data from these experiments are set forth in FIG. 13 (A-R).

This Example demonstrated that the bispecific anti-human PD-1/LAG-3 Nanobodies F023700931 and F023700924 gave rise to increased IL-2 levels following T-cell receptor agonist stimulation of peripheral blood mononuclear cell (PBMC) obtained from multiple donors (A-R).

Example 10: Mixed Lymphocyte Reaction (MLR) Assay

Human peripheral blood mononuclear cells (PBMCs) were purified from leukopacks and frozen down in liquid nitrogen freezer. Frozen human PBMCs were thawed, diluted in complete RPMI (RPMI+10% human serum), centrifuged at 450×g for 5 minutes, and the cell pellet resuspended with complete RPMI (Gibco RPMI 1640 media (Thermofisher Scientific; 11875-119); human serum (Sigma-Aldrich; H4522-100 mL). Monocytes were enriched using Human Monocyte Enrichment kit (STEMCELL technologies; 19059). Cells were transferred to 6-well plates at 1×10$^6$ cells/ml (5 ml/well) in complete RPMI containing 100 ng/ml GM-CSF (R&D Systems; 215-GM-110) and 50 ng/ml of human IL-4 (R&D Systems; 204-IL-010/CF). Monocytes were incubated at 37° C. for 5 days to allow for dendritic cell (DC) differentiation. Monocyte-derived dendritic cells (Mo-DC) were harvested on Day 6, counted, and used in MLR assay as stimulators.

On the day of experiment initiation, frozen human PBMCs were thawed and diluted two times in complete RPMI containing penicillin/streptomycin. CD4 T cells from each donor were enriched using EasySep Human CD4 T cell isolation kit (STEMCELL technologies; 17952). Isolated CD4 T cells were suspended at 1×10$^6$ cells/ml in complete RPMI. Mo-DC were mixed at 1:10 ratio (1×10$^5$ cells/ml) with CD4$^+$ T-cells (1×10$^6$ cells/ml) and cell mixture plated in a U-bottom 96-well plate at 200 ul/well. Nanobodies were serially diluted using a 4-fold dilution series and 5× working stocks were prepared. 50 µL of each dilution was added to the 200 cultures to give 1× final concentration of nano/anti bodies. Culture supernatants were collected at Day 5 post-experiment initiation for IFNγ quantitation using V-plex Human Pro-inflammatory Panel I (Mesoscale Discovery; K15052D-1). The data from these experiments are set forth in FIG. 14 (A-F).

This Example demonstrated that the bispecific anti-human PD-1/LAG-3 Nanobodies F023700931 and F023700924 gave rise to increased IFN-gamma levels following primary CD4 T-cell stimulation with allogeneic Mo-DCs obtained from different donors (a-f).

Example 11: Engineered 3A9.hLAG-3 Assay

3A9.hLAG3 is a human LAG-3 transgene expressing mouse 3A9 T-cell hybridoma. LK35.2 (ATCC; HB-98) is a mouse B-cell hybridoma that bears surface I-Ad$^k$ and I-Ed$^k$ molecules that present a specific antigen (i.e. hen egg lysozyme (HEL) peptide DGSTDYGILQINSRWW) to the class II restricted 3A9 T-cell hybridoma. Counted 3A9.hLAG3 cells and resuspend at 4×10$^6$ cells/ml of fresh medium [RPMI (Invitrogen, 61870-036)+10% FBS+Pen Strep]. Counted LK35.2 cells and resuspend at 1×10$^6$ cells/ml of fresh media. Added 25 µL 3A9.hLAG3 cells (1E5 cells) to wells in a 96-well flat bottom tissue culture plate (Corning 3610). Prepared a 4× (200 uM) solution of human albumin (Sigma, A8763) and added 25 µL to the cells. Diluted Nanobodies to 5× concentration in complete medium and add 20 ul of 5× Nanobody to cells. Incubated 3A9.hLAG3 cells with Nanobodies for 30 minutes at 37° C.

Figure 15C:
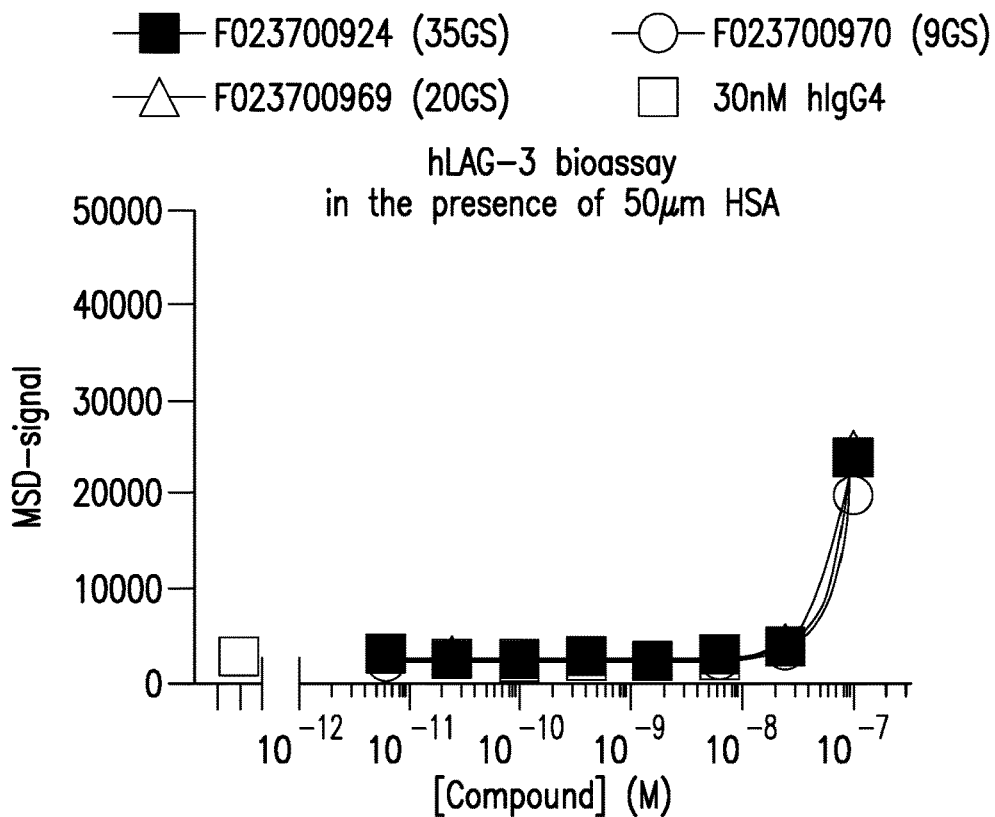
FIG. 15 (A-D). Activation assay of 3A9 T-cells expressing human LAG3 in the presence of HSA and in the presence of (A) F023700656 (11B09 (E1D)), F023700842 or control IgG4; (B) F023700931 (*Pichia* or CHO expressed), F023700924 (*Pichia* or CHO expressed), F023700933 or F023700962 or control Nanobody (IRR00085 or IRR00087; RSV binders); (C) F023700924, F023700969, F023700970 or control Nanobody; (D) F023700931, F023701016, or F023701017 or control Nanobody.
Figure 15D:
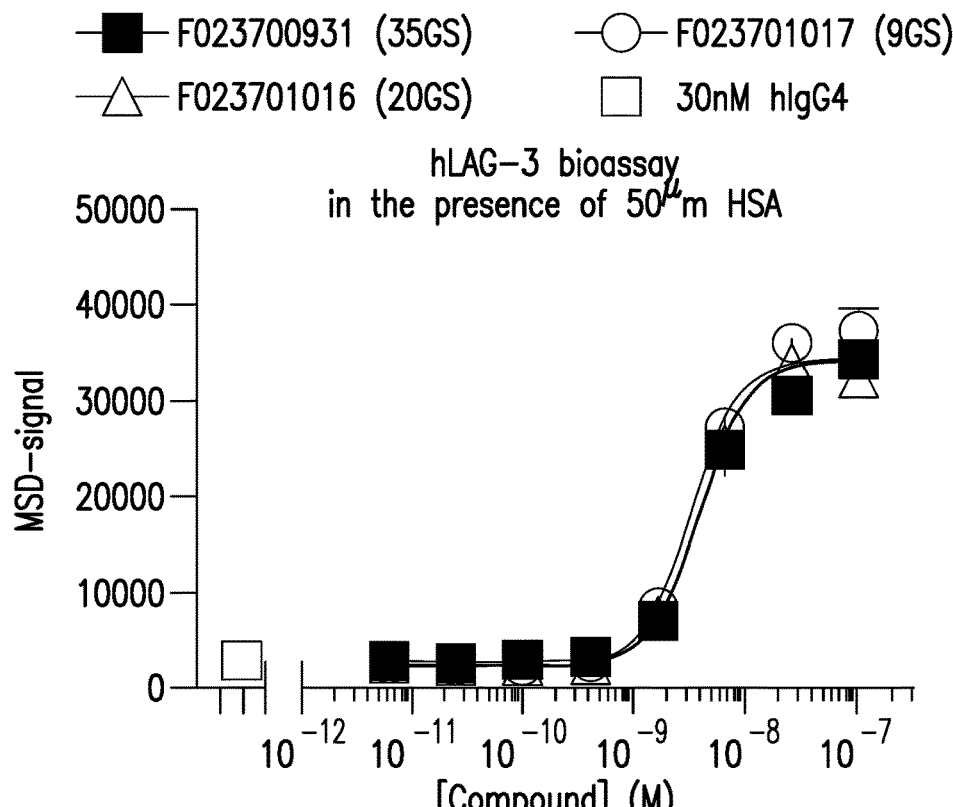

Prepared 500 µM HEL peptide (GenScript custom peptide) stock solution and stored at −20 C. Diluted HEL peptide stock 1:20 (25 uM) in cell culture medium and then further diluted HEL peptide 1:833 onto LK35.2 cells (final HEL concentration=∼30 nM). Incubated LK35.2 cells with peptide for 30 minutes at 37 C. Added 33 µL peptide treated LK35.2 cells to the 96-well plate containing Nanobody treated 3A9.hLAG-3 cells. Incubated culture at 37° C. for 24 hours. Spinned plates at 300×g for 5 minutes and collected supernatant for IL-2 analysis (IL-2 Mesoscale V-Plex; Mesoscale K152QQD-4). The data from these experiments were set forth in FIG. 15 (A-D).

This Example demonstrated that the anti-human LAG-3 Nanobody monovalent module F023700842 bound to human LAG-3 expressed by the T-cell line, blocked LAG-3's interaction with MHC Class II expressed by the co-culture cell line to relieve the suppression that MHC Class II was providing to the T-cell; thereby, allowing the T-cell to respond to a greater degree to the T-cell receptor agonist based on inhibiting the MHC Class II-mediated suppression. The potency of inhibiting the MHC Class II by the anti-human LAG-3 Nanobody monovalent module F023700842 was similar to that of the parental Nanobody F023700656 from which it was derived (FIG. 15 (A)). Furthermore, this Example demonstrated that the bispecific anti-human PD-1/LAG-3 Nanobodies F023700931 and F023700924 bound to human LAG-3 expressed by the T-cell line, blocked LAG-3's interaction with MHC Class II; thereby, allowing the T-cell to respond to a greater degree to the T-cell receptor agonist based on inhibiting the MHC Class II-mediated suppression (FIG. 15 (B)). The monospecific, bivalent controls anti-human PD-1 F023700933 and anti-human LAG-3 F023700962 were also shown. Additionally, this Example showed that the bispecific anti-human PD-1/LAG-3 Nanobody F023700969 and F023700970 containing 20GS or 9GS linkers, respectively, had similar potency as the parent F023700924 molecule containing 35GS linkers (FIG. 15

(C)). Similarly, the bispecific anti-human PD-1/LAG-3 Nanobody F023701016 and F023701017, containing 20GS or 9GS linkers, respectively, had similar potency to the parent F023700931 molecule containing 35GS linkers (FIG. 15 (D)).

Example 12: Engineered Bispecific Jurkat.hPD-1.LAG-3 Bioassay

Generation of Jurkat.LAG-3.PD-1 cells (DT1088-Clone G10PD1)

A human LAG-3 transgene was introduced into Jurkat cells (Je6.2.11) using a retroviral delivery system with puromycin as a selection marker. Limiting dilution was conducted to pick a clone (DT1088G10) with optimal LAG-3 and CD3 expression. A human PD-1 transgene was introduced into DT1088G10 clone using a Lentiviral delivery system with Genticin as a selection marker. Cells were FACS-sorted for high LAG-3 and PD-1 expression. Sorted cell pool was maintained and subcultured in RPMI complete media [RPMI (Corning 10-040-CV) supplemented with 10% FBS (Hyclone SH30910.03)+1 mM sodium pyruvate (BioWhittaker, 13-115E)+2 mM L-glutamine (Corning Cell-Gro, 25-005-CI)+10 mM HEPES (Corning, 26-060-CI)+1× non-essential amino acids (Sigma, M7145)+0.2 ug/ml puromycin (Sigma P9620), +0.5 mg/ml G418 (Gibco 10131-027)].

Generation of the Raji.PD-L1 Expressing Cells

A human PD-L1 transgene was introduced into Raji cells (ATCC CCL-86) using a retroviral delivery system with puromycin as a selection marker. The cells were sorted to enrich for PD-L1 and Class-II (endogenous) expression. The enriched pool of cells were maintained and subcultured in RPMI complete media (RPMI media supplemented with 10% Hyclone FBS+2 mM L-glutamine+10 mM HEPES+ 0.25 ug/ml puromycin).

Stock SED toxin was prepared by reconstituting SED (Toxin technology DT303) at 1 mg/ml in sterile distilled water and storing at −80° C. Raji.PD-L1 cells were preloaded with toxin by incubating a suspension of 0.87× $10^6$Raji-PD-L1 cells/ml with SED toxin (1.3×=130 ng/ml, final 100 ng/ml) in RPMI media containing 10% dialyzed FBS (Hyclone SH30079.03) for 30 minutes in a 37° C. incubator. A suspension of 8×$10^6$ Jurkat.LAG-3.PD-1 cells/ml in RPMI media containing 10% dialyzed FBS was prepared. Nanobodies were prepared as an 8 point, 4-fold dose titration (12×=120 μg/ml) of Nanobodies with a starting assay concentration of 10 ug/ml.

45 ul Jurkat.LAG-3.PD-1 cell suspension (8×$10^6$ cells/ml) was incubated with 45 ul of Nanobody titration at room temperature for 30 minutes in a round bottom plate (Corning 3359). At the end of 30 minutes, 36 uL human albumin (Sigma, A8763; 15×=450 uM to get a final assay concentration of 30 uM) was added to the Jurkat.LAG-3.PD-1+ Nanobody mixture. 115 ul SED-loaded Raji.PD-L1 cells were added to assay plates (Thermoscientific #167008). To the SED-loaded Raji.PD-L1 cells, 35 uL mixture of Jurkat-.LAG-3.PD-1+Nanobodies+albumin was carefully layered. Assay plates were incubated for 24 hours at 37° C. in a 5% $CO_2$ incubator. Following 24 hour incubation, 75 uL supernatant was transferred to a plate (Corning #3605) and frozen at −80 degrees. Samples were analyzed using the MSD IL-2 V-plex kit (Mesoscale devices Cat #K151QQD). EC50 values were calculated using the GraphPad prism Software. The data from these experiments are set forth in FIG. 16 (A-B).

Figure 16A:
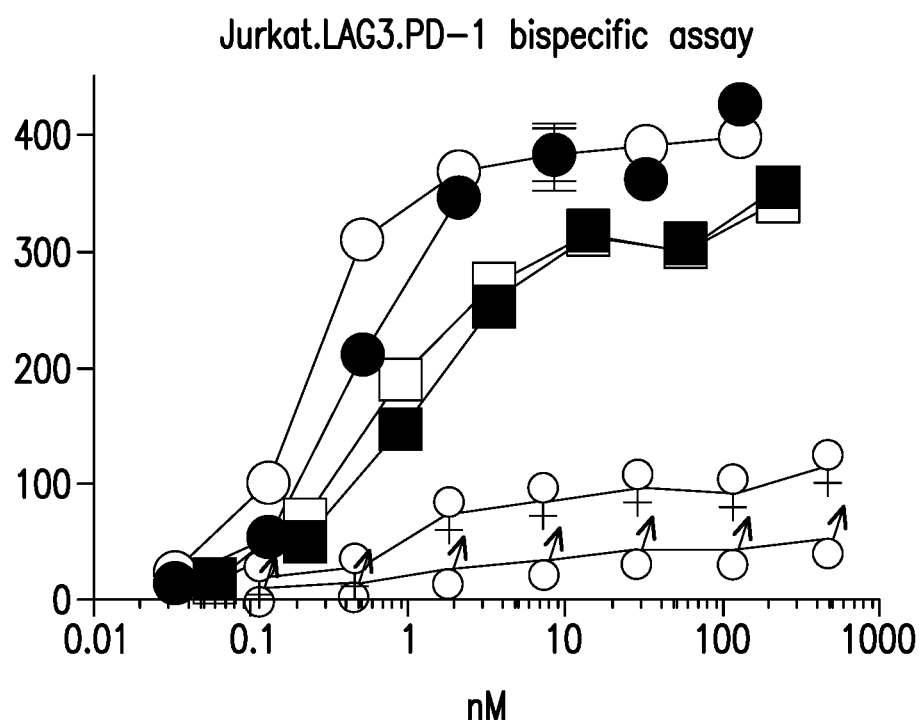
FIG. 16 (A-B). Activation of Jurkat T-cells expressing human LAG3 and human PD1 and Raji antigen-presenting cells in the presence of (A) F023700931 (*Pichia* or CHO expressed), F023700924 (*Pichia* or CHO expressed), F023700933 or F023700862 [should this be F023700892] or control Nanobody or (B) F023700924, F023700969, F023700970, F023700931, F023701016, F023701017, F023700933 or F023700962 or control Nanobody.
Figure 16B:
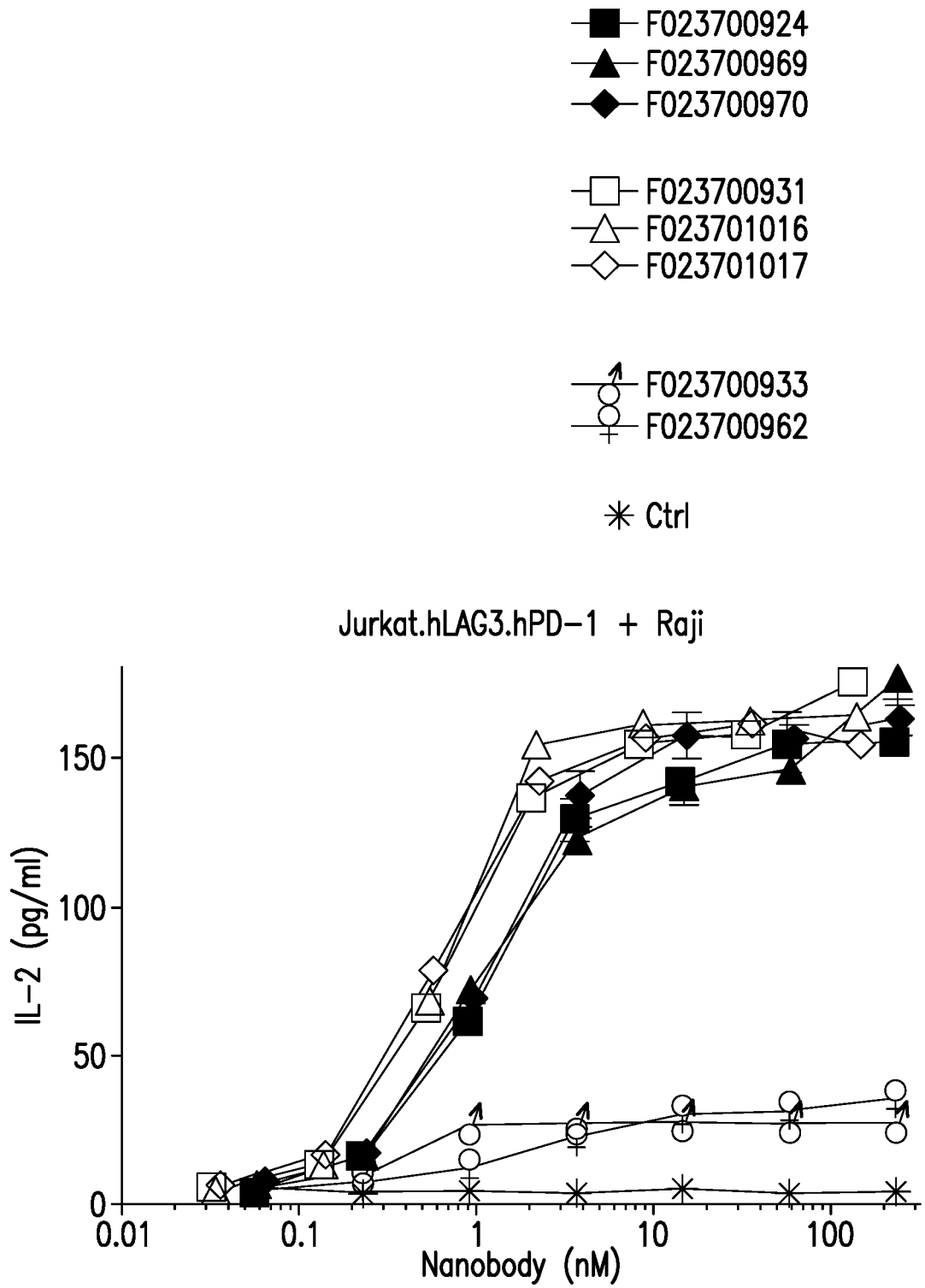

This Example demonstrated that the bispecific anti-human PD-1/LAG-3 Nanobodies F023700931 and F023700924 bound to both human PD-1 and human LAG-3 expressed by the T-cell line, blocked PD-1's interaction with PD-L1, blocks LAG-3's interaction with MHC Class II; thereby, allowing the T-cell to respond, to a greater degree, to the T-cell receptor agonist based on inhibiting the dual PD-L1-mediated and MHC Class II-mediated suppression (FIG. 16 (A)). The monospecific, bivalent controls anti-human PD-1 F023700933 and anti-human LAG-3 F023700862 were only able to block one of the two inhibitory mechanisms individually leading to the T-cell responding in a much more modest fashion to the T-cell receptor agonist. Additionally, this Example showed that the bispecific anti-human PD-1/LAG-3 Nanobody F023700969 and F023700970 containing 20GS or 9GS linkers, respectively, had similar potency to the parent F023700924 molecule containing 35GS linkers. Similarly, the bispecific anti-human PD-1/LAG-3 Nanobody F023701016 and F023701017 containing 20GS or 9GS linkers, respectively, had similar potency as the parent F023700931 molecule containing 35GS linkers (FIG. 16 (B)).

Example 13: Human T-Cell Clone+JY.hPD-L1 Assay

Generation and Culture of Human CD4+ T Cell Clone

MHC class II allo-antigen specific CD4+ T cell clone BC4-49 was generated by 2 rounds of mixed leukocyte reaction with the EBV-transformed B-cell line JY and cloned by limiting dilution. The clone was re-stimulated with allo-specific antigens at an interval of every 2 weeks and cultured in Yssel's medium (IMDM, Gibco 12440-053; human serum AB, Gemimi 100512; penicilin/streptomycin, Mediatech 30-002-CI; human albumin, Sigma A9080; ITS-X, Gibco 51500056; Transferin, Roche 10652202001; PA Bioxtra Sigma p5585; LA-OA-Albumin, Sigma L9655). Fresh PBMCs were isolated from two human buffy coats provided by Stanford Blood Center and pooled at 1:1 cell ratio. PBMCs were irradiated in a gamma irradiator at dose 4000 rads before use. Wildtype JY cells were prepared and irradiated at dose 5000 rads. T cell clones were cultured with feeders in 24-well plate at 1 mL per well with final concentrations of CD4+ T cells 0.2×$10^6$/mL, irradiated PBMCs 1×$10^6$/mL, irradiated JY 0.1×$10^6$/mL, and 100 ng/mL PHA (Sigma L9017). Recombinant human IL-2 (R&D Systems; 202-IL/CF) was added at final concentration of 100 ng/mL on day 3 after re-stimulation, and was replenished every 3-4 days throughout the expansion. Cells were passaged to an optimal concentration between 0.5-1.0×$10^6$/mL. On day 7 after re-stimulation, abundant level of LAG-3 and moderate level of PD-1 were expressed on T cell surface.

Human CD4+ T Cell Functional Assay

Allo-antigen specific CD4+ T cells were harvested from 24 well culture plates on day 7 after antigen re-stimulation, then washed twice with 20 mL PBS (Hyclone, SH3002802)

containing 2 mM EDTA (Invitrogen, 15575-38) by centrifugation. The pellets were re-suspended into single cell suspension in Yssel's medium. Tested Nanobodies were titrated by 5-fold serially dilutions in Yssel's medium starting from highest concentration of 133 nM with total 7 dilutions in a volume of 100 µL in 96 well U-bottom culture plates (Falcon, 353077). Fifty microliters of T cell suspension at a density of $4 \times 10^5$ cells/mL was added into wells containing titrated Nanobodies. The Nanobody/T cell mixture was pre-incubated for 1 hour in an incubator at 37° C. with 5% $CO_2$. Human PD-L1 transgene expressing JY cells (JY.hPD-L1) were used in co-cultures to provide allo-specific antigens. JY.hPD-L1 cells cultured in T-75 flask (Thermo Scientific, 156499) in RPMI medium (Corning Cellgro, 10-040-CV) with 10% FCS were harvested and irradiated in a gamma irradiator at a dose of 5000 rads, then washed twice with PBS containing 2 mM EDTA by centrifugation. The pellet was re-suspended with Yssel's medium, and filtered with 40 µm cell strainer before plating. 50 µL/well of JY.hPD-L1 suspension at a concentration of $2 \times 10^5$ cells/mL was dispensed into pre-incubated Nanobody-T cells mixture, with T cell to JY.hPD-L1 cell ratio at 2:1. All conditions were run in duplicates. After approximately 3-day culture, 100 µL of supernatant per well was harvested for human IFNγ quantification. Human IFNγ ELISA was performed to assess IFNγ level on pooled supernatant from duplicates by using hIFNγ Quantikine kit (R&D Systems, SIF50). Assays were run following the standard protocol provided by manufacturer. EC50 values were calculated using the GraphPad prism software. The data from these experiments are set forth in FIG. 17 (A-C).

Figure 17A:
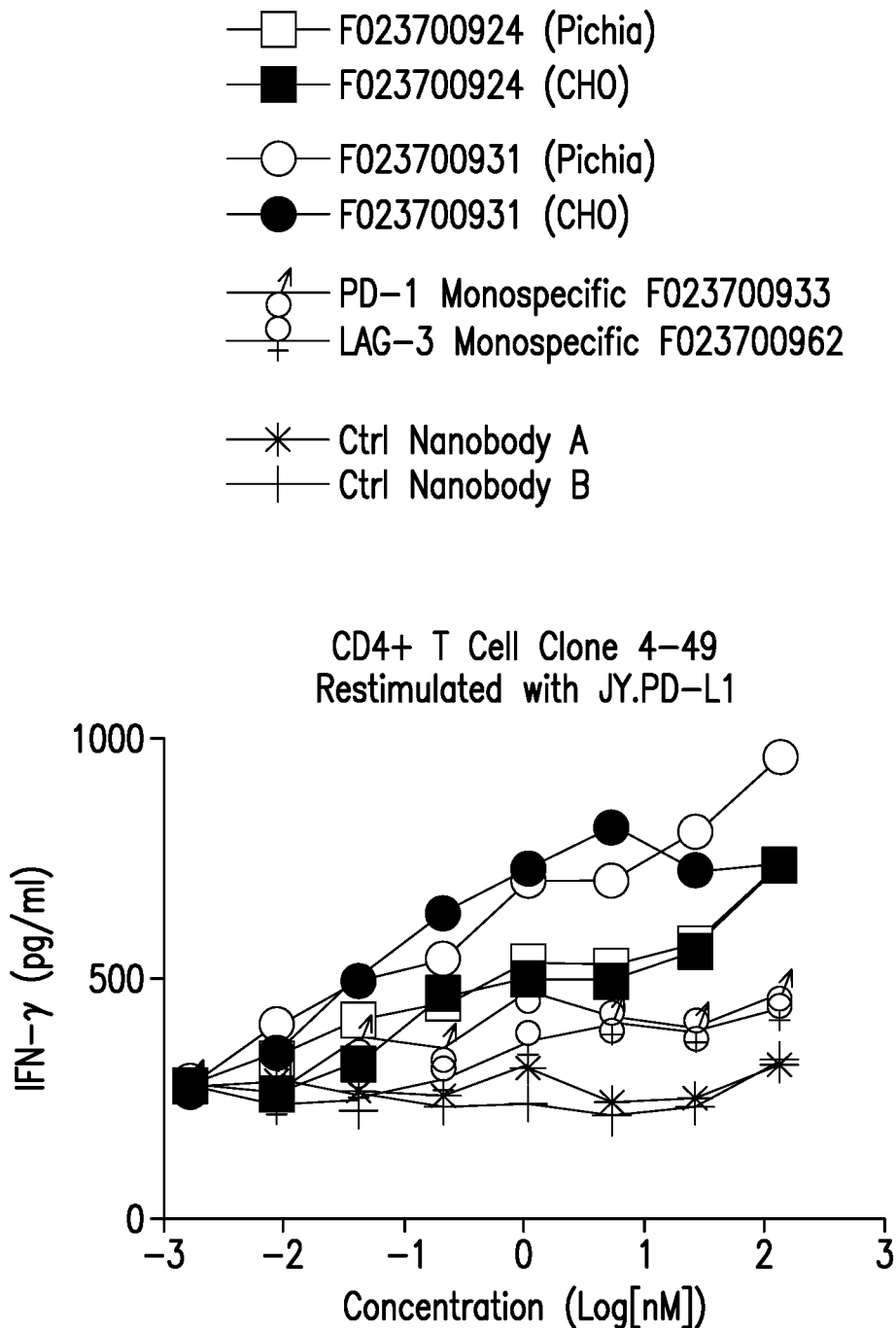
FIG. 17 (A-C). Human T-cell clone activation (interferon-gamma production) in the presence of JY cells expressing human PDL1 in the presence of varying concentrations of (A) F023700931 (*Pichia* or CHO expressed), F023700924 (*Pichia* or CHO expressed), F023700933 or F023700962 or control Nanobody; (B) F023700924, F023700969, F023700970, F023700933 or F023700962 or control Nanobody; or (C) F023700931, F023701016, F023701017, F023700933 or F023700962 or control Nanobody.
Figure 17B:
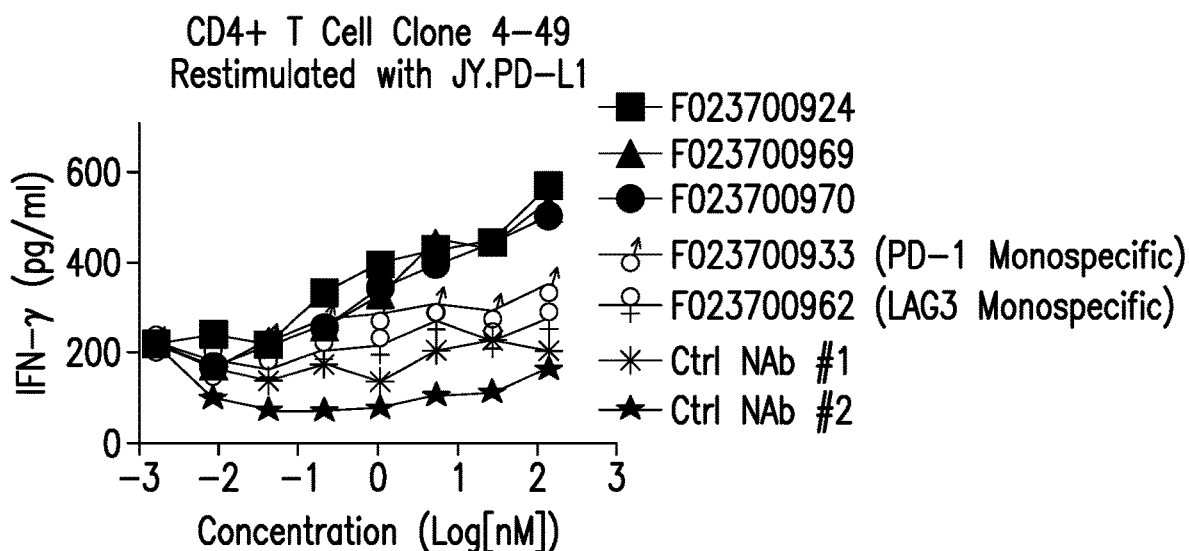
Figure 17C:
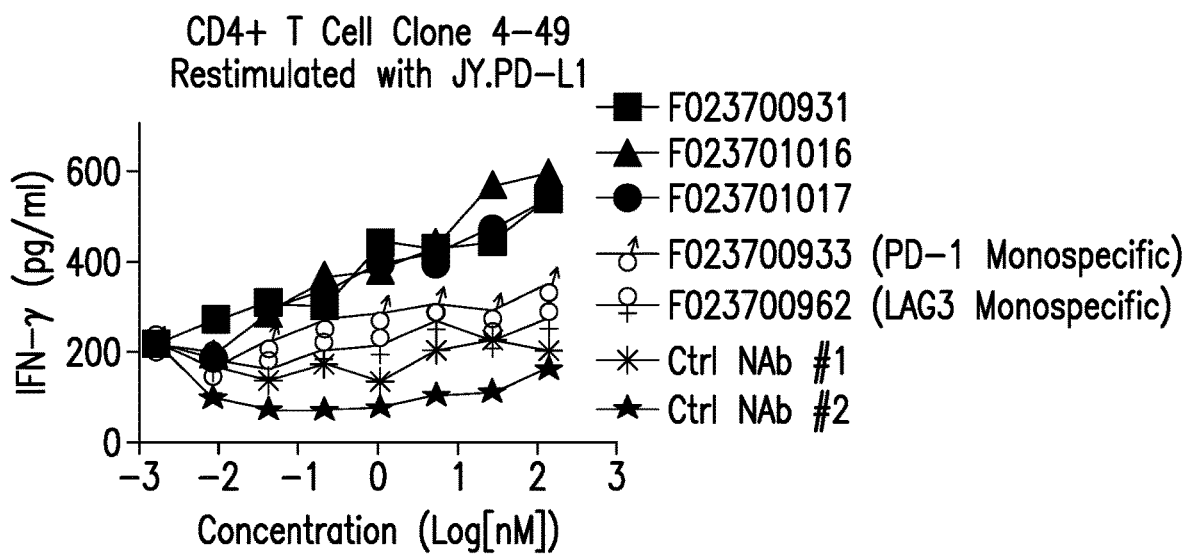
Figure 19A:
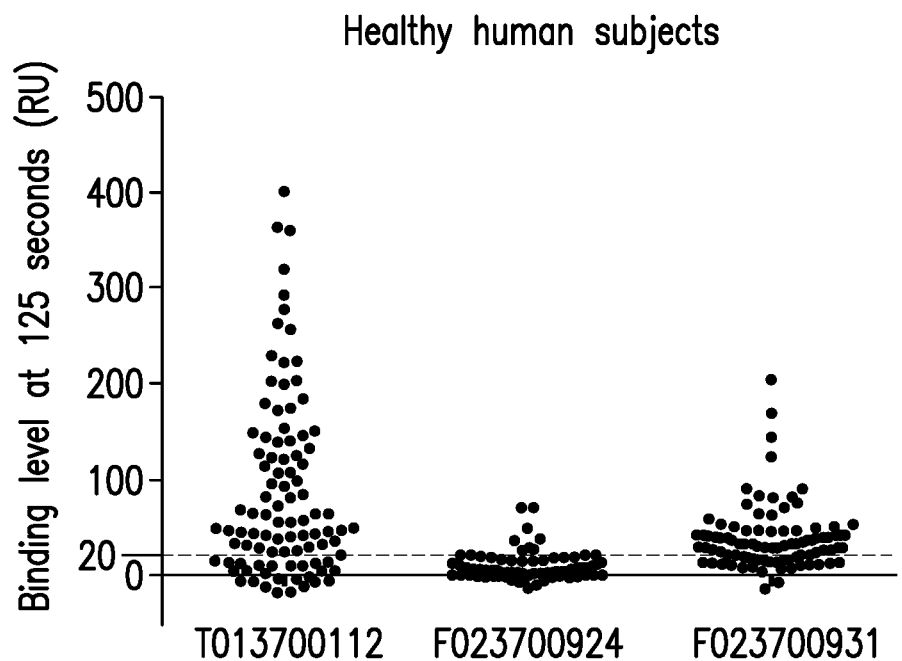
FIG. 19 (A-I). Serum preAb reactivity to F023700924 and F023700931 and a trivalent control Nanobody T013700112 (lacking mutations to reduce pre-existing antibody binding) by healthy human subject sera at (A) 125 seconds and (B) 360 seconds; by cancer patient sera at (C) 125 seconds or (D) 360 seconds; or by sera of patients suffering from (E) melanoma, (F) non-small cell lung cancer (NSCLC), (G) head & neck cancer, (H) gastric cancer or (I) colorectal cancer.
Figure 19B:
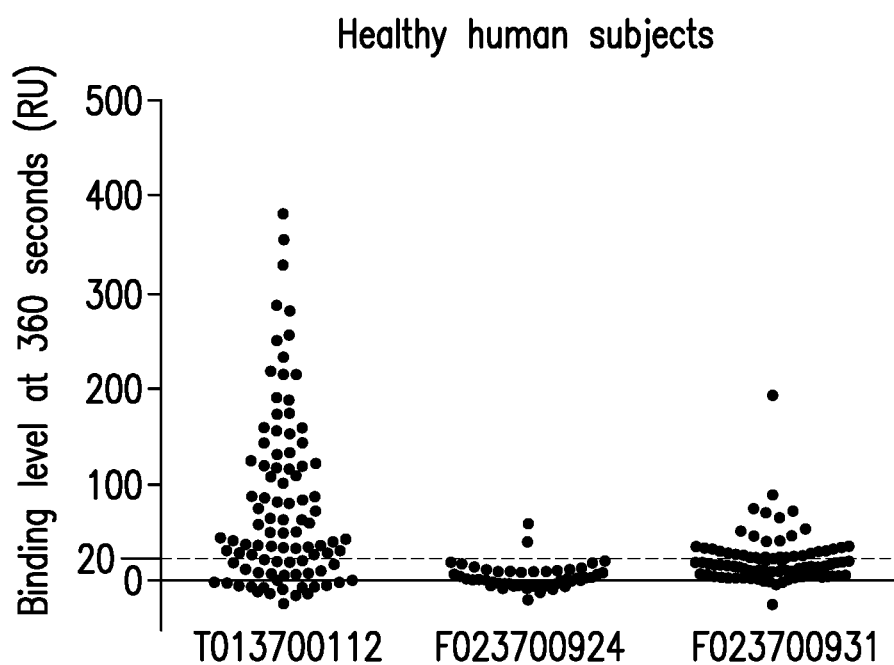
Figure 19C:
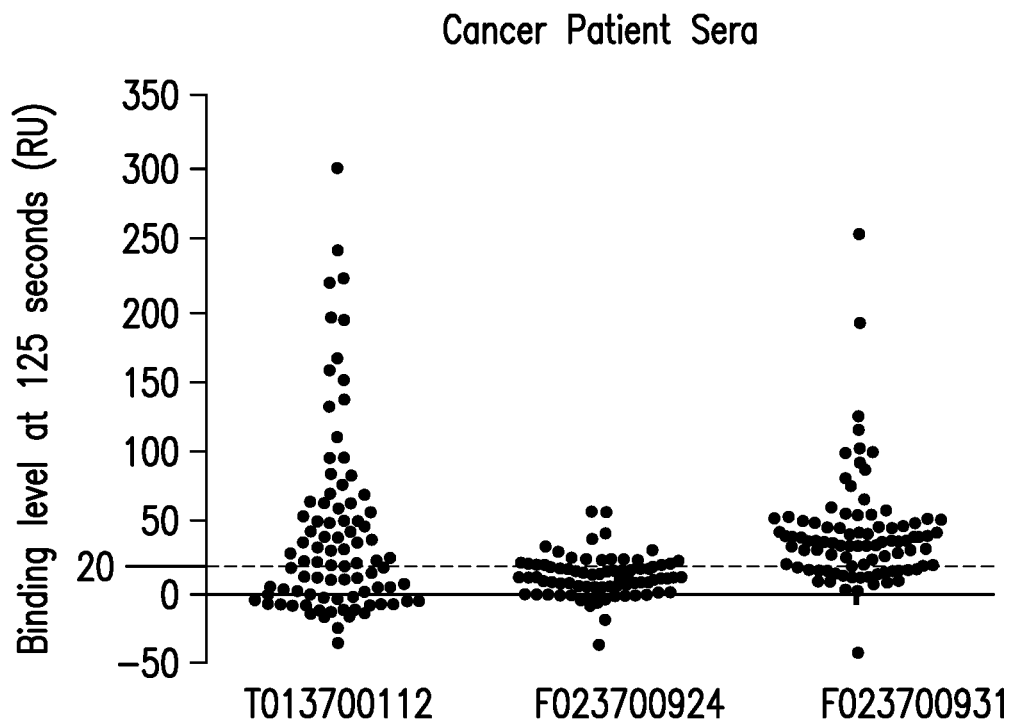
Figure 19D:
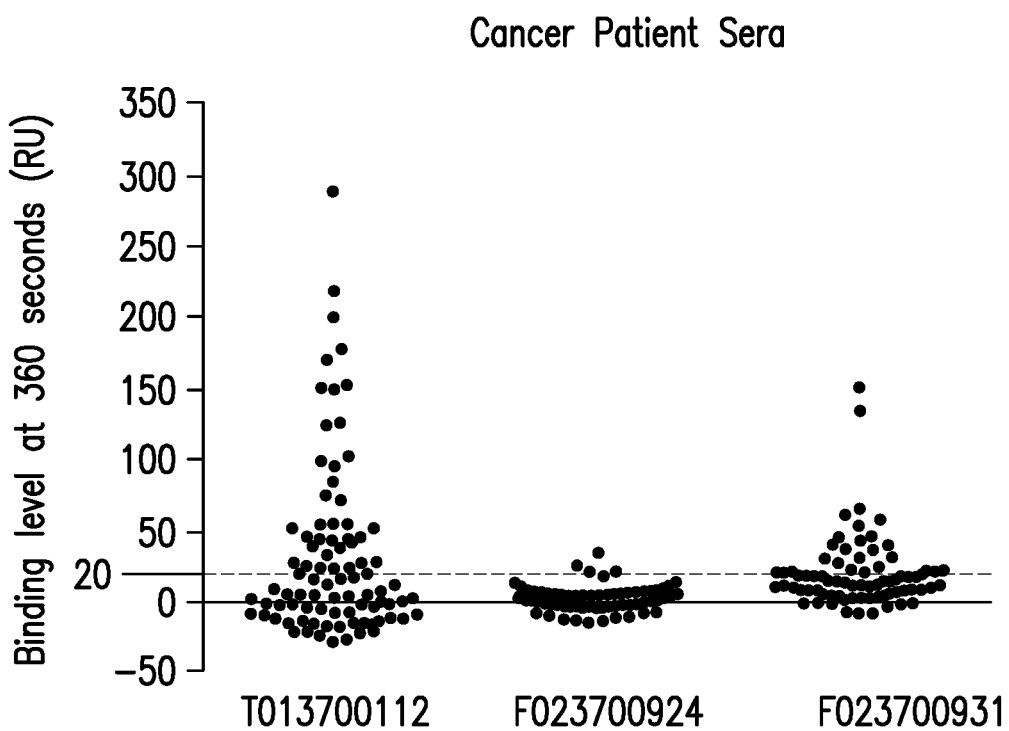
Figure 19E:
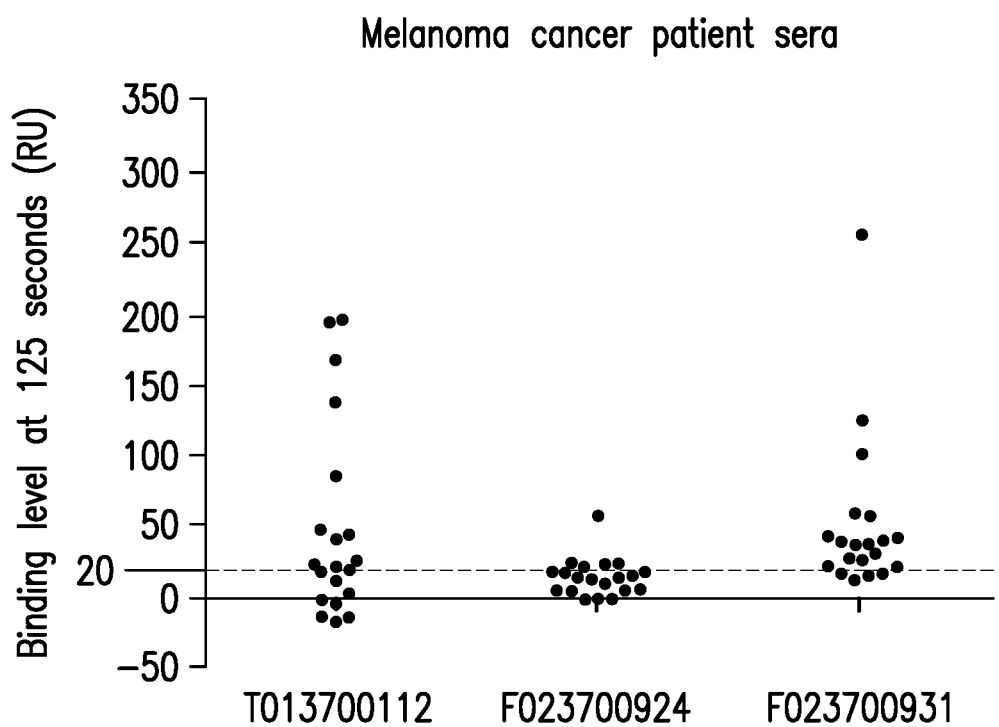
Figure 19F:
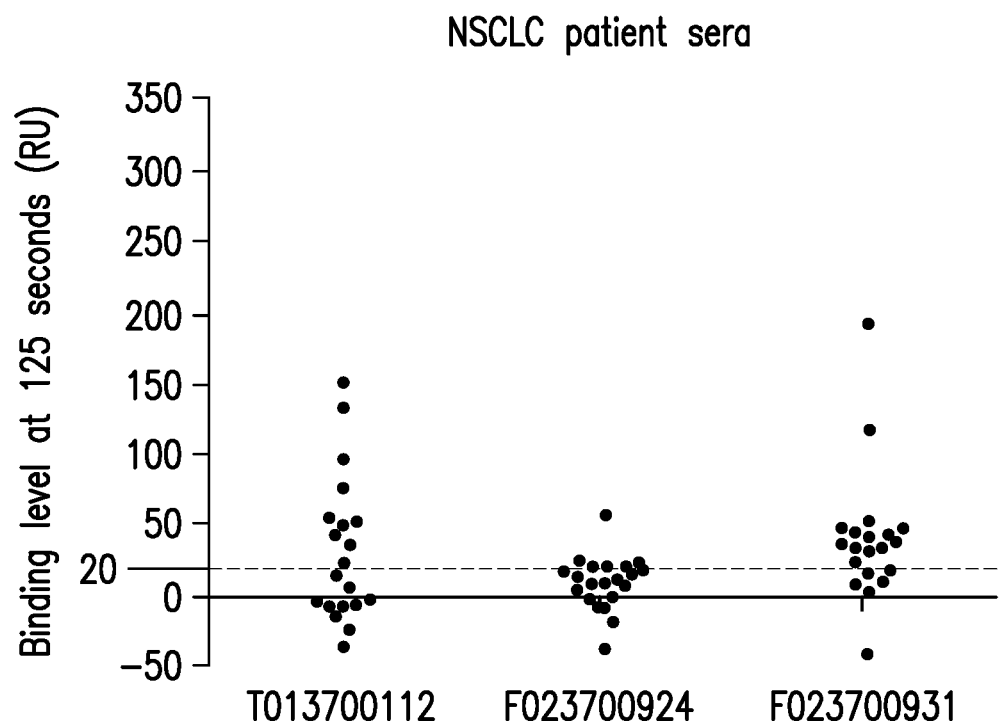
Figure 19G:
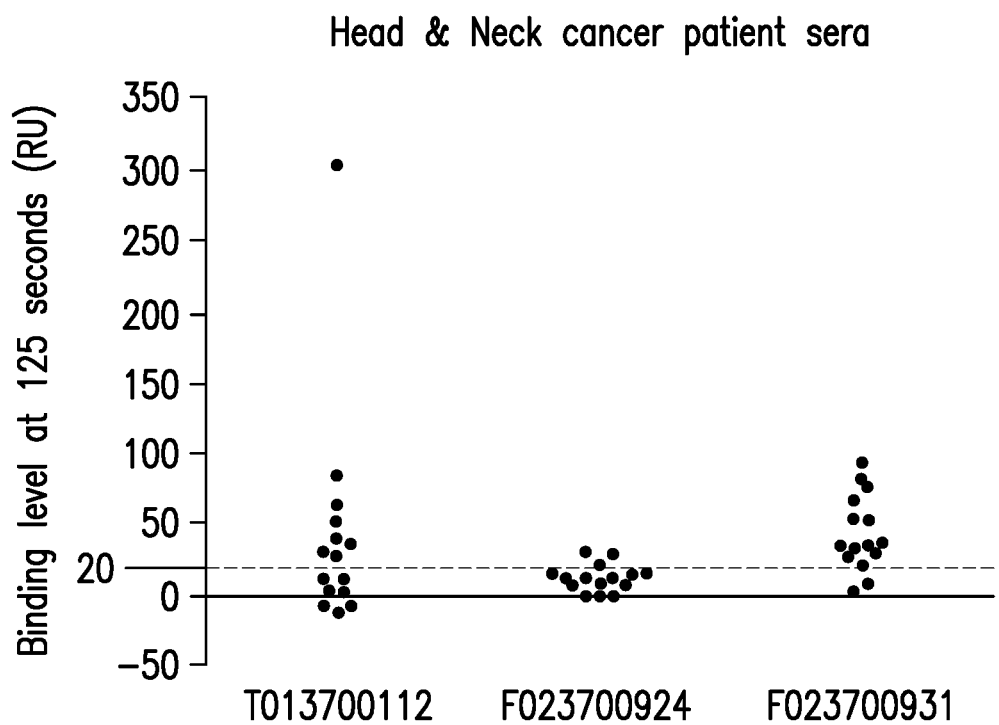
Figure 19H:
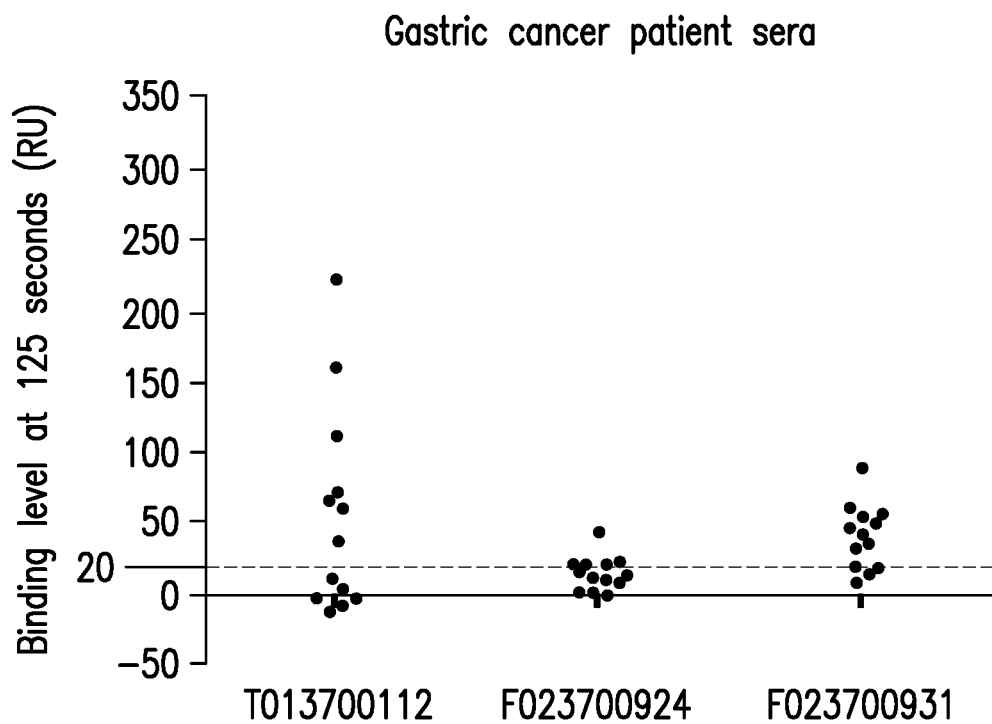
Figure 19I:
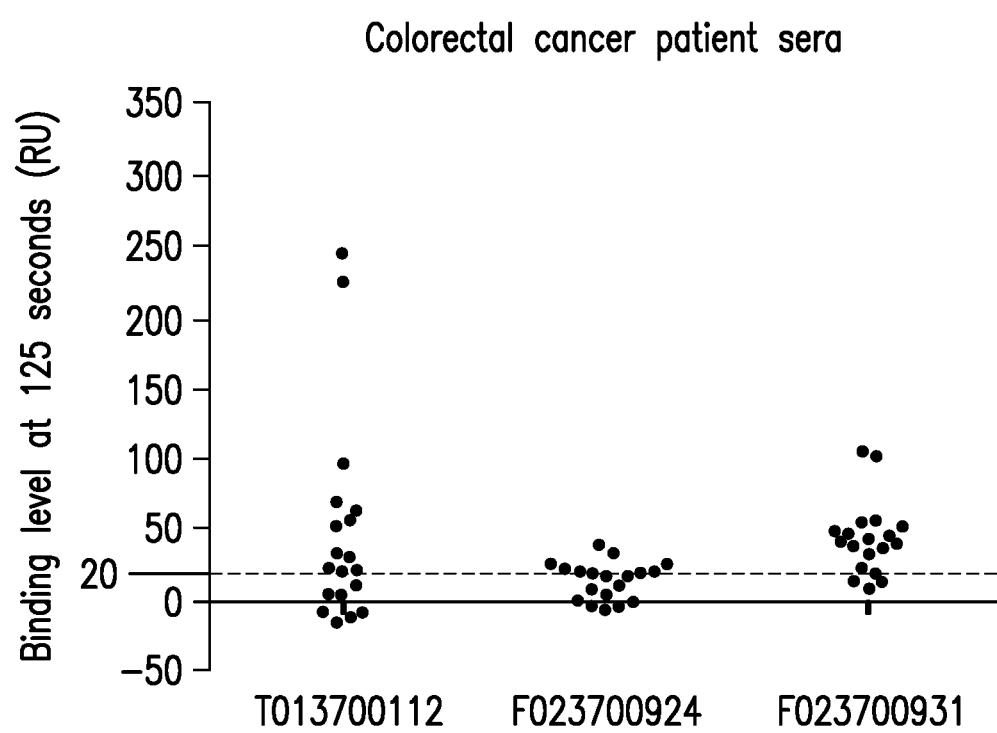

This Example demonstrated that the bispecific anti human PD 1/LAG-3 Nanobodies F023700931 and F023700924 bound to both human PD-1 and human LAG 3 expressed by the T-cell clone, blocked PD-1's interaction with PD-L1, blocked LAG-3's interaction with MHC Class II; thereby, allowing the T-cell to respond, to a greater degree, to the allogeneic stimulation based on inhibiting the dual PD-L1-mediated and MHC Class II-mediated suppression (FIG. 17 (A)). The monospecific, bivalent controls anti-human PD-1 F023700933 and anti-human LAG-3 F023700862 were only able to block one of the two inhibitory mechanisms individually leading to the T-cell responding, in a much more modest fashion, to the allogeneic stimulation. Additionally, this Example showed that the bispecific anti-human PD-1/LAG-3 Nanobody F023700969 and F023700970, containing 20GS or 9GS linkers, respectively, had similar potency as the parent F023700924 molecule containing 35GS linkers (FIG. 17 (C)). Similarly, the bispecific anti human PD-1/LAG-3 Nanobody F023701016 and F023701017, containing 20GS or 9GS linkers, respectively, had similar potency as the parent F023700931 molecule containing 35GS linkers (FIG. 17 (B)).

Example 14: Evaluation of Pre-Antibody Binding to F023700924 and F023700931

Binding of pre-existing antibodies to Nanobodies captured on human serum albumin (HSA) was evaluated using the ProteOn XPR36 (Bio-Rad Laboratories, Inc.). PBS/Tween (phosphate buffered saline, pH 7.4, 0.005% Tween 20) was used as running buffer and the experiments were performed at 25° C. The ligand lanes of a ProteOn GLC Sensor Chip were activated with EDC/NHS (flow rate 30 µL/min) and human serum albumin (has) was injected at 10 µg/ml in ProteOn Acetate buffer pH 4.5 (flow rate 100 µl/min) to render immobilization levels of approximately 3600 RU. After immobilization, surfaces were deactivated with ethanolamine HCl (flow rate 30 µL/min). Nanobodies were injected for 2 minutes at 45 µL/min over the HSA surface to render a Nanobody capture level of approximately 600 RU for trivalent F023700924 and approximately 1000RU for pentavalent F023700931. The samples containing pre-existing antibodies were diluted 1:10 in PBS-Tween20 (0.005%) before being injected for 2 minutes at 45 µl/min followed by a subsequent 400 seconds dissociation step. After each cycle (i.e. before a new Nanobody capture and blood sample injection step), the HSA surfaces were regenerated with a 2 minute injection of HCl (100 mM) at 45 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane containing HSA only. Binding levels of pre-existing antibodies were determined by setting report points at 125 seconds (5 seconds after end of association). As a reference, the samples containing pre-existing antibodies were also tested for binding to a trivalent Nanobody not modified for reducing the binding of these pre-existing antibodies (T013700112). The data from these experiments are set forth in FIG. 19 (A-I).

Bispecific anti-human PD-1/LAG-3 Nanobodies F023700924 had three Nanobody modules (one PD-1 module, one LAG-3 module, and one anti-albumin module); whereas, F023700931 has five Nanobody modules (duplicate PD-1 modules, duplicate LAG-3 modules, and one anti-albumin module). One component of the sequence optimization approach was to incorporate amino acid substitutions into the Nanobody framework that decreased the reactivity present in human sera to the Nanobody modules. This Example demonstrated the pre-existing reactivity found in a panel of serum from healthy human donors to the 3-module bispecific anti-human PD-1/LAG-3 Nanobody F023700924 was reduced compared to the pre-existing reactivity to a different 3-module Nanobody T013700112 construct that does not contain these framework amino acid substitutions at two timepoints. Reactivity of the 5-module bispecific anti-human PD-1/LAG-3 Nanobodies F023700931 was higher than the 3-module F023700924 (FIG. 19 (A-B)). In addition, this Example demonstrated the pre-existing reactivity found in a panel of serum from cancer patients to the 3-module bispecific anti-human PD-1/LAG-3 Nanobodies F023700924 is reduced compared to the pre-existing reactivity to a different 3-module Nanobody T013700112 construct that does not contain these framework amino acid substitutions at two timepoints. Reactivity of the 5-module bispecific anti-human PD-1/LAG-3 Nanobodies F023700931 was higher than the 3-module F023700924 (FIG. 19 (C-D)). Lastly, the reactivity of the panel of serum from cancer patients towards F023700924 and F023700931 was separated based on cancer indication (FIG. 19 (E-I)).

Example 15: Affinity Measurement of Sequence Optimized Human LAG-3 Nanobodies by Surface Plasmon Resonance Kinetic analysis of Nanobodies was performed by surface plasmon resonance (SPR) technology, using the Biacore T100 instrument (GE Healthcare). HBS-EP+(0.01 M HEPES pH 7.4, 0.15 M NaCl, 3 mM EDTA, 0.05% v/v Surfactant P20) was used as running buffer and the experiments were performed at 25° C. Two flow channels of a Series S Sensor Chip CM5 were activated with EDC (200 mM)/NHS (50 mM) and anti-Human IgG(Fc) (GE Healthcare, BR100839) was injected at 5 µg/ml in the supplied immobilization buffer (10 mM sodium acetate pH5.0) to render immobilization levels of approximately 2000 R.U. After immobilization, surfaces were deactivated with 1M ethanolamine/HCl (pH 8.5). The flow rate during the sensor preparation was set on 5 µL/min.

In the kinetic analysis, 62.5 nM human LAG3-hFc was injected for 1 minute at 10 µL/min over one anti-Human IgG(Fc) surface to render a capture level of approximately 600 RU. 2.5 fold serial dilutions of the Nanobodies (i.e., 5 µM down to 3.3 nM for F023700842) were made in running buffer before being injected for 2 minutes at 45 µL/min followed by a subsequent 900 seconds dissociation. After each cycle (i.e. before a new human LAG3-hFc capture and Nanobody injection step) the anti-hIgG(Fc) surfaces were regenerated with a 2 minute injection of $MgCl_2$ (3M) at 10 µL/min.

Sensorgram processing and data analysis was performed with Biacore T100 Evaluation Software Version 2.0.4 (GE Healthcare). Sensorgrams showing Nanobody binding were obtained after double referencing by subtracting 1) human LAG3-hFc/anti-hIgG(Fc) dissociation and 2) non-specific binding to reference flow channel. Processed curves were evaluated via fitting with the model 'Langmuir with Mass Transport'.

This Example demonstrated that the anti-human LAG-3 monovalent Nanobody F023700842 bound with high affinity to human LAG-3.

TABLE E

Affinity Measurement of Human LAG-3 Nanobodies by Surface Plasmon Resonance.

| | | ka (1/Ms) | kd (1/s) | KD (M) |
|---|---|---|---|---|
| F023700929 | Human PD-1-Fc | 2.0E+06 | 5.9E−04 | 2.9E−10 |
| F023701192 | | 2.5E+06 | 3.2E−03 | 1.3E−09 |
| F023701193 | | 3.2E+06 | 7.5E−03 | 2.4E−09 |
| F023700842 | Human LAS-3-Fc | 9.2E+05 | 1.9E−02 | 2.1E−08 |
| F023700924 | Human Serum | 6.4E+04 | 7.7E−03 | 1.2E−07 |
| F023700931 | Albumin | 3.2E+04 | 8.2E−03 | 2.5E−07 |
| F023700924 | Rhesus Serum | 6.9E+04 | 7.9E−03 | 1.2E−07 |
| F023700931 | Albumin | 3.2E+04 | 8.4E−03 | 2.7E−07 |

Example 16: Affinity Measurement of Sequence Optimized Human PD-1 Nanobodies by Surface Plasmon Resonance Kinetic analysis of the Nanobodies was performed by SPR technology, using the Biacore T100 instrument (GE Healthcare). HBS-EP+(0.01 M HEPES pH 7.4, 0.15 M NaCl, 3 mM EDTA, 0.05% v/v Surfactant P20) was used as running buffer and the experiments were performed at 25° C. Two flow channels of a Series S Sensor Chip CM5 were activated with EDC (200 mM)/NHS (50 mM). hPD-1-hFc was injected (4 times) at 5 µg/ml in suitable immobilization buffer (10 mM sodium acetate pH4.5) over one surface to render immobilization levels of 303 RU. After immobilization, surfaces were deactivated with 1M ethanolamine/HCl (pH 8.5). The flow rate during the sensor preparation was set on 5 µl/min.

In the kinetic analysis, 2.5 Fold serial dilutions of the Nanobodies (i.e. 1 µM down to 0.46 nM for F023700929, F023701192 and F023701193) were made in running buffer before being injected for 2 minutes at 45 µl/min followed by subsequent 900 seconds dissociation. After each cycle (i.e. before a new Nanobody injection step) the hPD1-hFc surfaces were regenerated with a 1 minute injection 10 mM Glycine pH1.5 at 45 µl/min. Sensorgram processing and data analysis was performed with Biacore T100 Evaluation Software Version 2.0.4 (GE Healthcare). Sensorgrams showing Nanobody binding were obtained after double referencing by subtracting 1) non-specific binding to reference flow channel and 2) HBS-EP+injection. Processed curves were evaluated via fitting with the model 'Langmuir with Mass Transport'.

This Example demonstrated that the anti-human PD-1 monovalent Nanobody F023700929 bound with high affinity to human PD-1. In addition, this Example demonstrated that additional amino acid variants of sequence optimized anti-human PD-1 monovalent F023700929 (i.e., F023701192 and F023701193) bound with high affinity to human PD-1.

TABLE F

Affinity Measurement of Sequence Optimized Human PD-1 Nanobodies by Surface Plasmon Resonance.

| | ka (1/Ms) | T(ka) | kd (1/s) | T(kd) | Rmax (RU) | T(Rmax) | KD (M) | kt (RU/Ms) | $Chi^2$ $(RU^2)$ | $Chi^2$/Rmax (%) |
|---|---|---|---|---|---|---|---|---|---|---|
| F023700929 | 2.0E+06 | 220 | 5.9E−04 | 150 | 32.0 | 500 | 2.9E−10 | 2.9E+15 | 1.8 | 5 |
| F023701192 | 2.5E+06 | 63 | 3.2E−03 | 66 | 27.9 | 380 | 1.3E−09 | 8.7E+07 | 0.8 | 3 |
| F023701193 | 3.2E+06 | 49 | 7.5E−03 | 49 | 29.5 | 450 | 2.4E−09 | 4.2E+07 | 1.2 | 4 |

Example 17: Affinity Measurement of Sequence Optimized Multispecific Human PD-1/LAG-3 to Albumin of Different Species by Surface Plasmon Resonance Kinetic analysis of the Nanobodies was performed by SPR technology, using the Biacore T100 instrument (GE Healthcare). HBS-EP+(0.01M HEPES pH 7.4, 0.15M NaCl, 3 mM EDTA, 0.05% v/v Surfactant P20) was used as running buffer and the experiments were performed at 25° C. Four flow channels of a Series S Sensor Chip CM5 were activated with EDC (200 mM)/NHS (50 mM) and Human Serum Albumin (Sigma, cat. A3782, lot. SLBD7204V) or Rhesus Serum Albumin (BioWorld, cat. 22070099-1, lot. L15091001DA) were injected at 5 µg/ml in 10 mM Sodium Acetate buffer pH 4.5 to render immobilization levels between 179 and 312 RU on three flow channels, respectively. After immobilization, surfaces were deactivated with 1M ethanolamine/HCl (pH 8.5). The flow rate during the sensor preparation was set on 5 µl/min.

In the kinetic analysis, three fold serial dilutions of the Nanobodies (i.e. 6 µM down to 2.7 nM) were prepared in running buffer before being injected for 2 minutes at 45 µl/min followed by subsequent 900 seconds dissociation. After each cycle (i.e. before a new Nanobody concentration was injected) all surfaces were regenerated with a 10 second injection of 10 mM Glycine pH 1.5 at 100 µl/min. Sensorgram processing and data analysis was performed with Biacore T100 Evaluation Software Version 2.0.4 (GE Healthcare). Sensorgrams showing Nanobody binding were obtained after double referencing by subtracting 1) non-specific binding to reference flow channel and 2) average of two HBS-EP+injections on the specific flow channel. Processed curves were evaluated via fitting with the model 'Langmuir with Mass Transport'.

This Example demonstrated that the bispecific anti human PD1/LAG-3 Nanobodies F023700931 and F023700924 bound to both human albumin and rhesus albumin with similar affinity.

TABLE G

Affinity Measurement of Sequence Optimized Multispecific Human PD-1/LAG-3 to Albumin of Different Species by Surface Plasmon Resonance.

| | | HSA | | | RhSA | | | MSA | | |
| --- | --- | --- | --- | --- | --- | --- | --- | --- | --- | --- |
| Nanobody | Valency | Ka (1/Ms) ($\times 10^4$) | Kd (1/Ms) ($\times 10^{-3}$) | KD (M) ($\times 10^{-7}$) | Ka (1/Ms) ($\times 10^4$) | Kd (1/Ms) ($\times 10^{-3}$) | KD (M) ($\times 10^{-7}$) | Ka (1/Ms) ($\times 10^5$) | Kd (1/Ms) ($\times 10^{-1}$) | KD (M) ($\times 10^{-6}$) |
| F023700924-CHO-EXP1 | Trimer | 6.4 | 7.7 | 1.2 | 6.9 | 7.9 | 1.2 | >5.0 | <6.0 | −1.9 |
| F023700931-CHO-EXP1 | Pentamer | 3.2 | 8.2 | 2.5 | 3.2 | 8.4 | 2.7 | >5.0 | <6.0 | −4.1 |

We claim:

1. A polynucleotide encoding a PD1 binder comprising one or more immunoglobulin single variable domains (ISVDs) that bind PD1, each ISVD comprising (i) a CDR1 comprising the amino acid sequence IHAMG (SEQ ID NO: 3) or GSIASIHAMG (SEQ ID NO: 6); a CDR2 comprising the amino acid sequence VITXSGGITYYADSVKG (SEQ ID NO: 4) or VITXSGGITY (SEQ ID NO: 7); and a CDR3 comprising the amino acid sequence DKHQSSXYDY (SEQ ID NO: 5), and (ii) a substitution of a leucine at position 11 with valine and a substitution of a isoleucine at position 89 with leucine, wherein the positions are numbered according to Kabat, and optionally, further comprising a half-life extender and/or a C-terminal extender.

2. A vector comprising the polynucleotide of claim 1.

3. A host cell comprising the polynucleotide of claim 1.

4. A method for making a PD1 binder comprising:
   introducing a polynucleotide encoding a PD1 binder comprising one or more immunoglobulin single variable domains (ISVDs) that bind PD1, each ISVD comprising (i) a CDR1 comprising the amino acid sequence IHAMG (SEQ ID NO: 3) or GSIASIHAMG (SEQ ID NO: 6); a CDR2 comprising the amino acid sequence VITXSGGITYYADSVKG (SEQ ID NO: 4) or VITXSGGITY (SEQ ID NO: 7); and a CDR3 comprising the amino acid sequence DKHQSSXYDY (SEQ ID NO: 5), and (ii) a substitution of a leucine at position 11 with valine and a substitution of a isoleucine at position 89 with leucine, wherein the positions are numbered according to Kabat, and optionally, further comprising a half-life extender and/or a C-terminal extender into a host cell and culturing the host cell in a medium under conditions favorable to expression of said PD1 binder from said polynucleotide and, optionally, purifying the PD1 binder from said host cell and/or said medium.

5. The polynucleotide of claim 1, wherein each ISVD that binds PD1 independently comprises an amino acid sequence selected from the group consisting of

```
                                        (SEQ ID NO: 57)
DVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(SEQ ID NO: 99)
EVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(amino acids 1-119 of SEQ ID NO: 101)
DVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(SEQ ID NO: 103)
DVQLVESGGGVVQPGGSLRLSCAASGSIASIHAMGWFRQAPGKEREFVAV
ITVSGGITYYADSVKGRFTISRDNSKNTVYLQMNSLRPEDTALYYCAGDK
HQSSFYDYWGQGTLVTVSS;

(SEQ ID NO: 104)
DVQLVESGGGVVQPGGSLRLSCAASGSIASIHAMGWFRQAPGKEREFVAV
ITVSGGITYYADSVKGRFTISRDQSKNTVYLQMNSLRPEDTALYYCAGDK
HQSSFYDYWGQGTLVTVSS;
and (SEQ ID NO: 105)
DVQLVESGGGVVQPGGSLRLSCAASGSIASIHAMGWFRQAPGKEREFVAV
ITVSGGITYYADSVKGRFTISRDPSKNTVYLQMNSLRPEDTALYYCAGDK
HQSSFYDYWGQGTLVTVSS.
```

6. The polynucleotide of claim 1, wherein the polynucleotide further encodes a C-terminal extender, which is an alanine residue.

7. The polynucleotide of claim 1, wherein the polynucleotide further encodes a half-life extender comprising an ISVD that binds human serum albumin wherein the ISVD comprises a CDR1 comprising the amino acid sequence GFTFSSFGMS (SEQ ID NO: 60) or SFGMS (SEQ ID NO:151); a CDR2 comprising the amino acid sequence SISGSGSDTLYADSVKG (SEQ ID NO: 61) or SISGSGSDTL (SEQ ID NO:152); and a CDR3 comprising the amino acid sequence GGSLSR (SEQ ID NO: 62).

8. The polynucleotide of claim 1, wherein the polynucleotide further encodes a half-life extender comprising an ISVD that binds human serum albumin wherein the ISVD comprises the amino acid sequence

```
                                       (SEQ ID NO: 142)
EVQLVESGGGVVQPGNSLRLSCAASGETFSSFGMSWVRQAPGKGLEWVSS
ISGSGSDTLYADSVKGRFTISRDNAKTTLYLQMNSLRPEDTALYYCTIGG
SLSRSSQGTLVTVSS.
```

9. The polynucleotide of claim 1, wherein the polynucleotide encodes (i) an ISVD that binds PD1 comprising the amino acid sequence DVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSSWYDYWGQGTLVTVSS (SEQ ID NO:57); (ii) a half-life extender comprising an ISVD that binds human serum albumin and comprises the amino acid sequence EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS (SEQ ID NO: 142); and, (iii) a C-terminal extender comprising an alanine residue.

10. The polynucleotide of claim 9, wherein the polynucleotide further encodes a polypeptide linker that links the C-terminus of the ISVD that binds PD1 to the N-terminus of the ISVD that binds human serum albumin, wherein the polypeptide linker comprises the amino acid sequence set forth in SEQ ID NO: 58.

11. The method of claim 4, wherein each ISVD that binds PD1 independently comprises an amino acid sequence selected from the group consisting of

```
                                        (SEQ ID NO: 57)
DVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(SEQ ID NO: 99)
EVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(amino acids 1-119 of SEQ ID NO: 101)
DVQLVESGGGVVQPGGSLRLSCAASGSIASIHAMGWFRQAPGKEREFVAV
ITWSGGITYYADSVKGRFTISRDNSKNTVYLQMNSLRPEDTALYYCAGDK
HQSSWYDYWGQGTLVTVSS;

(SEQ ID NO: 103)
DVQLVESGGGVVQPGGSLRLSCAASGSIASIHAMGWFRQAPGKEREFVAV
ITVSGGITYYADSVKGRFTISRDNSKNTVYLQMNSLRPEDTALYYCAGDK
HQSSFYDYWGQGTLVTVSS;

(SEQ ID NO: 104)
DVQLVESGGGVVQPGGSLRLSCAASGSIASIHAMGWFRQAPGKEREFVAV
ITVSGGITYYADSVKGRFTISRDQSKNTVYLQMNSLRPEDTALYYCAGDK
HQSSFYDYWGQGTLVTVSS;
and (SEQ ID NO: 105)
DVQLVESGGGVVQPGGSLRLSCAASGSIASIHAMGWFRQAPGKEREFVAV
ITVSGGITYYADSVKGRFTISRDPSKNTVYLQMNSLRPEDTALYYCAGDK
HQSSFYDYWGQGTLVTVSS.
```

12. The method of claim 4, wherein the polynucleotide further encodes a C-terminal extender, which is an alanine residue.

13. The method of claim 4, wherein the polynucleotide further encodes a half-life extender comprising an ISVD that binds human serum albumin wherein the ISVD comprises a CDR1 comprising the amino acid sequence GFTFSSFGMS (SEQ ID NO: 60) or SFGMS (SEQ ID NO:151); a CDR2 comprising the amino acid sequence SISGSGSDTLYADSVKG (SEQ ID NO: 61) or SISGSGSDTL (SEQ ID NO:152); and a CDR3 comprising the amino acid sequence GGSLSR (SEQ ID NO: 62).

14. The method of claim 4, wherein the polynucleotide further encodes a half-life extender comprising an ISVD that binds human serum albumin wherein the ISVD comprises the amino acid sequence

```
                                       (SEQ ID NO: 142)
EVQLVESGGGVVQPGNSLRLSCAASGETFSSFGMSWVRQAPGKGLEWVSS
ISGSGSDTLYADSVKGRFTISRDNAKTTLYLQMNSLRPEDTALYYCTIGG
SLSRSSQGTLVTVSS.
```

15. The method of claim 4, wherein the polynucleotide encodes (i) an ISVD that binds PD1 comprising the amino acid sequence DVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSSWYDYWGQGTLVTVSS (SEQ ID NO:57); (ii) a half-life extender comprising an ISVD that binds human serum albumin and comprises the amino acid sequence EVQLVESGGGVVQPGNSLRLSCAASGFTFSSFGMSWVRQAPGK-GLEWVSSISGSGSDTLYADSVKGRFTISRDNAKT TLYLQMNSLRPEDTALYYC-TIGGSLSRSSQGTLVTVSS (SEQ ID NO: 142); and, (iii) a C-terminal extender comprising an alanine residue.

16. The method of claim 15, wherein the polynucleotide further encodes a polypeptide linker that links the C-terminus of the ISVD that binds PD1 to the N-terminus of the ISVD that binds human serum albumin, wherein the polypeptide linker comprises the amino acid sequence set forth in SEQ ID NO: 58.

* * * * *